(12) United States Patent
Diehn et al.

(10) Patent No.: US 12,286,634 B2
(45) Date of Patent: Apr. 29, 2025

(54) REGULATORY SEQUENCES FOR MODULATING TRANSGENE EXPRESSION IN PLANTS

(71) Applicants: CORTEVA AGRISCIENCE LLC, Indianapolis, IN (US); PIONEER HI-BRED INTERNATIONAL, INC., Johnston, IA (US)

(72) Inventors: Scott Diehn, West Des Moines, IA (US); Ajit Nott, Johnston, IA (US); David Selinger, Hockessin, DE (US); Carl Simmons, Des Moines, IA (US); Priyanka Bhyri, Johnston, IA (US); Venkata S Tavva, Hyderabad (IN)

(73) Assignees: PIONEER HI-BRED INTERNATIONAL, INC., IA (US); Corteva AgriScience LLC, IN (US)

( * ) Notice: Subject to any disclaimer, the term of this patent is extended or adjusted under 35 U.S.C. 154(b) by 303 days.

(21) Appl. No.: 17/645,631

(22) Filed: Dec. 22, 2021

(65) Prior Publication Data

US 2022/0119830 A1    Apr. 21, 2022

Related U.S. Application Data

(63) Continuation of application No. 16/429,846, filed on Jun. 3, 2019, now Pat. No. 11,242,535, which is a continuation of application No. 15/660,390, filed on Jul. 26, 2017, now Pat. No. 10,344,290, which is a continuation of application No. 14/660,076, filed on Mar. 17, 2015, now abandoned, which is a continuation of application No. 13/701,848, filed as application No. PCT/US2011/039691 on Jun. 9, 2011, now abandoned.

(60) Provisional application No. 61/372,515, filed on Aug. 11, 2010.

(30) Foreign Application Priority Data

Jun. 9, 2010  (IN) .......................... 1340/DEL/2010

(51) Int. Cl.
  *C12N 15/82*  (2006.01)
(52) U.S. Cl.
  CPC .............................. *C12N 15/8216* (2013.01)
(58) Field of Classification Search
  None
  See application file for complete search history.

(56) References Cited

U.S. PATENT DOCUMENTS 6,252,138 B1   6/2001 Karlmi et al.
10,344,290 B2  7/2019 Scott et al.
11,242,535 B2  2/2022 Diehn et al.
2007/0204367 A1* 8/2007 Flasinski et al. .. C12N 15/8216
                                                    536/23.6
2011/0201059 A1  8/2011 Hall et al.
2012/0198584 A1  8/2012 Nuccio
2013/0145502 A1  6/2013 Diehn et al.
2015/0184177 A1  7/2015 Diehn et al.

FOREIGN PATENT DOCUMENTS

CN         1361282 A       7/2002
EP       1 817 419 B1      8/2007
EP        1817419 A2       8/2007
WO       1993019189 A1     9/1993
WO       2006094976 A3     9/2006
WO     WO-2006094976 A2    9/2006

OTHER PUBLICATIONS

Rose (2008) Curr Top Microbial Immunol 326:277-90, 283-84.*
Gallegos & Rose (2015) Plant Sci 237:8-15.*
Kim et al. (1994) Plant Mol Biol 24:105-17.*
Dolferus et al. (1994) Plant Physiol 105:1075-87.*
Saha et al. (2007) In Silica Biol 7(1 ):7-19.*
Rose, Curr Top Microbiol Immunol, 326:277-90 (2008).
Crane, Phil Trans Biol Sci 359(1444): 735-37 (2004).
Narsai et al., Plant Cell, 19:3418-36 (2007).
Clancy et al. "Maize Shrunken-1 intron and exon regions increase gene expression in maize protoplasts." Plant Science. (1994) 98:151-161.
Luehrsen, Kenneth R. & Virginia Walbot. "Intron enhancement of gene expression and the splicing efficiency of introns in maize cells." Molecular and General Genetics. (1991) 225:81-93.
Maas et al. "The combination of a novel stimulatory element in the first exon of the maize Shrunken-1 gene with the following intron 1 enhances reporter expression up to 1000-fold." Plant Molecular Biology. (1991) 16:199-207.
Database Accession No. AC202950.
Chemical Book Bgl II_CAGATCTG_2008.
Gallegos & Rose (2015) Plant Sol 237:8-15.
The International Search Report and Written Opinion for International Application PCT/US2011/039691.
Donald R.G., et al., "Mutation of Either G Box or I Box Sequences Profoundly Affects Expression from the Arabidopsis rbcS-1A Promoter," The EMBO Journal, 1990, vol. 9, No. 6, pp. 1717-1726.
International Preliminary Report on Patentability for International Application No. PCT/US2011/039691, mailed Dec. 20, 2012, 22 Pages.
Saha D., et al., "In Silico Analysis of the Lateral Organ Junction (LOJ) Gene and Promoter of Arabidopsis Thaliana," In Silico Biology, 2007, vol. 7, No. 1, pp. 7-19.

* cited by examiner

*Primary Examiner* — Russell T Boggs

(57) ABSTRACT

The invention relates to gene expression regulatory sequences, specifically introns that act as enhancers of gene expression, the promoter and terminator sequences endogenously associated with these introns. Presence of these intronic enhancer sequences in proximity to promoter sequences leads to enhancement of gene expression. Methods of finding such new intronic enhancer sequences and using them to generate transgenic plants are also described.

14 Claims, 13 Drawing Sheets

Specification includes a Sequence Listing.

```
                        SEQUENCE LISTING

<160> NUMBER OF SEQ ID NOS: 146

<210> SEQ ID NO 1
<211> LENGTH: 978
<212> TYPE: DNA
<213> ORGANISM: zea mays

<400> SEQUENCE: 1
gtgcagcgtg acccggtcgt gccctctct agagataatg agcattgcat gtctaagtta      60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg     300 caaatagctt cacctatata atacttcatc cattttatta gtacatccat ttagggttta    360
gggttaatgg tttttataga ctaattttt tagtacatct attttattct attttagcct     420
ctaaattaag aaaactaaaa ctctatttta gttttttat ttaataattt agatataaaa      480
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc cctccacac cctctttccc      900 caacctcgtg ttgttcggag cgcacacaca cacaaccaga tctccccaa atccacccgt    960 cggcacctcc gcttcaag                                                  978

<210> SEQ ID NO 2
<211> LENGTH: 1013
<212> TYPE: DNA
<213> ORGANISM: zea mays

<400> SEQUENCE: 2
gtacgccgct cgtcctcccc cccccccctc tctaccttct ctagatcggc gttccggtcc      60
atgcatggtt agggcccggt agttctactt ctgttcatgt ttgtgttaga tccgtgtttg    120
tgttagatcc gtgctgctag cgttcgtaca cggatgcgac ctgtacgtca gacacgttct    180
gattgctaac ttgccagtgt ttctctttgg ggaatcctgg gatggctcta gccgttccgc    240
agacgggatc gatttcatga tttttttgt ttcgttgcat aggggtttggt ttgcccttt    300 cctttatttc aatatatgcc gtgcacttgt ttgtcgggtc atcttttcat gcttttttt     360
```

| | |
|---|---|
| gtcttggttg tgatgatgtg gtctggttgg gcggtcgttc tagatcggag tagaattctg | 420 |
| tttcaaacta cctggtggat ttattaattt tggatctgta tgtgtgtgcc atacatattc | 480 |
| atagttacga attgaagatg atggatggaa atatcgatct aggataggta tacatgttga | 540 |
| tgcgggtttt actgatgcat atacagagat gcttttttgtt cgcttggttg tgatgatgtg | 600 |
| gtgtggttgg gcggtcgttc attcgttcta gatcggagta gaatactgtt tcaaactacc | 660 |
| tggtgtattt attaattttg aactgtatg tgtgtgtcat acatcttcat agttacgagt | 720 |
| ttaagatgga tggaaatatc gatctaggat aggtatacat gttgatgtgg gttttactga | 780 |
| tgcatataca tgatggcata tgcagcatct attcatatgc tctaaccttg agtacctatc | 840 |
| tattataata aacaagtatg ttttataatt attttgatct tgatatactt ggatgatggc | 900 |
| atatgcagca gctatatgtg gattttttta gccctgcctt catacgctat ttatttgctt | 960 |
| ggtactgttt cttttgtcga tgctcaccct gttgtttggt gttacttctg cag | 1013 |

<210> SEQ ID NO 3
<211> LENGTH: 16656
<212> TYPE: DNA
<213> ORGANISM: Artificial Sequence
<220> FEATURE:
<223> OTHER INFORMATION: Vector Sequence

<400> SEQUENCE: 3

| | |
|---|---|
| gtttacccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagcaag | 180 |
| ctggtacgat tgtaatacga ctcactatag ggcgaattga gcgctgttta aacgctcttc | 240 |
| aactggaaga gcggttacca gagctggtca cctttgtcca ccaagatgga actgcggcct | 300 |
| cgaagcttgg cgcgccgtgc agcgtgaccg ggtcgtgccc ctctctagag ataatgagca | 360 |
| ttgcatgtct aagttataaa aaattaccac atatttttt tgtcacactt gtttgaagtg | 420 |
| cagtttatct atctttatac atatatttaa actttactct acgaataata taatctatag | 480 |
| tactacaata atatcagtgt tttagagaat catataaatg aacagttaga catggtctaa | 540 |
| aggacaattg agtattttga caacaggact ctacagtttt atcttttag tgtgcatgtg | 600 |
| ttctcctttt tttttgcaaa tagcttcacc tatataatac ttcatccatt ttattagtac | 660 |
| atccatttag ggtttagggt taatggtttt tatagactaa ttttttagt acatctattt | 720 |
| tattctattt tagcctctaa attaagaaaa ctaaaactct attttagttt ttttatttaa | 780 |
| taatttagat ataaaataga ataaaataaa gtgactaaaa attaaacaaa tacccctttaa | 840 |
| gaaattaaaa aaactaagga aacatttttc ttgtttcgag tagataatgc cagcctgtta | 900 |
| aacgccgtcg acgagtctaa cggacaccaa ccagcgaacc agcagcgtcg cgtcgggcca | 960 |
| agcgaagcag acggcacggc atctctgtcg ctgcctctgg accctctcg agagttccgc | 1020 |
| tccaccgttg gacttgctcc gctgtcggca tccagaaatt gcgtggcgga gcggcagacg | 1080 |
| tgagccggca cggcaggcgg cctcctcctc ctctcacggc accggcagct acggggatt | 1140 |
| cctttcccac cgctccttcg cttttccttc ctcgccgcc gtaataaata gacacccct | 1200 |
| ccacacccctc ttttccccaac ctcgtgttgt tcggagcgca cacacacaca accagatctc | 1260 |
| ccccaaatcc acccgtcggc acctccgctt caagcgatcg caggtacccg actttaactt | 1320 |
| agcctaggat ccacacgaca ccatggtccg tcctgtagaa accccaaccc gtgaaatcaa | 1380 |

```
aaaactcgac ggcctgtggg cattcagtct ggatcgcgaa actgtggaa ttgatcagcg    1440
ttggtgggaa agcgcgttac aagaaagccg ggcaattgct gtgccaggca gttttaacga    1500
tcagttcgcc gatgcagata ttcgtaatta tgcgggcaac gtctggtatc agcgcgaagt    1560
ctttataccg aaaggttggg caggccagcg tatcgtgctg cgtttcgatg cggtcactca    1620
ttacggcaaa gtgtgggtca ataatcagga agtgatggag catcagggcg gctatacgcc    1680
atttgaagcc gatgtcacgc cgtatgttat tgccggaaa agtgtacgta agttctgct    1740
tctacctttg atatatatat aataattatc attaattagt agtaatataa tatttcaaat    1800
atttttttca aaataaaaga atgtagtata tagcaattgc ttttctgtag tttataagtg    1860
tgtatatttt aatttataac ttttctaata tatgaccaaa atttgttgat gtgcaggtat    1920
caccgtttgt gtgaacaacg aactgaactg gcagactatc ccgccgggaa tggtgattac    1980
cgacgaaaac ggcaagaaaa agcagtctta cttccatgat ttctttaact atgccggaat    2040
ccatcgcagc gtaatgctct acaccacgcc gaacacctgg gtggacgata tcaccgtggt    2100
gacgcatgtc gcgcaagact gtaaccacgc gtctgttgac tggcaggtgg tggccaatgg    2160
tgatgtcagc gttgaactgc gtgatgcgga tcaacaggtg gttgcaactg acaaggcac    2220
tagcgggact ttgcaagtgg tgaatccgca cctctggcaa ccgggtgaag ttatctcta    2280
tgaactgtgc gtcacagcca aaagccagac agagtgtgat atctacccgc ttcgcgtcgg    2340
catccggtca gtggcagtga agggcgaaca gttcctgatt aaccacaaac cgttctactt    2400
tactggcttt ggtcgtcatg aagatgcgga cttgcgtggc aaaggattcg ataacgtgct    2460
gatggtgcac gaccacgcat taatggactg gattggggcc aactcctacc gtacctcgca    2520
ttacccttac gctgaagaga tgctcgactg gcagatgaa catggcatcg tggtgattga    2580
tgaaactgct gctgtcggct taacctctc tttaggcatt ggtttcgaag cgggcaacaa    2640
gccgaaagaa ctgtacagcg aagaggcagt caacggggaa actcagcaag cgcacttaca    2700
ggcgattaaa gagctgatag cgcgtgacaa aaaccaccca agcgtggtga tgtggagtat    2760
tgccaacgaa ccggatacccc gtccgcaagg tgcacgggaa tatttcgcgc cactggcgga    2820
agcaacgcgt aaactcgacc cgacgcgtcc gatcacctgc gtcaatgtaa tgttctgcga    2880
cgctcacacc gataccatca gcgatctctt tgatgtgctg tgcctgaacc gttattacgg    2940
atggtatgtc caaagcggcg atttggaaac ggcagagaag gtactggaaa aagaacttct    3000
ggcctggcag gagaaactgc atcagccgat tatcatcacc gaatacggcg tggatacgtt    3060
agccgggctg cactcaatgt acaccgacat gtggagtgaa gagtatcagt gtgcatggct    3120
ggatatgtat caccgcgtct ttgatcgcgt cagcgccgtc gtcggtgaac aggtatggaa    3180
tttcgccgat tttgcgacct cgcaaggcat attgcgcgtt ggcggtaaca agaaagggat    3240
cttcactcgc gaccgcaaac cgaagtcggc ggcttttctg ctgcaaaaac gctggactgg    3300
catgaacttc ggtgaaaaac cgcagcaggg aggcaaacaa tgaatcaaca actctcctgg    3360
cgcaccatcg tcggctacag cctcggtgac gtggggcaac ctagacttgt ccatcttctg    3420
gattggccaa cttaattaat gtatgaaata aaaggatgca cacatagtga catgctaatc    3480
actataatgt gggcatcaaa gttgtgtgtt atgtgtaatt actagttatc tgaataaaag    3540
agaaagagat catccatatt tcttatccta aatgaatgtc acgtgtcttt ataattcttt    3600
gatgaaccag atgcatttca ttaaccaaat ccatatacat ataaatatta atcatatata    3660
attaatatca attgggttag caaaacaaat ctagtctagg tgtgttttgc gaattgcggc    3720
cgcgatctga gcttctagag gatccccatc gatgggcccc ggccgaagct tgcatgcctg    3780
```

```
cagtgcagcg tgacccggtc gtgcccctct ctagagataa tgagcattgc atgtctaagt   3840
tataaaaaat taccacatat ttttttttgtc acacttgttt gaagtgcagt ttatctatct   3900
ttatacatat atttaaactt tactctacga ataatataat ctatagtact acaataatat   3960
cagtgtttta gagaatcata taaatgaaca gttagacatg gtctaaagga caattgagta   4020
ttttgacaac aggactctac agttttatct ttttagtgtg catgtgttct ccttttttt    4080
tgcaaatagc ttcacctata taatacttca tccattttat tagtacatcc atttaggggtt  4140
tagggttaat ggttttata gactaatttt tttagtacat ctattttatt ctattttagc    4200
ctctaaatta agaaaactaa aactctattt tagttttttt atttaataat ttagatataa   4260
aatagaataa aataaagtga ctaaaaatta acaaatacc ctttaagaaa ttaaaaaaac    4320
taaggaaaca ttttcttgt ttcgagtaga taatgccagc ctgttaaacg ccgtcgacga    4380
gtctaacgga caccaaccag cgaaccagca gcgtcgcgtc gggccaagcg aagcagacgg   4440
cacggcatct ctgtcgctgc ctctggaccc ctctcgagag ttccgctcca ccgttggact   4500
tgctccgctg tcggcatcca gaaattgcgt ggcggagcgg cagacgtgag ccggcacggc   4560
aggcggcctc ctcctcctct cacggcaccg gcagctacgg gggattcctt tcccaccgct   4620
ccttcgcttt cccttcctcg cccgccgtaa taaatagaca cccctccac accctctttc     4680
cccaacctcg tgttgttcgg agcgcacaca cacacaacca gatctccccc aaatccaccc   4740
gtcggcacct ccgcttcaag gtacgccgct cgtcctcccc ccccccctc tctaccttct    4800
ctagatcggc gttccggtcc atgcatggtt agggcccggt agttctactt ctgttcatgt   4860
ttgtgttaga tccgtgtttg tgttagatcc gtgctgctag cgttcgtaca cggatgcgac   4920
ctgtacgtca gacacgttct gattgctaac ttgccagtgt ttctctttgg ggaatcctgg   4980
gatggctcta gccgttccgc agacgggatc gatttcatga tttttttgt tttcgttgcat   5040
agggtttggt ttgccctttt cctttatttc aatatatgcc gtgcacttgt ttgtcgggtc   5100
atcttttcat gctttttttt gtcttggttg tgatgatgtg gtctggttgg gcggtcgttc   5160
tagatcggag tagaattctg tttcaaacta cctggtggat ttattaattt tggatctgta    5220
tgtgtgtgcc atacatattc atagttacga attgaagatg atggatggaa atatcgatct   5280
aggataggta tacatgttga tgcgggtttt actgatgcat atacagagat gcttttttgtt  5340
cgcttggttg tgatgatgtg gtgtggttgg gcggtcgttc attcgttcta gatcggagta    5400
gaatactgtt tcaaactacc tggtgtattt attaattttg gaactgtatg tgtgtgtcat    5460
acatcttcat agttacgagt ttaagatgga tggaaatatc gatctaggat aggtatacat    5520
gttgatgtgg gttttactga tgcatataca tgatggcata tgcagcatct attcatatgc   5580
tctaaccttg agtacctatc tattataata aacaagtatg ttttataatt attttgatct    5640
tgatatactt ggatgatggc atatgcagca gctatatgtg gatttttta gccctgcctt    5700
catacgctat ttatttgctt ggtactgttt cttttgtcga tgctcaccct gttgtttggt    5760
gttacttctg caggtcgact ttaacttagc ctaggatcca cacgacacca tgtcccccga   5820
gcgccgcccc gtcgagatcc gcccggccac cgccgccgac atggccgccg tgtgcgacat   5880
cgtgaaccac tacatcgaga cctccaccgt gaacttccgc accgagccgc agaccccgca   5940
ggagtggatc gacgacctgg agcgcctcca ggaccgctac ccgtggctcg tggccgaggt   6000
ggagggcgtg gtgccggca tcgcctacgc cggcccgtgg aaggcccgca acgcctacga    6060
ctggaccgtg gagtccaccg tgtacgtgtc ccaccgccac cagcgcctcg gcctcggctc   6120
```

```
caccctctac acccacctcc tcaagagcat ggaggcccag ggcttcaagt ccgtggtggc    6180
cgtgatcggc ctcccgaacg acccgtccgt gcgcctccac gaggccctcg gctacaccgc    6240
ccgcggcacc ctccgcgccg ccggctacaa gcacggcggc tggcacgacg tcggcttctg    6300
gcagcgcgac ttcgagctgc cggccccgcc gcgcccggtg cgcccggtga cgcagatctg    6360
agtcgaaacc tagacttgtc catcttctgg attggccaac ttaattaatg tatgaaataa    6420
aaggatgcac acatagtgac atgctaatca ctataatgtg ggcatcaaag ttgtgtgtta    6480
tgtgtaatta ctagttatct gaataaaaga gaaagagatc atccatattt cttatcctaa    6540
atgaatgtca cgtgtcttta taattctttg atgaaccaga tgcatttcat taaccaaatc    6600
catatacata taaatattaa tcatatataa ttaatatcaa ttgggttagc aaaacaaatc    6660
tagtctaggt gtgttttgcg aatgcggccg ccaccgcgt ggagctcagg cctccaattc    6720
gtcaacttcg tccacagaca tcaacatctt atcgtccttt gaagataaga taataatgtt    6780
gaagataaga gtgggagccc ccactaaaac attgctttgt caaaagctaa aaagatgat    6840 gcccgacagc cacttgtgtg aagcatgaga agccggtccc tccactaaga aaattagtga    6900
agcatcttcc agtggtccct ccactcacag ctcaatcagt gagcaacagg acgaaggaaa    6960
tgacgtaagc catgacgtct aatcccaact tcgtccacag acatcaacat cttatcgtcc    7020
tttgaagata agataataat gttgaagata agagtgggag ccaccactaa acattgctt    7080 tgtcaaaagc taaaaagat gatgcccgac agccacttgt gtgaagcatg agaagccggt    7140
ccctccacta agaaaattag tgaagcatct tccagtggtc cctccactca gctcaatc    7200 agtgagcaac aggacgaagg aaatgacgta agccatgacg tctaatccca caagaatttc    7260
cttatataag gaacacaaat cagaaggaag agatcaatcg aaatcaaaat cggaatcgaa    7320
atcaaaatcg gaatcgaaat ctctcatcta acgtacgacc atgacttcga agtttatga    7380 tccagaacaa aggaaacgga tgataactgg tccgcagtgg tgggccagat gtaaacaaat    7440
gaatgttctt gattcattta ttaattatta tgattcagaa aaacatgcag aaaatgctgt    7500 tatttttta catggtaacg cggcctcttc ttatttatgg cgacatgttg tgccacatat    7560
tgagccagta gcgcggtgta ttataccaga ccttattggt atgggcaaat caggcaaatc    7620
tggtaatggt tcttataggt tacttgatca ttacaaatat cttactgcat ggtttgaact    7680
tcttaattta ccaaagaaga tcattttttgt cggccatgat tgggggtgctt gtttggcatt    7740 tcattatagc tatgagcatc aagataagat caaagcaata gttcacgctg aaagtgtagt    7800
agatgtgatt gaatcatggg atgaatggcc tgatattgaa gaagatattg cgttgatcaa    7860
atctgaagaa ggagaaaaaa tggttttgga gaataacttc ttcgtggaaa ccatgttgcc    7920
atcaaaaatc atgagaaagt tagaaccaga agaatttgca gcatatcttg aaccattcaa    7980
agagaaaggt gaagttcgtc gtccaacatt atcatggcct cgtgaaatcc cgttagtaaa    8040
aggtggtaaa cctgacgttg tacaaattgt taggaattat aatgcttatc tacgtgcaag    8100
tgatgattta ccaaaaatgt ttattgaatc ggacccagga ttcttttcca atgctattgt    8160
tgaaggtgcc aagaagtttc ctaatactga atttgtcaaa gtaaaaggtc ttcattttttc    8220 gcaagaagat gcacctgatg aaatgggaaa atatatcaaa tcgttcgttg agcgagttct    8280
caaaaatgaa caatgaccgt taacctagac ttgtccatct tctggattgg ccaacttaat    8340
taatgtatga aataaaagga tgcacacata gtgacatgct aatcactata atgtgggcat    8400
caaagttgtg tgttatgtgt aattactagt tatctgaata aaagagaaag agatcatcca    8460
tatttcttat cctaaatgaa tgtcacgtgt ctttataatt ctttgatgaa ccagatgcat    8520
```

```
ttcattaacc aaatccatat acatataaat attaatcata tataattaat atcaattggg    8580
ttagcaaaac aaatctagtc taggtgtgtt ttgcgagctc gaattcattc cgattaatcg    8640
tggcctcttg ctcttcagga tgaagagcta tgtttaaacg tgcaagcgct actagacaat    8700
tcagtacatt aaaaacgtcc gcaatgtgtt attaagttgt ctaagcgtca atttgtttac    8760
accacaatat atcctgccac cagccagcca acagctcccc gaccggcagc tcggcacaaa    8820
atcaccactc gatacaggca gcccatcagt ccgggacggc gtcagcggga gagccgttgt    8880
aaggcggcag actttgctca tgttaccgat gctattcgga agaacggcaa ctaagctgcc    8940
gggtttgaaa cacggatgat ctcgcggagg gtagcatgtt gattgtaacg atgacagagc    9000
gttgctgcct gtgatcaaat atcatctccc tcgcagagat ccgaattatc agccttctta    9060
ttcatttctc gcttaaccgt gacaggctgt cgatcttgag aactatgccg acataatagg    9120
aaatcgctgg ataaagccgc tgaggaagct gagtggcgct atttctttag aagtgaacgt    9180
tgacgatcgt cgggcccagg tagaatccgc ctgagtcgca agggtgactt cgcctatatt    9240
ggacgacggc gcgcagaggg cgacctcttt ttgggttacg attgtaggat tatcactaaa    9300
acaatacatg aacatattca aatggcaatc tctctaaggc attggaaata aatacaaata    9360
acagttgggt ggagtttttc gacctgaggg cgttaacctt ctgttaacct aaaagctctt    9420
gcccaaacag cagaatcggc gctaattgcc agcggcggaa cttttccagt ttcgcgaaaa    9480
atatcgccac tggcaaggaa tgggtttgag atggcgaagt ctgtcctaaa agcagcgcct    9540
gtagttgtag ggttgacggc cttgatggag cgtcatgccg atgccctctc gagccaactt    9600
caagcacatc atcttaaggt tttcccgccg cattccgaga agggcattcg aacattcggg    9660
ccatcggagg cgtccaagct gctcggcgtt ggcgagtcat atttacggca gaccgcgtct    9720
gagatgccag agttgaatgt tagcatgagc ccgggtggca ggcgaatgtt ctcaattgaa    9780
gatatccatg tgattcggaa gtatatggat caggtcggcc gcgggaaccg gcgctacctg    9840
ccacatcgtc gaggcggcga gcagcttcag gttatctctg tgatgaattt caaaggtggg    9900
tcgggtaaga ccaccaccgc cgcgcatctg gcgcagtacc tcgctatgcg cggatatcga    9960
gtcttggcca ttgatctcga tcctcaagcg agcctttctg cactctttgg gagccaaccg   10020
gagacggacg ttggcccgaa cgaaacgctc tacggcgcta taaggtatga tgatgagcag   10080
gtggcaatcg aacgagtcgt ccgagggact tacattcccg acctccacct gattcctggt   10140
aaccttgagc tgatggagtt tgaacacgat acgccacgcg cgctgatgaa ccgcaaagag   10200
ggcgacacgc tcttttatgg tcgcatcagc caagtaattg aagatatcgc ggataactat   10260
gacgtcgtgg tcatcgactg ccctccccag cttgggtatc tcacgctatc cgcattgact   10320
gcggcgacgt ccattcttgt cacggtccat ccgcagatgc tggatgtgat gtcgatgaac   10380
cagtttctgg caatgacatc gaaccttttg cgtgaaatcg agaatgctgg cgccaagttc   10440
aagtttaatt ggatgcgcta tctgataacc cgtttcgaac cgagcgacgg accacagaac   10500
caaatggtag gttatctgcg gtcgattttt ggcgaaaatg tcctcaattt tccgatgctt   10560
aaaaccaccg cggtttcgga cgctggcctg acaaaccaga ctctattcga agtggagcgt   10620
ggcctgttca cgcgctcgac ctatgatcga gccttggagg cgatgaacgc cgtcaacgac   10680
gagatcgaaa cactgatcaa aaaagcatgg ggtaggccca catgagccgg aagcacatcc   10740
ttggcgtctc aactgacgcc cctgagacgt cgcccgccga caataggacg gcaaagaacc   10800
gctccatgcc gctcctcggc gtaacaagga aggagcgcga tccggcaacg aagctcacag   10860
```

```
cgaacattgg taacgcactg cgagagcaaa acgatcgtct tagccgtgcc gaagagatcg   10920
agcggcgtct cgctgaaggt caggcagtga tagagttgga tgcctcgtca atagaaccgt   10980
ctttcgtgca ggatcgtatg cgaggggaca ttgacgggct ccttacttcg atccgggaac   11040
aaggacagca agtcccaatc cttgtgcgac cgcatccgag ccagccgggc cgatatcagg   11100
ttgccttcgg ccaccgccgg ctacgcgccg tttcagaact cggacttccg gtcagagcgg   11160
tcgttcgcga actgacggac gagcaagtgg tcgtagcaca gggtcaggaa acaatgagc    11220 gcgaagatct taccttcatc gaaaaggcgc gcttcgcaca tcgcctgaac aggcagtttt   11280
ctcgagagat tgtcatcgcc gcgatgtcga tcgacaagag caatttgtcc aagatgcttc   11340
tgctcgttga cgccctcccc tctgaactga ccgatgctat tggtgccgct cctggtgttg   11400
gacggccgag ttggcaacaa cttgccgagc tgattgagaa agtttcttca ccggccgacg   11460
tggctaaata tgctatgtcg gaggaagttc aagcgctgcc atcggcagaa cgattcaagg   11520
cggtgatcgc tagtctgaag cccagtcggg ttgcgcgtgg acttcccgag gtcatggcca   11580
ccccagacgg caccagaatt gcacaggtga cgcagagcaa ggccaaactg gaaatcacga   11640
ttgacaggaa ggcgacgccc gattttgcga ccttcgtgct cgatcatgtg ccagcgctgt   11700
atcaagcgta ccacgctgag aaccaacgga acgggggaga gtaaaccgca aaagaaaaga   11760 gcccctcaa cgtcgccgtc gcggaagccc ttctgtctct ctagcgcgaa cagaatcgca    11820
tttcctcgaa tcctcgtcaa gagttttag cgccgttttg gtgagctgat ttcctttgcc    11880
tgctgaaagg tgaaagatga tgcagacagg aagtgtaacg acgccattcg ggcggcggcc   11940
aatgacgctt gcgcttgtgc ggcgccagac ggcgctggcc gatatcaaac aaggcaagac   12000
agcggacaag tggaaggtct ttagagacgc gtccgcggct atggaactac ttggaatcca   12060
gtccaacagt cttgccgtcc ttgatgcgct attgagcttt cacccggaaa cggagttgcg   12120
tcaggaggca cagctgatcg tcttcccgtc gaatgctcag cttgcccttc gggcgcatgg   12180
gatggctggc gcgactttgc gtaggcacat cgccatgctc gtggagtcag gcttgatcgt   12240
ccggaaggat agcgccaacg gaaagcgtta cgctcgtaag gatggcgctg gtcagatcga   12300
gcgcgcgttt ggcttcgatt tgtctccgct tctcgcgcgg tccgaagagc tagcgatgat   12360
ggcacagcag gtgatggccg atcgagcagc attcaggatg ccaaagaaa gtctgacgat    12420 ttgccgacgg gacgttcgga agctaattac ggcagctatg gaagagggag cggagggcga   12480
ctggcaagct gtcgaggaag tctatgtgga acttgtgggt agaattccac gcgccccgac   12540
gcttgctgat gtagagtcaa ttctcgaaga gatgtggatg ctccaggaag agataatcaa   12600
ccggttggaa attagagaca attcagaaaa taatagcacc aatgctgccc agagcgagca   12660
gcacatacag aattcaaaac ccgaatccgt taatgaactt gaacctcgct ctgaaaagga   12720
gcagggcgct aagccgagtg aaatagaccg ggcaaggagc gagccgataa aagcgttccc   12780
cctcgggatg atcctgaaag catgcccgac cattggcaat tatgggccga gcggtgcggt   12840
tgctagctgg cgtgacctca tgtcggctgc ggtggtggtt cggtctatgc tgggggtcag   12900
cccgtcggct taccaagacg cgtgtgaggc aatgggaccg gagaatgcgg cagcagcgat   12960
ggcgtgcatt ttggagcgag cgaacttcat caattcgccc gggggctatc tccgagatct   13020
gacacggcgg agcgagcttg ggaagttttc acttggcccg atgataatgg cgctcttgaa   13080
ggctagcggg caggggacgt tgcggttttgg ctagaattag cgagtatgga gcaggatggt   13140
ctgtggtcag ctgaccacag acctaatagg ttgaaaacat gagcgttttt tggatgatcg   13200
acagaccatc cgattcccgg agtaccaagc gtgctctgat gggagcgata acattactca   13260
```

```
acaagcacga aggccccatg ccgatcgttg atcgtgaagg agagcctgct ctacatgcgg    13320
cggtattttg ccggccgagg catgtagtcg cggagcactg cctatttact gccctaggca    13380
caaacgttga ctcttggatc gagctggcag acaaagcaat aacccacaca gaggacgatt    13440
aatggctgac gaagagatcc agaatccgcc ggacggtact gctgctgccg aagttgagcc    13500
ggctgctcct agaggtagaa gagcaaagaa agcaccagcc gaaacagccc gcacgggatc    13560
gttcaaatcc gtgaagccga aaacccgcgg cctcagcaac cgagaaaaac tggagaagat    13620
cggtcaaatc gaagctcagg tcgctggcgg cgcaaccttg aaggacgccg ttaagatcgt    13680 gggtattttcc gttcagacct attatcaatg gaagagagct gcggttcaac ctgtctcaca    13740
gaatccggcc gtgtctgttt cagttgacga tgaactcggc gagttcatcc aactcgagga    13800
ggaaaatatg catggcatgc ccgttccata cagaagctgg gcgaacaaac gatgctcgcc    13860
ttccagaaaa ccgaggatgc gaaccacttc atccgggtc agcaccaccg gcaagcgccg    13920
cgacggccga ggtcttccga tctcctgaag ccagggcaga tccgtgcaca gcaccttgcc    13980
gtagaagaac agcaaggccg ccaatgcctg acgatgcgtg gagaccgaaa ccttgcgctc    14040
gttcgccagc caggacagaa atgcctcgac ttcgctgctg cccaaggttg ccgggtgacg    14100
cacaccgtgg aaacggatga aggcacgaac ccagtggaca taagcctgtt cggttcgtaa    14160
gctgtaatgc aagtagcgta tgcgctcacg caactggtcc agaaccttga ccgaacgcag    14220
cggtggtaac ggcgcagtgg cggttttcat ggcttgttat gactgttttt ttggggtaca    14280
gtctatgcct cgggcatcca agcagcaagc gcgttacgcc gtgggtcgat gtttgatgtt    14340
atggagcagc aacgatgtta cgcagcaggg cagtcgccct aaaacaaagt taaacatcat    14400
gagggaagcg gtgatcgccg aagtatcgac tcaactatca gaggtagttg gcgtcatcga    14460
gcgccatctc gaaccgacgt tgctggccgt acatttgtac ggctccgcag tggatggcgg    14520
cctgaagcca cacagtgata ttgatttgct ggttacggtg accgtaaggc ttgatgaaac    14580
aacgcggcga gctttgatca cgacctttt ggaaacttcg gcttccctg gagagagcga    14640 gattctccgc gctgtagaag tcaccattgt tgtgcacgac gacatcattc cgtggcgtta    14700
tccagctaag cgcgaactgc aatttggaga atggcagcgc aatgacattc ttgcaggtat    14760
cttcgagcca gccacgatcg acattgatct ggctatcttg ctgacaaaag caagagaaca    14820
tagcgttgcc ttggtaggtc cagcggcgga ggaactcttt gatccggttc ctgaacagga    14880
tctatttgag gcgctaaatg aaaccttaac gctatggaac tcgccgcccg actgggctgg    14940
cgatgagcga aatgtagtgc ttacgttgtc ccgcatttgg tacagcgcag taaccggcaa    15000
aatcgcgccg aaggatgtcg ctgccgactg gcaatggag cgcctgccgg cccagtatca    15060
gcccgtcata cttgaagcta gacaggctta tcttggacaa gaagaagatc gcttggcctc    15120
gcgcgcagat cagttggaag aatttgtcca ctacgtgaaa ggcgagatca ccaaggtagt    15180
cggcaaataa tgtctaacaa ttcgttcaag ccgacgccgc ttcgcggcgc ggcttaactc    15240
aagcgttaga tgcactatac gtaaccaact agtgcgctct tccgcttcct cgctcactga    15300
ctcgctgcgc tcggtcgttc ggctgcggcg agcggtatca gctcactcaa aggcggtaat    15360
acggttatcc acagaatcag gggataacgc aggaaagaac atgtgagcaa aaggccagca    15420
aaaggccagg aaccgtaaaa aggccgcgtt gctggcgttt ttccataggc tccgcccccc    15480
tgacgagcat cacaaaaatc gacgctcaag tcagaggtgg cgaaacccga caggactata    15540
aagataccag gcgtttcccc ctggaagctc cctcgtgcgc tctcctgttc cgaccctgcc    15600
```

```
gcttaccgga tacctgtccg cctttctccc ttcgggaagc gtggcgcttt ctcatagctc    15660
acgctgtagg tatctcagtt cggtgtaggt cgttcgctcc aagctgggct gtgtgcacga    15720
accccccgtt cagcccgacc gctgcgcctt atccggtaac tatcgtcttg agtccaaccc    15780
ggtaagacac gacttatcgc cactggcagc agccactggt aacaggatta gcagagcgag    15840
gtatgtaggc ggtgctacag agttcttgaa gtggtggcct aactacggct acactagaag    15900
gacagtattt ggtatctgcg ctctgctgaa gccagttacc ttcggaaaaa gagttggtag    15960
ctcttgatcc ggcaaacaaa ccaccgctgg tagcggtggt ttttttgttt gcaagcagca    16020
gattacgcgc agaaaaaaag gatctcaaga agatcctttg atcttttcta cggggtctga    16080
cgctcagtgg aacgaaaact cacgttaagg gattttggtc atgagattat caaaaaggat    16140
cttcacctag atccttttaa attaaaaatg aagcgtaccg acgatcttgc tgcgttcgga    16200
tattttcgtg gagttcccgc cacagacccg gattgaaggc gagatccagc aactcgcgcc    16260
agatcatcct gtgacggaac tttggcgcgt gatgactggc caggacgtcg ccgaaagag     16320 cgacaagcag atcacgcttt tcgacagcgt cggatttgcg atcgaggatt tttcggcgct    16380
gcgctacgtc cgcgaccgcg ttgagggatc aagccacagc agcccactcg accttctagc    16440
cgacccagac gagccaaggg atcttttttgg aatgctgctc cgtcgtcagg ctttccgacg    16500
tttgggtggt tgaacagaag tcattatcgc acggaatgcc aagcactccc gaggggaacc    16560
ctgtggttgg catgcacata caaatggacg aacggataaa ccttttcacg ccctttaaa    16620 tatccgatta ttctaataaa cgctctttc tcttag                              16656
```

<210> SEQ ID NO 4
<211> LENGTH: 814
<212> TYPE: DNA
<213> ORGANISM: Zea mays

<400> SEQUENCE: 4

```
gtgagcgctt acacctctcc gttcctcccc gctgccttgc gcgcgcacgc tttcgtgtag      60
atctgggtcg ccgcgtctcc gtctttgttt agccggccgt agagcctccg ctctaggtgc     120
ctcaagctcc tcttcagttc ttctagctcc ggtagggttt ccctttttgcg catagcgggg    180 gcggctgatg cacggttggc tacctcagct attcgtcagg ctactcgtca gtattttcgg    240
cgcactttgc tagcttagat catcgccgtt tgttttgcgc ttcgtccgtc gccgactcga    300
cgaaccggcc aatcaccacc ctcgccgatc cattactctt aaatccggac cacgccatat    360
cggatcgaac caaacgttca cgcgttgtcg actaaagcat tgtgtggttg atttattaat    420
cggctgatgc agtagaaatc ctatagagtg tacatcagtt tctagtttca agcatgtaat    480
tgagcttgtg aggtgcagta ttttgttgat gtacaaggct tagggcattg ttttgctgaa    540
gggcctgtga tcatgtgtaa tctaatgtgg agtattaaac gtgtgtgtag ggttgatgaa    600
attatgctag taatggcttt caagtaacac gttattgtg atctgtgaca tctttaaaca    660
atatgcagtt tgttttcctt aaattcgttg ctgaaattgt gacattggtc atgcttgaga    720
aggaatcatt ccgtgaaatc aggttgcgat gcctatgata acacttgctg gaatctgttg    780
tgcttttctg atcactgttt ttttgcaat ccag                                 814
```

<210> SEQ ID NO 5
<211> LENGTH: 727
<212> TYPE: DNA
<213> ORGANISM: zea mays

<400> SEQUENCE: 5

-continued

```
gtagtccttg acgcgttcga gcttgagtag gcgaaggcgg cactttgaga gcggcgccac    60
ggcgaggagc cacgccgccg cctcggagcc cttctgtcgc ttctgcttcc aaccgacacg   120
ggaaggggcg gcgggtggtt cacatttctt ctctttcttc tcgtctccct atttgcggtc   180
gcccgggaga ccgggctgct tgcccatccc gccaggagaa ccatgtccca ctccggcgg    240 ccgtgaatta gggtttggct tgtgatctg  tgtagggatc tagctatatg tgatggtgct   300
tgtctagatc tatgtttgtt aagcctggtt cgttgatctg gtgagatggt gcatgatcga   360
ggtttgattg ttttaatcta gaatgttgga tagagaatta gaacagggat tagccgaaat   420
tacgcattat tttccatgat ccaatgaagt tagtagttat gtagcataat tgttgttgat   480
ttatgccaat atgtgtgtta gatctgagtg ccctgaaatc gtttaaatgc actggcattc   540
acgatctgta aattttcata ggccaaattc gtgttgcctg tttatgccct tgaagtatgg   600
atatagagtt agtatgttta atgtaaaacg atgtatagta catctattcg tactattatt   660
agatattcaa aaaatgaat  acatattagc attagaccct ttgaaccaat tttattttgc   720
tatttag                                                             727

<210> SEQ ID NO 6
<211> LENGTH: 834
<212> TYPE: DNA
<213> ORGANISM: Zea mays

<400> SEQUENCE: 6
gtacgcccgc tctctcgctc cctctctacc tcctcgactc catctccttg aatttcactc    60
gttactacac cgaccgctac cacccgcgct gcgccctgtg ataatcggtg caccgtgcgc   120
cggcggatga ttgtattctt gaatctgcct tgttgatagc tcttggcgcc caccgagtgc   180
atcaacaaga caacaagaaa ccggtcccta tacgaatggt attggctacc gtgttcagtt   240
cgtccgcgcg gttgttggga aaaaaaatg  gacggtttag ttaggctggt gcgcagccgg   300
acaggacaaa tacacccgtg cggtggttag gcagcggaga ttgacgcatc attgcgacct   360
cgcaaatggt ccttgtctcc ctggtggttg tatgctctgt ccaacatccc gttgaggaac   420
tgcgcttggt gtgtgtggtc cagttcctgc aattagcgtg gttgttgttc gtcgcggcat   480
cttcgtggga tttggtagat ctgcaagaaa gtgagtgctg cttttcaatg gagttcttta   540
gcaatcagtg agatttggtt tgccataggc cgccttcttt tcctgggtct actgattgag   600
ccctcccagt cccatgtgct tgccattaag caacttgaca atcaatgaaa aggtgagggg   660
gtccgaagga gtaattacga agcaaataac ttgactgtgc agatttattg cactgaataa   720
cagaaatgac acacaaagtg ttttttttta aaaaacttt  agacagaaaa tcaaaggat   780 atacctctcc tcttcgtaac atagaattct tatctcataa attcgttcgt gcag         834

<210> SEQ ID NO 7
<211> LENGTH: 982
<212> TYPE: DNA
<213> ORGANISM: Zea mays

<400> SEQUENCE: 7
gtaaactcct acgcctccct tcgatgcctc cagcgtctcc ttcccgcgtt ccttagctgt    60
agttattact gccttgatct gtactccctc cgttttagtt gtcgctggat agtgcaaaat   120
tgaactatcc agcaacaact aaaaagaaac ggagggagta tctatcttgt tgtaggctct   180
ctcacttgta gctgcccgaa taccttgact gttcttcacc tcacgttaga aacacaggga   240
```

| | |
|---|---|
| ttccgcatgc ctgttcgtgg tcgctgtgcg cgtgagccta aatttaggcc gcatagagca | 300 |
| tgcggcagct agattgtacc gagcggtgaa actttgccag tgcaaccaag agagggcatg | 360 |
| aggcggcggc acgtcccgc tgcacggctg ctcgtggttg gggcgagatc tcgcgtgatt | 420 |
| gagtctgcga aaaagcgcag ctgcgatcta gatcgacgtg gttgctcgtg atctcgtctc | 480 |
| ccatccagat gtggtgaggc agttaggctg agatccggcc ccttgtgcca tgtccgtgtg | 540 |
| gaccgagtca ggctggtgtc gttttatttg tactcgcaaa gtgctgatgc tacgattttt | 600 |
| atttatgttt atgtatagag tgtaaaatac gatttttatt tatatttatg tatagaatgt | 660 |
| aaaacacaaa tacatacgtg ttgtgttggg gtggatgcga aattgagttt atagccaaaa | 720 |
| attgggtttt tatttgtaca taattttaaa ttaaatgtga atgagtatga tgatggtgga | 780 |
| aatgaaaact agtgcgtttt atatagtaga gaaaagatag ggagtaggtg ggcttcatcc | 840 |
| agatctttcg gttatgtcgg ggtttgtttg gtcatggcag gcagggccac atgagatttc | 900 |
| tgtacggggt ttgaattgac actgcatcgt cttcgactga cattatgtgc tattgtatct | 960 |
| atgaactgga aaacttttac ag | 982 |

<210> SEQ ID NO 8
<211> LENGTH: 856
<212> TYPE: DNA
<213> ORGANISM: Zea mays

<400> SEQUENCE: 8

| | |
|---|---|
| gtaaggttcc cttccctcct cccctcacac ccctgttcgt gttccttcgg atcggatctc | 60 |
| agtggtgatg ttagacgtcc gcggctgcct acgtagtggc attgccgccc gaaaggtttg | 120 |
| tttaggtggg gtagatccga acaggccgg atctggacca tgtccgcggc ggggcggcgg | 180 |
| gacttgatcg cgtagctgtc gtgtgcattt ctccctacca gtggcggaat cggcgatgtg | 240 |
| gacctaaggg ctaaggctta tctgctgcct tgaccatttc gtcgctgaca aaaacaaagt | 300 |
| gacaatcatg ccgttctctg tttgtttatc tggatcgtta ttacgctgtg aatcctgcga | 360 |
| tatgtggcta agtgattttt cttctttttc tgggggcagt ttagcctttg acccagtcct | 420 |
| aggtgtggtc actaggactg tgtagcatga tgagtgaggt tgcagcaggc tgattgctag | 480 |
| tggacgtttt ttttccccaat ttgttaggtt ttcacgctcc aggttgtgca agtaattttg | 540 |
| ctagtgattg tgtgatccat cttcaacgtt gaaccttgtt tttccccta aaaccccaa | 600 |
| caggaaatct tgccccgact tctattgcaa aaattgtaac gcttagcacc ctgattgact | 660 |
| caattcctgt cactaggcat gctcggtcaa aagcagatga tttaccactt agaaactgcc | 720 |
| ctgcccctgc tttccacata gcatttcgaa cttttttgact actattgaca ccccctaac | 780 |
| ttgccgaact atttctctct tcagctacta tttacctagt tataattaca taaatgtttg | 840 |
| tgtgtatctt gtgcag | 856 |

<210> SEQ ID NO 9
<211> LENGTH: 1020
<212> TYPE: DNA
<213> ORGANISM: zea mays

<400> SEQUENCE: 9

| | |
|---|---|
| gtaaatctca aatttatcat gtattttcaa atgatataaa attcggatac gaataatttt | 60 |
| ttgacatttt ttctctagag agcaaataat acataaaaca aattatacaa aatttttattc | 120 |
| ttatttataa taatatgttc aataacataa gaaaaaatca gcatcaaatt tcatatatat | 180 |
| ctatattaaa atattaaatt tatgctaata atttggatac ccatttttatc atcatcttat | 240 |

-continued

```
tccgatatgg tatttcctgc aatcaaacac atgcccaggg aacgctcgca cccgaagatt      300
ggcgtaaccg aaccgatgcg acctttggcc cgtttcaaaa tgaaatgggc cggtcaatgc      360
gcggcccatc cggccgatga tatcacgacc cagcgtgcat cctatgaaac ctctgccccg      420
gggctagggt ttcctcccag ccgtcatcgc ttcacgtccg ctacagaccg gcgaggagac      480
gaaaggtaag ccacccactg ccgccgctct cgtttcaccc catttcgtcc ggccgtctaa      540
ttcgttggcc ggcccgttct gttcgtggaa gcgctcggat ctgctctgta tatgcttgtt      600
ctcgttcggt tttgccggtc ggagttgtct cgcgaggcgt agcttgtgcg tcaggctctc      660
ttttgccttg tagatttcct gcatctgctc ttactgatag cttttgctgt taatcttgag      720
agagttatgc cacgagtctc tttgatattc tattggggta atgatatgtg gggatactgt      780
aatgtttctg atattcttgc tatggttggt ttgggcatga agtagaattt gtaatggtgc      840
ttttaggatc ctgttttttgg tgctaactct gtcaacacta gactgagaat tgttgttaac      900
aagtagcttt catgttgcac gacaagatcc ttctgtgttt cattccagtt ctcatgattt      960
tatttctttt ttgcatcttc atccgcctga cataatggtc tttatctact tgcaattcag     1020
```

<210> SEQ ID NO 10
<211> LENGTH: 841
<212> TYPE: DNA
<213> ORGANISM: zea mays

<400> SEQUENCE: 10

```
gtatacaacc gacctcgtct cccccgattt ctcaactacg tagtgtatgt acgcatcggt       60
aggtagatgg gaatttcggg ccactggttt gggggggttta atttgcgcta tcgtttcggt     120
ttgcctgtgg tttcggaggt agatttgggt cgcaggtagg ttgtcgcttg gatctgggag     180
aggcgaggag ctaaattcgc atagcttgta ataactcacc ccggttgcta tgaaaagccg     240
taggccgtag ctgctgctgc tgctgtaatt tactacttat tttcttctaa tatagggggat     300 tcccttcctg caactttttt ttaaatacgg ttcttggtta ctggctggct tagtgcagtg     360
ggaccttgtt gccatgaatg attgttgcgc aatttagtag atcattagat tagcacgacg     420
tacctaatca tgggtcccgt gaattttagc ctagtcccca ttatttgccc cttagtcacg     480
catgtgtttg gtgtacttca aggaatctgt ccatatgcat cggatctatg ggttcggcca     540
tgatgttgac attgaactgt ggccgttcat gttcgacttt accttgcgcc cgagcaaaaa     600
gaaggataaa tcgtgtgtac caatctggct atacggcagc tcgatatgtc tgaatgaaga     660
ttgggagtat tcttctgttt atttatttgt caattttttat tctgaatatt catttgttct     720
ccagtttagt agtgcatcat taacacttca attctaggtc tattgctatg gtatagtagc     780 actcttttcaa tctttcatgt gtacagctga tgccttatgt tgatcccctt ccttgcttta     840
g                                                                      841
```

<210> SEQ ID NO 11
<211> LENGTH: 1044
<212> TYPE: DNA
<213> ORGANISM: zea mays

<400> SEQUENCE: 11

```
gtccgtgccg ggcggcccgg atggacatct atagcccgca ggtcatggat agatagataa       60
tttcgcgtcc gtgataaagc cggactgcta cgtttccgac gggagtaatt atttacacac      120
tcttcagcac caacggcatc tcgtggacgc tggatcccaa taccaaattg ctacaagctc      180
```

```
aatgatgtct gggtgggctt ctggcccatt tagaatatca tctctatacg tctttataca     240
gaacgaaaaa aaaacgagcg gccaagatgg tgttggagta tagatcggac ggcaaagccg     300
tgctctccgc cttttaaaag gctgtccgac tcgacccttc tcctctccgt cgcatttccc     360
gtccggtctt tccgttaccc ggcggcttta aaccctagtt cccattccat cttcgtttcc     420
gctccgccgc cgtcgatgga gttctggggt gacctcccct actttctctc tcgcaaactc     480
aattctccgt gatacctgcg cttcttcgt tttgttgcgg ttcctctgtt tgattttgg      540
gcgttttagc cttttattta aggccctggg aatcatgggc atggtttgat tggctactgc     600
tagcacttgt ttgcgaatgt tttagggccc tgtgaatcgt ggctattgtt tggttcgcta     660
ctacttacta ctagggcatc gttgttctac aatcagcagt tatgtggcat tgcctatttg     720
cacagtatgg aaaaaagtag attaaaatgg ttgaaatcat acgtggccgt gtcctgtttc     780
aatagggtct tattatagga cgtgacggtg atgccactga attaggatgt tgttcttttt    840
gtaccattgt taaacagcac cagatcattc ttaatgtaac ctacatcaga ttgtttgttt    900
tgttctacta caagtatgtt cagcatggca ggaggaagtg tgctcctaaa tctgttgttt    960
aggcgcattg cgaaatgttt gttctaacag catcaggttt gcattcttaa tttaacctat   1020
cttgtattgc tctgtctttt gcag                                          1044
```

```
<210> SEQ ID NO 12
<211> LENGTH: 648
<212> TYPE: DNA
<213> ORGANISM: zea mays

<400> SEQUENCE: 12
gtaagcgacg acaacgagca gtgggcggca ggattgagcc cccccatacc ttctctctct      60
gggtttcgct ctctctcgcg tgctcagaaa gtttcggagg cggcggtttt cgctctctct     120
cgagcgctcc gtccaagcgt ttttcttca gaaccagtcc tttttgattc cagactaaaa     180
tttattgctt ttattattag caataaattt catggttcaa aaatgcgaca gttttttac     240
ttgaatagag acatttattt taaccaaaga aaatcatat atatataata aaaacaaatt     300
agtggcatcc atacatatgg atgcccaaac aattatcggt tgaggaagtc aacaggaaag     360
tatcttaaag gttggaaacg tggcaaatcg aggagcatga gctggtaggg cactcgcagt     420
gggtggagcc ggtttgctga cgcggaagga accgaccatt catgactcgc ttggcacgcg     480
gtgaggtgag tgtgagtgtg agtcagcctc tcgatctggg ttgggttttg gtctataaaa     540
tacccggcc tccatctctt ctctggggttg tggttgtggc ctcctatcct tgcacgcaca      600
cgcaaacgca tcccatcctg tcctcgcgtt actactagtt agttagag                 648
```

```
<210> SEQ ID NO 13
<211> LENGTH: 632
<212> TYPE: DNA
<213> ORGANISM: Zea mays

<400> SEQUENCE: 13
gtgaggagcc ttctctctct ctctctctct ttctctgtct ctctctcttc ctaacctttc      60
ttcccttcgt cctcgtcccc cacgctctgc tcttgtggaa ttttctatta gcgtctgccg     120
ccatttgttt cggctacttt gtgcgcgcgc aagcgcaaac cacgggggtc tctctcgtgt     180
tcgccattct gccgaatcgc cactgcaagc tcttctaccg cttctgtgt gctctgacat     240
ctggactccg gagtccggac gtccgcggct ctgtttgctg cgcttgtttt cttttttcca     300
gctatgcttc gtttcttctc gaattccatt tttttatctc tcttttttcc ctcgtggacg     360
```

| | | | | | |
|---|---|---|---|---|---|
| aagcaaagca | agcaagacga | ccttgcatct | gagactctga | gactgtactg | tttcttttgc | 420 |
| cattgggttt | ttccctaaga | ttccttttt g | gctgccaatg | ttcagtccga | cagcagcacc | 480 |
| cgctgcaacc | atttcagcac | ttcttccgcc | tctgtttcca | taatatttct | tctttttttt | 540 |
| ttccatctct | ttttttttgt | gtgtgctata | gcttttgctt | gactgaaacg | cagcacacac | 600 |
| cttacacaac | caaacatttt | tttttggcgc | ag | | | 632 |

<210> SEQ ID NO 14
<211> LENGTH: 1405
<212> TYPE: DNA
<213> ORGANISM: zea mays
<400> SEQUENCE: 14

| | | | | | |
|---|---|---|---|---|---|
| gtatatactc | tctctctctc | atccgcctct | tgattcatgc | ggcccttgtg | atgtgtgtga | 60 |
| tcttgttact | tggccggctg | tggttctttt | tgtgtctctt | gattcatgcg | ggtaggatta | 120 |
| atctttgttt | aatccgcaaa | aaaggccttg | attattcgat | actatctatc | tgtaatccgc | 180 |
| aaaaaggcga | tgaactttcc | atgttctcgg | tagtgactgt | tctgtatcga | ttctgctgtc | 240 |
| tcatcaacta | gtcgtcggtc | gcaaggactc | gatcgcacgt | ccatttcgac | ggtagctaca | 300 |
| acaagcattt | cctgcagaat | aatatctcgg | ttttatttct | agaaggacgg | tcgttgtagt | 360 |
| ttatttaaag | ggaaaaaaag | atcagttgta | gtagatatgc | gctctagagt | ccagaatggc | 420 |
| ttaaaggacg | atggttacgg | atggaaacct | tttcctctca | tcgcgtgccg | atagcgaaac | 480 |
| ggaagctttt | gtcagtccag | ggaggggaaa | aaatttcaag | gtgttgagca | gcccccttcgt | 540 |
| tggatatagc | agagcaggcg | acgtgcaaga | caattaaagc | aatgcctacg | agagcggacc | 600 |
| ctgatatttt | tgtatgtgtg | attgtgatac | gtgtctggct | ttaggctttg | gaccgagaaa | 660 |
| tagctcgctt | ttccacaggg | gggaaataag | gtgccccttg | gaaatgacag | tcggtattgg | 720 |
| gttcagaacc | aggctttgag | attacaatag | agaaactggc | agcttgagct | gacgtagcgt | 780 |
| tttatcagaa | gtcgtcaata | tcgcctgcta | cgtatatctt | atagtttaat | tgttacttgg | 840 |
| gacatcggtc | tctagcttgt | ctggacaact | ggttctcctc | ctcctgatcg | gatttgattt | 900 |
| tttttacgag | ccgtcaaatg | catggtttgc | tataggatat | tcatatttca | gagacgtcta | 960 |
| tcgcttctta | gcctaccacc | gcaactctgc | tgtggaccac | cattattatt | ggttctcctc | 1020 |
| atcgggcttc | ggggttcaca | agtctgcata | ttcttctcta | gttttttctt | tgctagcttt | 1080 |
| caggctgttt | tcaatgctac | ttcagacaga | gacgtcaatt | tttgtctgac | gcctattgag | 1140 |
| gaccgcgggg | atagtagggt | tttcagatcc | agagcactaa | accaactact | accccggccgc | 1200 |
| cgccgccgcc | ggtacatgta | aaaaaggct | tcgacctgcg | agatgaacgc | aacggagagc | 1260 |
| attcaacaaa | ccaaaaccgc | ataaccaaaa | tgttcagact | agcgcgtggt | agtagtagta | 1320 |
| cttgcagtca | tgtcatgcag | tttgccacgc | cgccgcgtgc | acgcagtttg | ccacgctagc | 1380 |
| taatctgttc | tcattccgct | cgcag | | | | 1405 |

<210> SEQ ID NO 15
<211> LENGTH: 1361
<212> TYPE: DNA
<213> ORGANISM: zea mays
<400> SEQUENCE: 15

| | | | | | |
|---|---|---|---|---|---|
| gtaagcagga | gagagagctc | tttgagtttg | atcgatcctt | aagacaatac | tgtagacttg | 60 |
| gcacaaccat | gccccgtcc | atatcccgac | cgtccgattg | ctgaatccac | ccccgcatac | 120 |

-continued

| | |
|---|---|
| ctcatctgcc atccattctc gctcccgccc tcgacccgc cgccatgcgc gcagccgcct | 180 |
| ccgcccaaca accatgcggg atcctcgccc aacagccatg cgcgccgact acgcctccac | 240 |
| cagatccagc cttcctatag tcatcctgtc atccaacagg gatcctggcc acatagagtt | 300 |
| tcgcccgaat cgatcgccga ttgactccgc tagggttcgg cccgatcgtc gcttcgtcct | 360 |
| ctcggctccc gcggggaccc cgccgagatg tctgaccgga gctcgccggc tgcgccgacg | 420 |
| ttcttccttt tggcccgcag gccgaggcat gggacgtcac cttcaaggtg aggcatccga | 480 |
| tcgattttc tttctttctt tactacactc ctttgcgata tggggacgac actcggtagt | 540 |
| ggcgtgaggt gaggtaaatc gcgttagttt agttgtaggg tttgatcgct tcaggggaga | 600 |
| ccaggggttg ggctttccgt gttgaaccgt caatcggacg tagtagtagt gcggattcgg | 660 |
| ggtttgatcg atggaaagag gggttgtccg cactcttggt gtggttatag ggttttgcga | 720 |
| tttgtttgtc tgtgtaggcc tgtttcgtct cgaggagtag attttcattg ctactaacaa | 780 |
| tccctatgtg gtttggtgaa cacgtatttt ggtctgtata tggtttaaac gtgaagacta | 840 |
| tggtagtgtg agaccatgat ttggatcctt ttctgtggca ttatagttaa aatcgtgagg | 900 |
| atgcacctat atctatcttt tagcgcttag ggtattgtta tagacgagat ccctctcttg | 960 |
| ggctctaaaa atagcaagaa aaagacatct tttgggcaag ttaacgtcct gtattattct | 1020 |
| gaacgagata tgtttacttt cttataagtt tgatgttttg gtctggaata tggttgcgtt | 1080 |
| catcttccaa ttagtgtgtt tgcagtatgt gttggtgtag tttctctgtg ggcattttgt | 1140 |
| ggccacagaa atgatagatt ttaagaaagg tttaggtaga agggtaccttt aagtgttgtc | 1200 |
| cagtacaaag taacaatttg tagcacttgt ttcttttctt ttgtttgact atatgaaatt | 1260 |
| tcggccatgt aattgtttca aaataataag atcgaatagt gttgcacact acttcccagt | 1320 |
| cctatgtata cttataagat ttttcctctt tgatatttca g | 1361 |

<210> SEQ ID NO 16
<211> LENGTH: 703
<212> TYPE: DNA
<213> ORGANISM: zea mays

<400> SEQUENCE: 16

| | |
|---|---|
| gtgagatttc gagagattcg tccgtaccag ggcttggatc tacgctccgg ccaccttcag | 60 |
| gcttcggttc gccgcccacc aaccgagcct aggagtccgc cattcattca aacgccctcg | 120 |
| acggcgactg cgcatcggtt cagatccagg cgtcctttca ccggcagctc cgcctcccat | 180 |
| gcaatcttgc tcgttgttgt tgtcccctcc ctggactcgg gtgtactgga agtccatgcg | 240 |
| gataaagaa actcttttgt tggtatggac gccataatgc gttttgttgc ggaatttttt | 300 |
| tgcggcttgg cgtgctgtca ataccggttt agttttccaa tttttttgca gggttcaacc | 360 |
| aaacctcctg ctgacagacc cttctctgtt cagtttgctt acccaactga cttttttttc | 420 |
| ttgttcatat tctagttgga tgctgagtgg catgccggtc gatatttggg aaagcagatt | 480 |
| tttatgttgg caagtgtgag tgcgagttct ttgctgaaac tttaagcttc acctgagatc | 540 |
| tgatattgtc ggtgccaaat tgctgtacat ttgactattt gaggacacgt tcttaggtaa | 600 |
| atcattggaa gacatatttc acttcgcgta ggacacgtac ttctccaaga tgatgccttc | 660 |
| acctgtctca aacctttgtg attttatat actcgcttgg cag | 703 |

<210> SEQ ID NO 17
<211> LENGTH: 1341
<212> TYPE: DNA
<213> ORGANISM: zea mays

<400> SEQUENCE: 17

| | | | | | |
|---|---|---|---|---|---|
| gtgaggccgc | gaccaagaag | gcgtaggcgg | cggcgctggc | cgtggcgggg | cggtggcacg | 60 |
| atacgctggc | cggctgggcg | acgccgtagc | ctgtaggtct | ctctcgcagg | aaaaagtttc | 120 |
| tgtgttccaa | tggaagtaag | atacaaccgt | tggattctaa | tggaagtaag | atcgaacggt | 180 |
| tgtgatagat | acaaacgaaa | ctgaagatct | tttatagtat | acatagatag | atcgacttaa | 240 |
| gcaaaaaaat | cttaggcccc | gtttgtttcg | ttggattgaa | ttccattttg | ataattataa | 300 |
| tttagtcaaa | actaattaag | tttatatatt | tatatatacg | atatatttgt | atattatcct | 360 |
| aaatcatacg | agagagatag | ttatatacta | tatttatgtt | atagcgaaac | aaatagatga | 420 |
| gtgtgctata | agttgtacat | cggaaaaata | gcatgtaaat | ctatagaatc | aatttccatc | 480 |
| tctcacccca | ttaatttgag | ataggcttat | atgataactt | tggaaagttg | tggaatgtca | 540 |
| cattctttta | aaaaaataga | ctattttatt | agtaagattc | aaatttctcg | aaataaaaga | 600 |
| aaacaaacga | gaccttaaag | ataatgttcc | tataacaatc | taataacaac | tcaaagagta | 660 |
| agaaataaaa | aaagtaacgg | cgtgtttggt | ttgcaggttg | gactgcttct | ggagtcatcc | 720 |
| ggacctatgt | ccgagcctac | attatcattt | ggtttgaatc | gcggaacgat | gtcgtccgtc | 780 |
| actgcgttgt | tctaataata | tactaacaca | tggaattagc | tcacttcgca | agaaagtgca | 840 |
| agaccgcttc | gtccggagcc | aggccacgat | ggatgagtca | aaccatcaaa | ccaaacacgc | 900 |
| tgtaataatt | ccgaaaccgc | ccgcggagca | tcgcagctac | tgacaagtgg | gttcggaagg | 960 |
| ggatcccgtg | tcgtgggtcc | acacgtcacc | gtgtgcggcg | tgctctaact | gcccgggccc | 1020 |
| ggccagtggc | gggtagggggg | ggagagggac | tgagcctgca | taaatcgtca | gcgaataggc | 1080 |
| cgcccgcacg | acttctcttc | ccaattccca | tagatcgatc | gccgacccct | cgagcaacgc | 1140 |
| gatcgcccgc | cgacccgacg | gcggcatgga | caccgagtac | gtcgaccacc | ccgcccgtcg | 1200 |
| ccgccgcgat | cagacggcgc | atctcttttt | cgcacgcggg | ggcctttttc | ctttctctat | 1260 |
| cccccatctt | tgtcgatttc | ttttatttt | cttccccct | tgaggatgat | gatgatcgcc | 1320 |
| tcgggccgtc | ggctcctgca | g | | | | 1341 |

<210> SEQ ID NO 18
<211> LENGTH: 1125
<212> TYPE: DNA
<213> ORGANISM: zea mays

<400> SEQUENCE: 18

| | | | | | |
|---|---|---|---|---|---|
| gtactaataa | actgatgatt | cattcattca | tggcacggcc | taccaatgca | aataaatcta | 60 |
| tctcacgcta | tgagaagaaa | accgagagag | agagagagag | agagagagag | ggcttgcctt | 120 |
| cccgccggc | cgttagtgct | caattgggca | cgcgattacc | gaggcaagca | gaggcctcgg | 180 |
| gtcgggtggg | gcttgtttga | cggggacggc | agatccacgt | ctctgtcacg | tgactccagg | 240 |
| cggtggtcgc | ttgctccatg | tgccgcgtcg | catcccgatc | tctggctgtg | gttgcctggc | 300 |
| tggcaagggc | caaccgcccg | tcgtcagcga | tgaggatgct | tgtagtgtcg | tgtcgacttt | 360 |
| tgcaaaaaca | acgtgcccag | ccctgggttt | gtgcgccgcc | gcaccagcca | aaacaaagac | 420 |
| gaaaccgaaa | gactcgtcaa | aaggcaaaac | caagtgagga | aagacaactg | accatagcaa | 480 |
| aaaacacaac | tttgctagtt | ggtttccacg | tatctttgcc | gcatgaactg | gtcccggccg | 540 |
| tcacgtttgc | ttatagttcc | accacaataa | tagtcgaccc | gtggtcccgt | tggttttgat | 600 |
| tgagagtaga | gagcatccac | cggacagtta | aaagtgtgtt | tcattgttt | ttcccctaat | 660 |

```
aatctagtac ttattctcta cgtccacata atttagtcgt tttgggttta ttctaaatta      720
aactatttta attttaatca acaatatata taattaaatt attttaaact taaaagaatt      780
atatattatg atagtttaat tcatgataaa tttagtaaaa ttacttttgt attgtaaaac      840
cttataaaag gttcgatata tatataactg gtcaaaattg ataggaacg acttagaaca       900 aacttaaaat aactaaatta aactaaatta tatggacgaa ggggtaggta cctactccac      960
agtacttaat ttcctctagt agttaaccga aacacggtag atactgaatg aatgtgttgc     1020
aagaaacata ctgatctgtc tacttttgct tctcccctct tcgcctcttc aataattcgg     1080
tgtgcaaaga tgttgagaag agaaccgtga ataccgattt tgcag                    1125
```

<210> SEQ ID NO 19
<211> LENGTH: 894
<212> TYPE: DNA
<213> ORGANISM: Zea mays

<400> SEQUENCE: 19

```
gtgaggcatc cgatcgattt ttctttcttt ctttactaca ctcctttgcg atatggggac       60
gacactcggt agtggcgtga ggtgaggtaa atcgcgttag tttagttgta gggtttgatc      120
gcttcagggg ggaccagggg ttgggctttc cgtgttgaac cgtcaatcgg acgtagtagt      180
agtgcggatt cggggtttga tcgatggaaa gaggggttgt ccgcactctt ggtgtggtta      240
tagggttttg cgatttgttt gtctgtgtag gcctgtttcg tctcgaggag tagatttttca     300 ttgctactaa caatccctat gtggtttggt gaacacgtat tttggtctgt atatggttta      360
aacgtgaaga ctatggtagt gtgagaccat gatttggatc cttttctgtg gcattatagt      420
taaaatcgtg aggatgcacc tatatctatc ttttagcgct tagggtattg ttatagacga      480
gatcccctct ttgggctcta aaatagcaa gaaaaagaca tcttttgggc aagttaatgt       540
cctgtattat tctgaacgag atatgtttac tttcttataa gtttgatgtt tggtctgga       600 atatggttgc gttcatcttc caattagtgt gtttgcagta tgtgttggtg tagtttctct      660
gtgggcattt tgtggccaca gaaatgatag attttaagaa aggtttaggc agaagggtac      720
cttaagtgtt gtccagtaca aagtaacaat ttgtagcact tgtttctttt cttttgtttg      780
attatatgaa atttcggcca tgtaattgtt tcaaaataat aagatcgaat agtgttgcac      840
actacttccc agtcctatgt atacttataa gattttcct ctttgatatt tcag             894
```

<210> SEQ ID NO 20
<211> LENGTH: 33
<212> TYPE: DNA
<213> ORGANISM: Artificial Sequence
<220> FEATURE:
<223> OTHER INFORMATION: intron_TS1 fwd primer

<400> SEQUENCE: 20

```
caagcgatcg caggtgagcg cttacacctc tcc                                    33
```

<210> SEQ ID NO 21
<211> LENGTH: 35
<212> TYPE: DNA
<213> ORGANISM: Artificial Sequence
<220> FEATURE:
<223> OTHER INFORMATION: Intron_TS1 rev primer

<400> SEQUENCE: 21

```
tcgggtacct ggattgcaaa aaaaacagtg atcag                                  35
```

```
<210> SEQ ID NO 22
<211> LENGTH: 33
<212> TYPE: DNA
<213> ORGANISM: Artificial Sequence
<220> FEATURE:
<223> OTHER INFORMATION: Intron TS4_forward primer

<400> SEQUENCE: 22
caagcgatcg caggtagtcc ttgacgcgtt cga                                  33

<210> SEQ ID NO 23
<211> LENGTH: 32
<212> TYPE: DNA
<213> ORGANISM: Artificial Sequence
<220> FEATURE:
<223> OTHER INFORMATION: Intron TS4_reverse primer

<400> SEQUENCE: 23
tcgggtacct aaatagcaaa ataaaattgg tt                                   32

<210> SEQ ID NO 24
<211> LENGTH: 33
<212> TYPE: DNA
<213> ORGANISM: Artificial Sequence
<220> FEATURE:
<223> OTHER INFORMATION: Intron_TS5 forward primer

<400> SEQUENCE: 24
caagcgatcg caggtacgcc cgctctctcg ctc                                  33

<210> SEQ ID NO 25
<211> LENGTH: 29
<212> TYPE: DNA
<213> ORGANISM: Artificial Sequence
<220> FEATURE:
<223> OTHER INFORMATION: Intron_TS5 reverse primer

<400> SEQUENCE: 25
tcgggtacct gcacgaacga atttatgag                                       29

<210> SEQ ID NO 26
<211> LENGTH: 33
<212> TYPE: DNA
<213> ORGANISM: Artificial Sequence
<220> FEATURE:
<223> OTHER INFORMATION: Intron_TS6 forward primer

<400> SEQUENCE: 26
caagcgatcg caggtaaact cctacgcctc cct                                  33

<210> SEQ ID NO 27
<211> LENGTH: 29
<212> TYPE: DNA
<213> ORGANISM: Artificial Sequence
<220> FEATURE:
<223> OTHER INFORMATION: Intron_TS6 reverse primer

<400> SEQUENCE: 27
tcgggtacct gtaaagttt tccagttca                                        29

<210> SEQ ID NO 28
<211> LENGTH: 34
<212> TYPE: DNA
<213> ORGANISM: Artificial Sequence
<220> FEATURE:
<223> OTHER INFORMATION: Intron_TS7 forward primer
```

```
<400> SEQUENCE: 28
caagcgatcg caggtaaggt tcccttccct cctc                          34

<210> SEQ ID NO 29
<211> LENGTH: 30
<212> TYPE: DNA
<213> ORGANISM: Artificial Sequence
<220> FEATURE:
<223> OTHER INFORMATION: Intron_TS7 reverse primer

<400> SEQUENCE: 29
tcgggtacct gcacaagata cacacaaaca                               30

<210> SEQ ID NO 30
<211> LENGTH: 35
<212> TYPE: DNA
<213> ORGANISM: Artificial Sequence
<220> FEATURE:
<223> OTHER INFORMATION: Intron_TS8 forward primer

<400> SEQUENCE: 30
caagcgatcg caggtaaatc tcaaatttat catgt                         35

<210> SEQ ID NO 31
<211> LENGTH: 33
<212> TYPE: DNA
<213> ORGANISM: Artificial Sequence
<220> FEATURE:
<223> OTHER INFORMATION: Intron_TS8 reverse primer

<400> SEQUENCE: 31
tcgggtacct gaattgcaag tagataaaga cca                           33

<210> SEQ ID NO 32
<211> LENGTH: 33
<212> TYPE: DNA
<213> ORGANISM: Artificial Sequence
<220> FEATURE:
<223> OTHER INFORMATION: Intron_TS10 forward primer

<400> SEQUENCE: 32
caagcgatcg caggtataca accgacctcg tct                           33

<210> SEQ ID NO 33
<211> LENGTH: 29
<212> TYPE: DNA
<213> ORGANISM: Artificial Sequence
<220> FEATURE:
<223> OTHER INFORMATION: Intron_TS10 reverse primer

<400> SEQUENCE: 33
tcgggtacct aaagcaagga agggatca                                 29

<210> SEQ ID NO 34
<211> LENGTH: 35
<212> TYPE: DNA
<213> ORGANISM: Artificial Sequence
<220> FEATURE:
<223> OTHER INFORMATION: Intron_TS11 forward primer

<400> SEQUENCE: 34
caagcgatcg caggtccgtg ccgggcggcc cggat                         35

<210> SEQ ID NO 35
<211> LENGTH: 32
```

```
<212> TYPE: DNA
<213> ORGANISM: Artificial Sequence
<220> FEATURE:
<223> OTHER INFORMATION: Intron_TS11 reverse primer

<400> SEQUENCE: 35
tcgggtacct gcaaaagaca gagcaataca ag                                    32

<210> SEQ ID NO 36
<211> LENGTH: 33
<212> TYPE: DNA
<213> ORGANISM: Artificial Sequence
<220> FEATURE:
<223> OTHER INFORMATION: Intron_TS12 primer

<400> SEQUENCE: 36
caagcgatcg caggtaagcg acgacaacga gca                                   33

<210> SEQ ID NO 37
<211> LENGTH: 28
<212> TYPE: DNA
<213> ORGANISM: Artificial Sequence
<220> FEATURE:
<223> OTHER INFORMATION: Intron_TS12 reverse primer

<400> SEQUENCE: 37
tcgggtacct ctaactaact agtagtaa                                         28

<210> SEQ ID NO 38
<211> LENGTH: 33
<212> TYPE: DNA
<213> ORGANISM: Artificial Sequence
<220> FEATURE:
<223> OTHER INFORMATION: Intron_TS13 forward primer

<400> SEQUENCE: 38
caagcgatcg caggtgagga gccttctctc tct                                   33

<210> SEQ ID NO 39
<211> LENGTH: 35
<212> TYPE: DNA
<213> ORGANISM: Artificial Sequence
<220> FEATURE:
<223> OTHER INFORMATION: Intron_TS13 reverse primer

<400> SEQUENCE: 39
tcgggtacct gcgccaaaaa aaaatgtttg gttgt                                 35

<210> SEQ ID NO 40
<211> LENGTH: 34
<212> TYPE: DNA
<213> ORGANISM: Artificial Sequence
<220> FEATURE:
<223> OTHER INFORMATION: Intron_TS14 forwrad primer

<400> SEQUENCE: 40
caagcgatcg caggtatata ctctctctct ctca                                  34

<210> SEQ ID NO 41
<211> LENGTH: 36
<212> TYPE: DNA
<213> ORGANISM: Artificial Sequence
<220> FEATURE:
<223> OTHER INFORMATION: Intron_TS14 reverse primer

<400> SEQUENCE: 41
```
tcgggtacct gcgagcggaa tgagaacaga ttagct          36

<210> SEQ ID NO 42
<211> LENGTH: 43
<212> TYPE: DNA
<213> ORGANISM: Artificial Sequence
<220> FEATURE:
<223> OTHER INFORMATION: Intron_TS15 forward primer

<400> SEQUENCE: 42
cctccgcttc aagcgatcgc aggtaagcag gagagagagc tct          43

<210> SEQ ID NO 43
<211> LENGTH: 41
<212> TYPE: DNA
<213> ORGANISM: Artificial Sequence
<220> FEATURE:
<223> OTHER INFORMATION: Intron_TS15 reverse primer

<400> SEQUENCE: 43
aggctaagtt aaagtcgggt acctgaaata tcaaagagga a          41

<210> SEQ ID NO 44
<211> LENGTH: 34
<212> TYPE: DNA
<213> ORGANISM: Artificial Sequence
<220> FEATURE:
<223> OTHER INFORMATION: Intron_TS16 forward primer

<400> SEQUENCE: 44
caagcgatcg caggtgagat ttcgagagat tcgt          34

<210> SEQ ID NO 45
<211> LENGTH: 34
<212> TYPE: DNA
<213> ORGANISM: Artificial Sequence
<220> FEATURE:
<223> OTHER INFORMATION: Intron_TS16 reverse primer

<400> SEQUENCE: 45
tcgggtacct gccaagcgag tatataaaaa tcac          34

<210> SEQ ID NO 46
<211> LENGTH: 42
<212> TYPE: DNA
<213> ORGANISM: Artificial Sequence
<220> FEATURE:
<223> OTHER INFORMATION: Intron_TS17 forward primer

<400> SEQUENCE: 46
cctccgcttc aagcgatcgc aggtgaggcc gcgaccaaga ag          42

<210> SEQ ID NO 47
<211> LENGTH: 43
<212> TYPE: DNA
<213> ORGANISM: Artificial Sequence
<220> FEATURE:
<223> OTHER INFORMATION: Intron_TS17 reverse primer

<400> SEQUENCE: 47
aggctaagtt aaagtcgggt acctgcagga gccgacggcc cga          43

<210> SEQ ID NO 48
<211> LENGTH: 43
<212> TYPE: DNA
<213> ORGANISM: Artificial Sequence

```
<220> FEATURE:
<223> OTHER INFORMATION: Intron_TS24 forward primer

<400> SEQUENCE: 48
cctccgcttc aagcgatcgc aggtactaat aaactgatga ttc                    43

<210> SEQ ID NO 49
<211> LENGTH: 44
<212> TYPE: DNA
<213> ORGANISM: Artificial Sequence
<220> FEATURE:
<223> OTHER INFORMATION: Intron_TS24 reverse primer

<400> SEQUENCE: 49
aggctaagtt aaagtcgggt acctgcaaaa tcggtattca cggt                   44

<210> SEQ ID NO 50
<211> LENGTH: 46
<212> TYPE: DNA
<213> ORGANISM: Artificial Sequence
<220> FEATURE:
<223> OTHER INFORMATION: Intron_TS27 forward primer

<400> SEQUENCE: 50
cctccgcttc aagcgatcgc aggtgaggca tccgatcgat ttttct                 46

<210> SEQ ID NO 51
<211> LENGTH: 47
<212> TYPE: DNA
<213> ORGANISM: Artificial Sequence
<220> FEATURE:
<223> OTHER INFORMATION: Intron_TS27 reverse primer

<400> SEQUENCE: 51
aggctaagtt aaagtcgggt acctgaaata tcaaagagga aaaatct                47

<210> SEQ ID NO 52
<211> LENGTH: 100
<212> TYPE: DNA
<213> ORGANISM: zea mays

<400> SEQUENCE: 52
gtccgttccc gtcccagatc cgtccatggc ttcgtccaga tctgacctgt cctgacacac  60
cctcacccgg atctgtccct ccttcccctc tcccctgcag                        100

<210> SEQ ID NO 53
<211> LENGTH: 147
<212> TYPE: DNA
<213> ORGANISM: zea mays

<400> SEQUENCE: 53
gtctgcttcg tcctcgctag gtttcatttc gcggtctgtt tgtgccgttg gggctagatc  60
cgggtcgtgg ttcaacagat ctgcttcgtt ttggtacaga tctgcgttcg ctcgaatcga  120
gcatgacgtt ttcatgtgat tatgcag                                      147

<210> SEQ ID NO 54
<211> LENGTH: 82
<212> TYPE: DNA
<213> ORGANISM: zea mays

<400> SEQUENCE: 54
gtgcgtgcat gcgcacgctc tgcttctgcc tccctttccc ttttcctccg aaagaactga  60
```
aacggaacgc atcttcgctc ag                                            82

<210> SEQ ID NO 55
<211> LENGTH: 85
<212> TYPE: DNA
<213> ORGANISM: zea mays

<400> SEQUENCE: 55
gtgcgtcact gtccaggtgc ttggcttgga tcagaatatt gttggcggtg acactgtctt    60
ctctcgatcg atcgatcgat gacag                                         85

<210> SEQ ID NO 56
<211> LENGTH: 107
<212> TYPE: DNA
<213> ORGANISM: zea mays

<400> SEQUENCE: 56
gtcggtttcc aatctgttga ccatggatcc acagatcgga gcagttcttt catagtactc    60
agcgatctgt ttgggtccta aatttccttt ccccggctgt tgtttag                 107

<210> SEQ ID NO 57
<211> LENGTH: 604
<212> TYPE: DNA
<213> ORGANISM: zea mays

<400> SEQUENCE: 57
gtatgtttcg ttttttatttc cttcgtgtca tatttctggg tgcgagtttt gtgcctagat   60
gattcgtatg tgttcgagtt ggcggtgctc taatctttgt tttaaggttg ttatatggca   120
tgttagtgtc atcaacgatt catgattaat agactcagta gctaccattt catgatttat   180
gcagcgtatc agaggcaaga tataaatctt gggttcaaag ttgcacttga ttagctgata   240
ttatttttgt attggctagt ccatgttttt ggttggaatt tagtcttgaa tgatagtgtt   300
gcatccggtt tgctctatgt ttaagccgct acacacctgt gaaggcttgt gtgtagtttc   360
tagaatcagt attttgacaa tattacagtc atattgcaat agttgcatgt gctagtgtaa   420
gaattgttct gttcatttt tatacatgct ttgttctctt ttgttttttc atcaatgaaa    480
aaaacataaa agatacagtt tttttatttg tctaaatatg ggtgggttaa cctttcaccc   540
tgctggtcat ggaatatgtg ttttcaatta cttatctgca acttgtggat gcggactctt   600
tcag                                                                604

<210> SEQ ID NO 58
<211> LENGTH: 659
<212> TYPE: DNA
<213> ORGANISM: zea mays

<400> SEQUENCE: 58
gtaagtatcg attgctgatt gctgcggatc gcgtaccgtg gtcacgctgc ttagttcagc    60
tctaacaact gatcgctcct cctccactgt taccgattaa tggcttgatc ggtgccgagt   120
ctgttttagg tcgtgcccgg ctctctgctc gggcggcacg tgtggtccgg tgttgcagcg   180
gatgtagaat tttgaccttg ttctctagct gtgaatgaca gtattatagg cacagactta   240
tagattgatg tgcgttttgc gttgaactgc tcatcgaaca gatgctccca attcggtagt   300
ttatggcttg tttggataca tgcgtgaagt tttcagctga taagatttta ggaaatgttg   360 ttttttggcat taagtgtttt tataatgtat gggtctaagg gaggcccaga gtgtctacct   420
tccgttattt tgatctctga attgccgcct ttcacacgaa gggcggtcac gcgtgtcacg   480

```
tgaagggtgg tcacatgatc tgcagcatag cactactaga tgttggacct tagtgtatct    540
atgcacaaat tttctgatta gatacttgct gaaagctatt tcttcttgcg ctatgatgga    600
ccatactagc tattttgtga ttctagcgcc cttacaaaat atttatcact gctttgcag     659

<210> SEQ ID NO 59
<211> LENGTH: 9794
<212> TYPE: DNA
<213> ORGANISM: Artificial Sequence
<220> FEATURE:
<223> OTHER INFORMATION: Vector Sequence

<400> SEQUENCE: 59
ttcctggcct tttgctggcc ttttgctcac atgttctttc ctgcgttatc ccctgattct     60
gtggataacc gtattaccgc ctttgagtga gctgataccg ctcgccgcag ccgaacgacc    120
gagcgcagcg agtcagtgag cgaggaagcg gaagagcgcc caatacgcaa accgcctctc    180
cccgcgcgtt ggccgattca ttaatgcagc tggcacgaca ggtttcccga ctggaaagcg    240
ggcagtgagc gcaacgcaat taatacgcgt accgctagcc aggaagagtt tgtagaaacg    300
caaaaaggcc atccgtcagg atggccttct gcttagtttg atgcctggca gtttatggcg    360
ggcgtcctgc ccgccaccct ccgggccgtt gcttcacaac gttcaaatcc gctcccggcg    420
gatttgtcct actcaggaga gcgttcaccg acaaacaaca gataaaacga aaggcccagt    480
cttccgactg agcctttcgt tttatttgat gcctggcagt ccctactct cgcgttcatg     540 gagctccaaa taatgatttt attttgactg atagtgacct gttcgttgca acaaattgat    600
aagcaatgct ttttataat gccaactttg tatagaaaag ttgggccgaa ttcgagctcg    660
gtacggccag aatccggtaa gtgactaggg tcacgtgacc ctagtcactt aaattcggcc    720
agaatggccc ggaccgggtt accaaaaaag cttcggccgg ggccgcactg tcaagctatt    780
attagcttct ttaataagtc caatgtgaac aaaccgtcta gggttagatg gattgctttc    840
acagatttcc ttactggtct aggaatccct gtaaatatag agcacataga tggaaaaaat    900
aaccatctgg ctgatgctct gtccagatta gtaactggtt tgttttttgc agaaccacaa    960
tgtcaagaca agttccagga cgatttaggg aaattggaag cagctcttca ggagaagaaa   1020
gaggctccgc aagcaatgca cgtagaatat gtctccctgt tgatcagatc agcggaccgc   1080
attacccgct cgctctgctt tatgagggac tcgtctcaca gcagaattta tcatgcagg    1140 ccaggcaaag aaccaatgaa ggccttaatc tgcgaacaga agtcatgcca atccaaaggc   1200
gacttaggga atacgaggac tgtgcactcc aagagtgcat tcaatcagca agacaactgg   1260
tggccctcca ccagcacaaa ctcgcttaca tcagaagcaa agctacaagg acaacgcat   1320 atgccgatag ctacccaca tgcaatcggg accacgagca actgtgtgaa gtggtcgagc   1380
tattagaagg aatctcggaa agaatcagcg atacagctgt ctaggacagc tggcttcaat   1440 tatgagcgt gatggacccc cccgcaataa tccaaagttt ggtgtgcttt tagtagtgcg    1500
tctttatgga ccactacttt attgtaataa tcgatgcttt ttgtagtgcg ctcttcgtgc   1560
gctctacttt atgcttttgc ttttgtaagt gcgctgtaag tgcgcctgtc tttcttcaga   1620
tgcttatcct ttaagcatct tttgcttttt gcgtggcatc ctttagttca caatttaaag   1680
aatgacgatg gggcccaaga tgtgcacccg gttctctaaa ttgcctatat aaggatatgc   1740
catagccttg ttttttgcaag tcaggaatac ctgagcataa cttggctaag caaaagtttg   1800
taagtgttct aagctttcat ttgtaaactt tctgtttggt tttaataaaa tctctcgtca   1860
```

```
atcgttgtga acatatattg tttgtttgta ttgttgtatc ttatttgttg tggtgataag   1920
gatcttcgat atcccggact ggcgccaggt ccgccttgtt tctcctctgt ctcttgatct   1980
gactaatctt ggtttatgat tcgttgagta attttgggga aagcttcgtc cacagttttt   2040
ttttcgatga acagtgccgc agtggcgctg atcttgtatg ctatcctgca atcgtggtga   2100
acttatttct tttatatcct tcactcccat gaaaaggcta gtaatctttc tcgatgtaac   2160
atcgtccagc actgctatta ccgtgtggtc catccgacag tctggctgaa cacatcatac   2220
gatattgagc aaagatcgat ctatcttccc tgttctttaa tgaaagacgt cattttcatc   2280
agtatgatct aagaatgttg caacttgcaa ggaggcgttt ctttctttga atttaactaa   2340
ctcgttgagt ggccctgttt ctcggacgta aggcctttgc tgctccacac atgtccattc   2400
gaattttacc gtgtttagca agggcgaaaa gtttgcatct tgatgattta gcttgactat   2460
gcgattgctt tcctggaccc gtgcagctgg cgccttggga tccatgggca acagcgtgct   2520
caacagcgga cgcaccacca tctgcgacgc ctacaacgtg ccgcgcacg acccgttcag   2580 cttccagcac aagagcctcg acaccgtgca gcgcgagtgg accagtgga agaagaacaa   2640 ccacagcctc tacctcgacc cgatcgtggg caccgtggcc agcttcctcc tcaagaaggt   2700
gggcagcctc gtgggcaagc gcatcctcag cgagctgcgc aacctcatct cccgagcgg   2760 cagcaccaac ctcatgcagg acatcctccg cgagaccgag cagttcctca accagcgcct   2820
cgacaccgac ccctcgcca gggtgaacgc cgagctgacc ggcctccagg ccaacgtgga   2880
ggagttcaac cgccaggtgg acaacttcct caacccgaac cgcaacgccg tgccgctcag   2940
catcaccagc agcgtgaaca ccatgcagca gctcttcctc aaccgcctcc cgcagttcca   3000
gatgcagggc taccagctcc tgctcctgcc gctcttcgcc caggccgcca acctccacct   3060
cagcttcatc cgcgacgtga tcctcaacgc cgacagtgg ggcatcagcg ccgccaccct   3120
ccgcacctac cgcgactacc tcaagaacta cacccgcgac tacagcaact actgcatcaa   3180
cacctaccag agcgccttca agggcctcaa cacccgcctc cacggcaccc tcgagttccg   3240
cacctacatg ttcctcaacg tcttcgagta cgtgagcatc tggagcctct tcaagtacca   3300
gagcctcctc gtgagcagcg gcgccaacct ctacgccagc ggcagcggcc cgcagcagac   3360
ccagagcttc accagccagg actggccgtt cctctacagc ctcttccagg tgaacagcaa   3420
ctacgtgctc aacggcttca gcggcgccag gctcagcaac accttcccga acatcggcgg   3480
cctcccgggc agcaccacca cccacgccct cctcgcggcc agggtgaact acagcggcgg   3540
catcagcagc ggcgacatcg cgccagccc gttcaaccag aacttcaact gcagcacctt   3600
cctcccgccg ctcctcaccc cgttcgtgcg cagctggctc gatagcggca gcgaccgcga   3660
gggcgtggcc accgtgacca actggcagac cgagagcttc gagaccacac tcgggctcag   3720
gagcggcgcc ttcaccgccc gcggcaacag caactacttc ccggactact tcatccggaa   3780
catctccggc gttccgttgg tggtccgtaa cgaggatctc aggaggccgc tgcactacaa   3840
cgagatccgc aacatcgctt cgcccagcgg gacccccaggt ggagcacggg cctacatggt   3900
gtccgtgcac aaccggaaga caacatcca cgcggtccat gagaacggca gcatgatcca   3960
cctggctcct aacgactaca cggggttcac aatctctccg atccatgcta ctcaagtcaa   4020
caaccagacc aggacgttca tctcggagaa gttcggcaac cagggagact ccttgaggtt   4080
cgagcagaac aacacaactg cccgctacac ccttcggggc aacgggaaca gctacaacct   4140
ctacctgcgc gtcagctcca tcggcaactc gacgatcagg gtcacgatca acggaagggt   4200
ctacactgcg accaacgtga acacgacaac taacaacgac ggcgtcaacg caacggcgc   4260
```

```
taggttctcc gacatcaaca tcgggaacgt tgtggcaagc tccaactcgg atgtccctct    4320
tgacatcaac gtcaccttca actctggaac gcagttcgat ctgatgaaca caatgctggt    4380
gccaactaac atcagccctc tgtactgata cgtagttcgc gcctaggttt ttgtgatctg    4440
atgataagtg gttggttcgt gtctcatgca cttgggaggt gatctatttc acctggtgta    4500
gtttgtgttt ccgtcagttg gaaaaactta tccctatcga tttcgttttc attttctgct    4560
tttcttttat gtaccttcgt ttgggcttgt aacgggcctt tgtatttcaa ctctcaataa    4620
taatccaagt gcatgttaaa caatttgtca tctgtttcgg ctttgatata ctactggtga    4680
agatgggccg tactactgca tcacaacgaa aaataataat aagatgaaaa acttgaagtg    4740
gaaaaaaaaa aaaacttgaa tgttcactac tactcattga ccataatgtt aacatacat    4800 agctcaatag tattttgtg aatatggcaa cacaaacagt ccaaaacaat tgtctcttac    4860
tataccaaac caagggcgcc gcttgtttgc cactctttgt gtgcaatagt gtgattacca    4920
catctccaca ttcaatatat tccctgaatt atctgacgat tttgatggct cactgttttc    4980
ccaagtcttg aattgtcttc tgtgcgccag tcaaatgcat atgtgttgag tttatctttt    5040
aaatatcaag cttttgtttt taacttttgt ttgtaaccaa aaactcacag taggagtttg    5100
atcacataat tttatgtttg cctttgcaat ttctagtgag tctttgatta aaagcttgaa    5160
aagaaaatgc agccaagctt accaagtaag ttatgtgtat taaccagagg aagagagaat    5220
cttgcaaaat ttcaacaaac acaaaagaa gtattactac gattggtgga gaaagaaaac    5280
gattccaaat cttgaactgt tgttgtaaaa gcatagcaga aagtgggaga caaccgaaat    5340
agaaatgact ataacttaat ttaatgttat cattataatt tcttctagca aatatttaga    5400
aagtaaatat cacatcaacc tttaatgtaa ttaagctttc tcttttgat tcatgtgaga    5460 tgaaagaaa aaaagaaga gaaagtgta gaaacacat catttctaag ctgaaggtac    5520
atagtaccct tgtacttttg gtttcacctg catagagaaa acccacaaga atatgacagt    5580
ctgatttgtc agtctcattc tcaagcaaca tttctctatc cgttacttc atggtgaata    5640 acacaatcca tcatcaatac tttgtgttac tcagaaactg aaagttattc cgagtcttgc    5700
atatctttgg acctactcgt ttttctacca ttattgctga ttgttaagct ctcgctactt    5760
gaatcggcat tgttggagtg ggaaggttca aaaaattgga gttatgacta gttgtctctt    5820
tctatgtacg atggagaaaa tgaataaaca actgagaaaa tggctcttgt ttagttgatg    5880
atgctcttaa gctttccact ggttgccata tatgatttgg gcatttcact ttgatcttaa    5940 tgggcccttgt aaagcccaag actcatgatt atctttagtt gatgctctta attaggtgtg    6000
ggcaaataat tcaaactgta tgtacccgac caaaccaaa gcaaaaataa tcgaaccaaa    6060
ccgaaaattt aaaaataacc gaatgaaaac taaatcctat aactgaaaga actgaaaccg    6120
aatcaaaata tttaatgtaa ccaaaaatat ccgaaatata attatattgt caaaaatatt    6180
aataatttct agattaaata attaaaaata cttaaaaatt tatataaaat agtaaaaata    6240
ctcgaaaata accacaaata ttcaaaaaca accgaaatat cccaaaatat tcaaagcaaa    6300
ataaccgaat ggataccaaa ttttaaaacc gaaaaaactg gaacaaaacc aaaatcgaac    6360
caaaatttca aaaatcgaat aaatactaaa ctttagaaca aaaaaaacg ataaccgaat    6420 gtatacgaac caaagccgaa ttagataacc gaacgtccag gactactctt aatctttccg    6480
ccacttatga tttgggctat tacttttgttt ataatgagcc ttttcaagct caagttcatg    6540
attgtccgtg agatgagaaa ctgacttgtt ggattcgaaa ccctagctag tattggttaa    6600
```

```
tacttaatac ataaatgacc tgcattgaca tcatcatcca agaaaataaa aattgtatgc    6660
ttgagatatt tagttttcct agctaggttt tctttatttt agtaccgaat ctttaggtgt    6720
gccacgttaa tttagaccca ttttttcata cttaccaact gagtctagtt taatcatgac    6780
tataatcgta taaatgatt cagtcgacgt cattgcgaac gtatataaaa tcatccaaat     6840
tgacgtcatt ccaaagaggt aagcatgctt atctaagagt ccgagcatac taaacaagac    6900
gacattttat ttgcactcca aatcaaattt tgtattgcct aaagaaaaac aatcaaactc    6960
aagtttctta aaattaattt cattcaaact aatcactttc aatatctcac atattattca    7020
tgccattcct atttgtctaa acatgattta aaaaaaaaag taaaatacaa agattactat    7080
gcaaaaactc tataaaaaaa aattcaaatt tcttatttat ttgtgacatc aaatttcaa     7140
aataatttt ttaattatcg gttgatccgg tcagtcgata aaaacataaa ctttcagcga     7200
ccgttaaaac tttcctacta ccgatttaga gaaaatctta gcttgaaacg taattgtaac    7260
ctgccttcat gcaagtcgca agatatgtca tcctaagttg tatatgtttt ctcaaaagat    7320
gtatttactt gagaaaatac gtttcaacgt tgatggacaa ccaattaaga atcaagcacc    7380
tttcgtaatc aatttaggct tatcgtctaa ggtatactga tttacgacag ttgactagac    7440
ttataaggaa caaataata gaataatttc gtcaagaaaa attgattttg gactcatact     7500
ttacataata ttttactctt aaatttattt aagtggctcc tcgcatgatc ccaaagagca    7560
agcctagact atatggaaaa gtttctaaac acttcaccta atcatagaga ctaagatggt    7620
aattcgtaaa cgacaaagcc tagtgacact gtccattgta aaattccaca tcatattagt    7680
attaaacata tacatgtagt ttcctgaaca catgtagtat caaacacact tcgtggcttc    7740
ttcctcgaaa cctggtaccc taggcttaag gtttaaacag cccgggcgcg ccgtcccatt    7800
ctggccgaat ttaagtgact agggtcacgt gaccctagtc acttaccgga ttctggccgt    7860
accgagctcg aattcaaagg tcacccggtc cgggcctaga aggcctaagt gactagggtc    7920
acgtgaccct agtcacttat tcccgggcaa ctttattata caaagttggc attataaaaa    7980
agcattgctt atcaatttgt tgcaacgaac aggtcactat cagtcaaaat aaaatcatta    8040
tttggagctc catgcatggt agcgttatcc cctatagtga gtcgtattac atggtcatag    8100
ctgtttcctg gcagctctgg cccgtgtctc aaaatctctg atgttacatt gcacaagata    8160
aaaatatatc atcatgaaca ataaaactgt ctgcttacat aaacagtaat acaaggggtg    8220
ttatgagcca tattcaacgg gaaacgtcga ggccgcgatt aaattccaac atggatgctg    8280
atttatatgg gtataaatgg gctcgcgata atgtcgggca atcaggtgcg acaatctatc    8340
gcttgtatgg gaagcccgat gcgccagagt tgtttctgaa acatggcaaa ggtagcgttg    8400
ccaatgatgt tacagatgag atggtcagac taaactggct gacggaattt atgcctcttc    8460
cgaccatcaa gcattttatc cgtactcctg atgatgcatg ttactcacc actgcgatcc    8520
ccggaaaaac agcattccag gtattagaag aatatcctga ttcaggtgaa atattgttg     8580
atgcgctggc agtgttcctg cgccggttgc attcgattcc tgtttgtaat tgtccttta     8640
acagcgatcg cgtatttcgt ctcgctcagg cgcaatcacg aatgaataac ggtttggttg    8700
atgcgagtga tttgatgac gagcgtaatg gctggcctgt tgaacaagtc tggaaagaaa     8760
tgcataaact tttgccattc tcaccggatt cagtcgtcac tcatggtgat ttctcacttg    8820
ataaccttat ttttgacgag gggaaattaa taggttgtat tgatgttgga cgagtcggaa    8880
tcgcagaccg ataccaggat cttgccatcc tatggaactg cctcggtgag ttttctcctt    8940
cattacagaa acggcttttt caaaaatatg gtattgataa tcctgatatg aataaattgc    9000
```

```
agtttcattt gatgctcgat gagtttttct aatcagaatt ggttaattgg ttgtaacact    9060
ggcagagcat tacgctgact tgacgggacg gcgcaagctc atgaccaaaa tcccttaacg    9120
tgagttacgc gtcgttccac tgagcgtcag accccgtaga aaagatcaaa ggatcttctt    9180
gagatccttt ttttctgcgc gtaatctgct gcttgcaaac aaaaaaacca ccgctaccag    9240
cggtggtttg tttgccggat caagagctac caactctttt tccgaaggta actggcttca    9300
gcagagcgca gataccaaat actgtccttc tagtgtagcc gtagttaggc caccacttca    9360
agaactctgt agcaccgcct acatacctcg ctctgctaat cctgttacca gtggctgctg    9420
ccagtggcga taagtcgtgt cttaccgggt tggactcaag acgatagtta ccggataagg    9480
cgcagcggtc gggctgaacg gggggttcgt gcacacagcc cagcttggag cgaacgacct    9540
acaccgaact gagatacccta cagcgtgagc attgagaaag cgccacgctt cccgaaggga    9600
gaaaggcgga caggtatccg gtaagcggca gggtcggaac aggagagcgc acgagggagc    9660
ttccaggggg aaacgcctgg tatctttata gtcctgtcgg gtttcgccac ctctgacttg    9720
agcgtcgatt tttgtgatgc tcgtcagggg ggcggagcct atggaaaaac gccagcaacg    9780
cggccttttt acgg                                                      9794
```

<210> SEQ ID NO 60
<211> LENGTH: 51162
<212> TYPE: DNA
<213> ORGANISM: Artificial Sequence
<220> FEATURE:
<223> OTHER INFORMATION: Vector sequence

<400> SEQUENCE: 60

```
tctagagctc gttcctcgag gaacggtacc tgcggggaag cttacaataa tgtgtgttgt      60
taagtcttgt tgcctgtcat cgtctgactg actttcgtca taaatcccgg cctccgtaac     120
ccagctttgg gcaagctcac ggatttgatc cggcggaacg ggaatatcga gatgccgggc     180
tgaacgctgc agttccagct ttcccttttcg ggacaggtac tccagctgat tgattatctg    240
ctgaagggtc ttggttccac ctcctggcac aatgcgaatg attacttgag cgcgatcggg    300
catccaattt tctcccgtca ggtgcgtggt caagtgctac aaggcacctt tcagtaacga    360
gcgaccgtcg atccgtcgcc gggatacgga caaaatggag cgcagtagtc catcgagggc    420
ggcgaaagcc tcgccaaaag caatacgttc atctcgcaca gctccagat ccgatcgagg     480
gtcttcggcg taggcagata gaagcatgga tacattgctt gagagtattc cgatggactg    540
aagtatggct tccatctttt ctcgtgtgtc tgcatctatt tcgagaaagc ccccgatgcg    600
gcgcaccgca acgcgaattg ccatactatc cgaaagtccc agcaggcgcg cttgatagga    660
aaaggtttca tactcggccg atcgcagacg ggcactcacg accttgaacc cttcaacttt    720
cagggatcga tgctggttga tggtagtctc actcgacgtg gctctggtgt gttttgacat    780
agcttcctcc aaagaaagcg gaaggtctgg atactccagc acgaaatgtg cccgggtaga    840
cggatggaag tctagccctg ctcaatatga aatcaacagt acatttacag tcaatactga    900
atatacttgc tacatttgca attgtcttat aacgaatgtg aaataaaaat agtgtaacaa    960
cgcttttact catcgataat cacaaaaaca tttatacgaa caaaaataca aatgcactcc   1020
ggtttcacag gataggcggg atcagaatat gcaactttg acgttttgtt ctttcaaagg    1080
gggtgctgga aaaccaccg cactcatggg cctttgcgct gctttggcaa atgacggtaa    1140
acgagtggcc ctctttgatg ccgacgaaaa ccggcctctg acgcgatgga gagaaaacgc   1200
```

```
cttacaaagc agtactggga tcctcgctgt gaagtctatt ccgccgacga aatgcccctt   1260
cttgaagcag cctatgaaaa tgccgagctc gaaggatttg attatgcgtt ggccgatacg   1320
cgtggcggct cgagcgagct caacaacaca atcatcgcta gctcaaacct gcttctgatc   1380
cccaccatgc taacgccgct cgacatcgat gaggcactat ctacctaccg ctacgtcatc   1440
gagctgctgt tgagtgaaaa tttggcaatt cctacagctg ttttgcgcca acgcgtcccg   1500
gtcggccgat tgacaacatc gcaacgcagg atgtcagaga cgctagagag ccttccagtt   1560
gtaccgtctc ccatgcatga aagagatgca tttgccgcga tgaaagaacg cggcatgttg   1620
catcttacat tactaaacac gggaactgat ccgacgatgc gcctcataga gaggaatctt   1680
cggattgcga tggaggaagt cgtggtcatt tcgaaactga tcagcaaaat cttggaggct   1740
tgaagatggc aattcgcaag cccgcattgt cggtcggcga agcacggcgg cttgctggtg   1800
ctcgacccga gatccaccat cccaacccga cacttgttcc ccagaagctg gacctccagc   1860
acttgcctga aaaagccgac gagaaagacc agcaacgtga gcctctcgtc gccgatcaca   1920
tttacagtcc cgatcgacaa cttaagctaa ctgtggatgc ccttagtcca cctccgtccc   1980
cgaaaaagct ccaggttttt ctttcagcgc gaccgcccgc gcctcaagtg tcgaaaacat   2040
atgacaacct cgttcggcaa tacagtccct cgaagtcgct acaaatgatt taaggcgcg   2100 cgttggacga tttcgaaagc atgctggcag atggatcatt tcgcgtggcc ccgaaaagtt   2160
atccgatccc ttcaactaca gaaaaatccg ttctcgttca gacctcacgc atgttcccgg   2220
ttgcgttgct cgaggtcgct cgaagtcatt ttgatccgtt ggggttggag accgctcgag   2280
cttccggcca caagctggct accgccgcgc tcgcgtcatt cttgctgga gagaagccat   2340 cgagcaattg gtgaagaggg acctatcgga accctcacc aaatattgag tgtaggtttg   2400
aggccgctgg ccgcgtcctc agtcacctt tgagccagat aattaagagc caaatgcaat   2460
tggctcaggc tgccatcgtc ccccgtgcg aaacctgcac gtccgcgtca agaaataac   2520 cggcacctct tgctgttttt atcagttgag ggcttgacgg atccgcctca gtttgcggc   2580 gcagccgcaa aatgagaaca tctatactcc tgtcgtaaac ctcctcgtcg cgtactcgac   2640
tggcaatgag aagttgctcg cgcgatagaa cgtcgcgggg tttctctaaa aacgcgagga   2700
gaagattgaa ctcacctgcc gtaagtttca cctcaccgcc agcttcggac atcaagcgac   2760
gttgcctgag attaagtgtc cagtcagtaa aacaaaaaga ccgtcggtct ttggagcgga   2820
caacgttggg gcgcacgcgc aaggcaaccc gaatgcgtgc aagaaactct ctcgtactaa   2880
acggcttagc gataaaatca cttgctccta gctcgagtgc aacaacttta tccgtctcct   2940
caaggcggtc gccactgata attatgattg gaatatcaga ctttgccgcc agatttcgaa   3000
cgatctcaag cccatcttca cgacctaaat ttagatcaac aaccacgaca tcgaccgtcg   3060
cggaagagag tactctagtg aactgggtgc tgtcggctac cgcggtcact ttgaaggcgt   3120
ggatcgtaag gtattcgata ataagatgcc gcatagcgac atcgtcatcg ataagaagaa   3180
cgtgtttcaa cggctcacct ttcaatctaa aatctgaacc cttgttcaca gcgcttgaga   3240
aattttcacg tgaaggatgt acaatcatct ccagctaaat gggcagttcg tcagaattgc   3300
ggctgaccgc ggatgacgaa aatgcgaacc aagtatttca attttatgac aaaagttctc   3360
aatcgttgtt acaagtgaaa cgcttcgagg ttacagctac tattgattaa ggagatcgcc   3420
tatggtctcg ccccggcgtc gtgcgtccgc cgcgagccag atctcgccta cttcataaac   3480
gtcctcatag gcacggaatg gaatgatgac atcgatcgcc gtagagagca tgtcaatcag   3540
tgtgcgatct tccaagctag caccttgggc gctactttg acaagggaaa acagtttctt   3600
```

```
gaatccttgg attggattcg cgccgtgtat tgttgaaatc gatcccggat gtcccgagac   3660
gacttcactc agataagccc atgctgcatc gtcgcgcatc tcgccaagca atatccggtc   3720
cggccgcata cgcagacttg cttggagcaa gtgctcggcg ctcacagcac ccagcccagc   3780
accgttcttg gagtagagta gtctaacatg attatcgtgt ggaatgacga gttcgagcgt   3840
atcttctatg gtgattagcc tttcctgggg ggggatggcg ctgatcaagg tcttgctcat   3900
tgttgtcttg ccgcttccgg tagggccaca tagcaacatc gtcagtcggc tgacgacgca   3960
tgcgtgcaga aacgcttcca aatccccgtt gtcaaaatgc tgaaggatag cttcatcatc   4020
ctgattttgg cgtttccttc gtgtctgcca ctggttccac ctcgaagcat cataacggga   4080
ggagacttct ttaagaccag aaacacgcga gcttggccgt cgaatggtca agctgacggt   4140
gcccgaggga acggtcggcg gcagacagat ttgtagtcgt tcaccaccag gaagttcagt   4200
ggcgcagagg gggttacgtg gtccgacatc ctgctttctc agcgcgcccg ctaaaatagc   4260
gatatcttca agatcatcat aagagacggg caaaggcatc ttggtaaaaa tgccggcttg   4320
gcgcacaaat gcctctccag gtcgattgat cgcaatttct tcagtcttcg ggtcatcgag   4380
ccattccaaa atcggcttca gaagaaagcg tagttgcgga tccacttcca tttacaatgt   4440
atcctatctc taagcggaaa tttgaattca ttaagagcgg cggttcctcc cccgcgtggc   4500
gccgccagtc aggcggagct ggtaaacacc aaagaaatcg aggtcccgtg ctacgaaaat   4560
ggaaacggtg tcaccctgat tcttcttcag ggttggcggt atgttgatgg ttgccttaag   4620
ggctgtctca gttgtctgct caccgttatt ttgaaagctg ttgaagctca tcccgccacc   4680
cgagctgccg gcgtaggtgc tagctgcctg gaaggcgcct tgaacaacac tcaagagcat   4740
agctccgcta aaacgctgcc agaagtggct gtcgaccgag cccggcaatc ctgagcgacc   4800
gagttcgtcc gcgcttggcg atgttaacga gatcatcgca tggtcaggtg tctcggcgcg   4860
atcccacaac acaaaaacgc gcccatctcc ctgttgcaag ccacgctgta tttcgccaac   4920
aacggtggtg ccacgatcaa gaagcacgat attgttcgtt gttccacgaa tatcctgagg   4980
caagacacac tttacatagc ctgccaaatt tgtgtcgatt gcggtttgca agatgcacgg   5040
aattattgtc ccttgcgtta ccataaaatc ggggtgcggc aagagcgtgg cgctgctggg   5100
ctgcagctcg gtgggtttca tacgtatcga caaatcgttc tcgccggaca cttcgccatt   5160
cggcaaggag ttgtcgtcac gcttgccttc ttgtcttcgg cccgtgtcgc cctgaatggc   5220
gcgtttgctg accccttgat cgccgctgct atatgcaaaa atcggtgttt cttccggccg   5280
tggctcatgc cgctccggtt cgcccctcgg cggtagagga gcagcaggct gaacagcctc   5340
ttgaaccgct ggaggatccg gcggcacctc aatcggagct ggatgaaatg gcttggtgtt   5400
tgttgcgatc aaagttgacg gcgatgcgtt ctcattcacc ttcttttggc gcccacctag   5460
ccaaatgagg cttaatgata acgcgagaac gacacctccg acgatcaatt tctgagaccc   5520
cgaaagacgc cggcgatgtt tgtcggagac cagggatcca gatgcatcaa cctcatgtgc   5580
cgcttgctga ctatcgttat tcatcccttc gccccttca ggacgcgttt cacatcgggc    5640
ctcaccgtgc ccgtttgcgg cctttggcca acgggatcgt aagcggtgtt ccagatacat   5700
agtactgtgt ggccatccct cagacgccaa cctcgggaaa ccgaagaaat ctcgacatcg   5760
ctccctttaa ctgaatagtt ggcaacagct tccttgccat caggattgat ggtgtagatg   5820
gagggtatgc gtacattgcc cggaaagtgg aataccgtcg taaatccatt gtcgaagact   5880
tcgagtggca acagcgaacg atcgccttgg gcgacgtagt gccaattact gtccgccgca   5940
```

-continued

```
ccaagggctg tgacaggctg atccaataaa ttctcagctt tccgttgata ttgtgcttcc    6000
gcgtgtagtc tgtccacaac agccttctgt tgtgcctccc ttcgccgagc cgccgcatcg    6060
tcggcgggt  aggcgaattg gacgctgtaa tagagatcgg gctgctcttt atcgaggtgg    6120
gacagagtct tggaacttat actgaaaaca taacggcgca tcccggagtc gcttgcggtt    6180
agcacgatta ctggctgagg cgtgaggacc tggcttgcct tgaaaaatag ataatttccc    6240
cgcggtaggg ctgctagatc tttgctattt gaaacggcaa ccgctgtcac cgtttcgttc    6300
gtggcgaatg ttacgaccaa agtagctcca accgccgtcg agaggcgcac cacttgatcg    6360
ggattgtaag ccaaataacg catgcgcgga tctagcttgc ccgccattgg agtgtcttca    6420
gcctccgcac cagtcgcagc ggcaaataaa catgctaaaa tgaaaagtgc ttttctgatc    6480
atggttcgct gtggcctacg tttgaaacgg tatcttccga tgtctgatag gaggtgacaa    6540
ccagacctgc cgggttggtt agtctcaatc tgccgggcaa gctggtcacc ttttcgtagc    6600
gaactgtcgc ggtccacgta ctcaccacag gcattttgcc gtcaacgacg agggtccttt    6660
tatagcgaat ttgctgcgtg cttggagtta catcatttga agcgatgtgc tcgacctcca    6720
ccctgccgcg tttgccaaga atgacttgag gcgaactggg attgggatag ttgaagaatt    6780
gctggtaatc ctggcgcact gttggggcac tgaagttcga taccaggtcg taggcgtact    6840
gagcggtgtc ggcatcataa ctctcgcgca ggcgaacgta ctcccacaat gaggcgttaa    6900
cgacggcctc ctcttgagtt gcaggcaatc gcgagacaga cacctcgctg tcaacggtgc    6960
cgtccggccg tatccataga tatacgggca caagcctgct caacggcacc attgtggcta    7020
tagcgaacgc ttgagcaaca tttcccaaaa tcgcgatagc tgcgacagct gcaatgagtt    7080
tggagagacg tcgcgccgat ttcgctcgcg cggtttgaaa ggcttctact tccttatagt    7140
gctcggcaag gctttcgcgc gccactagca tggcatattc aggccccgtc atagcgtcca    7200
cccgaattgc cgagctgaag atctgacgga gtaggctgcc atcgcccac  attcagcggg    7260
aagatcgggc ctttgcagct cgctaatgtg tcgtttgtct ggcagccgct caaagcgaca    7320
actaggcaca gcaggcaata cttcatagaa ttctccattg aggcgaattt ttgcgcgacc    7380
tagcctcgct caacctgagc gaagcgacg  tacaagctgc tggcagattg ggttgcgccg    7440
ctccagtaac tgcctccaat gttgccggcg atcgccggca aagcgacaat gagcgcatcc    7500
cctgtcagaa aaacatatc  gagttcgtaa agaccaatga tcttggccgc ggtcgtaccg    7560
gcgaaggtga ttacaccaag cataagggtg agcgcagtcg cttcggttag gatgacgatc    7620
gttgccacga ggtttaagag gagaagcaag agaccgtagg tgataagttg cccgatccac    7680
ttagctgcga tgtcccgcgt gcgatcaaaa atatatccga cgaggatcag aggcccgatc    7740
gcgagaagca ctttcgtgag aattccaacg gcgtcgtaaa ctccgaaggc agaccagagc    7800
gtgccgtaaa ggacccactg tgcccttgg  aaagcaagga tgtcctggtc gttcatcgga    7860
ccgatttcgg atgcgatttt ctgaaaaacg gcctgggtca cggcgaacat tgtatccaac    7920
tgtgccggaa cagtctgcag aggcaagccg gttacactaa actgctgaac aaagtttggg    7980
accgtctttt cgaagatgga aaccacatag tcttggtagt tagcctgccc aacaattaga    8040
gcaacaacga tggtgaccgt gatcacccga gtgataccgc tacgggtatc gacttcgccg    8100
cgtatgacta aaatacccctg aacaataatc caaagagtga cacaggcgat caatggcgca    8160
ctcaccgcct cctggatagt ctcaagcatc gagtccaagc ctgtcgtgaa ggctacatcg    8220
aagatcgtat gaatggccgt aaacggcgcc ggaatcgtga aattcatcga ttggacctga    8280
acttgactgg tttgtcgcat aatgttggat aaaatgagct cgcattcggc gaggatgcgg    8340
```

```
gcggatgaac aaatcgccca gccttagggg agggcaccaa agatgacagc ggtcttttga    8400
tgctccttgc gttgagcggc cgcctcttcc gcctcgtgaa ggccggcctg cgcggtagtc    8460
atcgttaata ggcttgtcgc ctgtacattt tgaatcattg cgtcatggat ctgcttgaga    8520
agcaaaccat tggtcacggt tgcctgcatg atattgcgag atcgggaaag ctgagcagac    8580
gtatcagcat tcgccgtcaa gcgtttgtcc atcgtttcca gattgtcagc cgcaatgcca    8640
gcgctgtttg cggaaccggt gatctgcgat cgcaacaggt ccgcttcagc atcactaccc    8700
acgactgcac gatctgtatc gctggtgatc gcacgtgccg tggtcgacat tggcattcgc    8760
ggcgaaaaca tttcattgtc taggtccttc gtcgaaggat actgattttt ctggttgagc    8820
gaagtcagta gtccagtaac gccgtaggcc gacgtcaaca tcgtaaccat cgctatagtc    8880
tgagtgagat tctccgcagt cgcgagcgca gtcgcgagcg tctcagcctc cgttgccggg    8940
tcgctaacaa caaactgcgc ccgcgcgggc tgaatatata gaaagctgca ggtcaaaact    9000
gttgcaataa gttgcgtcgt cttcatcgtt tcctacctta tcaatcttct gcctcgtggt    9060
gacgggccat gaattcgctg agccagccag atgagttgcc ttcttgtgcc tcgcgtagtc    9120
gagttgcaaa gcgcaccgtg ttggcacgcc ccgaaagcac ggcgacatat tcacgcatat    9180
cccgcagatc aaattcgcag atgacgcttc cactttctcg tttaagaaga aacttacggc    9240
tgccgaccgt catgtcttca cggatcgcct gaaattcctt tcggtacat ttcagtccat    9300 cgacataagc cgatcgatct gcggttggtg atggatagaa aatcttcgtc atacattgcg    9360
caaccaagct ggctcctagc ggcgattcca gaacatgctc tggttgctgc gttgccagta    9420
ttagcatccc gttgttttt cgaacggtca ggaggaattt gtcgacgaca gtcgaaaatt    9480
tagggtttaa caaataggcg cgaaactcat cgcagctcat cacaaaacgg cggccgtcga    9540
tcatggctcc aatccgatgc aggagatatg ctgcagcggg agcgcatact tcctcgtatt    9600
cgagaagatg cgtcatgtcg aagccggtaa tcgacggatc taactttact tcgtcaactt    9660
cgccgtcaaa tgcccagcca agcgcatggc cccggcacca gcgttggagc cgcgctcctg    9720
cgccttcggc gggcccatgc aacaaaaatt cacgtaaccc cgcgattgaa cgcatttgtg    9780
gatcaaacga gagctgacga tggataccac ggaccagacg gcggttctct tccggagaaa    9840
tcccaccccg accatcactc tcgatgagag ccacgatcca ttcgcgcaga aaatcgtgtg    9900
aggctgctgt gttttctagg ccacgcaacg gcgccaaccc gctgggtgtg cctctgtgaa    9960
gtgccaaata tgttcctcct gtggcgcgaa ccagcaattc gccaccccgg tccttgtcaa    10020
agaacacgac cgtacctgca cggtcgacca tgctctgttc gagcatggct agaacaaaca    10080
tcatgagcgt cgtcttaccc ctcccgatag gcccgaatat tgccgtcatg ccaacatcgt    10140
gctcatgcgg gatatagtcg aaaggcgttc cgccattggt acgaaatcgg gcaatcgcgt    10200
tgccccagtg gcctgagctg gcgccctctg gaaagttttc gaaagagaca aaccctgcga    10260
aattgcgtga agtgattgcg ccagggcgtg tgcgccactt aaaattcccc ggcaattggg    10320
accaataggc cgcttccata ccaataccttc ttggacaac cacggcacct gcatccgcca    10380
ttcgtgtccg agcccgcgcg cccctgtccc caagactatt gagatcgtct gcatagacgc    10440
aaaggctcaa atgatgtgag cccataacga attcgttgct cgcaagtgcg tcctcagcct    10500
cggataattt gccgatttga gtcacggctt tatcgccgga actcagcatc tggctcgatt    10560
tgaggctaag tttcgcgtgc gcttgcgggc gagtcaggaa cgaaaactc tgcgtgaaa    10620 caagtggaaa atcgagggat agcagcgcgt tgagcatgcc cggccgtgtt tttgcagggt    10680
```

```
attcgcgaaa cgaatagatg gatccaacgt aactgtcttt tggcgttctg atctcgagtc   10740
ctcgcttgcc gcaaatgact ctgtcggtat aaatcgaagc gccgagtgag ccgctgacga   10800
ccggaaccgg tgtgaaccga ccagtcatga tcaaccgtag cgcttcgcca atttcggtga   10860
agagcacacc ctgcttctcg cggatgccaa gacgatgcag gccatacgct ttaagagagc   10920
cagcgacaac atgccaaaga tcttccatgt tcctgatctg gcccgtgaga tcgttttccc   10980 ttttccgct tagcttggtg aacctcctct ttaccttccc taaagccgcc tgtgggtaga   11040
caatcaacgt aaggaagtgt tcattgcgga ggagttggcc ggagagcacg cgctgttcaa   11100
aagcttcgtt caggctagcg gcgaaaacac tacggaagtg tcgcggcgcc gatgatggca   11160
cgtcggcatg acgtacgagg tgagcatata ttgacacatg atcatcagcg atattgcgca   11220
acagcgtgtt gaacgcacga caacgcgcat tgcgcatttc agtttcctca agctcgaatg   11280
caacgccatc aattctcgca atggtcatga tcgatccgtc ttcaagaagg acgatatggt   11340
cgctgaggtg gccaatataa gggagataga tctcaccgga tctttcggtc gttccactcg   11400
cgccgagcat cacaccattc ctctcccctcg tggggggaacc ctaattggat ttgggctaac   11460
agtagcgccc ccccaaactg cactatcaat gcttcttccc gcggtccgca aaaatagcag   11520
gacgacgctc gccgcattgt agtctcgctc cacgatgagc cgggctgcaa accataacgg   11580
cacgagaacg acttcgtaga gcgggttctg aacgataacg atgacaaagc cggcgaacat   11640
catgaataac cctgccaatg tcagtggcac cccaagaaac aatgcgggcc gtgtggctgc   11700
gaggtaaagg gtcgattctt ccaaacgatc agccatcaac taccgccagt gagcgtttgg   11760
ccgaggaagc tcgcccccaaa catgataaca atgccgccga cgacgccggc aaccagccca   11820
agcgaagccc gcccgaacat ccaggagatc ccgatagcga caatgccgag aacagcgagt   11880
gactggccga acgaccaag gataaacgtg catatattgt taaccattgt ggcgggtca   11940 gtgccgccac ccgcagattg cgctgcggcg ggtccggatg aggaaatgct ccatgcaatt   12000
gcaccgcaca agcttggggc gcagctcgat atcacgcgca tcatcgcatt cgagagcgag   12060
aggcgattta gatgtaaacg gtatctctca aagcatcgca tcaatgcgca cctccttagt   12120
ataagtcgaa taagacttga ttgtcgtctg cggatttgcc gttgtcctgg tgtggcggtg   12180
gcggagcgat taaaccgcca gcgccatcct cctgcgagcg gcgctgatat gacccccaaa   12240
catcccacgt ctcttcggat tttagcgcct cgtgatcgtc ttttggaggc tcgattaacg   12300
cgggcaccag cgattgagca gctgtttcaa cttttcgcac gtagccgttt gcaaaaccgc   12360
cgatgaaatt accggtgttg taagcggaga tcgcccgacg aagcgcaaat tgcttctcgt   12420
caatcgtttc gccgcctgca taacgacttt tcagcatgtt tgcagcggca gataatgatg   12480
tgcacgcctg gagcgcaccg tcaggtgtca gaccgagcat agaaaaattt cgagagttta   12540
tttgcatgag gccaacatcc agcgaatgcc gtgcatcgag acggtgcctg acgacttggg   12600
ttgcttggct gtgatcttgc cagtgaagcg tttcgccggt cgtgttgtca tgaatcgcta   12660
aaggatcaaa gcgactctcc accttagcta tcgccgcaag cgtagatgtc gcaactgatg   12720
gggcacactt gcgagcaaca tggtcaaact cagcagatga gagtggcgtg gcaaggctcg   12780
acgaacagaa ggagaccatc aaggcaagag aaagcgaccc cgatctctta agcatacctt   12840
atctccttag ctcgcaacta acaccgcctc tcccgttgga agaagtgcgt tgttttatgt   12900
tgaagattat cgggagggtc ggttactcga aaattttcaa ttgcttcttt atgatttcaa   12960
ttgaagcgag aaacctcgcc cggcgtcttg gaacgcaaca tggaccgaga accgcgcatc   13020
catgactaag caaccggatc gacctattca ggccgcagtt ggtcaggtca ggctcagaac   13080
```

```
gaaaatgctc ggcgaggtta cgctgtctgt aaacccattc gatgaacggg aagcttcctt   13140
ccgattgctc ttggcaggaa tattggccca tgcctgcttg cgctttgcaa atgctcttat   13200
cgcgttggta tcatatgcct tgtccgccag cagaaacgca ctctaagcga ttatttgtaa   13260
aaatgtttcg gtcatgcggc ggtcatgggc ttgacccgct gtcagcgcaa gacggatcgg   13320
tcaaccgtcg gcatcgacaa cagcgtgaat cttggtggtc aaaccgccac gggaacgtcc   13380
catacagcca tcgtcttgat cccgctgttt ccgtcgccg catgttggtg gacgcggaca    13440
caggaactgt caatcatgac gacattctat cgaaagcctt ggaaatcaca ctcagaatat   13500
gatcccagac gtctgcctca cgccatcgta caaagcgatt gtagcaggtt gtacaggaac   13560
cgtatcgatc aggaacgtct gcccagggcg ggcccgtccg gaagcgccac aagatgacat   13620
tgatcacccg cgtcaacgcg cggcacgcga cgcggcttat ttgggaacaa aggactgaac   13680
aacagtccat tcgaaatcgg tgacatcaaa gcggggacgg ttatcagtg gcctccaagt    13740 caagcctcaa tgaatcaaaa tcagaccgat ttgcaaacct gatttatgag tgtgcggcct   13800
aaatgatgaa atcgtccttc tagatcgcct ccgtggtgta gcaacacctc gcagtatcgc   13860
cgtgctgacc ttggccaggg aattgactgg caagggtgct ttcacatgac cgctcttttg   13920
gccgcgatag atgatttcgt tgctgctttg ggcacgtaga aggagagaag tcatatcgga   13980
gaaattcctc ctggcgcgag agcctgctct atcgcgacgg catcccactg tcgggaacag   14040
accggatcat tcacgaggcg aaagtcgtca acacatgcgt tataggcatc ttcccttgaa   14100
ggatgatctt gttgctgcca atctggaggt gcggcagccg caggcagatg cgatctcagc   14160
gcaacttgcg gcaaaacatc tcactcacct gaaaaccact agcgagtctc gcgatcagac   14220
gaaggccttt tacttaacga cacaatatcc gatgtctgca tcacaggcgt cgctatccca   14280
gtcaatacta aagcggtgca ggaactaaag attactgatg acttaggcgt gccacgaggc   14340
ctgagacgac gcgcgtagac agttttttga aatcattatc aaagtgatgg cctccgctga   14400
agcctatcac ctctgcgccg gtctgtcgga gagatgggca agcattatta cggtcttcgc   14460
gcccgtacat gcattggacg attgcagggt caatggatct gagatcatcc agaggattgc   14520
cgcccttacc ttccgtttcg agttggagcc agcccctaaa tgagacgaca tagtcgactt   14580
gatgtgacaa tgccaagaga gagatttgct taacccgatt ttttttgctca agcgtaagcc   14640 tattgaagct tgccggcatg acgtccgcgc cgaaagaata tcctacaagt aaaacattct   14700
gcacaccgaa atgcttggtg tagacatcga ttatgtgacc aagatcctta gcagtttcgc   14760
ttggggaccg ctccgaccag aaataccgaa gtgaactgac gccaatgaca ggaatccctt   14820
ccgtctgcag ataggtacca tcgatagatc tgctgcctcg cgcgtttcgg tgatgacggt   14880
gaaaacctct gacacatgca gctcccggag acggtcacag cttgtctgta agcggatgcc   14940
gggagcagac aagcccgtca gggcgcgtca gcgggtgttg gcgggtgtcg gggcgcagcc   15000
atgacccagt cacgtagcga tagcggagtg tatactggct taactatgcg gcatcagagc   15060
agattgtact gagagtgcac catatgcggt gtgaaatacc gcacagatgc gtaaggagaa   15120
aataccgcat caggcgctct tccgcttcct cgctcactga ctcgctgcgc tcggtcgttc   15180
ggctgcggcg agcggtatca gctcactcaa aggcggtaat acgttatcc acagaatcag    15240 gggataacgc aggaaagaac atgtgagcaa aaggccagca aaaggccagg aaccgtaaaa   15300
aggccgcgtt gctggcgttt ttccataggc tccgccccc tgacgagcat cacaaaaatc    15360
gacgctcaag tcagaggtgg cgaaacccga caggactata aagataccag gcgtttcccc   15420
```

```
ctggaagctc cctcgtgcgc tctcctgttc cgaccctgcc gcttaccgga tacctgtccg   15480
cctttctccc ttcgggaagc gtggcgcttt ctcatagctc acgctgtagg tatctcagtt   15540
cggtgtaggt cgttcgctcc aagctgggct gtgtgcacga accccccgtt cagcccgacc   15600
gctgcgcctt atccggtaac tatcgtcttg agtccaaccc ggtaagacac gacttatcgc   15660
cactggcagc agccactggt aacaggatta gcagagcgag gtatgtaggc ggtgctacag   15720
agttcttgaa gtggtggcct aactacggct acactagaag gacagtattt ggtatctgcg   15780
ctctgctgaa gccagttacc ttcggaaaaa gagttggtag ctcttgatcc ggcaaacaaa   15840
ccaccgctgg tagcggtggt ttttttgttt gcaagcagca gattacgcgc agaaaaaaag   15900
gatctcaaga agatcctttg atcttttcta cggggtctga cgctcagtgg aacgaaaact   15960
cacgttaagg gattttggtc atgagattat caaaaaggat cttcacctag atccttttaa   16020
attaaaaatg aagttttaaa tcaatctaaa gtatatatga gtaaacttgg tctgacagtt   16080
accaatgctt aatcagtgag gcacctatct cagcgatctg tctatttcgt tcatccatag   16140
ttgcctgact ccccgtcgtg tagataacta cgatacggga gggcttacca tctggcccca   16200
gtgctgcaat gataccgcga gacccacgct caccggctcc agatttatca gcaataaacc   16260
agccagccgg aagggccgag cgcagaagtg gtcctgcaac tttatccgcc tccatccagt   16320
ctattaattg ttgccgggaa gctagagtaa gtagttcgcc agttaatagt ttgcgcaacg   16380
ttgttgccat tgctgcaggg ggggggggggg gggggactt ccattgttca ttccacggac   16440
aaaaacagag aaaggaaacg acagaggcca aaaagcctcg ctttcagcac ctgtcgtttc   16500
ctttcttttc agagggtatt ttaaataaaa acattaagtt atgacgaaga agaacggaaa   16560
cgccttaaac cggaaaattt tcataaatag cgaaacccg cgaggtcgcc gccccgtaac   16620
ctgtcggatc accggaaagg acccgtaaag tgataatgat tatcatctac atatcacaac   16680
gtgcgtggag gccatcaaac cacgtcaaat aatcaattat gacgcaggta tcgtattaat   16740
tgatctgcat caacttaacg taaaaacaac ttcagacaat acaaatcagc gacactgaat   16800
acggggcaac ctcatgtccc ccccccccc cccctgcag gcatcgtggt gtcacgctcg   16860
tcgtttggta tggcttcatt cagctccggt tcccaacgat caaggcgagt tacatgatcc   16920
cccatgttgt gcaaaaagc ggttagctcc ttcggtcctc cgatcgttgt cagaagtaag   16980
ttggccgcag tgttatcact catggttatg gcagcactgc ataattctct tactgtcatg   17040
ccatccgtaa gatgcttttc tgtgactggt gagtactcaa ccaagtcatt ctgagaatag   17100
tgtatgcggc gaccgagttg ctcttgcccg gcgtcaacac gggataatac cgcgccacat   17160
agcagaactt taaaagtgct catcattgga aaacgttctt cggggcgaaa actctcaagg   17220
atcttaccgc tgttgagatc cagttcgatg taacccactc gtgcacccaa ctgatcttca   17280
gcatctttta ctttcaccag cgtttctggg tgagcaaaaa caggaaggca aaatgccgca   17340
aaaaagggaa taagggcgac acggaaatgt tgaatactca tactcttcct ttttcaatat   17400
tattgaagca tttatcaggg ttattgtctc atgagcggat acatatttga atgtatttag   17460
aaaaataaac aaatagggt tccgcgcaca tttccccgaa aagtgccacc tgacgtctaa   17520
gaaaccatta ttatcatgac attaacctat aaaaataggc gtatcacgag gccctttcgt   17580
cttcaagaat tggtcgacga tcttgctgcg ttcggatatt ttcgtggagt tcccgccaca   17640
gacccggatt gaaggcgaga tccagcaact cgcgccagat catcctgtga cggaactttg   17700
gcgcgtgatg actggccagg acgtcggccg aaagagcgac aagcagatca cgcttttcga   17760
cagcgtcgga tttgcgatcg aggattttc ggcgctgcgc tacgtccgcg accgcgttga   17820
```

```
gggatcaagc cacagcagcc cactcgacct tctagccgac ccagacgagc caagggatct   17880
ttttggaatg ctgctccgtc gtcaggcttt ccgacgtttg ggtggttgaa cagaagtcat   17940
tatcgtacgg aatgccaagc actcccgagg ggaaccctgt ggttggcatg cacatacaaa   18000
tggacgaacg gataaacctt tcacgccct tttaaatatc cgttattcta ataaacgctc    18060
ttttctctta ggtttacccg ccaatatatc ctgtcaaaca ctgatagttt aaactgaagg   18120
cgggaaacga caatctgatc atgagcgag aattaaggga gtcacgttat gaccccgcc     18180
gatgacgcgg gacaagccgt tttacgtttg gaactgacag aaccgcaacg ttgaaggagc   18240
cactcagcaa gctggtacga ttgtaatacg actcactata gggcgaattg agcgctgttt   18300
aaacgctctt caactggaag agcggttact accggctgga tggcggggcc ttgatcgtgc   18360
accgccggcg tccggataag tgactagggt cacgtgaccc tagtcactta tcgagctagt   18420
taccctatga ggtgacatga agcgctcacg gttactatga cggttagctt cacgactgtt   18480
ggtggcagta gcgtacgact tagctatagt tccggtagat ctgaagttcc tattccgaag   18540
ttcctattct tcaaaaggta taggaacttc ctcgaattgt tgtggtgggg tatagaggtt   18600
tgatataggg ggaactgctg tagagcgtgg agatataggg ggaaagagaa cgctgatgtg   18660
acaagtgagt gagatatagg gggagaaatt taggggaac gccgaacaca gtctaaagaa    18720
gcttgggacc caaagcactc tgttcggggg ttttttttt tgtctttcaa cttttttgctg   18780
taatgttatt caaaataaga aaagcacttg gcatggctaa gaaatagagt tcaacaactg   18840
aacagtacag tgtattatca atggcataaa aaacaaccct tacagcattg ccgtatttta   18900
ttgatcaaac attcaactca acactgacga gtggtcttcc accgatcaac ggactaatgc   18960
tgctttgtca gatcaccggt taagtgacta gggtcacgtg accctagtca cttaggttac   19020
cagagctggt caccttttgtc caccaagatg gaactgcggc cgctcattaa ttaagtcagg   19080
cgcgcctcta gttgaagaca cgttcatgtc ttcatcgtaa gaagacactc agtagtcttc   19140
ggccagaatg gccatctgga ttcagcaggc ataacttcgt ataatgtatg ctatacgaag   19200
ttatctctag aactagtgga tctcgatgtg tagtctacga gaagggttaa ccgtctcttc   19260
gtgagaataa ccgtggccta aaaataagcc gatgaggata aataaaatgt ggtggtacag   19320
tacttcaaga ggtttactca tcaagaggat gcttttccga tgagctctag tagtacatcg   19380
gacctcacat acctccattg tggtgaaata ttttgtgctc atttagtgat gggtaaattt   19440
tgtttatgtc actctaggtt ttgacatttc agttttgcca ctcttaggtt ttgacaaata   19500
atttccattc cgcggcaaaa gcaaacaat tttattttac ttttaccact cttagctttc    19560
acaatgtatc acaaatgcca ctctagaaat tctgtttatg ccacagaatg tgaaaaaaaa   19620
cactcactta tttgaagcca aggtgttcat ggcatgaaa tgtgacataa agtaacgttc    19680
gtgtataaga aaaaattgta ctcctcgtaa caagagacgg aaacatcatg agacaatcgc   19740
gtttggaagg ctttgcatca cctttggatg atgcgcatga atggagtcgt ctgcttgcta   19800
gccttcgcct accgcccact gagtccgggc ggcaactacc atcggcgaac gacccagctg   19860
acctctaccg accggacttg aatgcgctac cttcgtcagc gacgatggcc gcgtacgctg   19920
gcgacgtgcc cccgcatgca tggcggcaca tggcgagctc agaccgtgcg tggctggcta   19980
caaatacgta ccccgtgagt gccctagcta gaaacttaca cctgcaactg cgagagcgag   20040
cgtgtgagtg tagccgagta gatccccgg tcgccaccat ggcctcctcc gagaacgtca    20100
tcaccgagtt catgcgcttc aaggtgcgca tggagggcac cgtgaacggc cacgagttcg   20160
```

```
agatcgaggg cgagggcgag ggccgccct acgagggcca caacaccgtg aagctgaagg    20220
tgaccaaggg cggccccctg cccttcgcct gggacatcct gtcccccag ttccagtacg    20280 gctccaaggt gtacgtgaag caccccgccg acatcccga ctacaagaag ctgtccttcc    20340
ccgagggctt caagtgggag cgcgtgatga acttcgagga cggcggcgtg gcgaccgtga    20400
cccaggactc ctccctgcag gacggctgct tcatctacaa ggtgaagttc atcggcgtga    20460
acttcccctc cgacggcccc gtgatgcaga agaagaccat gggctgggag gcctccaccg    20520
agcgcctgta ccccgcgac ggcgtgctga agggcgagac ccacaaggcc ctgaagctga    20580
aggacggcgg ccactacctg gtggagttca agtccatcta catggccaag aagcccgtgc    20640
agctgcccgg ctactactac gtggacgcca agctggacat caccctccac aacgaggact    20700
acaccatcgt ggagcagtac gagcgcaccg agggccgcca ccacctgttc ctgtagcggc    20760
ccatggatat tcgaacgcgt aggtaccaca tggttaacct agacttgtcc atcttctgga    20820
ttggccaact taattaatgt atgaaataaa aggatgcaca catagtgaca tgctaatcac    20880
tataatgtgg gcatcaaagt tgtgtgttat gtgtaattac tagttatctg aataaaagag    20940
aaagagatca tccatatttc ttatcctaaa tgaatgtcac gtgtctttat aattctttga    21000
tgaaccagat gcatttcatt aaccaaatcc atatacatat aaatattaat catatataat    21060
taatatcaat tgggttagca aaacaaatct agtctaggtg tgttttgcga atgcggccat    21120
aacttcgtat aatgtatgct atacgaagtt atctagaagg ccatttaaat cctgaggatc    21180
tggtcttcct aaggacccgg gatatcgcta tcaactttgt atagaaaagt tgaacgagaa    21240
acgtaaaatg atataaatat caatatatta aattagattt tgcataaaaa acagactaca    21300
taatactgta aaacacaaca tatccagtca ctatggtcga cctgcagact ggctgtgtat    21360
aagggagcct gacatttata ttccccagaa catcaggtta atggcgtttt tgatgtcatt    21420
ttcgcggtgg ctgagatcag ccacttcttc cccgataacg agaccggca cactggccat    21480 atcggtggtc atcatgcgcc agctttcatc cccgatatgc accacggggt aaagttcacg    21540
ggggacttta tctgacagca gacgtgcact ggccaggggg atcaccatcc gtcgcccggg    21600
cgtgtcaata atatcactct gtacatccac aaacagacga taacggctct ctctttata    21660 ggtgtaaacc ttaaactgca tttcaccagc ccctgttctc gtcggcaaaa gagccgttca    21720
tttcaataaa ccgggcgacc tcagccatcc cttcctgatt ttccgctttc agcgttcgg    21780 cacgcagacg acgggcttca ttctgcatgg ttgtgcttac cgaaccggag atattgacat    21840
catatatgcc ttgagcaact gatagctgtc gctgtcaact gtcactgtaa tacgctgctt    21900
catagcatac ctctttttga catacttcgg gtatacatat cagtatatat tcttataccg    21960
caaaaatcag cgcgcaaata cgcatactgt tatctggctt ttagtaagcc ggatcctcta    22020
gattacgccc cgcctgccac tcatcgcagt actgttgtaa ttcattaagc attctgccga    22080
catggaagcc atcacaaacg gcatgatgaa cctgaatcgc cagcggcatc agcaccttgt    22140
cgccttgcgt ataatatttg cccatggtga aacgggggc gaagaagttg tccatattgg    22200
ccacgtttaa atcaaaactg gtgaaactca cccaggatt ggctgagacg aaaaacatat    22260
tctcaataaa cccttaggg aaataggcca ggttttcacc gtaacacgcc acatcttgcg    22320
aatatatgtg tagaaactgc cggaaatcgt cgtggtattc actccagagc gatgaaaacg    22380
tttcagtttg ctcatggaaa acggtgtaac aagggtgaac actatcccat atcaccagct    22440
caccgtcttt cattgccata cggaattccg gatgagcatt catcaggcgg gcaagaatgt    22500
gaataaaggc cggataaaac ttgtgcttat ttttctttac ggtctttaaa aaggccgtaa    22560
```

```
tatccagctg aacggtctgg ttataggtac attgagcaac tgactgaaat gcctcaaaat   22620
gttctttacg atgccattgg gatatatcaa cggtggtata tccagtgatt tttttctcca   22680
ttttagcttc cttagctcct gaaaatctcg acggatccta actcaaaatc cacacattat   22740
acgagccgga agcataaagt gtaaagcctg gggtgcccta atgcggccgc catagtgact   22800
ggatatgttg tgttttacag tattatgtag tctgtttttt atgcaaaatc taatttaata   22860
tattgatatt tatatcattt tacgtttctc gttcaacttt attatacaaa gttgatagat   22920
atcggaccga ttaaacttta attcggtccg atgcatgtat acgaagttcc tattccgaag   22980
ttcctattct acatagagta taggaacttc acctggtggc gccgctagtg gatccccgg   23040
gctgcagtgc agcgtgaccc ggtcgtgccc ctctctagag ataatgagca ttgcatgtct   23100
aagttataaa aaattaccac atatttttt tgtcacactt gtttgaagtg cagtttatct   23160
atctttatac atatatttaa actttactct acgaataata taatctatag tactacaata   23220
atatcagtgt tttagagaat catataaatg aacagttaga catggtctaa aggacaattg   23280
agtattttga caacaggact ctacagtttt atctttttag tgtgcatgtg ttctcctttt   23340
tttttgcaaa tagcttcacc tatataatac ttcatccatt ttattagtac atccatttag   23400
ggtttagggt taatggtttt tatagactaa ttttttttagt acatctattt tattctattt   23460
tagcctctaa attaagaaaa ctaaaactct attttagttt ttttatttaa taatttagat   23520
ataaaataga ataaaataaa gtgactaaaa attaaacaaa taccctttaa gaaattaaaa   23580
aaactaagga aacatttttc ttgtttcgag tagataatgc cagcctgtta aacgccgtcg   23640
acgagtctaa cggacaccaa ccagcgaacc agcagcgtcg cgtcgggcca agcgaagcag   23700
acggcacggc atctctgtcg ctgcctctgg accctctcg agagttccgc tccaccgttg   23760
gacttgctcc gctgtcggca tccagaaatt gcgtggcgga gcggcagacg tgagccggca   23820
cggcaggcgg cctcctcctc ctctcacggc accggcagct acgggggatt cctttcccac   23880
cgctccttcg ctttcccttc ctcgcccgcc gtaataaata gacacccct ccacaccctc   23940
tttccccaac ctcgtgttgt tcggagcgca cacacacaca accagatctc ccccaaatcc   24000
acccgtcggc acctccgctt caaggtacgc cgctcgtcct cccccccccc cctctctacc   24060
ttctctagat cggcgttccg gtccatgcat ggttagggcc cggtagttct acttctgttc   24120
atgtttgtgt tagatccgtg tttgtgttag atccgtgctg ctagcgttcg tacacggatg   24180
cgacctgtac gtcagacacg ttctgattgc taacttgcca gtgtttctct ttggggaatc   24240
ctgggatggc tctagccgtt ccgcagacgg gatcgatttc atgattttt ttgtttcgtt   24300
gcatagggtt tggtttgccc ttttcctttta tttcaatata tgccgtgcac ttgtttgtcg   24360
ggtcatcttt tcatgcttt ttttgtcttg gttgtgatga tgtggtctgg ttgggcggtc   24420
gttctagatc ggagtagaat tctgtttcaa actacctggt ggatttatta attttggatc   24480
tgtatgtgtg tgccatacat attcatagtt acgaattgaa gatgatggat ggaaatatcg   24540
atctaggata ggtatacatg ttgatgcggg ttttactgat gcatatacag agatgctttt   24600
tgttcgcttg gttgtgatga tgtggtgtgg ttggcggtc gttcattcgt tctagatcgg   24660
agtagaatac tgtttcaaac tacctggtgt atttattaat tttggaactg tatgtgtgtg   24720
tcatacatct tcatagttac gagtttaaga tggatggaaa tatcgatcta ggataggtat   24780
acatgttgat gtgggtttta ctgatgcata tacatgatgg catatgcagc atctattcat   24840
atgctctaac cttgagtacc tatctattat aataaacaag tatgttttat aattattttg   24900
```

```
atcttgatat acttggatga tggcatatgc agcagctata tgtggatttt tttagccctg    24960
ccttcatacg ctatttattt gcttggtact gtttcttttg tcgatgctca ccctgttgtt    25020
tggtgttact tctgcaggtc gactttaact tagcctagga tccacacgac accatgtccc    25080
ccgagcgccg ccccgtcgag atccgcccgg ccaccgccgc cgacatggcc gccgtgtgcg    25140
acatcgtgaa ccactacatc gagacctcca ccgtgaactt ccgcaccgag ccgcagaccc    25200
cgcaggagtg gatcgacgac ctggagcgcc tccaggaccg ctacccgtgg ctcgtggccg    25260
aggtggaggg cgtggtggcc ggcatcgcct acgccggccc gtggaaggcc cgcaacgcct    25320
acgactggac cgtggagtcc accgtgtacg tgtcccaccg ccaccagcgc ctcggcctcg    25380
gctccaccct ctacacccac ctcctcaaga gcatggaggc ccagggcttc aagtccgtgg    25440
tggccgtgat cggcctcccg aacgaccgt ccgtgcgcct ccacgaggcc ctcggctaca    25500
ccgcccgcgg caccctccgc gccgccggct acaagcacgg cggctggcac gacgtcggct    25560
tctggcagcg cgacttcgag ctgccggccc cgccgcgccc ggtgcgcccg gtgacgcaga    25620
tctgagtcga aacctagact tgtccatctt ctggattggc aacttaatt aatgtatgaa    25680
ataaaaggat gcacacatag tgacatgcta atcactataa tgtgggcatc aaagttgtgt    25740
gttatgtgta attactagtt atctgaataa aagagaaaga gatcatccat atttcttatc    25800
ctaaatgaat gtcacgtgtc tttataattc tttgatgaac cagatgcatt tcattaacca    25860
aatccatata catataaata ttaatcatat ataattaata tcaattgggt tagcaaaaca    25920
aatctagtct aggtgtgttt tgcgaattgc ggccgctcta gcgtatacga agttcctatt    25980
ccgaagttcc tattctctag aaagtatagg aacttctgat tccgatgact tgtaggttc    26040
ctagctcaag ccgctcgtgt ccaagcgtca cttacgatta gctaatgatt acggcatcta    26100
ggaccgacta gtaagtgact agggtcacgt gaccctagtc acttatacgt agaattaatt    26160
cattccgatt aatcgtggcc tcttgctctt caggatgaag agctatgttt aaacgtgcaa    26220
gcgctactag acaattcagt acattaaaaa cgtccgcaat gtgttattaa gttgtctaag    26280
cgtcaatttg tttacaccac aatatatcct gccaccagcc agccaacagc tccccgaccg    26340
gcagctcggc acaaaatcac cactcgatac aggcagccca tcagtccggg acggcgtcag    26400
cgggagagcc gttgtaaggc ggcagacttt gctcatgtta ccgatgctat tcggaagaac    26460
ggcaactaag ctgccgggtt tgaaacacgg atgatctcgc ggagggtagc atgttgattg    26520
taacgatgac agagcgttgc tgcctgtgat caaatatcat ctccctcgca gagatccgaa    26580
ttatcagcct tcttattcat ttctcgctta accgtgacag gctgtcgatc ttgagaacta    26640
tgccgacata ataggaaatc gctggataaa gccgctgagg aagctgagtg gcgctatttc    26700
tttagaagtg aacgttgacg atcgtcgacc gtaccccgat gaattaattc ggacgtacgt    26760
tctgaacaca gctggatact tacttgggcg attgtcatac atgacatcaa caatgtaccc    26820
gtttgtgtaa ccgtctcttg gaggttcgta tgacactagt ggttccccctc agcttgcgac    26880
tagatgttga ggcctaacat tttattagag agcaggctag ttgcttagat acatgatctt    26940
caggccgtta tctgtcaggg caagcgaaaa ttggccattt atgacgacca atgccccgca    27000
gaagctccca tctttgccgc catagacgcc gcgcccccct ttggggtgt agaacatcct    27060
tttgccagat gtggaaaaga agttcgttgt cccattgttg gcaatgacgt agtagccggc    27120
gaaagtgcga gacccatttg cgctatatat aagcctacga tttccgttgc gactattgtc    27180
gtaattggat gaactattat cgtagttgct ctcagagttc tcgtaatttg atggactatt    27240
gtcgtaattg cttatggagt tgtcgtagtt gcttggagaa atgtcgtagt tggatgggga    27300
```

```
gtagtcatag ggaagacgag cttcatccac taaaacaatt ggcaggtcag caagtgcctg    27360
ccccgatgcc atcgcaagta cgaggcttag aaccaccttc aacagatcgc gcatagtctt    27420
ccccagctct ctaacgcttg agttaagccg cgccgcgaag cggcgtcggc ttgaacgaat    27480
tgttagacat tatttgccga ctaccttggt gatctcgcct ttcacgtagt gaacaaattc    27540
ttccaactga tctgcgcgcg aggccaagcg atcttcttgt ccaagataag cctgcctagc    27600
ttcaagtatg acgggctgat actgggccgg caggcgctcc attgcccagt cggcagcgac    27660
atccttcggc gcgattttgc cggttactgc gctgtaccaa atgcgggaca acgtaagcac    27720
tacatttcgc tcatcgccag cccagtcggg cggcgagttc catagcgtta aggtttcatt    27780
tagcgcctca aatagatcct gttcaggaac cggatcaaag agttcctccg ccgctggacc    27840
taccaaggca acgctatgtt ctcttgcttt tgtcagcaag atagccagat caatgtcgat    27900
cgtggctggc tcgaagatac ctgcaagaat gtcattgcgc tgccattctc caaattgcag    27960
ttcgcgctta gctggataac gccacggaat gatgtcgtcg tgcacaacaa tggtgacttc    28020
tacagcgcgg agaatctcgc tctctccagg ggaagccgaa gtttccaaaa ggtcgttgat    28080
caaagctcgc cgcgttgttt catcaagcct tacagtcacc gtaaccagca aatcaatatc    28140
actgtgtggc ttcaggccgc catccactgc ggagccgtac aaatgtacgg ccagcaacgt    28200
cggttcgaga tggcgctcga tgacgccaac tacctctgat agttgagtcg atacttcggc    28260
gatcaccgct tccctcatga tgtttaactc ctgaattaag ccgcgccgcg aagcggtgtc    28320
ggcttgaatg aattgttagg cgtcatcctg tgctcccgag aaccagtacc agtacatcgc    28380
tgtttcgttc gagacttgag gtctagtttt atacgtgaac aggtcaatgc cgccgagagt    28440
aaagccacat tttgcgtaca aattgcaggc aggtacattg ttcgtttgtg tctctaatcg    28500
tatgccaagg agctgtctgc ttagtgccca cttttcgca aattcgatga gactgtgcgc    28560
gactcctttg cctcggtgcg tgtgcgacac aacaatgtgt tcgatagagg ctagatcgtt    28620
ccatgttgag ttgagttcaa tcttcccgac aagctcttgg tcgatgaatg cgccatagca    28680
agcagagtct tcatcagagt catcatccga gatgtaatcc ttccggtagg ggctcacact    28740
tctggtagat agttcaaagc cttggtcgga taggtgcaca tcgaacactt cacgaacaat    28800
gaaatggttc tcagcatcca atgtttccgc cacctgctca gggatcaccg aaatcttcat    28860
atgacgccta acgcctggca cagcggatcg caaacctggc gcggcttttg gcacaaaagg    28920
cgtgacaggt ttgcgaatcc gttgctgcca cttgttaacc cttttgccag atttggtaac    28980
tataatttat gttagaggcg aagtcttggg taaaaactgg cctaaaattg ctggggattt    29040
caggaaagta aacatcacct tccggctcga tgtctattgt agatatatgt agtgtatcta    29100
cttgatcggg ggatctgctg cctcgcgcgt ttcggtgatg acggtgaaaa cctctgacac    29160
atgcagctcc cggagacggt cacagcttgt ctgtaagcgg atgccgggag cagacaagcc    29220
cgtcagggcg cgtcagcggg tgttggcggg tgtcggggcg cagccatgac ccagtcacgt    29280
agcgatagcg gagtgtatac tggcttaact atgcggcatc agagcagatt gtactgagag    29340
tgcaccatat gcggtgtgaa ataccgcaca gatgcgtaag gagaaaatac cgcatcaggc    29400
gctcttccgc ttcctcgctc actgactcgc tgcgctcggt cgttcggctg cggcgagcgg    29460
tatcagctca ctcaaaggcg gtaatacggt tatccacaga atcagggat aacgcaggaa    29520 agaacatgtg agcaaaaggc cagcaaaagg ccaggaaccg taaaaaggcc gcgttgctgg    29580
cgttttccca taggctccgc cccctgacg agcatcacaa aaatcgacgc tcaagtcaga    29640
```

```
ggtggcgaaa cccgacagga ctataaagat accaggcgtt tcccnctgga agctccctcg    29700
tgcgctctcc tgttccgacc ctgccgctta ccggatacct gtccgccttt ctcccttcgg    29760
gaagcgtggc gctttctcat agctcacgct gtaggtatct cagttcggtg taggtcgttc    29820
gctccaagct gggctgtgtg cacgaacccc cgttcagcc cgaccgctgc gccttatccg     29880
gtaactatcg tcttgagtcc aacccggtaa gacacgactt atcgccactg gcagcagcca   29940
ctggtaacag gattagcaga gcgaggtatg taggcggtgc tacagagttc ttgaagtggt    30000
ggcctaacta cggctacact agaaggacag tatttggtat ctgcgctctg ctgaagccag   30060
ttaccttcgg aaaaagagtt ggtagctctt gatccggcaa acaaaccacc gctggtagcg   30120
gtggtttttt tgtttgcaag cagcagatta cgcgcagaaa aaaggatctc aagaagatc    30180
ctttgatctt ttctacgggg tctgacgctc agtggaacga aaactcacgt taagggattt   30240
tggtcatgag attatcaaaa aggatcttca cctagatcct tttaaattaa aaatgaagtt    30300
ttaaatcaat ctaaagtata tatgagtaaa cttggtctga cagttaccaa tgcttaatca    30360
gtgaggcacc tatctcagcg atctgtctat ttcgttcatc catagttgcc tgactccccg    30420
tcgtgtagat aactacgata cgggagggct taccatctgg ccccagtgct gcaatgatac    30480
cgcgagaccc acgctcaccg gctccagatt tatcagcaat aaaccagcca gccggaaggg   30540
ccgagcgcag aagtggtcct gcaactttat ccgcctccat ccagtctatt aattgttgcc    30600
gggaagctag agtaagtagt tcgccagtta atagtttgcg caacgttgtt gccattgctg    30660
cagggggggg gggggggggg gacttccatt gttcattcca cggacaaaaa cagagaaagg   30720
aaacgacaga ggccaaaaag cctcgctttc agcacctgtc gtttcctttc ttttcagagg   30780
gtattttaaa taaaaacatt aagttatgac gaagaagaac ggaaacgcct taaaccggaa   30840
aattttcata aatagcgaaa acccgcgagg tcgccgcccc gtaacctgtc ggatcaccgg   30900
aaaggacccg taaagtgata atgattatca tctacatatc acaacgtgcg tggaggccat    30960
caaaccacgt caaataatca attatgacgc aggtatcgta ttaattgatc tgcatcaact    31020
taacgtaaaa acaacttcag acaatacaaa tcagcgacac tgaatacggg gcaacctcat   31080
gtcccccccc ccccccccc tgcaggcatc gtggtgtcac gctcgtcgtt tggtatggct     31140
tcattcagct ccggttccca acgatcaagg cgagttacat gatcccccat gttgtgcaaa   31200
aaagcggtta gctccttcgg tcctccgatc gttgtcagaa gtaagttggc cgcagtgtta    31260
tcactcatgg ttatggcagc actgcataat tctcttactg tcatgccatc cgtaagatgc    31320
ttttctgtga ctggtgagta ctcaaccaag tcattctgag aatagtgtat gcggcgaccg   31380
agttgctctt gcccggcgtc aacacgggat aataccgcgc cacatagcag aactttaaaa    31440
gtgctcatca ttggaaaacg ttcttcgggg cgaaaactct caaggatctt accgctgttg    31500
agatccagtt cgatgtaacc cactcgtgca cccaactgat cttcagcatc ttttactttc    31560
accagcgttt ctgggtgagc aaaaacagga aggcaaaatg ccgcaaaaaa gggaataagg   31620
gcgacacgga aatgttgaat actcatactc ttccttttttc aatattattg aagcatttat   31680
cagggttatt gtctcatgag cggatacata tttgaatgta tttagaaaaa taaacaaata    31740
ggggttccgc gcacatttcc ccgaaaagtg ccacctgacg tctaagaaac cattattatc    31800
atgacattaa cctataaaaa taggcgtatc acgaggccct ttcgtcttca agaattcgga    31860
gcttttgcca ttctcaccgg attcagtcgt cactcatggt gatttctcac ttgataacct    31920
tattttttgac gaggggaaat taataggttg tattgatgtt ggacgagtcg gaatcgcaga   31980
ccgataccag gatcttgcca tcctatggaa ctgcctcggt gagttttctc cttcattaca    32040
```

```
gaaacggctt tttcaaaaat atggtattga taatcctgat atgaataaat tgcagtttca    32100
tttgatgctc gatgagtttt tctaatcaga attggtaat tggttgtaac actggcagag     32160
cattacgctg acttgacggg acggcggctt tgttgaataa atcgaacttt tgctgagttg    32220
aaggatcaga tcacgcatct tcccgacaac gcagaccgtt ccgtggcaaa gcaaaagttc    32280
aaaatcacca actggtccac ctacaacaaa gctctcatca accgtggctc cctcactttc    32340
tggctggatg atggggcgat tcaggcctgg tatgagtcag caacaccttc ttcacgaggc    32400
agacctcagc gccagaaggc cgccagagag gccgagcgcg gccgtgaggc ttggacgcta    32460
gggcagggca tgaaaaagcc cgtagcgggc tgctacgggc gtctgacgcg gtggaaaggg    32520 ggagggatg ttgtctacat ggctctgctg tagtgagtgg gttgcgctcc ggcagcggtc     32580
ctgatcaatc gtcacccttt ctcggtcctt caacgttcct gacaacgagc ctccttttcg    32640
ccaatccatc gacaatcacc gcgagtccct gctcgaacgc tgcgtccgga ccggcttcgt    32700
cgaaggcgtc tatcgcggcc cgcaacagcg gcgagagcgg agcctgttca acggtgccgc    32760
cgcgctcgcc ggcatcgctg tcgccggcct gctcctcaag cacggcccca acagtgaagt    32820
agctgattgt catcagcgca ttgacggcgt ccccggccga aaaacccgcc tgcagagga     32880 agcgaagctg cgcgtcggcc gtttccatct gcggtgcgcc cggtcgcgtg ccggcatgga    32940
tgcgcgcgcc atcgcggtag gcgagcagcg cctgcctgaa gctgcgggca ttcccgatca    33000
gaaatgagcg ccagtcgtcg tcggctctcg gcaccgaatg cgtatgattc tccgccagca    33060
tggcttcggc cagtgcgtcg agcagcgccc gcttgttcct gaagtgccag taaagcgccg    33120
gctgctgaac ccccaaccgt tccgccagtt tgcgtgtcgt cagaccgtct acgccgacct    33180
cgttcaacag gtccagggcg gcacggatca ctgtattcgg ctgcaacttt gtcatgcttg    33240
acactttatc actgataaac ataatatgtc caccaactta tcagtgataa agaatccgcg    33300
cgttcaatcg gaccagcgga ggctggtccg gaggccagac gtgaaaccca acatacccct    33360
gatcgtaatt ctgagcactg tcgcgctcga cgctgtcggc atcggcctga ttatgccggt    33420
gctgccgggc ctcctgcgcg atctggttca ctcgaacgac gtcaccgccc actatggcat    33480
tctgctggcg ctgtatgcgt tggtgcaatt tgcctgcgca cctgtgctgg gcgcgctgtc    33540
ggatcgtttc gggcggcggc caatcttgct cgtctcgctg gccggcgcca ctgtcgacta    33600
cgccatcatg gcgacagcgc cttttccttg ggttctctat atcgggcgga tcgtggccgg    33660
catcaccggg gcgactgggg cggtagccgg cgcttatatt gccgatatca ctgatggcga    33720
tgagcgcgcg cggcacttcg gcttcatgag cgcctgtttc gggttcggga tggtcgcggg    33780
acctgtgctc ggtgggctga tgggcggttt ctccccccac gctccgttct tcgccgcggc    33840
agccttgaac ggcctcaatt tcctgacggg ctgtttcctt tgccggagt cgcacaaagg     33900 cgaacgccgg ccgttacgcc gggaggctct caacccgctc gcttcgttcc ggtgggcccg    33960
gggcatgacc gtcgtcgccg ccctgatggc ggtcttcttc atcatgcaac ttgtcggaca    34020
ggtgccggcc gcgctttggg tcattttcgg cgaggatcgc tttcactggg acgcgaccac    34080
gatcggcatt tcgcttgccg catttggcat tctgcattca ctcgcccagg caatgatcac    34140
cggccctgta gccgcccggc tcggcgaaag gcgggcactc atgctcggaa tgattgccga    34200
cggcacaggc tacatcctgc ttgccttcgc gacacgggga tggatggcgt tcccgatcat    34260
ggtcctgctt gcttcgggtg gcatcggaat gccggcgctg caagcaatgt tgtccaggca    34320
ggtggatgag gaacgtcagg ggcagctgca aggctcactg gcggcgctca ccagcctgac    34380
```

```
ctcgatcgtc ggacccctcc tcttcacggc gatctatgcg gcttctataa caacgtggaa    34440
cgggtgggca tggattgcag gcgctgccct ctacttgctc tgcctgccgg cgctgcgtcg    34500
cgggctttgg agcggcgcag ggcaacgagc cgatcgctga tcgtggaaac gataggccta    34560
tgccatgcgg gtcaaggcga cttccggcaa gctatacgcg ccctaggagt gcggttggaa    34620
cgttggccca gccagatact cccgatcacg agcaggacgc cgatgatttg aagcgcactc    34680
agcgtctgat ccaagaacaa ccatcctagc aacacggcgg tccccgggct gagaaagccc    34740
agtaaggaaa caactgtagg ttcgagtcgc gagatccccc ggaaccaaag gaagtaggtt    34800
aaacccgctc cgatcaggcc gagccacgcc aggccgagaa cattggttcc tgtaggcatc    34860
gggattggcg gatcaaacac taaagctact ggaacgagca gaagtcctcc ggccgccagt    34920
tgccaggcgg taaaggtgag cagaggcacg ggaggttgcc acttgcgggt cagcacggtt    34980
ccgaacgcca tggaaaccgc ccccgccagg cccgctgcga cgccgacagg atctagcgct    35040
gcgtttggtg tcaacaccaa cagcgccacg cccgcagttc cgcaaatagc ccccaggacc    35100
gccatcaatc gtatcgggct acctagcaga gcggcagaga tgaacacgac catcagcggc    35160
tgcacagcgc ctaccgtcgc cgcgacccccg cccggcaggc ggtagaccga aataaacaac    35220
aagctccaga atagcgaaat attaagtgcg ccgaggatga agatgcgcat ccaccagatt    35280
cccgttggaa tctgtcggac gatcatcacg agcaataaac ccgccggcaa cgcccgcagc    35340
agcataccgg cgacccctcg gcctcgctgt tcgggctcca cgaaaacgcc ggacagatgc    35400
gccttgtgag cgtccttggg gccgtcctcc tgtttgaaga ccgacagccc aatgatctcg    35460
ccgtcgatgt aggcgccgaa tgccacggca tctcgcaacc gttcagcgaa cgcctccatg    35520
ggcttttcct cctcgtgctc gtaaacggac ccgaacatct ctggagcttt cttcagggcc    35580
gacaatcgga tctcgcggaa atcctgcacg tcggccgctc caagccgtcg aatctgagcc    35640
ttaatcacaa ttgtcaattt taatcctctg tttatcggca gttcgtagag cgcgccgtgc    35700
gtcccgagcg atactgagcg aagcaagtgc gtcgagcagt gcccgcttgt tcctgaaatg    35760
ccagtaaagc gctggctgct gaaccccccag ccggaactga ccccacaagg ccctagcgtt    35820
tgcaatgcac caggtcatca ttgacccagg cgtgttccac caggccgctg cctcgcaact    35880
cttcgcaggc ttcgccgacc tgctcgcgcc acttcttcac gcgggtggaa tccgatccgc    35940
acatgaggcg gaaggtttcc agcttgagcg ggtacggctc ccggtgcgag ctgaaatagt    36000
cgaacatccg tcgggccgtc ggcgacagct tgcggtactt ctcccatatg aatttcgtgt    36060
agtggtcgcc agcaaacagc acgacgattt cctcgtcgat caggacctgg caacgggacg    36120
ttttcttgcc acggtccagg acgcggaagc ggtgcagcag cgacaccgat tccaggtgcc    36180
caacgcggtc ggacgtgaag cccatcgccg tcgcctgtag gcgcgacagg cattcctcgg    36240
ccttcgtgta ataccggcca ttgatcgacc agcccaggtc ctggcaaagc tcgtagaacg    36300
tgaaggtgat cggctcgccg ataggggtgc gcttcgcgta ctccaacacc tgctgccaca    36360
ccagttcgtc atcgtcggcc cgcagctcga cgccggtgta ggtgatcttc acgtccttgt    36420
tgacgtggaa aatgaccttg ttttgcagcg cctcgcgcgg gattttcttg ttgcgcgtgg    36480
tgaacagggc agagcgggcc gtgtcgtttg gcatcgctcg catcgtgtcc ggccacggcg    36540
caatatcgaa caaggaaagc tgcatttcct tgatctgctg cttcgtgtgt ttcagcaacg    36600
cggcctgctt ggcctcgctg acctgttttg ccaggtcctc gccggcggtt tttcgcttct    36660
tggtcgtcat agttcctcgc gtgtcgatgg tcatcgactt cgccaaacct gccgcctcct    36720
gttcgagacg acgcgaacgc tccacggcgg ccgatggcgc gggcagggca gggggagcca    36780
```

```
gttgcacgct gtcgcgctcg atcttggccg tagcttgctg gaccatcgag ccgacggact   36840
ggaaggtttc gcggggcgca cgcatgacgg tgcggcttgc gatggtttcg gcatcctcgg   36900
cggaaaaccc cgcgtcgatc agttcttgcc tgtatgcctt ccggtcaaac gtccgattca   36960
ttcaccctcc ttgcgggatt gccccgactc acgccgggc aatgtgccct tattcctgat    37020
ttgacccgcc tggtgccttg gtgtccagat aatccacctt atcggcaatg aagtcggtcc   37080
cgtagaccgt ctggccgtcc ttctcgtact tggtattccg aatcttgccc tgcacgaata   37140
ccagcgaccc cttgcccaaa tacttgccgt gggcctcggc ctgagagcca aaacacttga   37200
tgcggaagaa gtcggtgcgc tcctgcttgt cgccggcatc gttgcgccac tcttcattaa   37260
ccgctatatc gaaaattgct tgcggcttgt tagaattgcc atgacgtacc tcggtgtcac   37320
gggtaagatt accgataaac tggaactgat tatggctcat atcgaaagtc tccttgagaa   37380
aggagactct agtttagcta acattggtt ccgctgtcaa gaactttagc ggctaaaatt     37440
ttgcgggccg cgaccaaagg tgcgagggc ggcttccgct gtgtacaacc agatattttt     37500
caccaacatc cttcgtctgc tcgatgagcg gggcatgacg aaacatgagc tgtcggagag   37560
ggcaggggtt tcaatttcgt ttttatcaga cttaaccaac ggtaaggcca acccctcgtt   37620
gaaggtgatg gaggccattg ccgacgccct ggaaactccc ctacctcttc tcctggagtc   37680
caccgacctt gaccgcgagg cactcgcgga gattgcgggt catcctttca agagcagcgt   37740
gccgcccgga tacgaacgca tcagtgtggt tttgccgtca cataaggcgt ttatcgtaaa   37800
gaaatgggc gacgacaccc gaaaaaagct gcgtggaagg ctctgacgcc aagggttagg    37860
gcttgcactt ccttctttag ccgctaaaac ggccccttct ctgcgggccg tcggctcgcg   37920
catcatatcg acatcctcaa cggaagccgt gccgcgaatg gcatcgggcg ggtgcgcttt   37980
gacagttgtt ttctatcaga acccctacgt cgtgcggttc gattagctgt ttgtcttgca   38040
ggctaaacac tttcggtata tcgtttgcct gtgcgataat gttgctaatg atttgttgcg   38100
tagggggttac tgaaaagtga gcgggaaaga agagtttcag accatcaagg agcgggccaa   38160
gcgcaagctg gaacgcgaca tgggtgcgga cctgttggcc gcgctcaacg acccgaaaac   38220
cgttgaagtc atgctcaacg cggacggcaa ggtgtggcac gaacgccttg gcgagccgat   38280
gcggtacatc tgcgacatgc ggcccagcca gtcgcaggcg attatagaaa cggtggccgg   38340
attccacggc aaagaggtca cgcggcattc gcccatcctg gaaggcgagt tcccttgga    38400
tggcagccgc tttgccggcc aattgccgcc ggtcgtggcc gcgccaacct ttgcgatccg   38460
caagcgcgcg gtcgccatct tcacgctgga acagtacgtc gaggcgggca tcatgacccg   38520
cgagcaatac gaggtcatta aaagcgccgt cgcggcgcat cgaaacatcc tcgtcattgg   38580
cggtactggc tcgggcaaga ccacgctcgt caacgcgatc atcaatgaaa tggtcgcctt   38640
caacccgtct gagcgcgtcg tcatcatcga ggacaccggc gaaatccagt gcgccgcaga   38700
gaacgccgtc caataccaca ccagcatcga cgtctcgatg acgctgctgc tcaagacaac   38760
gctgcgtatg cgccccgacc gcatcctggt cggtgaggta cgtggccccg aagcccttga   38820
tctgttgatg gcctggaaca ccgggcatga aggaggtgcc gccaccctgc acgcaaacaa   38880
ccccaaagcg ggcctgagcc ggctcgccat gcttatcagc atgcacccgg attcaccgaa   38940
acccattgag ccgctgattg gcgaggcggt tcatgtggtc gtccatatcg ccaggacccc   39000
tagcggccgt cgagtgcaag aaattctcga agttcttggt tacgagaacg ccagtacat    39060
caccaaaacc ctgtaaggag tatttccaat gacaacggct gttccgttcc gtctgaccat   39120
```

```
gaatcgcggc atttttgttct accttgccgt gttcttcgtt ctcgctctcg cgttatccgc   39180
gcatccggcg atggcctcgg aaggcaccgg cggcagcttg ccatatgaga gctggctgac   39240
gaacctgcgc aactccgtaa ccggcccggt ggccttcgcg ctgtccatca tcggcatcgt   39300
cgtcgccggc ggcgtgctga tcttcggcgg cgaactcaac gccttcttcc gaaccctgat   39360
cttcctggtt ctggtgatgg cgctgctggt cggcgcgcag aacgtgatga gcaccttctt   39420
cggtcgtggt gccgaaatcg cggccctcgg caacggggcg ctgcaccagg tgcaagtcgc   39480
ggcggcggat gccgtgcgtg cggtagcggc tggacggctc gcctaatcat ggctctgcgc   39540
acgatcccca tccgtcgcgc aggcaaccga gaaaacctgt tcatgggtgg tgatcgtgaa   39600
ctggtgatgt tctcgggcct gatggcgttt gcgctgattt tcagcgccca agagctgcgg   39660
gccaccgtgg tcgtctgat  cctgtggttc ggggcgctct atgcgttccg aatcatggcg   39720
aaggccgatc cgaagatgcg gttcgtgtac ctgcgtcacc gccggtacaa gccgtattac   39780
ccggcccgct cgaccccgtt ccgcgagaac accaatagcc aagggaagca ataccgatga   39840
tccaagcaat tgcgattgca atcgcgggcc tcggcgcgct tctgttgttc atcctctttg   39900
cccgcatccg cgcggtcgat gccgaactga aactgaaaaa gcatcgttcc aaggacgccg   39960
gcctggccga tctgctcaac tacgccgctg tcgtcgatga cggcgtaatc gtgggcaaga   40020
acggcagctt tatggctgcc tggctgtaca agggcgatga caacgcaagc agcaccgacc   40080
agcagcgcga agtagtgtcc gcccgcatca accaggccct cgcgggcctg ggaagtgggt   40140
ggatgatcca tgtggacgcc gtgcggcgtc ctgctccgaa ctacgcggag cggggcctgt   40200
cggcgttccc tgaccgtctg acggcagcga ttgaagaaga gcgctcggtc ttgccttgct   40260
cgtcggtgat gtacttcacc agctccgcga agtcgctctt cttgatggag cgcatgggga   40320
cgtgcttggc aatcacgcgc accccccggc cgttttagcg gctaaaaaag tcatggctct   40380
gccctcgggc ggaccacgcc catcatgacc ttgccaagct cgtcctgctt ctcttcgatc   40440
ttcgccagca gggcgaggat cgtggcatca ccgaaccgcg ccgtgcgcgg gtcgtcggtg   40500
agccagagtt tcagcaggcc gcccaggcgg cccaggtcgc cattgatgcg ggccagctcg   40560
cggacgtgct catagtccac gacgcccgtg attttgtagc cctggccgac ggccagcagg   40620
taggccgaca ggctcatgcc ggccgccgcc gccttttcct caatcgctct tcgttcgtct   40680
ggaaggcagt acaccttgat aggtgggctg cccttcctgg ttggcttggt ttcatcagcc   40740
atccgcttgc cctcatctgt tacgccggcg gtagccggcc agcctcgcag agcaggattc   40800
ccgttgagca ccgccaggtg cgaataaggg acagtgaaga aggaacaccc gctcgcgggt   40860
gggcctactt cacctatcct gcccggctga cgccgttgga tacaccaagg aaagtctaca   40920
cgaacccttt ggcaaaatcc tgtatatcgt gcgaaaaagg atggatatac cgaaaaaatc   40980
gctataatga ccccgaagca gggttatgca gcggaaaagc gctgcttccc tgctgttttg   41040
tggaatatct accgactgga aacaggcaaa tgcaggaaat tactgaactg aggggacagg   41100
cgagagacga tgccaaagag ctacaccgac gagctggccg agtgggttga atcccgcgcg   41160
gccaagaagc gccggcgtga tgaggctgcg gttgcgttcc tggcggtgag gcggatgtc   41220
gaggcggcgt tagcgtccgg ctatgcgctc gtcaccattt gggagcacat gcgggaaacg   41280
gggaaggtca agttctccta cgagacgttc cgctcgcacg ccaggcggca catcaaggcc   41340
aagcccgccg atgtgcccgc accgcaggcc aaggctgcgg aacccgcgcc ggcacccaag   41400
acgccggagc cacggcggcc gaagcagggg ggcaaggctg aaaagccggc cccgctgcg   41460
gcccccgaccg gcttcacctt caacccaaca ccggacaaaa aggatctact gtaatggcga   41520
```

```
aaattcacat ggttttgcag ggcaagggcg gggtcggcaa gtcggccatc gccgcgatca    41580
ttgcgcagta caagatggac aaggggcaga caccettgtg catcgacacc gacccggtga    41640
acgcgacgtt cgagggctac aaggccctga acgtccgccg gctgaacatc atggccggcg    41700
acgaaattaa ctcgcgcaac ttcgacaccc tggtcgagct gattgcgccg accaaggatg    41760
acgtggtgat cgacaacggt gccagctcgt tcgtgcctct gtcgcattac ctcatcagca    41820
accaggtgcc ggctctgctg caagaaatgg ggcatgagct ggtcatccat accgtcgtca    41880
ccggcggcca ggctctcctg gacacggtga gcggcttcgc ccagctcgcc agccagttcc    41940
cggccgaagc gcttttcgtg gtctggctga acccgtattg ggggcctatc gagcatgagg    42000
gcaagagctt tgagcagatg aaggcgtaca cggccaacaa ggcccgcgtg tcgtccatca    42060
tccagattcc ggccctcaag gaagaaacct acggccgcga tttcagcgac atgctgcaag    42120
agcggctgac gttcgaccag gcgctggccg atgaatcgct cacgatcatg acgcggcaac    42180
gcctcaagat cgtgcggcgc ggcctgtttg aacagctcga cgcggcggcc gtgctatgag    42240
cgaccagatt gaagagctga tccgggagat tgcggccaag cacggcatcg ccgtcggccg    42300
cgacgacccg gtgctgatcc tgcataccat caacgcccgg ctcatggccg acagtgcggc    42360
caagcaagag gaaatccttg ccgcgttcaa ggaagagctg aagggatcg cccatcgttg    42420 gggcgaggac gccaaggcca aagcggagcg gatgctgaac gcggccctgg cggccagcaa    42480
ggacgcaatg gcgaaggtaa tgaaggacag cgccgcgcag gcggccgaag cgatccgcag    42540
ggaaatcgac gacggccttg gccgccagct cgcggccaag gtcgcggacg cgcggcgcgt    42600
ggcgatgatg aacatgatcg ccggcggcat ggtgttgttc gcggccgccc tggtggtgtg    42660
ggcctcgtta tgaatcgcag aggcgcagat gaaaaagccc ggcgttgccg ggctttgttt    42720
ttgcgttagc tgggcttgtt tgacaggccc aagctctgac tgcgcccgcg ctcgcgctcc    42780
tgggcctgtt tcttctcctg ctcctgcttg cgcatcaggg cctggtgccg tcgggctgct    42840
tcacgcatcg aatcccagtc gccggccagc tcgggatgct ccgcgcgcat cttgcgcgtc    42900
gccagttcct cgatcttggg cgcgtgaatg cccatgcctt ccttgatttc gcgcaccatg    42960
tccagccgcg tgtgcagggt ctgcaagcgg gcttgctgtt gggcctgctg ctgctgccag    43020
gcggcctttg tacgcggcag ggacagcaag ccggggggcat tggactgtag ctgctgcaaa    43080
cgcgcctgct gacggtctac gagctgttct aggcggtcct cgatgcgctc cacctggtca    43140
tgctttgcct gcacgtagag cgcaagggtc tgctggtagg tctgctcgat gggcgcggat    43200
tctaagaggg cctgctgttc cgtctcggcc tcctgggccg cctgtagcaa atcctcgccg    43260
ctgttgccgc tggactgctt tactgccggg gactgctgtt gccctgctcg cgccgtcgtc    43320
gcagttcggc ttgcccccac tcgattgact gcttcatttc gagccgcagc gatgcgatct    43380
cggattgcgt caacggacgg ggcagcgcgg aggtgtccgg cttctccttg ggtgagtcgg    43440
tcgatgccat agccaaaggt ttccttccaa aatgcgtcca ttgctggacc gtgtttctca    43500
ttgatgcccg caagcatctt cggcttgacc gccaggtcaa gcgcgccttc atgggcggtc    43560
atgacggacg ccgccatgac cttgccgccg ttgttctcga tgtagccgcg taatgaggca    43620
atggtgccgc ccatcgtcag cgtgtcatcg acaacgatgt acttctggcc ggggatcacc    43680 tcccccctcga aagtcgggtt gaacgccagg cgatgatctg aaccggctcc ggttcgggcg    43740
accttctccc gctgcacaat gtccgtttcg acctcaaggc caaggcggtc ggccagaacg    43800
accgccatca tggccggaat cttgttgttc cccgccgcct cgacggcgag gactggaacg    43860
```

```
atgcgggget tgtcgtcgcc gatcagcgtc ttgagctggg caacagtgtc gtccgaaatc   43920
aggcgctcga ccaaattaag cgccgcttcc gcgtcgccct gcttcgcagc ctggtattca   43980
ggctcgttgg tcaaagaacc aaggtcgccg ttgcgaacca ccttcgggaa gtctccccac   44040
ggtgcgcgct cggctctgct gtagctgctc aagacgcctc cctttttagc cgctaaaact   44100
ctaacgagtg cgcccgcgac tcaacttgac gctttcggca cttacctgtg ccttgccact   44160
tgcgtcatag gtgatgcttt tcgcactccc gatttcaggt actttatcga aatctgaccg   44220
ggcgtgcatt acaaagttct tccccacctg ttggtaaatg ctgccgctat ctgcgtggac   44280
gatgctgccg tcgtggcgct gcgacttatc ggccttttgg ccatataga tgttgtaaat   44340
gccaggtttc agggccccgg ctttatctac cttctggttc gtccatgcgc cttggttctc   44400
ggtctggaca attctttgcc cattcatgac caggaggcgg tgtttcattg ggtgactcct   44460
gacggttgcc tctggtgtta aacgtgtcct ggtcgcttgc cggctaaaaa aaagccgacc   44520
tcggcagttc gaggccggct ttccctagag ccgggcgcgt caaggttgtt ccatctattt   44580
tagtgaactg cgttcgattt atcagttact ttcctcccgc tttgtgtttc ctcccactcg   44640
tttccgcgtc tagccgaccc ctcaacatag cggcctcttc ttgggctgcc tttgcctctt   44700
gccgcgcttc gtcacgctcg gcttgcaccg tcgtaaagcg ctcggcctgc ctggccgcct   44760
cttgcgccgc caacttcctt tgctcctggt gggcctcggc gtcggcctgc gccttcgctt   44820
tcaccgctgc caactccgtg cgcaaactct ccgcttcgcg cctggtggcg tcgcgctcgc   44880
cgcgaagcgc ctgcatttcc tggttggccg cgtccagggt cttgcggctc tcttctttga   44940
atgcgcgggc gtcctggtga gcgtagtcca gctcggcgcg cagctcctgc gctcgacgct   45000
ccacctcgtc ggcccgctgc gtcgccagcg cggcccgctg ctcggctcct gccagggcgg   45060
tgcgtgcttc ggccagggct tgccgctggc gtgcggccag ctcggccgcc tcggcggcct   45120
gctgctctag caatgtaacg cgcgcctggg cttcttccag ctcgcgggcc tgcgcctcga   45180
aggcgtcggc cagctccccg cgcacggctt ccaactcgtt gcgctcacga tcccagccgg   45240
cttgcgctgc ctgcaacgat tcattggcaa gggcctgggc ggcttgccag agggcggcca   45300
cggcctggtt gccggcctgc tgcaccgcgt ccggcacctg gactgccagc ggggcggcct   45360
gcgccgtgcg ctggcgtcgc cattcgcgca tgccggcgct ggcgtcgttc atgttgacgc   45420
gggcggcctt acgcactgca tccacggtcg ggaagttctc ccgtcgcct tgctcgaaca   45480
gctcgtccgc agccgcaaaa atgcggtcgc gcgtctcttt gttcagttcc atgttggctc   45540
cggtaattgg taagaataat aatactctta cctaccttat cagcgcaaga gtttagctga   45600
acagttctcg acttaacggc aggttttta gcggctgaag ggcaggcaaa aaaagccccg   45660
cacggtcggc gggggcaaag ggtcagcggg aaggggatta gcgggcgtcg ggcttcttca   45720
tgcgtcgggg ccgcgcttct tgggatggag cacgacgaag cgcgcacgcg catcgtcctc   45780
ggccctatcg gcccgcgtcg cggtcaggaa cttgtcgcgc gctaggtcct ccctggtggg   45840
caccaggggc atgaactcgg cctgctcgat gtaggtccac tccatgaccg catcgcagtc   45900
gaggccgcgt tccttcaccg tctcttgcag gtcgcggtac gcccgctcgt tgagcggctg   45960
gtaacgggcc aattggtcgt aaatggctgt cggccatgag cggcctttcc tgttgagcca   46020
gcagccgacg acgaagccgg caatgcaggc ccctggcaca accaggccga cgccggggc   46080
aggggatggc agcagctcgg caaccaggaa cccgccgcg atgatgccga tgccggtcaa   46140
ccagcccttg aaactatccg gccccgaaac acccctgcgc attgcctgga tgctgcgccg   46200
gatagcttgc aacatcagga gccgtttctt ttgttcgtca gtcatggtcc gccctcacca   46260
```

```
gttgttcgta tcggtgtcgg acgaactgaa atcgcaagag ctgccggtat cggtccagcc   46320
gctgtccgtg tcgctgctgc cgaagcacgg cgaggggtcc gcgaacgccg cagacggcgt   46380
atccggccgc agcgcatcgc ccagcatggc cccggtcagc gagccgccgg ccaggtagcc   46440
cagcatggtg ctgttggtcg ccccggccac cagggccgac gtgacgaaat cgccgtcatt   46500
ccctctggat tgttcgctgc tcggcggggc agtgcgccgc gccggcggcg tcgtggatgg   46560
ctcgggttgg ctggcctgcg acggccggcg aaaggtgcgc agcagctcgt tatcgaccgg   46620
ctgcggcgtc ggggccgccg ccttgcgctg cggtcggtgt tccttcttcg gctcgcgcag   46680
cttgaacagc atgatcgcgg aaaccagcag caacgccgcg cctacgcctc ccgcgatgta   46740
gaacagcatc ggattcattc ttcggtcctc cttgtagcgg aaccgttgtc tgtgcggcgc   46800
gggtggcccg cgccgctgtc tttggggatc agccctcgat gagcgcgacc agtttcacgt   46860
cggcaaggtt cgcctcgaac tcctggccgt cgtcctcgta cttcaaccag gcatagcctt   46920
ccgccggcgg ccgacggttg aggataaggc gggcagggcg ctcgtcgtgc tcgacctgga   46980
cgatggcctt tttcagcttg tccgggtccg gctccttcgc gccctttttcc ttggcgtcct   47040 taccgtcctg gtcgccgtcc tcgccgtcct ggccgtcgcc ggcctccgcg tcacgctcgg   47100
catcagtctg gccgttgaag gcatcgacgg tgttgggatc gcggcccttc tcgtccagga   47160
actcgcgcag cagcttgacc gtgccgcgcg tgatttcctg ggtgtcgtcg tcaagccacg   47220
cctcgacttc ctccgggcgc ttcttgaagg ccgtcaccag ctcgttcacc acggtcacgt   47280
cgcgcacgcg gccggtgttg aacgcatcgg cgatcttctc cggcaggtcc agcagcgtga   47340
cgtgctgggt gatgaacgcc ggcgacttgc cgatttcctt ggcgatatcg cctttcttct   47400
tgcccttcgc cagctcgcgg ccaatgaagt cggcaatttc gcgcggggtc agctcgttgc   47460
gttgcaggtt ctcgataacc tggtcggctt cgttgtagtc gttgtcgatg aacgccggga   47520
tggacttctt gccggcccac ttcgagccac ggtagcggcg ggcgccgtga ttgatgatat   47580
agcggcccgg ctgctcctgg ttctcgcgca ccgaaatggg tgacttcacc ccgcgctctt   47640
tgatcgtggc accgatttcc gcgatgctct ccggggaaaa gccggggttg tcggccgtcc   47700
gcggctgatg cggatcttcg tcgatcaggt ccaggtccag ctcgataggg ccggaaccgc   47760
cctgagacgc cgcaggagcg tccaggaggc tcgacaggtc gccgatgcta tccaacccca   47820
ggccggacgg ctgcgccgcg cctgcggctt cctgagcggc cgcagcggtg tttttcttgg   47880
tggtcttggc ttgagccgca gtcattggga aatctccatc ttcgtgaaca cgtaatcagc   47940
cagggcgcga acctctttcg atgccttgcg cgcggccgtt ttcttgatct tccagaccgg   48000
cacaccggat gcgagggcat cggcgatgct gctgcgcagg ccaacggtgg ccggaatcat   48060
catcttgggg tacgcggcca gcagctcggc ttggtggcgc gcgtggcgcg gattccgcgc   48120
atcgaccttg ctgggcacca tgccaaggaa ttgcagcttg gcgttcttct ggcgcacgtt   48180
cgcaatggtc gtgaccatct tcttgatgcc ctggatgctg tacgcctcaa gctcgatggg   48240
ggacagcaca tagtcggccg cgaagagggc ggccgccagg ccgacgccaa gggtcggggc   48300
cgtgtcgatc aggcacacgt cgaagccttg gttcgccagg gccttgatgt tcgccccgaa   48360
cagctcgcgg cgtcgtcca gcgacagccg ttcggcgttc gccagtaccg ggttggactc   48420
gatgagggcg aggcgcgcgg cctggccgtc gccggctgcg ggtgcggttt cggtccagcc   48480
gccggcaggg acagcgccga acagcttgct tgcatgcagg ccggtagcaa agtccttgag   48540
cgtgtaggac gcattgccct gggggtccag gtcgatcacg gcaacccgca agccgcgctc   48600
```

| | | | | | |
|---|---|---|---|---|---|
| gaaaaagtcg | aaggcaagat | gcacaagggt | cgaagtcttg | ccgacgccgc | ctttctggtt | 48660 |
| ggccgtgacc | aaagttttca | tcgtttggtt | tcctgttttt | tcttggcgtc | cgcttcccac | 48720 |
| ttccggacga | tgtacgcctg | atgttccggc | agaaccgccg | ttacccgcgc | gtacccctcg | 48780 |
| ggcaagttct | tgtcctcgaa | cgcggcccac | acgcgatgca | ccgcttgcga | cactgcgccc | 48840 |
| ctggtcagtc | ccagcgacgt | tgcgaacgtc | gcctgtggct | tcccatcgac | taagacgccc | 48900 |
| cgcgctatct | cgatggtctg | ctgccccact | tccagcccct | ggatcgcctc | ctggaactgg | 48960 |
| ctttcggtaa | gccgtttctt | catggataac | acccataatt | tgctccgcgc | cttggttgaa | 49020 |
| catagcggtg | acagccgcca | gcacatgaga | gaagtttagc | taaacatttc | tcgcacgtca | 49080 |
| acacctttag | ccgctaaaac | tcgtccttgg | cgtaacaaaa | caaaagcccg | gaaaccgggc | 49140 |
| tttcgtctct | tgccgcttat | ggctctgcac | ccggctccat | caccaacagg | tcgcgcacgc | 49200 |
| gcttcactcg | gttgcggatc | gacactgcca | gcccaacaaa | gccggttgcc | gccgccgcca | 49260 |
| ggatcgcgcc | gatgatgccg | gccacaccgg | ccatcgccca | ccaggtcgcc | gccttccggt | 49320 |
| tccattcctg | ctggtactgc | ttcgcaatgc | tggacctcgg | ctcaccatag | gctgaccgct | 49380 |
| cgatggcgta | tgccgcttct | ccccttggcg | taaacccag | cgccgcaggc | ggcattgcca | 49440 |
| tgctgcccgc | cgctttcccg | accacgacgc | gcgcaccagg | cttgcggtcc | agaccttcgg | 49500 |
| ccacggcgag | ctgcgcaagg | acataatcag | ccgccgactt | ggctccacgc | gcctcgatca | 49560 |
| gctcttgcac | tcgcgcgaaa | tccttggcct | ccacggccgc | catgaatcgc | gcacgcggcg | 49620 |
| aaggctccgc | agggccggcg | tcgtgatcgc | cgccgagaat | gcccttcacc | aagttcgacg | 49680 |
| acacgaaaat | catgctgacg | gctatcacca | tcatgcagac | ggatcgcacg | aacccgctga | 49740 |
| attgaacacg | agcacggcac | ccgcgaccac | tatgccaaga | atgcccaagg | taaaaattgc | 49800 |
| cggcccgcc | atgaagtccg | tgaatgcccc | gacggccgaa | gtgaagggca | ggccgccacc | 49860 |
| caggccgccg | ccctcactgc | ccggcacctg | gtcgctgaat | gtcgatgcca | gcacctgcgg | 49920 |
| cacgtcaatg | cttccgggcg | tcgcgctcgg | gctgatcgcc | catcccgtta | ctgccccgat | 49980 |
| cccggcaatg | gcaaggactg | ccagcgctgc | cattttggg | gtgaggccgt | tcgcggccga | 50040 |
| ggggcgcagc | ccctggggg | atgggaggcc | cgcgttagcg | ggccgggagg | gttcgagaag | 50100 |
| gggggcacc | cccttcggc | gtgcgcggtc | acgcgcacag | ggcgcagccc | tggttaaaaa | 50160 |
| caaggtttat | aaatattggt | ttaaaagcag | gttaaaagac | aggttagcgg | tggccgaaaa | 50220 |
| acgggcggaa | acccttgcaa | atgctggatt | ttctgcctgt | ggacagcccc | tcaaatgtca | 50280 |
| ataggtgcgc | ccctcatctg | tcagcactct | gcccctcaag | tgtcaaggat | cgcgcccctc | 50340 |
| atctgtcagt | agtcgcgccc | ctcaagtgtc | aataccgcag | ggcacttatc | cccaggcttg | 50400 |
| tccacatcat | ctgtgggaaa | ctcgcgtaaa | atcaggcgtt | ttcgccgatt | tgcgaggctg | 50460 |
| gccagctcca | cgtcgccggc | cgaaatcgag | cctgcccctc | atctgtcaac | gccgcgccgg | 50520 |
| gtgagtcggc | ccctcaagtg | tcaacgtccg | cccctcatct | gtcagtgagg | gccaagtttt | 50580 |
| ccgcgaggta | tccacaacgc | cggcggccgc | ggtgtctcgc | acacggcttc | gacggcgttt | 50640 |
| ctggcgcgtt | tgcagggcca | tagacggccg | ccagcccagc | ggcgagggca | accagcccgg | 50700 |
| tgagcgtcgg | aaaggcgctg | gaagcccgt | agcgacgcgg | agaggggcga | gacaagccaa | 50760 |
| gggcgcaggc | tcgatgcgca | gcacgacata | gccggttctc | gcaaggacga | gaatttccct | 50820 |
| gcggtgcccc | tcaagtgtca | atgaaagttt | ccaacgcgag | ccattcgcga | gagccttgag | 50880 |
| tccacgctag | atgagagctt | tgttgtaggt | ggaccagttg | gtgattttga | acttttgctt | 50940 |
| tgccacggaa | cggtctgcgt | tgtcgggaag | atgcgtgatc | tgatccttca | actcagcaaa | 51000 | agttcgattt attcaacaaa gccacgttgt gtctcaaaat ctctgatgtt acattgcaca    51060 agataaaaat atatcatcat gaacaataaa actgtctgct tacataaaca gtaatacaag    51120 gggtgttatg agccatattc aacgggaaac gtcttgctcg ac                       51162

<210> SEQ ID NO 61
<211> LENGTH: 42
<212> TYPE: DNA
<213> ORGANISM: Artificial Sequence
<220> FEATURE:
<223> OTHER INFORMATION: sense primer for i1

<400> SEQUENCE: 61
ccatgcatac atccaacgcc attcgcttac acctgatatc cc                       42

<210> SEQ ID NO 62
<211> LENGTH: 46
<212> TYPE: DNA
<213> ORGANISM: Artificial Sequence
<220> FEATURE:
<223> OTHER INFORMATION: i1-sense oligonucleotide 2

<400> SEQUENCE: 62
ggactggcgc caggtccgtt cccgtcccag atccgtccat ggcttc                   46

<210> SEQ ID NO 63
<211> LENGTH: 46
<212> TYPE: DNA
<213> ORGANISM: Artificial Sequence
<220> FEATURE:
<223> OTHER INFORMATION: i1-sense oligonucleotide 3

<400> SEQUENCE: 63
gtccagatct gacctgtcct gacacaccct cacccggatc tgtccc                   46

<210> SEQ ID NO 64
<211> LENGTH: 45
<212> TYPE: DNA
<213> ORGANISM: Artificial Sequence
<220> FEATURE:
<223> OTHER INFORMATION: i1-sense oligonucleotide 4

<400> SEQUENCE: 64
tccttcccct ctccctgca gctggcgcct tgggatccat tcctg                     45

<210> SEQ ID NO 65
<211> LENGTH: 42
<212> TYPE: DNA
<213> ORGANISM: Artificial Sequence
<220> FEATURE:
<223> OTHER INFORMATION: i1-antisense oligonucleotide 1

<400> SEQUENCE: 65
ggacctggcg ccagtccggg atatcaggtg taagcgaatg gc                       42

<210> SEQ ID NO 66
<211> LENGTH: 49
<212> TYPE: DNA
<213> ORGANISM: Artificial Sequence
<220> FEATURE:
<223> OTHER INFORMATION: i1-antisenseoligonucleotide 2

<400> SEQUENCE: 66
aggacaggtc agatctggac gaagccatgg acgatctgg gacgggaac                 49

```
<210> SEQ ID NO 67
<211> LENGTH: 51
<212> TYPE: DNA
<213> ORGANISM: Artificial Sequence
<220> FEATURE:
<223> OTHER INFORMATION: i1-antisense oligonucleotide 3

<400> SEQUENCE: 67
ccagctgcag gggagagggg aaggagggac agatccgggt gagggtgtgt c         51

<210> SEQ ID NO 68
<211> LENGTH: 44
<212> TYPE: DNA
<213> ORGANISM: Artificial Sequence
<220> FEATURE:
<223> OTHER INFORMATION: i1-antisense oligonucleotide 4

<400> SEQUENCE: 68
ggtggaggcg ttgtaagctg gaatcaggaa tggatcccaa ggcg               44

<210> SEQ ID NO 69
<211> LENGTH: 48
<212> TYPE: DNA
<213> ORGANISM: Artificial Sequence
<220> FEATURE:
<223> OTHER INFORMATION: i2_flanking sense primer

<400> SEQUENCE: 69
ccatcagata tcccggactg gcgccaggtc tgcttcgtcc tcgctagg           48

<210> SEQ ID NO 70
<211> LENGTH: 56
<212> TYPE: DNA
<213> ORGANISM: Artificial Sequence
<220> FEATURE:
<223> OTHER INFORMATION: i2_sense oligonucleotide 2

<400> SEQUENCE: 70
tttcatttcg cggtctgttt gtgccgttgg ggctagatcc gggtcgtggt tcaaca   56

<210> SEQ ID NO 71
<211> LENGTH: 44
<212> TYPE: DNA
<213> ORGANISM: Artificial Sequence
<220> FEATURE:
<223> OTHER INFORMATION: i2_sense oligonucleotide 3

<400> SEQUENCE: 71
gatctgcttc gttttggtac agatctgcgt tcgctcgaat cgag               44

<210> SEQ ID NO 72
<211> LENGTH: 43
<212> TYPE: DNA
<213> ORGANISM: Artificial Sequence
<220> FEATURE:
<223> OTHER INFORMATION: i2_sense oligonucleotide 4

<400> SEQUENCE: 72
catgacgttt tcatgtgatt atgcagctgg cgccttggga tcc                43

<210> SEQ ID NO 73
<211> LENGTH: 52
<212> TYPE: DNA
<213> ORGANISM: Artificial Sequence
<220> FEATURE:
<223> OTHER INFORMATION: i2_antisense oligonucleotide 1
```

<400> SEQUENCE: 73
ggcacaaaca gaccgcgaaa tgaaacctag cgaggacgaa gcagacctgg cg         52

<210> SEQ ID NO 74
<211> LENGTH: 53
<212> TYPE: DNA
<213> ORGANISM: Artificial Sequence
<220> FEATURE:
<223> OTHER INFORMATION: i2_antisense oligonucleotide 2

<400> SEQUENCE: 74
ctgtaccaaa acgaagcaga tctgttgaac cacgacccgg atctagcccc aac        53

<210> SEQ ID NO 75
<211> LENGTH: 45
<212> TYPE: DNA
<213> ORGANISM: Artificial Sequence
<220> FEATURE:
<223> OTHER INFORMATION: i2_antisense oligonucleotide 3

<400> SEQUENCE: 75
cataatcaca tgaaaacgtc atgctcgatt cgagcgaacg cagat                 45

<210> SEQ ID NO 76
<211> LENGTH: 41
<212> TYPE: DNA
<213> ORGANISM: Artificial Sequence
<220> FEATURE:
<223> OTHER INFORMATION: i2_antisense flanking primer

<400> SEQUENCE: 76
gtggtaagcg aatgcaggaa tggatcccaa ggcgccagct g                     41

<210> SEQ ID NO 77
<211> LENGTH: 37
<212> TYPE: DNA
<213> ORGANISM: Artificial Sequence
<220> FEATURE:
<223> OTHER INFORMATION: i3_sense flanking primer

<400> SEQUENCE: 77
ccatcagtac tcgatatccc ggactggcgc caggtgc                          37

<210> SEQ ID NO 78
<211> LENGTH: 45
<212> TYPE: DNA
<213> ORGANISM: Artificial Sequence
<220> FEATURE:
<223> OTHER INFORMATION: i3_sense oligonucleotide 2

<400> SEQUENCE: 78
gtgcatgcgc acgtctgct tctgcctccc tttcccttt cctcc                   45

<210> SEQ ID NO 79
<211> LENGTH: 50
<212> TYPE: DNA
<213> ORGANISM: Artificial Sequence
<220> FEATURE:
<223> OTHER INFORMATION: i3_sense oligonucleotide 3

<400> SEQUENCE: 79
gaaagaactg aaacggaacg catcttcgct cagctggcgc cttgggatcc            50

<210> SEQ ID NO 80

```
<211> LENGTH: 39
<212> TYPE: DNA
<213> ORGANISM: Artificial Sequence
<220> FEATURE:
<223> OTHER INFORMATION: i3_antisense oligonucleotide 1

<400> SEQUENCE: 80
tgcgcatgca cgcacctggc gccagtccgg gatatcgag                              39

<210> SEQ ID NO 81
<211> LENGTH: 54
<212> TYPE: DNA
<213> ORGANISM: Artificial Sequence
<220> FEATURE:
<223> OTHER INFORMATION: i3_antisense oligo2

<400> SEQUENCE: 81
cgttccgttt cagttctttc ggaggaaaag ggaaagggag gcagaagcag agcg             54

<210> SEQ ID NO 82
<211> LENGTH: 43
<212> TYPE: DNA
<213> ORGANISM: Artificial Sequence
<220> FEATURE:
<223> OTHER INFORMATION: i3_antisense flanking primer

<400> SEQUENCE: 82
gtcgaggtga tgtggatccc aaggcgccag ctgagcgaag atg                        43

<210> SEQ ID NO 83
<211> LENGTH: 50
<212> TYPE: DNA
<213> ORGANISM: Artificial Sequence
<220> FEATURE:
<223> OTHER INFORMATION: i4_sense flanking primer

<400> SEQUENCE: 83
ccatcagata tcccggactg gcgccaggtg cgtcactgtc caggtgcttg                  50

<210> SEQ ID NO 84
<211> LENGTH: 50
<212> TYPE: DNA
<213> ORGANISM: Artificial Sequence
<220> FEATURE:
<223> OTHER INFORMATION: i4_s2_sense oligo 3

<400> SEQUENCE: 84
gcttggatca gaatattgtt ggcggtgaca ctgtcttctc tcgatcgatc                  50

<210> SEQ ID NO 85
<211> LENGTH: 45
<212> TYPE: DNA
<213> ORGANISM: Artificial Sequence
<220> FEATURE:
<223> OTHER INFORMATION: i4_sense oligonucleotide 3

<400> SEQUENCE: 85
gatcgatgac agctggcgcc ttgggatcca catcaatcac catgc                      45

<210> SEQ ID NO 86
<211> LENGTH: 49
<212> TYPE: DNA
<213> ORGANISM: Artificial Sequence
<220> FEATURE:
<223> OTHER INFORMATION: i4_antisense oligonucleotide 1

<400> SEQUENCE: 86
```
caatattctg atccaagcca agcacctgga cagtgacgca cctggcgcc  49

<210> SEQ ID NO 87
<211> LENGTH: 50
<212> TYPE: DNA
<213> ORGANISM: Artificial Sequence
<220> FEATURE:
<223> OTHER INFORMATION: i4_antisense oligonucleotide 2

<400> SEQUENCE: 87
cgccagctgt catcgatcga tcgatcgaga gaagacagtg tcaccgccaa  50

<210> SEQ ID NO 88
<211> LENGTH: 43
<212> TYPE: DNA
<213> ORGANISM: Artificial Sequence
<220> FEATURE:
<223> OTHER INFORMATION: i4_antisense flanking primer

<400> SEQUENCE: 88
gctggaacga tggaatgcat ggtgattgat gtggatccca agg  43

<210> SEQ ID NO 89
<211> LENGTH: 48
<212> TYPE: DNA
<213> ORGANISM: Artificial Sequence
<220> FEATURE:
<223> OTHER INFORMATION: i5_flanking sense primer

<400> SEQUENCE: 89
ccatcagata tcccggactg gcgccaggtc ggtttccaat ctgttgac  48

<210> SEQ ID NO 90
<211> LENGTH: 47
<212> TYPE: DNA
<213> ORGANISM: Artificial Sequence
<220> FEATURE:
<223> OTHER INFORMATION: i5_sense oligonucleotide 2

<400> SEQUENCE: 90
catggatcca cagatcggag cagttctttc atagtactca gcgatct  47

<210> SEQ ID NO 91
<211> LENGTH: 50
<212> TYPE: DNA
<213> ORGANISM: Artificial Sequence
<220> FEATURE:
<223> OTHER INFORMATION: i5_sense oligonucleotide 3

<400> SEQUENCE: 91
gtttgggtcc taaatttcct ttccccggct gttgtttagc tggcgccttg  50

<210> SEQ ID NO 92
<211> LENGTH: 50
<212> TYPE: DNA
<213> ORGANISM: Artificial Sequence
<220> FEATURE:
<223> OTHER INFORMATION: i5_antisense oligonucleotide 1

<400> SEQUENCE: 92
ctccgatctg tggatccatg gtcaacagat tggaaaccga cctggcgcca  50

<210> SEQ ID NO 93
<211> LENGTH: 45
<212> TYPE: DNA

<213> ORGANISM: Artificial Sequence
<220> FEATURE:
<223> OTHER INFORMATION: i5_antisense oligonucleotide 2

<400> SEQUENCE: 93
gaaatttagg acccaaacag atcgctgagt actatgaaag aactg        45

<210> SEQ ID NO 94
<211> LENGTH: 44
<212> TYPE: DNA
<213> ORGANISM: Artificial Sequence
<220> FEATURE:
<223> OTHER INFORMATION: i5_antisense flanking primer

<400> SEQUENCE: 94
cgatgtagat ctcaaggcgc cagctaaaca acagccgggg aaag        44

<210> SEQ ID NO 95
<211> LENGTH: 535
<212> TYPE: DNA
<213> ORGANISM: Zea mays

<400> SEQUENCE: 95
gtccgccttg tttctcctct gtctcttgat ctgactaatc ttggtttatg attcgttgag        60
taattttggg gaaagcttcg tccacagttt tttttcgatg aacagtgccg cagtggcgct       120
gatcttgtat gctatcctgc aatcgtggtg aacttatttc ttttatatcc tttactccca       180
tgaaaaggct agtaatcttt ctcgatgtaa catcgtccag cactgctatt accgtgtggt       240
ccatccgaca gtctggctga acacatcata cgatctatgg agcaaaaatc tatcttccct       300
gttctttaat gaaggacgtc attttcatta gtatgatcta ggaatgttgc aacttgcaag       360
gaggcgtttc tttctttgaa tttaactaac tcgttgagtg gccctgtttc tcggacgtaa       420
ggcctttgct gctccacaca tgtccattcg aattttaccg tgtttagcaa gggcgaaaag       480
tttgcatctt gatgatttag cttgactatg cgattgcttt cctggacccg tgcag           535

<210> SEQ ID NO 96
<211> LENGTH: 344
<212> TYPE: DNA
<213> ORGANISM: Zea mays

<400> SEQUENCE: 96
gtacagtaca cacacatatg tatatatgta tgatgtatcc cttcgatcga aggcatgcct        60
tggtcgaata actgagtagt cattttatta cgttattttg acaagtcagt agttcatcca       120
tttgtcccat tttttcagct aggaagtttg gttacactgg ccttggtcta ataactgagt       180
agtcatttta ttacgttgtt tcgacaagtc agtagctcat ccatctgtcc cattttttc       240 agctaggaag tttggttaca ctggacttgg tctaataact gagtagtcat tttattacgt       300
tgtttcgaca agtcattagc tcatccatct gtcccatttt tcag                       344

<210> SEQ ID NO 97
<211> LENGTH: 1014
<212> TYPE: DNA
<213> ORGANISM: Zea mays

<400> SEQUENCE: 97
gtatgcttgc tctcctgttc atctccgtgc taaacctctg tcctctgggt gggttttgc        60 tgggattttg agctaatctg ctggccgcgg tagaaaagac cgtgtcccct gatgagctca       120
agcgctcgcc ttagccgcgt ccttgtcccc cgccatttct tgcggtttcg ctgtgttccc       180

```
gtgactcgcc gggtgcgtca tcgcctgaat cttgtctggg ctctgctgac atgttcttgg      240
ctagttgggt ttatagattc ctctgatcta aaaccgtgcc tgtgctgcgc acagaactct      300
cccctgtcct ttcctggggt tttggttacg tggtggtagt aagcttggat ttgcacatgg      360
ataaagttgt tctaagctcc gtggtttgct tgagatcttg ctgttattgc gtgccgtgct      420
cacttctttt gcaatccgag gaatgaattt gtcgtttact cgttttggtg gattattagc      480
gcgaaaaaaa actctttttt tttgttcttt tactacgaaa agcatcttct tggattttgc      540
tatcttcttt tactacgaaa aactcttgag tctaggaatt tgaatttgtg atgtccattc      600
ttgcagtgcg ctgtgcttta tgggaagcc aaatcctatt attttctgcc tctagggtct      660
gaatggaatc agtactattg agacaaaatc aatccaatca agttgatttc tttctttaaa      720
aatattatca cagaactaag tgcttgtgcg gaatcagtac tggcttttgt ttggtggagg      780
atcaatactt gcttttgttt tggggtggca actgttttgc tataagattc catgtgttcc      840
tgttgagatg aatcatatat agtatagctg catactacaa atctgttttt caaatttagg      900
ttgctttggc atgatcaatt ttttttcaga cagtctttct aagtggtagc tcttgatttc      960
ttgttcttct acaactggtg ctgctgaatc ttgaccgtat agctcgaatt gcag           1014

<210> SEQ ID NO 98
<211> LENGTH: 1010
<212> TYPE: DNA
<213> ORGANISM: Zea mays

<400> SEQUENCE: 98
gtacgccgct cgtcctcccc ccccccccct ctctaccttc tctagatcgg cgttccggtc       60
catggttagg gcccggtagt tctacttctg ttcatgtttg tgttagatcc gtgtttgtgt      120
tagatccgtg ctgctagcgt tcgtacacgg atgcgacctg tacgtcagac acgttctgat      180
tgctaacttg ccagtgtttc tctttgggga atcctgggat ggctctagcc gttccgcaga      240
cgggatcgat ttcatgattt ttttttgtttc gttgcatagg gtttggtttg cccttttcct      300
ttatttcaat atatgccgtg cacttgtttg tcggtcatc ttttcatgct ttttttttgtc      360 ttggttgtga tgatgtggtc tggttgggcg gtcgttctag atcggagtag aattctgttt      420
caaactacct ggtggattta ttaattttgg atctgtatgt gtgtgccata catattcata      480
gttacgaatt gaagatgatg gatggaaata tcgatctagg ataggtatac atgttgatgc      540
gggttttact gatgcatata cagagatgct ttttgttcgc ttggttgtga tgatgtggtg      600
tggttgggcg gtcgttcatt cgttctagat cggagtagaa tactgtttca aactacctgg      660
tgtatttatt aatttttggaa ctgtatgtgt gtgtcataca tcttcatagt tacgagttta      720
agatggatgg aaatatcgat ctaggatagg tatacatgtt gatgtgggtt ttactgatgc      780
atatacatga tggcatatgc agcatctatt catatgctct aaccttgagt acctatctat      840
tataataaac aagtatgttt tataattatt ttgatcttga tatacttgga tgatggcata      900
tgcagcagct atatgtggat tttttttagcc ctgccttcat acgctattta tttgcttggt      960
actgtttctt ttgtcgatgc tcaccctgtt gtttggtgtt acttctgcag                1010

<210> SEQ ID NO 99
<211> LENGTH: 8
<212> TYPE: DNA
<213> ORGANISM: Artificial Sequence
<220> FEATURE:
<223> OTHER INFORMATION: motif
```

```
<400> SEQUENCE: 99 cagatctg                                                             8

<210> SEQ ID NO 100
<211> LENGTH: 5
<212> TYPE: DNA
<213> ORGANISM: Artificial Sequence
<220> FEATURE:
<223> OTHER INFORMATION: 5 bp motif

<400> SEQUENCE: 100 atctg                                                                5

<210> SEQ ID NO 101
<211> LENGTH: 867
<212> TYPE: DNA
<213> ORGANISM: Zea mays

<400> SEQUENCE: 101
gtatgggtga cgtggtggca ctcgatctgc tgggttcaga tctgattttc ttggtgacgg    60
gatggcttgc cggcgatggt gcaggccgtc cactccaacg accccctccgg gcagcttgag  120 gccaccacac agttcaggaa gctgcttcct atagttgaga ttgggatctt atgtgcagtt  180
agcattccag atggatagag tttaggggtt gagatttggg ccatgctcga ggtattaggc  240
catacccaaa cgtgagggta tggtcagttg tagctgtttc gggcaattgt tgtatacagg  300
acttgacttg tggattgtga gctatcaaaa ttagtcgttg caccctctca ttttcagatt  360
acttaattta ctgtctcgtc agaaaaaaaa caaaccctat cctatggcct ctgcaacatg  420
catatgacca tgtatgccca aaagttctga aaaagttat  actcctgaaa gcatttgatt  480
tcatgaacca ctattctatt ttttccagta gtgttctgct tgcagctggg gcaattatca  540
ttgcatccat gtgtgtgttt gcgcatgcat gtgtgtgtta tacattgttt tattgtctta  600
aaatggtata tgcagactat gtgtgtgttt gcgcattagt gtgtgttata cattgtttta  660
ttgtcttaaa aaggtcatgg agagtctgcg tacctctttt catattcttg tacatcgtag  720
atagcagctt tgatatcttg tgggattctt gtatttgttg gtgaatccag atgagtgcat  780
ggtacttctt tcttaattcc cactacaact ttatgtgaaa gttaagtagt aacttgctga  840 ttgagttttcc ataaatttct ctcgtag                                      867

<210> SEQ ID NO 102
<211> LENGTH: 847
<212> TYPE: DNA
<213> ORGANISM: Zea mays

<400> SEQUENCE: 102
gtgcgaccgg ctcgtattct cttccttgaa aagcatctcc atcaccatct tcgattgttt    60
tctgatctgt cgtcgaggag tgctgcaatt tgcagttgca gggcgttagt actcgaatcg  120
gggtgaagta ctgaagtggc ttaggttagg gttttttttt cgtcagatct gttgctagta  180
ctactaggat ctgaaatttc ctgcacgatt taagctgcca ccatcctgtg ttttaggtgt  240
atcgtggatt tcgtttgtta atactttgcg gcagaaataa caggatgttc cgatcgaatt  300
tggcatctcg tatttgttga tggtcacgcc aattcttgac agattgcgat gtcgtaataa  360
gtcatctgcc gttccgtgac cggtttggat ctggtttgtg tgtggatgaa ctgcgctatc  420
tttgtttctg ttattgtcga ctaggaattg attgaattcg cctttttacta tttcgtgaat  480 caagctctga ttctgtaact tttactcatg ttgttttcat ttcttcggcc tgatccaaaa  540
```

```
tttccagtg gaacgatgct ttcttttgtg ctgtacaact gcaatatttc gtgactcaag      600
ctctgattct gtaaaattta cccatgttgt tcccatttct cagatctgat gcaggaatga      660
cgctttagtt ctagtttgtg ctgtgcaact gtaatacgac tgtactgaaa tttctctctc      720
ctatgaattt gagatgctcg cctgccttct gattcaaata cttattacac taatggcacc      780
tcgcaatcat gttcctttga tcgttttatg atctgaacca cattaaacac ctttctattt      840
cacgcag                                                                847
```

\<210\> SEQ ID NO 103
\<211\> LENGTH: 1448
\<212\> TYPE: DNA
\<213\> ORGANISM: Zea mays

\<400\> SEQUENCE: 103

```
gtgaggccgc cgccggggg ttcctcagat ctggggccga tgctgggtcc gcctagatcc       60
acgcgtttct cggctgctcc ggcgaggatt atgttttttt agtgtccgtc gtttgttaat      120
aggatatgca cacgtttctc taagagtggg tgagatcttt gcgggggta gaaggtccgg       180 agttttgcta cccgttcgtt tatttagtgg gtttcacgct gatctggtca tctggcggtg      240
aagttcctat tattaggctg cggatgcctg ggtgagctcg aatgccattc tattttacc       300 ctcttccggg accgtagcaa ctgtctaggt agcacaaaat catcattttg ttaggaccga      360
agcgagtttc aggttgcatg attttttcgg aatggaagac aaatatctat gtctgtgtgg      420
ggtgggtggg tggggctcg gtacctctgg ggactaacaa ttggtgtatc ccttccccc       480 ttcaaaccct tcaaactatg tacttttta tgatatattt ttgttcacta ctggcaccgt      540
cccaactgtg gattttttc aagggtggct catgtgatgt gctactgttg ttttgctagt      600
attcgattca cgggccccaa gtagggctgg caaacaattc cttttccca cctcttggac      660 gtgtgatgag tgtgggcttt ggctttggat gcttgtagta gcttagctgg tggatctagg      720
ctttattgaa gttgtctttt aatgcctatc cgtgttcttg ccctgtgtcg gtgctgcagt      780
aaaaggtgta gctttcagtt gacatggccc gatctcgcct ggcgcctttc ttctagacta      840
aaactcggta atgaaggtg cgtgacggat ctgtcacaaa ttgattatgc aaacacgtag      900
caagttaggc agagcaccat ttggtaagta gatctggacc tggaagttcc tgggtggggg      960
ttctctgcca tctgtcaccc acgtgtcgtt tgttcactga cctttgaact tcccatttag     1020
atcagcatgg atggccctag tgctcatcag atacttgtcc gatatgtggg gcttttgttt     1080
taagcgggtc accaatcttt gacccgatgt gcatgtgcta ttttctatga ttgagacggc     1140
gacacaggaa gatgagcact tttggagtta cctggttggg ggtccatgag ttagctgctt     1200
acctgtgtgg ttgacaaatg gatgttggat gcttcagtct attaatcacc cgttatttat     1260
tttctgatac tgcaaatata aactggacag gttttgacat tctttctgaa tctactattg     1320
taccattgta ttgtacacag tttgaatttg cagcacaata taaccttgtg tggttttata     1380
tttacatcct agtgatccta accatatgat tgacatctaa aaaaaaactc ttgctctttt     1440
atggacag                                                             1448
```

\<210\> SEQ ID NO 104
\<211\> LENGTH: 169
\<212\> TYPE: DNA
\<213\> ORGANISM: Zea mays

\<400\> SEQUENCE: 104

```
gtccgtgcct tttttctttt cctttcaatt tcacccgcaa aaggttcatt ctttcatcga    60
tctgggtggt tttgaccggg ttctatggcc ctgttcgtcc agatctggtg atttcttggc   120
tgttctttcc atggggtttt gacaaaaaaa aaatcacttg tgatggcag               169

<210> SEQ ID NO 105
<211> LENGTH: 1500
<212> TYPE: DNA
<213> ORGANISM: zea mays

<400> SEQUENCE: 105 atcttttgt gtggagtgac ctgttttcaa gagctccatt gtagagtgac ctgttttgcc    60
aattttctct cggctatgtg aaccatcaaa tatggtaact aacaatatat aaaatataag   120
ataaattgtt gctatggtac atcagatttg tgtggcattg tccatcgcat atgaaacttt   180
ctatgttagg ctgcattcca ttataaagtc atgtctgttt tttacatagg ccgataaata   240
tatttttcat atctgtatcc taaaaggttt taggcttagt aggtctaaaa cagagtatat   300
gaagtgtgat ttcagtgcca tggggtatga ggatggcgat gttagtcttg atgggcaagt   360
ggtacccaag aaagacactt ttcgttactt aggatcaatg cttcaaaagg agggagacat   420
cgaggaggat gtcagtcata gaattaaagt cggatggttg aagtggcgac aagctgcggg   480
tgtcttatgc gaccaccggg tgccacgcaa actaaaaggc aaattctaca ggacagcaat   540
ccggccggct atgttgtatg gagcagaatg ttggcccact aaaagacgac atgtccaaca   600
actaagtgtg gcagagatgc gtatgttgcg ctggatatgt ggccacacaa ggagagatcg   660
agtccggaat gatgatatac gagagagagt aggagtggcg ccaattgagg agaagcttat   720
gcaacatcgc ttgagatggt ttggacatat ccaacgaaga cctgaagagg caccagtgca   780
tatcggaata attaggcgtc ccgaaaatgt gaagagaggt agaggtcgac caactttgac   840
gtggacagag gctgtgaaga gagacctgaa ggagtggaat aatgacaaag agctcgccgc   900
agataggaag gggtggaagt gtgcaattca cgtgccagaa ccctgattga tagtttcgct   960
tttcctcctt aatcgtttga ccttttcttg tgtccatttt agatcttgct ggtccttgtg  1020
ggttttatct cttttatgtg tttccccgtt tcgttgtttt cggttctcct ttgcctttgt  1080
ttcccttttc tgttctttgg gggttgagct ctgaggtttt catacggggt ttcatctcta  1140
gcctacccca acgtgcttgg gacaaaaagg ctttgttgtt gttgttgttg ttgtatctgt  1200
atcctaaaag gtgagagaga agggttatta agaaaaaccc tcgtcgctgg ccactgaagg  1260
ccgggcccaa tttagaacct agacctgctg ccaccgcact acaagaccga ggcctaaaag  1320
gcccatcagg aggcgcatcg gcgaatgccc caaactaaaa ccctaccccg gcaagtatat  1380
atatcctccc aacctcagtt cttgttccca ttatcacggc ggcggtggcg gagcgtaagg  1440
cgaaggagta gcagcagcag gcggcgccga gtagcggctc cccatctcga gcttgccacc  1500

<210> SEQ ID NO 106
<211> LENGTH: 1500
<212> TYPE: DNA
<213> ORGANISM: zea mays

<400> SEQUENCE: 106
ataagcgcta ctacttgaga aatgatttta cattcacac aaaatgatgg tttttatgca    60
atcaaactag cacctaaatg taaacaaaac atgcttgtca tgtatctcct ttaagcgcta   120
ttttgagaac tctgttttta caatgaattt atattttctc acataaattt aattcatttt   180
ttcttagaaa aaaaaagaa aatccttgag aaaacagagt tcccaaacta gccataaagt    240
```

```
tgcacggagt tttcttctag cgagattaca tcaattgttt gaggtacaag tatttcgtat      300
atgccaaatt attagcaccc tagttattta gattcttaaa tatgttttgg ggtaaaaata      360
taacatacca tgttataccc aacttttgtc aaagatttag gagagttttt ttaatcgaac      420
ttgatgttta gcgcctaaga attttattgg tacttgtaaa aaaaatgtta acatgccccc      480
attagaatgt aggaaaaaat gggagaaaaa actatgattt caatccctat gaattgattt      540
gttctatagc ctttgttttg ctagaatttg tctgaaaacg taagagtggg ttcgttttca      600
cacgaaaaga tctactcaaa tatcattatt ccttgtttac acccatagtt cattcaacta      660
cctattttat gttaattttt tctgttttca ctcctccaga tatctattct tcttaacttt      720 tttgttttc accccataac tttgcataga tatttctatc ttatttatgt ttttttctat      780
tgttgacttt ttcaatatga cattcaaaag aaggttgctg atattttcc caatcttgca      840 tttaaagagg accatactta aaaagactct agaagctttg agagcatctc taacaatacc      900
ttaaactagt gtctcaaatt aaaatacaag gctgtacgca gaaaaaacta ctccaacaat      960
gcttcatttt ataaaatttg gtcaaaattt ttttagtgca ctctcttata tgtctcaaat     1020 atactcacacc acaatgttct gccctataat ctagatttgg ggttttacta ttggagcaga    1080 atatttatt ggtgctctaa atcaaataaa atataaccat tttaaaatta tagggcattt     1140
ttatagatca cgtgttgttg gagatgctct aacaaaacca tttaaaagat gaacgttatc     1200
aatgtaataa tattttgatc tgtagtgttt ataaatatat atacaataat ttttaaaaac     1260
ttataataat atcattattg tatcatcaat ctataaacaa atttaagttt tcattaaaaa     1320
tagtaagtag tctgacattg actttttttt cattcgagaa ggacaaactg gaaagaaat     1380 atagcccagg ggtagttttg ggaaaaaaga tatttggatg ctggcgaatg tgacggccac    1440
gtctagtgga agcgcgtata aatcgtccct tctttctttc ctcacccgcc cctgatccac    1500

<210> SEQ ID NO 107
<211> LENGTH: 1500
<212> TYPE: DNA
<213> ORGANISM: zea mays

<400> SEQUENCE: 107
cgagcggatg ttgttccggc ccgccaagcg gcaatcagca gctcaggtag tgtctagcca       60
gtgacgcggg gcgcgctact gtatgtgtct cgccgcctcg ctgggggcac ttcgtgtcgg      120
tagtacagga aaaagggaag gagtcgagat cgttcgcttc actgtctgtg tttcgtgtcg      180
gtaggtaccg tatagtgggg gagaagagat cgttcgcatc agtgcttgtg tttcacttag      240
ttgaacgtat acgtatatc gtatttggcc cattgcaaag caaggtgccg gaccaagaca       300
ccatccatcc atttgttgta gtagcaaaac aacagattca tctgtttgga agtcctattt      360
tgagccatac gttctcagtc ccgttgttgg gacgtgggag aatcctaatc ccaaaaatct      420
gcaaccaagt cgggggggcta gtgaaggagg agaaatttac tattttgcca ctctcaattt     480
tggctgtctt ttattatgcc atcccgtgtc tatgactggt gggaccgtct gtgtctatga      540
tttgtgggtc cgatggcata ttggcgaagc ccacaaataa taatggcaaa attgccaatg      600
gctcagtgaa agagaggccg agcacagctg accgctgctg cgctgcacaa ggaggctgtg      660
tgcctgcacg tttttttttt ttgcctcagg gctcaggctc tcgcaatttg ggccctaacc      720
aatggacgct aaatcatcgg aaaccgctga ccgcatagca ccagtactgc tgctgttgct     780
gtctgatgaa gcgccctcca gttctccact acggccccta ccccacaccc ctgacaatgc     840
```

```
gaccgtttgc ttttatcacc acacaagtat actgaaacac acacacacac acacaaaaag    900
gggttcgctg ctgacttttc acctggcact gagagccgta atagcacttc ctgctcctgc    960
agcgtgcaat aatccgcgtt caagggatgg gtaaattggt cggatagatc gcaaatctta   1020
tcagatcgat ctcgtgccaa ggcagccatg ccccaccccc accgcgtttg gtgcgacacg   1080
gtccccagcc gcgcatatga tatgcgtgta cgagtagtcc gcaggttttc tctcgccagc   1140
aacgccatct caggacctgc ggagcaagta tataaaagca ctagcgattg ttgtttcacc   1200
cacaagattc caccatcacc acctcatttg ttagcggtaa tacctcgcct ccgttacccc   1260
gtgcttttaa ttccacggga aaccgaaaaa gaagagagag ggaaatgcca gcgaaattgc   1320
atggtggcct cgaaacgccg tccagactcc agagagaacc aggcatggct tcagagagag   1380
agagaaagcg gcgacaaaga accaaacgaa accaaaacaa aaaaaggctt tctttgcaaa   1440
gtcggacgca caaagcgggg agggcgaatt ccgcacgaaa cacgcagacc atatatgccc   1500
```

<210> SEQ ID NO 108
<211> LENGTH: 1500
<212> TYPE: DNA
<213> ORGANISM: zea mays

<400> SEQUENCE: 108

```
cccgccctcg tttttcagta aaaaaaatat ggtaatggaa gtgggagaga gttttcccaa     60
ctgtttccga tcgttttcat ccctatctat aaacatccac atgagtaggg gaggcggggt    120
ggcgagtgga cgacactgta gccaacctaa ggaccaaagc tttagcctta accattgcac    180
catgtgtcgc ttattgttat atagagtata taaatgtata tagtaacaat ttgaaaatta    240
aaattaaaat catgattgaa taaaaatctc atttaaataa aaaattacat atatgatata    300
tagaattcat aacaatgtac gagtaactaa ctagttctat acttaagcat aaatagaaag    360
cgtagcaatg tatgcacact ttgctagtcg atatttaga tactagttag aagtattaaa    420
tatagtctaa gtataaaact aattatatag atgaggacta acagcaaga cgaacctatt    480
aagtttaagt agtccatggt tcgtccatgt aaaataaata tttgctaata atagattaat    540
tagacttaat agatccatct cgtcgtttag tctttatcta tataattact tttgtagtta    600
gactatattt aattttagta attgacattt aaacatccga tatgatccag acttgatgtt    660
agtcaggaaa accaaacatc cccttaacca tattggtccc aatttttggt gcctttaccc    720
atcaaatgat attcacacaa tcacacatct gggcctaact ttcatcgttg ctgtccacga    780
cggcgacctg gaggcgaggt caattccttg gcccaagcat agcttggagc ttgcacgcta    840
agaagaggct ctcgtactct acaaacagta cagcacatac aggtgacaaa acgacacaca    900
tcaaccagcc aaataataaa tgagcttctt catgggcacg gcaagccgac aactaccaac    960
aagatacagg tgacaaaaag aaaacaagag gcccccactc accagtgggt cgtaggcaac   1020
gcacgcggac gcggtccagc gggcgagaag atccccgact gcgcccaaa gaagatacag   1080
gatcaaggat ttttaaccgc agtttttctat tccacgacct tatccacacc agcagattcg   1140
aaattcacgg acaggcccat ggacccggcg aaagccagcg gtggttcagc cctgacgtg    1200
cgggtcccac tctccagccg caccgcctag agaggcagag gcatcccttc gcgtggaagc   1260
aaacgaggcg tgataaagtg gggctcctcg gtcccggcgt tggccgcatc gacactcgcc   1320
gcgcaccacc accaccgctg cggctcacgg ctacgcagcc cgctctcccg acccccccgt   1380
gccctcctct ttttgctact agcacataga gtttcgcccg aatcgatcgc cgactgactc   1440
cgctagggtt cggcccgatc gccgcttcgt cctcccggct cccgcgggga ccccgccgag   1500
```

<210> SEQ ID NO 109
<211> LENGTH: 1500
<212> TYPE: DNA
<213> ORGANISM: zea mays

<400> SEQUENCE: 109

```
ttcgtgtata catttattta tcctatgtac atgcaatgta aatgatacat agtgcatatt      60
gaccttattt ttaacatgta cttctttcaa agcaaaccac ccgcgaagtg tcacaatgca     120
tacatccttc ggtgtcgagg gacctcatca tgaggcccct gcccccctaa gtctagcttc     180
caatgtcatt taaggaagaa gatgagtttc gaggccttta gggcctctga ggttctaccg     240
aacaatctag gttatctttg tctcttagat cccctgcatc agaccccctct tggacctcga     300
ccttggagcc cttcaaggtt ctgaagccct cttgagatct atggctctta atgtgggaac     360
ccaagcttct ctcttgacta agtacaagaa tgctccacat tgaggcatac aactagttgt     420
aaccccgggg caagaagtac catgggagta tggtcccata gccacaactg tctctactta     480
agacgaccat gtgatactaa tgttccgaat aaagcttttg cacatcacat taatgtgatg     540
gatgatattg tggtcaagca ggcatatggt agccaccaca aaggatatga agcatacca     600
aatccactat gaggagtgtg tcgcgtacct atgccacacc taaatgtgct aatttacctg     660
taagcattat aaaatataag caattacacc gtatctgatg gcatggactc gagtacataa     720
ctatgatatg atatatttct cactgccgca agatatgcat attacaatga catgttcaag     780
cgccattgtg gtccgcgtag agtcctcgtc tctaacaaga tgaagtaatc gagcatgttc     840
actacgaacc aacatgtgat cctcctcttc ttcgagctat aaaatattca tccagcttaa     900
atttcaaaat atgtgtgtca gagttaaaaa aatattcgat tcaaatctaa atatcagttc     960
tgtattcata tcctagaata ttcgaatcta tatttgaatt cagattacaa ggtagtgaat    1020
tgtgacatgt attcgttcct atccgatccg tcgttttga gcactaggtg cggtcactgt    1080
gacgcgtgga cttggcttcg cccactgcca tcgtggaccc acgtcatcag caagtgtcca    1140
tatccaccac ccgaccccgac gaccgcttgc cgtccgatcc gtgtgctccc gagggcaagg    1200
atggcatttc gccacgcgag atattttcg gtggcctgca caggccggca gtgcagcggc    1260
caaaacgagg tcaggtcagt cacgctgggc cccgcctcac gctcccgtcc tgctccgggt    1320
cccaacaaag ccgtccccgg gaggtgctcg tgtgctcgta gcgcggtggc gaccccgatg    1380
ccccgcatat tccactgggc gtccgcgccg tcggatggga tcaggacggc gcggcggcc    1440
ccgcgctcgg ctataaagac gctgcggggg acgcattccc tctccgtgct ttcttagagg    1500
```

<210> SEQ ID NO 110
<211> LENGTH: 1500
<212> TYPE: DNA
<213> ORGANISM: zea mays

<400> SEQUENCE: 110

```
tgcacccatc gatagcagcc tggctcaaca gttgaattgg tggttggggg ctatatatac      60
cctccaacca cctccactcc aaccatccaa gcattcatta ctgcatattc aatacaagag     120
caatagacac cactccaaag acacaattca agtgatcgat ccgctcaaag tctacaattc     180
aactctagcg catttagact tgtgagagga tcatttgtgt tttccttgtt gctcttgttt     240
gcttggttgg cttcttctt cctcattctt gttctcaaga aacttgtaat caaagcaaga     300
gacaccaagt ttgtaagtgg tccttgcggg gtctaagtga tccggttgat taagagaaaa     360
```

-continued

```
gctcactcgg tctaggtgac cgtttgagag agggaaagag ttgaaagaga cccggtcttt      420
gtgaccacct caacgggac taggttcttt agaaccgaac ttcggtaaaa caaatcattg       480
tgtcatccgc ttttatttc ttggttgatt tgttttcctc tctcccccgg actcggattt      540
attctaacgc taaccccggc ttgtagaatt aaatcgtgcg actcaagata tatagaaaaa      600
tttacacgac tgtcgcatgg aaacttttca tggcaccact tgatgtattt cctttcttga     660
tactttcctt ttcattttc aattaaagtt gttactcatt ttatctttac ggacactgag       720
tatacactag gagcaaactt gttagtaact ttatttgttt tgtcatctaa tcatcaaaac     780
cctcaacttg ggggtgattt cacttacaat atgaccaatc tcaactcctt tacgaatgc       840
cgatagacac atattctgga caatcacagt ctcccgtgca aaacgagggt aaacccgtca     900
atttgcgtat ggacgtaccg tccgcacgtg agcacaaacc gtctggtcca acgatcgtcg     960
accccatttt tttgaaccga attactggaa tccgcgtcta agccaccaca tctcatgata     1020
ctatatatta atacagtatt atatttagta tatacgatga tatggtaaaa taacatgat      1080
tactatatat taatacagta ttatctttag tatatacgat gatatggtaa ttttagatat     1140
tgtgataaga aactatatag gttggaaata gcctaaggtg aggcgagtac agccccggca     1200
cacaaccaat cacggtgacg ctctaggatt gggccatttg tgtggcact gtagcgaggc      1260
ccagctcggt ccatgagcag cattctggtc ggcttgacag atccatcacg ccatcggcaa     1320
aaatatctgg ctctcgagaa ccctcccggt cccagcgcgg taggcccacc tcgggatcct     1380
tatcctccgg tcggaccgtt gtttgcgcgg tcgccgcccg atccgatcat gacggcgccc     1440
gtcacgtccg tcgcgctata aatctgcggg gtagggcttc ctcactccct cgtgctctct     1500
```

<210> SEQ ID NO 111
<211> LENGTH: 1500
<212> TYPE: DNA
<213> ORGANISM: zea mays

<400> SEQUENCE: 111

```
tttggcctcc tctccttcac ggatcaccct tgcagtcgag cgtactctgg ccatctgatg      60
atgaattttt ttgcagtttt tacgaagctg atgttttta cagttttttg acgaagctcc      120
ctcttttgac gaagctaatt aaagatgatg gtttgctcaa gaatgcagtg aaaaagcttc     180
gactatggtt aaattttca acagcacaac actgcaatga caatgaatgt tgtggtaact      240
tcacacctac ctctctgttt tatatagtgc tgcaggtggg aaggtgaatg gccaagttgc     300
ctgcacccgc tgaacagtta cccgcacccg ctgaacggtg gaccactcga cgcttgggag     360
gcgaatcgcc agaccgtgcg tacccgccgc atggtgggcc acctcgtgct tggaatatt       420
taatcgtttc ttgacaacga gctcaggaa ggtgttttt ggatctacgg cattccgaag       480
ccttggagat ttttcacgga tcaagctcgt tacaaaaaac gatctagcac cgcgaaggag     540
ctattgttgg gagactactt catcgccaaa ggtccttta aagaaaacat cttcggaaga     600
tcagtacata caacgcgaag gtacatgccg aagctaccat ccaggagct tcggcatagc      660
gacatgcctt gagacgaagg gctgcaccga cttaagagg aaaagaccaa tcggtccatg      720
ataatttgtg tcatggttgt aactaattgc caaggacata aatgtaattc tgaccgggct     780
gcgtcctgtg cctataaata ggtgaacagt acctctgtac tgttcacgct ggattgtatt     840
cactcgtacg tcacgcttgg acctttgcct tctgtcaagc cgaaggtaca aatacaattc    900
aatgtaattc atgttcattt ataatgatat aaaaaagata tattaatgat gttatataac    960
tattcatttt actcctcatg tttcatatgc ttctttttc attaatatat aatatgatga    1020
```

```
tgaaggtacg tgcttcatga ccttcgtctg aagatcatta tatcctatga gaaataatga      1080
ttcgaaggac gaagacccct aaccattaat attttatgtt gccttattct taattcgaag      1140
catttaagaa caagttccca acatttcga tacctactca ttatctatta tcaaatttct       1200
tctaactaac gattactaag gtgcacggaa acaaaaatg aaaagtgttt agaggtgaac       1260
gccaacaaca aggggtgaga aaaagaaacc gccatgtagt gtgggctgct aggggacggc      1320
cgtgccccca tgtagcccct tatcccctgt gatcggatca tcacaaaata tctttggagc     1380
gcggttgata ttatcactat aattgggggt ttacacgaaa aatcgcacca tctagaggtt      1440
tatgaagcct ccaaaaaaat atctaaacaa caactacttc ctagtataaa gtgacagtag     1500

<210> SEQ ID NO 112
<211> LENGTH: 1500
<212> TYPE: DNA
<213> ORGANISM: zea mays

<400> SEQUENCE: 112
atggagtact catgtttaat aagattttc tttataaaga gagccttatt aaaactcaac         60
aggtataaga gttttaaaaa tgatcgtctt cgctcgcctt ctcattccgc tctgtaaatg      120
atcctttggc tctcaagttc caactgattg acgatgggac gttgggataa attccaggag     180
acaacattct aatataatta attactcgca atttaaagga cagagaaaac catgctactt      240
gcttcgatgt ttattttac aaaaattaaa acatagaga tacagaaaaa tctgaccacg         300
agaattgcta gactctagcg tcacatgaat tgggagttat tgtaagtttt tgggccaagg      360
tgctagcgtg gagagtgagt agagacaagc agcgtgtgtg cttggcaaaa taaaagtttt      420 acttttctt ttgcttctta aaagactgag aggtgcagtg gatgaaatct cggatcttga        480
caaatgattc gggcctttt gtgttgcttt ttctttgct tctttaaaga ctttgagagg        540
tgcggtgaag cttgagtgca gtaggtttcg aaaggcacga cttacacgaa aaaatggag      600 aaaagagaa acaacaaaa actggagatg cggggtatcg atccccgtac ctctcgcatg        660
ctaagcgagc gctctaccat ctgagctaca tccccttttg ttattattat aaaatagtta       720
atatttggta ataatgagct agactaagtt ggaccatgtg aagaaaaatt cattagccaa     780
ttacttagca tgtgaaaatc atgcgcactg gtgtgagatt tgtaagaggt atataaagta      840
tctatggtct catgatatta gaaagaggac atgaaaaatc aaggagttt atagtggaaa       900 aaggaggcgg acacaactgc atcgccaaat tcatcacacc tgcatgcaca accctgagtt      960
gagtgagttc cacgtcgtgc tctgtagcat agcagacccct gtggtggtac tacccgtaac    1020
atgttgttgg agatgtctaa agtgttggac aacagtgtgc cctatgcccc tatgtctata     1080
ggatctcgag catctcaacg aaggagacag tcaactaatc gctctactag aagtctagtt     1140
cagccatgat agtaggccca ccatcttacg agtgggacag atgataaagt tgttgcttac     1200
caacatccac gcaaggtcat atcccttgat attgaaaaga tgtcactgac acatgggacc    1260
tgcctgtatc accgagagcg gcaagtatgc aatttgcaat ggcacgatag taatcgacat    1320
taattaaagc aaaaaaatca atgttttttt aaacaaaagg gctaagagcc caagacagac   1380
gacgtagccc aactgaatgc cctcctgcag cccagcccaa cctgtgcgat cgggtcggtc     1440
aagcaaccca ttcgatcggg tcgccttcag acctgacctc tcaaatcaaa ccgggaccgg   1500

<210> SEQ ID NO 113
<211> LENGTH: 1500
<212> TYPE: DNA
```

<213> ORGANISM: zea mays

<400> SEQUENCE: 113

```
agttaagcta acttccgaca aaaaaattt cgagagccaa actttcgacg ggatggcttt      60
acttccgaga gtttagctaa cttcctagag tttagggcta acttcctagg gtttaggctc    120
taggaagttc actattttgg tgtagtggga tagatatccc ctaggtccac taaaggaata    180
aaagacctca cgaaaggccc aagggcccaa taactcgtaa ggtcattctt tcgtgggcct    240
ggggtggaac aaccagcaag ggggaacgac atgaggccga ttggtgcaaa cccgagcggc    300
ccacatcgtc gagcgaatga tcgcaacaga gacccgattt tccgcgcggg agcccccat     360
gcagcggagc cgtgcgagga taagtcggcg aggatcacgc aggataaact cgagaggttc    420
actatctttt agttacttgt tgttatcata cccacatgtg ttgccccacg gtcgaatata    480
taaggcctag ggggcacccc ttcagaacga tcgaccctat cttacttagc cacccacgta    540
aactctctgt gccttcaatc cagagagccc tcttgtaacc acgctcgtat actcaccagg    600
acgtagggtg ttacgcatct ctaagcgccc cgaacctgta atcttgtcc actgtctctc     660
gtgcgatcgg cacgaaccat tttgctacag tcgttgacac cgtcctactc ctaaaaacac    720
cttgagggc aaccccgggt gtgcggtcgg acccaaaaca ccgacaccgg gcccaagggc     780
cggaccgtcc gctcattttg gtgtccaaca ggtcgccttt taatatattg atcaggtagc    840
tatgaccgaa gaaaatgcac gccctctata tactacctac attcacaaat atatgacaca    900
attgaacttt ttcgaaaact ttgaccactc gttttattca aaatatttac tcaataatgt    960
aaaacttcaa gtaagcacaa attatcttaa gtgataaaac aaatcacaaa aaatgataac   1020
ttattatttt ttgaataaga tgagtgatca agtttttttt aaaaagtcaa cgacgtcata   1080
ttgaacagag ggagtattag agttctatta aatatttata ttatttcatt ataaaagtcg   1140
gtggctaaag ttcgtatttt gggaacaaat caagttaatt aatttattat ttttccgaaa   1200
gaagcgggta ggacacgaac caaaagcagg tagctacggg accccgcgat tttagcagat   1260
cgcagcaccg gcccgcgcac acccaccaaa cccggcccgc tactgaagtg acgtcactca   1320
agtgtccacg gccggcccca cccagtcata gctaactaca cgacacccac ctgtcttcct   1380
cggctcctcc accccggtcc tctcctgccg cgtcgcgttc gccccctcgca gcgggcaact   1440
cccaccgccg ccgcttcgca tccgcccatc tgcttccatc gtctcacgga ggtcgctcac   1500
```

<210> SEQ ID NO 114
<211> LENGTH: 1500
<212> TYPE: DNA
<213> ORGANISM: Zea mays

<400> SEQUENCE: 114

```
gaccggcgtc ccatctggcc agctccgcca gatggacaat gatggcgccc cacaagctct     60
atgacgacgg cggctctcag ctctcttacg gaagcagggc gacgtcagca aggactcgac    120
cgctccaaca gctgtccctc cgccaggctc cgtcgctcct ccgacagcca cgacatcacg    180
ccagcaaggt gccaagacct ctccggctgc acattggca tgtacctagg gcgctagctc      240
tctctccgct agacacgtag cactctgcta cacccccat tgtacacctg atcctctcc       300
ttacgactat aaaaggaagg accagggcct tcttagagga ggttggccgc gcggggacga    360
ggacgagaca ggcggctctct tggggccgct cgcttccctc accgcgtgg acgcttgtaa     420
cccccctact gcaagcgcac ccgacctggg cgcgggacga acacgaaggc cgcgggatct    480
ccacctctct cacgcccgtc tccggccacc tcgcctctcc cccttcgcg ctcacccacg      540
```

```
cgctcgaccc atctgggctg gggcacgcag cacactcact cgtcggctcg gggacccccc    600
ggtctcgaaa cgccgacaaa accgtaggaa ataaataact tccgagaggc aactggtagc    660
tctaggaaat aaacataact tcctacggta ttttataaaa gctgtaggaa gttagttttc    720
acatgctgac ccgtgtgttc ggtcaagcga gccactaact tcctagaggc ggccgtagga    780
agttagcatg ggcagctaac ttcctgcggc ctcctctaga aagttaactt ttaattgctg    840
atccgcgggt gtggtcaaat gagccgctaa cttcctacgg cctcctctag aaagttagat    900
ttcagctttt gaccagccaa acgaaaagct cgtgctcaag attacaggaa caatccaaag    960
attacaccaa tcatattaag attggaggat caagaaaagg agaatctaaa tcctaagagc   1020
tagtttgata acctcgtttt tttgacagtt ctctaccgat gttcgcacac gcagcagccc   1080
ttgttgccat tttttctccg cgtcctctgt gccccaggta gggatgctgc cctttataaa   1140
ctttcacctc caactcactc gtatctcctt tcgagagatt ctgatatttt ccatcaacaa   1200
gaaacagatt tgtaaaatta tcatcaggcc acatttcata gacccagctg acccacaat    1260 ttataaacac agtggtaatt ataacaagaa acaacattg tgagtggcaa aaatctaatt    1320
gtctcatctc ctttccgttc gccaattcga aatcgaatcc gttccctaat tcgaaatcga   1380
atggggtcgg tcttgtcgtg cgtgcgtggc tgcgcgagcg acttgactgc acccgacccc   1440
cctcctccca gtccccacac actgcacgcc gccgccgggt cctcctaggg tttcgccgcg   1500

<210> SEQ ID NO 115
<211> LENGTH: 1500
<212> TYPE: DNA
<213> ORGANISM: Zea mays

<400> SEQUENCE: 115
aactggacta gattcgtctc gtcttttaat cttcggctga caaattagtt ttataatccg     60
actacattta atacccgaaa cggaggttca aacattcgat gggacagggg ctaaatttta    120
gaggggtgta accaaacacc cccgtagtcc aaaactgcag gttaatgggt ctatgaccta    180 atttttggg acaccaaaac ataaaaattt ggaaaacaaa tatattctct agactcatag    240
gaacccctat agattttccc aaattatttt tgattttaa aattcaatct tttgaaccga    300
aaaaattcaa aatttacac agatcttgat tctgtgcagt gctggtgatg ggaaaagcg    360 aaaaaccatc ggtatgtttt tgacaaatat gaaaatggga caaaaacaac atgtgtgttt    420
tttcgaccgt ttccgctttt cttgttttag tcacaatagc tcgttttat ccacatatga    480 tatctcattt tagataatac atgaacaaat cataattgat tatatcatat ctcaacaaat    540
taacccgtaa tgaattattt ttctttgata gtcatatgta cattacaata tttcgcttcc    600
atatgtatgg atgtgatgtt ttaatcgatt gcaacactac ttttatttt atactctatg    660 tgacaattat ttccgctttt atttacatct tattccgatc tgttatcgat atcgatttgt    720
tccgtcccgt ttttatctta ttttctgatag ttccaattta atcttatttt cgaaataaag    780
tatgaaaata aaaataagag agattgttac gttcgatccg gttttgaacc ctagctatac    840
ttgcccgttg ttgcaactgg ccggccattc cataggcggg cacagtcagc actcagcagt    900
gacagagtgc gcgtgcgaca cacagtttca aatttcaaaa ctgaaacggg cggctataaa    960
cagaacccgc tgctcccagg agcctcacgc agataaattc acccacatca atggggccca   1020
aatatttata accatctatt ggtcccacat gttcgtgtca caacatcctc taccgcaggt   1080
aaagatagcc gtctcgccaa gaccccgagc ccgccggctc cgcgggaccc gccgccagct   1140
```

```
cacacccacc gttgccggcc gctgagccgt tcgaagccaa acggtcgtt aaccacccag      1200 gctgcgccgt cggctaccat cacgccgtta gccccgaacc agacggcggc taggtcttcc      1260
gcgccgcgcc gcgccatcac gggccggccg cggccgcctc tcccacgctg cctataaaag      1320
ccgccgcgag gctgagcagc attatcgctt cagctcggcg tcttcacaaa cgccggcgca      1380
aactctcgcc cgagcccgac agatcttcaa ttccccattc cgcccaccga tcgaccttca      1440
cgccagtctc ggtctcttcc gaaggcgtcg cgcgcggttg tttgagagga gaggaggaag      1500

<210> SEQ ID NO 116
<211> LENGTH: 1500
<212> TYPE: DNA
<213> ORGANISM: Zea mays

<400> SEQUENCE: 116
atgagctatt atccataaaa ttatctaata ttcattatta ttccataaat tgatcatttt        60
tgcaaggctc gcgagctgga acgagccggc tcggctcggc tcgctgcaaa acgagctcg        120 aaacaggagc tcagctcggc tcgtttgagg ctcgcgagcc gctccgagct cgagccggct      180
cgcgagcctc gagctaattt tccaaccctg gccctggcc agtgagctgg gcttccccgt        240
gagcgtccaa cggctcccct ccccccctcac gctcttctcg gtgagagctc tcaccccctc      300
tccgctaatc agctataata attacaaaat taattttag atttacttag cagataacaa       360
tatgtattat aacactacaa aaattgtat aatcatttaa aattccaaaa accgatgtat        420
aaaagtcaaa taacccaggg ttaaggggac ttgaatagga aaatgattgg atatgaggaa      480
aaataaggga cagatatttg aggagataga tatttaaata taaatagaaa ttatgaatgt      540
agggatttag gagggggaat ggttcaaaat agcctaagaa taagagtttg ccacctctct      600
tgagccatcg tccgctcgct ggcaggagtg atatatggc catatgggtg tttgttgggg       660
tcagttgacc ccgataaaat ttataaatct ttaaataaaa cactaaagtt tgaaaaaaca     720
ttgcatcata taatgaagct gacccctattc cgacatcatt cttttgctaaa ttcgccattg    780 ctcgctcatg cctaaaaaaa gacagagtaa gcacgttggg gggtgcttgg ttcttttagc     840
agcacaggct agcatggtaa ggctgcctaa tcttgctcag cttggccagc aaatataacc    900
atggacaatt taaatagcac aacgacatgc atgtcgtgac tgaaatagta caggaaggcc     960
cacccgtcgg ccagcctcca atcgcagaac gtggtagctt tctccgtccg ctcgccttgc    1020
cagcgcggga gagccgaatt ggccgcccgt ccgcttcaac gacgaggaaa agctagcttg    1080
cccagacaag ttagcttgct aagcaacgca aggttctaaa cacaactagt accaaacacc     1140
ccgtcgctaa tgcagtatcc aagaagatca ttagcttatc caatgctgaa ggcaaatgac    1200
acgtcagtgc aagctcactc acttgatcca gatctttcca tgcctatgcc tataacccta    1260
aataacggag ataagctaaa agatatttat ctcctgggcc cacctgccat cccgggccca    1320
ccgcaccagc aaggcctgca actttcacac ctaacccttc caagttaact gcattcacga    1380
cccacccccc cttcttctct ctcctggcca cctccgtcca ttccacactc cctcctccgg    1440
acgcaccttc cccgctatat aaggcacgcg ccccgagcac aggcgaagag cgtgcagagc    1500

<210> SEQ ID NO 117
<211> LENGTH: 1500
<212> TYPE: DNA
<213> ORGANISM: Zea mays

<400> SEQUENCE: 117
gtctttgagc tgaggtcttc ctgagagaag gtgattgtaa tgtgtgacca tttggatttg        60
```

```
atgaagggtc cttatactcc aacatgttgt accattctct gtgcttcctt cttctgcttc      120
ttgttagctg gctcagaact tgaacctccg tgattgggag caccagcttc gtagccgaag      180
gtgtcacaac ttgatcacct tgcgaagcca ttgtcgtggt cgtggaagtg agttctccgg      240
aggtgggcac caatgttggt cacttgttct cgaatgctgt gaattaagaa caaggcaaca      300
cagtcgctag ggattaaaga ccttcgtcct ccgaaacatt gtttcctctt ggattcaatg      360
atcatcggac gaaggccatg aaggacatgc cttcatcata tcataaataa ataaaaatgt      420
aaagagataa atacattgat gattactctt taatacattc atacttgtac tccgtaaaac      480
atgtataaat atcaataaaa ttcacgttat attgatacat tcggcttgct cgaaggtgaa      540
gatgcgagcg agtgattaca attcagcgtg aacagtaggg tgttattgtt catctattta      600
taggcacggg acgcatccca ggggaaatta cattcacgac cctcaacatt catctagaga      660
caacctagat taacaaggtc tatctggtct tttcttcttc tgcttgactt gaacagaaac      720
taaatggtag ctttgacatt tgactatgtt gattctacat taagtctgtc ttgagaattt      780
tcggcagaaa aaaagtagac ttatgtacca ttttaccgaa gatgtttttg ttgaaaactt      840
ttgtcggaaa agaagacacc caacacttta cgtcgccgcc ataagtcacc agcgtcgtac      900
catgacttat ggcgtctaaa aaagattcaa agaatcatat tacatccttt ataaaaccaa      960
acgtatattc ttttagtaaa aaattaaaat gcaaaaaaaa atggtttccc acagccctag     1020
caaaacacaa tcgccacttc attccacccc ccgtttcgat gatgggtggg gacaaaaata     1080
cagggaccca catgtcagtt aaaatctgac catgcatgag gtcatggcac ggaatagttc     1140
tttactacta ggcaaccagc acgttgtaca ctgactgtgg ggccaaccgt accttgggtc     1200
cacaagtcac tgtgtgcttg acaacacagc attggcagat ccatgtgtac gttctcagcg     1260
ccaggaaatt gcggccgtcc tttcctcctt ttccgttaag ccgataatct tcaatgacgc     1320
acgggtccaa gattagcttg ggcccatatg gcagtgtggg aagctgaatc cggacgcgtg     1380
acgcgaggtc tcgcgtggtg cggcgggcac tacgtcgtgg atggggaagg ggattaaata     1440
tcgtcggacg aggcgtggcc aaccccttc gctcctctcg ccgctttggg ttggggttta     1500
```

<210> SEQ ID NO 118
<211> LENGTH: 1329
<212> TYPE: DNA
<213> ORGANISM: Zea mays

<400> SEQUENCE: 118

```
gtaactgcga tcatccatcc tcccgcttcc actctcccctt cacctcctct gcttgctagg       60
tatacgaaca tacgatttat tacgggttat atgggggctt cgattcccag atctggcgat      120
ctattatcgt agctccgagt cctcgatcta gtaattgtgg gatatgcttg taagaggctc      180
tgagatgggt tgggttgggt tgggtcgctg tgacgattcc aacagcctcg tttcttaggg      240
ttggatcttc tcgtggtttc ctttttaatt aaataagtac ctgatgcaga atggtgcgtc      300
ctattagatg gaaccttgat cttgatgcat ctaaccttga tcttgttcgc tgtgatgatt      360
ccaacaggct cgtttcttag gcctgttcgt ctggttcgtc agatcagttt cgttgctttt      420
ggcctcgttg taaggtccat ccagatcgga gtagaatcga atgattattt tacggtagc      480 tgctggtctc attagatttg gatctgcatg ggttgaacat atgtattcat aattaatatg      540
gtgtatacgt actagtttgc tggtcttatt ttttagcct gattgcttct gcctttctgg      600
caacgcctga tccacgcgtt agctagagtg gatttttagtt ccttgtttac gcggccacac      660
```

```
ctgccgccta gaaaagctgc agcgagaact ctaattaaat ttggatctac atgtgctagc      720
atatatgttt gtaattaata tgatggatga atatgtgctt cagagttgag ttcctgttga      780
tgctgtagtt ctgcctgaat tgttgaggct gtagcttctg cctgattaaa atgcaccgtg      840
cctatctgtt aaactctagg gtgtgtgatt tagccggtga cggtggttta atatgtgtaa      900
tttcactgct tatagtaatg caattcacct ttgcttgaac atgcattgtc ttgttgcttt      960
gttctataca catgcttagc tattatctga tgagcatgca ctgttttgtt ctgtttgata     1020
tgcatgctca gaaatatgta gatgtgtggc tcctgctcgg ttgttcttta tcatccacct     1080
gttgaacatg catgttcttg tcgcttatct ttattatata ttaccttcgt tctcgaatat     1140
ttgtcgcccg ctagttcatt tttgaactaa accgtgacaa ataaaataga acgtagggag     1200
tggcatcatg ctgctactgt accttacggt ggcaactaca tcttgagcac gcatatatct     1260
tatagtgttc cttttctttt cctccttggt ctactgttat atgcttacct ttttttggtt     1320
tccttgcag                                                             1329
```

<210> SEQ ID NO 119
<211> LENGTH: 1076
<212> TYPE: DNA
<213> ORGANISM: Zea mays

<400> SEQUENCE: 119

```
gacggagatc aacgtcccta tttacattat aattaggaaa tgcatccttt gttattaata       60 aaaacactttt cacttatata tattgttaga tgtaagaaat cattatgggt atattaaaat      120
aaacatattt gtacaatgat tgatctctta cccaaataat tatttgtttt tattattagc      180
tagtatacga aaacatcacc acgtacaggt ttgacggatt cccacagaaa cagggatgaa      240
aaatacttct acatccctgt cccgtttacc catctgagaa agcgggaaat cgggcatagg      300
atccattgcc aaagatcgta gggctataac ctaagcgttg caacgaagcg aagcagacgg      360
tggagacgtt gacgcaaagc aatgaacttg aacggcatct ctctcgctgg ccctggcctt      420
ctcgaaggct ctgcgtgggt ccttgcgcag ttgcgccgca gcgggctggc agcatccgga      480
aattgcgtct tgcgtggcgg agcagacact aaggtactat tttacgttct atttagttgg      540
actgtggcgg taaactatga aaaaaactat tgcagactat gagctattaa aaagctaaaa      600
attatttagt gtaaaccact aaaaaccatt aaaaattctt tgatatatat tttcacagtt      660
ttataaaaaa tccactaaaa acaggtcaaa taagctttca atttttacact acgaaaaagt      720 cagcttttaa aaaaaactgc ttaaatccag tcctttagtt taatttttat cttttaggaa      780
acaaaagcca aaactaaaac caaaccaaac ctacctttaa aaccgatcta ataggaacgc      840
ggtgtttgga acaactagat attaatttta gaggttagac cgccacgaaa gcgtcactgc      900
acacggcatt ccctcccct agcgttatcg tcgcaccata aataaccatc ctctcctcgc      960 cttttccccac atctcatctt cgtctgtgtt cttgggcgta cgcggacaca gccccgatcc     1020
gaatcgtcgt ccttgcgagc ctcgccgatc ccccactccc ctcccctcgc ttcaag         1076
```

<210> SEQ ID NO 120
<211> LENGTH: 42
<212> TYPE: DNA
<213> ORGANISM: Artificial Sequence
<220> FEATURE:
<223> OTHER INFORMATION: TS2 fwd primer

<400> SEQUENCE: 120

```
cctccgcttc aagcgatcgc aggtaactgc gatcatccat cc                          42
```

<210> SEQ ID NO 121
<211> LENGTH: 46
<212> TYPE: DNA
<213> ORGANISM: Artificial Sequence
<220> FEATURE:
<223> OTHER INFORMATION: TS2 rev primer

<400> SEQUENCE: 121
aggctaagtt aaagtcgggt acctgcaagg aaaccaaaaa aaggta         46

<210> SEQ ID NO 122
<211> LENGTH: 42
<212> TYPE: DNA
<213> ORGANISM: Artificial Sequence
<220> FEATURE:
<223> OTHER INFORMATION: pTS2 fwd primer

<400> SEQUENCE: 122
tcgaagcttg gcgcgccgac ggagatcaac gtccctattt ac             42

<210> SEQ ID NO 123
<211> LENGTH: 42
<212> TYPE: DNA
<213> ORGANISM: Artificial Sequence
<220> FEATURE:
<223> OTHER INFORMATION: pTS2_TS2 rev primer

<400> SEQUENCE: 123
acaggacgga ccatggctgc aaggaaacca aaaaaggta ag              42

<210> SEQ ID NO 124
<211> LENGTH: 42
<212> TYPE: DNA
<213> ORGANISM: Artificial Sequence
<220> FEATURE:
<223> OTHER INFORMATION: pTS2 reverse primer

<400> SEQUENCE: 124
acaggacgga ccatggcctt gaagcgaggg gaggggagtg gg             42

<210> SEQ ID NO 125
<211> LENGTH: 33
<212> TYPE: DNA
<213> ORGANISM: Artificial Sequence
<220> FEATURE:
<223> OTHER INFORMATION: pTS1 fwd primer

<400> SEQUENCE: 125
cttggcgcgc ctgccacgca aactaaaagg caa                       33

<210> SEQ ID NO 126
<211> LENGTH: 42
<212> TYPE: DNA
<213> ORGANISM: Artificial Sequence
<220> FEATURE:
<223> OTHER INFORMATION: pTS1 rev primer

<400> SEQUENCE: 126
cctgcgatcg cggtggcaag ctcgagatgg ggagccgcta ct             42

<210> SEQ ID NO 127
<211> LENGTH: 39
<212> TYPE: DNA
<213> ORGANISM: Artificial Sequence
<220> FEATURE:

<223> OTHER INFORMATION: pTS27 fwd primer

<400> SEQUENCE: 127
tcgaagcttg gcgcgccccg gctataccgc tcccgccct                    39

<210> SEQ ID NO 128
<211> LENGTH: 42
<212> TYPE: DNA
<213> ORGANISM: Artificial Sequence
<220> FEATURE:
<223> OTHER INFORMATION: pTS27 rev primer

<400> SEQUENCE: 128
ggatgcctca cctgcgatcg caggacgaag cggcgatcgg gc                42

<210> SEQ ID NO 129
<211> LENGTH: 21
<212> TYPE: DNA
<213> ORGANISM: Artificial Sequence
<220> FEATURE:
<223> OTHER INFORMATION: GUS-F primer

<400> SEQUENCE: 129
cttacgtggc aaaggattcg a                                       21

<210> SEQ ID NO 130
<211> LENGTH: 20
<212> TYPE: DNA
<213> ORGANISM: Artificial Sequence
<220> FEATURE:
<223> OTHER INFORMATION: GUS-R primer

<400> SEQUENCE: 130
gccccaatcc agtccattaa                                         20

<210> SEQ ID NO 131
<211> LENGTH: 21
<212> TYPE: DNA
<213> ORGANISM: Artificial Sequence
<220> FEATURE:
<223> OTHER INFORMATION: Gr5-F primer

<400> SEQUENCE: 131
ggcagtttgg ttgatgctca t                                       21

<210> SEQ ID NO 132
<211> LENGTH: 26
<212> TYPE: DNA
<213> ORGANISM: Artificial Sequence
<220> FEATURE:
<223> OTHER INFORMATION: Gr5-R primer

<400> SEQUENCE: 132
tgctgtatat ctttgctttg aaccat                                  26

<210> SEQ ID NO 133
<211> LENGTH: 23
<212> TYPE: DNA
<213> ORGANISM: Artificial Sequence
<220> FEATURE:
<223> OTHER INFORMATION: GUS probe

<400> SEQUENCE: 133
aacgtgctga tggtgcacga cca                                     23

```
<210> SEQ ID NO 134
<211> LENGTH: 17
<212> TYPE: DNA
<213> ORGANISM: Artificial Sequence
<220> FEATURE:
<223> OTHER INFORMATION: Gr5 probe

<400> SEQUENCE: 134
ttgaagtcac aaagcca                                                    17

<210> SEQ ID NO 135
<211> LENGTH: 50976
<212> TYPE: DNA
<213> ORGANISM: Artificial Sequence
<220> FEATURE:
<223> OTHER INFORMATION: vector sequence

<400> SEQUENCE: 135
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagcaag    180
ctggtacgat tgtaatacga ctcactatag ggcgaattga gcgctgttta acgctcttc    240 aactggaaga gcggttaccc ggaccggaat tcgagctcgg tacgatatca acaagtttgt    300
acaaaaaagc aggtttaaac ttcgaaacgc gtggaccgaa gcttgcatgc ctgcagtgca    360
gcgtgacccg gtcgtgcccc tctctagaga taatgagcat tgcatgtcta agttataaaa    420
aattaccaca tatttttttt gtcacacttg tttgaagtgc agtttatcta tctttataca    480
tatatttaaa ctttactcta cgaataatat aatctatagt actacaataa tatcagtgtt    540
ttagagaatc atataaatga acagttagac atggtctaaa ggacaattga gtattttgac    600
aacaggactc tacagtttta tcttttagt gtgcatgtgt tctccttttt ttttgcaaat    660
agcttcacct atataatact tcatccattt tattagtaca tccatttagg gtttagggtt    720
aatggttttt atagactaat ttttttagta catctatttt attctatttt agcctctaaa    780
ttaagaaaac taaaactcta ttttagtttt tttatttaat aatttagata taaaatagaa    840
taaaataaag tgactaaaaa ttaaacaaat acccttaag aaattaaaaa aactaaggaa    900 acattttct tgtttcgagt agataatgcc agcctgttaa acgccgtcga cgagtctaac    960
ggacaccaac cagcgaacca gcagcgtcgc gtcgggccaa gcgaagcaga cggcacggca   1020
tctctgtcgc tgcctctgga cccctctcga gagttccgct ccaccgttgg acttgctccg   1080
ctgtcggcat ccagaaattg cgtggcgag cggcagacgt gagccggcac ggcaggcggc   1140
ctcctcctcc tctcacggca ccggcagcta cggggattc ctttcccacc gctccttcgc   1200
tttcccttcc tcgcccgccg taataaatag acaccccgc cacaccctct ttccccaacc   1260
tcgtgttgtt cggagcgcac acacacacaa ccagatctcc cccaaatcca cccgtcggca   1320
cctccgcttc aaggtacgcc gctcgtcctc cccccccccc cctctctacc ttctctagat   1380
cggcgttccg gtccatggtt agggcccggt agttctactt ctgttcatgt ttgtgttaga   1440
tccgtgtttg tgttagatcc gtgctgctag cgttcgtaca cggatgcgac ctgtacgtca   1500
gacacgttct gattgctaac ttgccagtgt ttctctttgg ggaatcctgg gatggctcta   1560
gccgttccgc agacgggatc gatttcatga ttttttttgt ttcgttgcat agggtttggt   1620
ttgccctttt cctttatttc aatatatgcc gtgcacttgt ttgtcgggtc atcttttcat   1680 gcttttttttt gtcttggttg tgatgatgtg gtctggttgg gcggtcgttc tagatcggag   1740
```

```
tagaattctg tttcaaacta cctggtggat ttattaattt tggatctgta tgtgtgtgcc   1800
atacatattc atagttacga attgaagatg atggatggaa atatcgatct aggataggta   1860
tacatgttga tgcgggtttt actgatgcat atacagagat gcttttttgtt cgcttggttg   1920 tgatgatgtg gtgtggttgg gcggtcgttc attcgttcta gatcggagta gaatactgtt   1980
tcaaactacc tggtgtattt attaattttg aactgtatg tgtgtgtcat acatcttcat    2040
agttacgagt ttaagatgga tggaaatatc gatctaggat aggtatacat gttgatgtgg   2100
gttttactga tgcatataca tgatggcata tgcagcatct attcatatgc tctaaccttg   2160
agtacctatc tattataata aacaagtatg ttttataatt attttgatct tgatatactt   2220
ggatgatggc atatgcagca gctatatgtg gatttttta gccctgcctt catacgctat    2280
ttatttgctt ggtactgttt cttttgtcga tgctcaccct gttgtttggt gttacttctg   2340
caggtcgact ctagacagct tcttgtaca aagtggtcga tatcgatcca ccatggtccg   2400
tcctgtagaa accccaaccc gtgaaatcaa aaaactcgac ggcctgtggg cattcagtct   2460
ggatcgcgaa aactgtggaa ttgatcagcg ttggtgggaa agcgcgttac aagaaagccg   2520
ggcaattgct gtgccaggca gttttaacga tcagttcgcc gatgcagata ttcgtaatta   2580
tgcgggcaac gtctggtatc agcgcgaagt ctttataccg aaaggttggg caggccagcg   2640
tatcgtgctg cgtttcgatg cggtcactca ttacggcaaa gtgtgggtca ataatcagga   2700
agtgatggag catcagggcg gctatacgcc atttgaagcc gatgtcacgc cgtatgttat   2760
tgccgggaaa agtgtacgta agtttctgct tctacctttg atatatatat aataattatc   2820
attaattagt agtaatataa tatttcaaat attttttca aaataaaga atgtagtata    2880 tagcaattgc ttttctgtag tttataagtg tgtatatttt aatttataac ttttctaata  2940
tatgaccaaa acatggtgat gtgcaggtat caccgtttgt gtgaacaacg aactgaactg   3000
gcagactatc ccgccgggaa tggtgattac cgacgaaaac ggcaagaaaa agcagtctta   3060
cttccatgat ttctttaact atgccggaat ccatcgcagc gtaatgctct acaccacgcc   3120
gaacacctgg gtggacgata tcaccgtggt gacgcatgtc gcgcaagact gtaaccacgc   3180
gtctgttgac tgccaggtgg tggccaatgg tgatgtcagc gttgaactgc gtgatgcgga   3240
tcaacaggtg gttgcaactg gacaaggcac tagcgggact ttgcaagtgg tgaatccgca   3300
cctctgccaa ccgggtgaag gttatctcta tgaactgtgc gtcacagcca aaagccagac   3360
agagtgtgat atctacccgc ttcgcgtcgg catccggtca gtggcagtga agggccaaca   3420
gttcctgatt aaccacaaac cgttctactt tactggcttt ggtcgtcatg aagatgcgga   3480
cttacgtggc aaaggattcg ataacgtgct gatggtgcac gaccacgcat taatggactg   3540
gattggggcc aactcctacc gtacctcgca ttacccttac gctgaagaga tgctcgactg   3600
ggcagatgaa catggcatcg tggtgattga tgaaactgct gctgtcggct ttaacctctc   3660
tttaggcatt ggtttcgaag cgggcaacaa gccgaaagaa ctgtacagcg aagaggcagt   3720 caacgggaa actcagcaag cgcacttaca ggcgattaaa gagctgatag cgcgtgacaa    3780
aaaccaccca agcgtggtga tgtggagtat tgccaacgaa ccggatacccc gtccgcaagt   3840 gcacgggaat atttcgccac tggcggaagc aacgcgtaaa ctcgacccga cgcgtccgat   3900
cacctgcgtc aatgtaatgt tctgcgacgc tcacaccgat accatcagcg atctctttga   3960
tgtgctgtgc ctgaaccgtt attacgatg gtatgtccaa agcggcgatt tggaaacggc   4020
agagaaggta ctggaaaaag aacttctggc ctggcaggag aaactgcatc agccgattat   4080
catcaccgaa tacggcgtgg atacgttagc cgggctgcac tcaatgtaca ccgacatgtg   4140
```

```
gagtgaagag tatcagtgtg catggctgga tatgtatcac cgcgtctttg atcgcgtcag    4200
cgccgtcgtc ggtgaacagg tatggaattt cgccgatttt gcgacctcgc aaggcatatt    4260
gcgcgttggc ggtaacaaga aagggatctt cactcgcgac cgcaaaccga agtcggcggc    4320
ttttctgctg caaaaacgct ggactggcat gaacttcggt gaaaaaccgc agcagggagg    4380
caaacaatga atcaacaact ctcctggcgc accatcgtcg gctacagcct cggtgacgtg    4440
gggcaaccta gacttgtcca tcttctggat tggccaactt aattaatgta tgaaataaaa    4500
ggatgcacac atagtgacat gctaatcact ataatgtggg catcaaagtt gtgtgttatg    4560
tgtaattact agttatctga ataaaagaga aagagatcat ccatatttct tatcctaaat    4620
gaatgtcacg tgtctttata attctttgat gaaccagatg catttcatta accaaatcca    4680
tatacatata aatattaatc atatataatt aatatcaatt gggttagcaa aacaaatcta    4740
gtctaggtgt gttttgcgaa ttgcggccgc gatctgagct tctagagtcg acctgcaggc    4800
atgcccgcgg atatcgatgg gccccggccg aagcttcggt ccgggtcacc tttgtccacc    4860
aagatggaac tgcggccgct cattaattaa gtcaggcgcg cctctagttg aagacacgtt    4920
catgtcttca tcgtaagaag acactcagta gtcttcggcc agaatggcca tctggattca    4980
gcaggcctag aaggccattt aaatcctgag gatctggtct tcctaaggac ccgggatatc    5040
ggaccgatta aactttaatt cggtccgaag cttgcatgcc tgcagtgcag cgtgacccgg    5100
tcgtgcccct ctctagagat aatgagcatt gcatgtctaa gttataaaaa attaccacat    5160 atttttttg tcacacttgt ttgaagtgca gtttatctat ctttatacat atatttaaac    5220
tttactctac gaataatata atctatagta ctacaataat atcagtgttt tagagaatca    5280
tataaatgaa cagttagaca tggtctaaag gacaattgag tattttgaca acaggactct    5340
acagttttat cttttagtg tgcatgtgtt ctccttttt tttgcaaata gcttcaccta    5400
tataatactt catccatttt attagtacat ccatttaggg tttagggtta atggtttta    5460 tagactaatt tttttagtac atctattta ttctatttta gcctctaaat taagaaaact    5520
aaaactctat tttagtttt ttatttaata atttagatat aaaatagaat aaaataaagt    5580
gactaaaaat taaacaaata ccctttaaga aattaaaaaa actaaggaaa catttttctt    5640
gtttcgagta gataatgcca gcctgttaaa cgccgtcgac gagtctaacg gacaccaacc    5700
agcgaaccag cagcgtcgcg tcgggccaag cgaagcagac ggcacggcat ctctgtcgct    5760
gcctctggac ccctctcgag agttccgctc caccgttgga cttgctccgc tgtcggcatc    5820
cagaaattgc gtggcggagc ggcagacgtg agccggcacg gcaggcgcc tcctcctcct    5880 ctcacggcac cggcagctac gggggattcc tttcccaccg ctccttcgct ttcccttcct    5940
cgcccgccgt aataaataga cacccctcc acacctctt tccccaacct cgtgttgttc    6000
ggagcgcaca cacacacaac cagatctccc ccaaatccac ccgtcggcac tccgcttca    6060 aggtacgccg ctcgtcctcc ccccccccc tctctacctt ctctagatcg gcgttccggt    6120
ccatggttag ggcccggtag ttctacttct gttcatgttt gtgttagatc cgtgtttgtg    6180
ttagatccgt gctgctagcg ttcgtacacg gatgcgacct gtacgtcaga cacgttctga    6240
ttgctaactt gccagtgttt ctctttgggg aatcctggga tggctctagc cgttccgcag    6300
acgggatcga tttcatgatt tttttgttt cgttgcatag ggtttggttt gcccttttcc    6360
tttatttcaa tatatgccgt gcacttgttt gtcgggtcat cttttcatgc ttttttttgt    6420
cttggttgtg atgatgtggt ctggttgggc ggtcgttcta gatcggagta gaattctgtt    6480
```

```
tcaaactacc tggtggattt attaattttg gatctgtatg tgtgtgccat acatattcat    6540
agttacgaat tgaagatgat ggatggaaat atcgatctag gataggtata catgttgatg    6600
cgggttttac tgatgcatat acagagatgc tttttgttcg cttggttgtg atgatgtggt    6660
gtggttgggc ggtcgttcat tcgttctaga tcggagtaga atactgtttc aaactacctg    6720
gtgtatttat taattttgga actgtatgtg tgtgtcatac atcttcatag ttacgagttt    6780
aagatggatg gaaatatcga tctaggatag gtatacatgt tgatgtgggt tttactgatg    6840
catatacatg atggcatatg cagcatctat tcatatgctc taaccttgag tacctatcta    6900
ttataataaa caagtatgtt ttataattat tttgatcttg atatacttgg atgatggcat    6960
atgcagcagc tatatgtgga tttttttagc cctgccttca tacgctattt atttgcttgg    7020
tactgtttct tttgtcgatg ctcaccctgt tgtttggtgt tacttctgca ggtcgaccgc    7080
cggggatcca cacgacacca tggctattga ggttaagcct atcaacgcag aggatacctg    7140
tgaccttagg catagagtgc tcagaccaaa ccagcctatc gaagcctgca tgtttgagtc    7200
tgaccttact aggagtgcat ttcaccttgg tggattctac ggaggtaaac tgatttccgt    7260
ggcttcattc caccaagctg agcactctga acttcaaggt aagaagcagt accagcttag    7320
aggtgtggct accttggaag gttatagaga gcagaaggct ggttccagtc tcgtgaaaca    7380
cgctgaagag attctcagaa agagaggtgc tgacatgatc tggtgtaatg ccaggacatc    7440
tgcttcagga tactacagga agttgggatt cagtgagcaa ggagaggtgt tcgatactcc    7500
tccagttgga cctcacatcc tgatgtataa gaggatcaca taagagatct gagtcgaaac    7560
ctagacttgt ccatcttctg gattggccaa cttaattaat gtatgaaata aaaggatgca    7620
cacatagtga catgctaatc actataatgt gggcatcaaa gttgtgtgtt atgtgtaatt    7680
actagttatc tgaataaaag agaaagagat catccatatt tcttatccta aatgaatgtc    7740
acgtgtcttt ataattcttt gatgaaccag atgcatttca ttaaccaaat ccatatacat    7800
ataaatatta atcatatata attaatatca attgggttag caaaacaaat ctagtctagg    7860
tgtgttttgc gaattgcggc cgccaccgcg gtggagctcg aattcattcc gattaatcgt    7920
ggcctcttgc tcttcaggat gaagagctat gtttaaacgt gcaagcgcta ctagacaatt    7980
cagtacatta aaaacgtccg caatgtgtta ttaagttgtc taagcgtcaa tttgtttaca    8040
ccacaatata tcctgccacc agccagccaa cagctccccg accggcagct cggcacaaaa    8100
tcaccactcg ataccaggcag cccatcagtc cgggacggcg tcagcgggag agccgttgta    8160
aggcggcaga ctttgctcat gttaccgatg ctattcggaa gaacggcaac taagctgccg    8220
ggtttgaaac acggatgatc tcgcggaggg tagcatgttg attgtaacga tgacagagcg    8280
ttgctgcctg tgatcaaata tcatctccct cgcagagatc cgaattatca gccttcttat    8340
tcatttctcg cttaaccgtg acaggctgtc gatcttgaga actatgccga cataatagga    8400
aatcgctgga taaagccgct gaggaagctg agtggcgcta tttctttaga agtgaacgtt    8460
gacgatcgtc gaccgtaccc cgatgaatta attcggacgt acgttctgaa cacagctgga    8520
tacttacttg ggcgattgtc atacatgaca tcaacaatgt acccgtttgt gtaaccgtct    8580
cttggaggtt cgtatgacac tagtggttcc cctcagcttg cgactagatg ttgaggccta    8640
acatttattt agagagcagg ctagttgctt agatacatga tcttcaggcc gttatctgtc    8700
agggcaagcg aaaattggcc atttatgacg accaatgccc cgcagaagct cccatctttg    8760
ccgccataga cgccgcgccc ccttttgggg gtgtagaaca tccttttgcc agatgtggaa    8820
aagaagttcg ttgtcccatt gttggcaatg acgtagtagc cggcgaaagt gcgagaccca    8880
```

```
tttgcgctat atataagcct acgatttccg ttgcgactat tgtcgtaatt ggatgaacta    8940
ttatcgtagt tgctctcaga gttgtcgtaa tttgatggac tattgtcgta attgcttatg    9000
gagttgtcgt agttgcttgg agaaatgtcg tagttggatg gggagtagtc atagggaaga    9060
cgagcttcat ccactaaaac aattggcagg tcagcaagtg cctgcccga tgccatcgca     9120
agtacgaggc ttagaaccac cttcaacaga tcgcgcatag tcttccccag ctctctaacg    9180
cttgagttaa gccgcgccgc gaagcggcgt cggcttgaac gaattgttag acattatttg    9240
ccgactacct tggtgatctc gcctttcacg tagtgaacaa attcttccaa ctgatctgcg    9300
cgcgaggcca agcgatcttc ttgtccaaga taagcctgcc tagcttcaag tatgacgggc    9360
tgatactggg ccggcaggcg ctccattgcc cagtcggcag cgacatcctt cggcgcgatt    9420
ttgccggtta ctgcgctgta ccaaatgcgg gacaacgtaa gcactacatt tcgctcatcg    9480
ccagcccagt cgggcggcga gttccatagc gttaaggttt catttagcgc ctcaaataga    9540
tcctgttcag gaaccggatc aaagagttcc tccgccgctg gacctaccaa ggcaacgcta    9600
tgttctcttg cttttgtcag caagatagcc agatcaatgt cgatcgtggc tggctcgaag    9660
atacctgcaa gaatgtcatt gcgctgccat tctccaaatt gcagttcgcg cttagctgga    9720
taacgccacg gaatgatgtc gtcgtgcaca acaatggtga cttctacagc gcggagaatc    9780
tcgctctctc caggggaagc cgaagtttcc aaaaggtcgt tgatcaaagc tcgccgcgtt    9840
gtttcatcaa gccttacagt caccgtaacc agcaaatcaa tatcactgtg tggcttcagg    9900
ccgccatcca ctgcggagcc gtacaaatgt acggccagca acgtcggttc gagatggcgc    9960
tcgatgacgc caactacctc tgatagttga gtcgatactt cggcgatcac cgcttccctc   10020
atgatgttta actcctgaat taagccgcgc cgcgaagcgg tgtcggcttg aatgaattgt   10080
taggcgtcat cctgtgctcc cgagaaccag taccagtaca tcgctgtttc gttcgagact   10140
tgaggtctag ttttatacgt gaacaggtca atgccgccga gagtaaagcc acattttgcg   10200
tacaaattgc aggcaggtac attgttcgtt tgtgtctcta atcgtatgcc aaggagctgt   10260
ctgcttagtg cccactttt cgcaaattcg atgagactgt gcgcgactcc tttgcctcgg    10320
tgcgtgtgcg acacaacaat gtgttcgata gaggctagat cgttccatgt tgagttgagt   10380
tcaatcttcc cgacaagctc ttggtcgatg aatgcgccat agcaagcaga gtcttcatca   10440
gagtcatcat ccgagatgta atccttccgg taggggctca cacttctggt agatagttca   10500
aagccttggt cggataggtg cacatcgaac acttcacgaa caatgaaatg gttctcagca   10560
tccaatgttt ccgccacctg ctcagggatc accgaaatct tcatatgacg cctaacgcct   10620
ggcacagcgg atcgcaaacc tggcgcggct tttggcacaa aaggcgtgac aggtttgcga   10680
atccgttgct gccacttgtt aacccttttg ccagatttgg taactataat ttatgttaga   10740
ggcgaagtct tgggtaaaaa ctggcctaaa attgctgggg atttcaggaa agtaaacatc   10800
accttccggc tcgatgtcta ttgtagatat atgtagtgta tctacttgat cggggggatct  10860
gctgcctcgc gcgtttcggt gatgacggtg aaaacctctg acacatgcag ctcccggaga   10920
cggtcacagc ttgtctgtaa gcggatgccg ggagcagaca agcccgtcag ggcgcgtcag   10980
cgggtgttgg cgggtgtcgg ggcgcagcca tgacccagtc acgtagcgat agcggagtgt   11040
atactggctt aactatgcgg catcagagca gattgtactg agagtgcacc atatgcggtg   11100
tgaaataccg cacagatgcg taaggagaaa ataccgcatc aggcgctctt ccgcttcctc   11160
gctcactgac tcgctgcgct cggtcgttcg gctgcggcga gcggtatcag ctcactcaaa   11220
```

-continued

```
ggcggtaata cggttatcca cagaatcagg ggataacgca ggaaagaaca tgtgagcaaa    11280
aggccagcaa aaggccagga accgtaaaaa ggccgcgttg ctggcgtttt tccataggct    11340
ccgcccccct gacgagcatc acaaaaatcg acgctcaagt cagaggtggc gaaacccgac    11400
aggactataa agataccagg cgtttccccc tggaagctcc ctcgtgcgct ctcctgttcc    11460
gaccctgccg cttaccggat acctgtccgc ctttctccct tcgggaagcg tggcgctttc    11520
tcatagctca cgctgtaggt atctcagttc ggtgtaggtc gttcgctcca agctgggctg    11580
tgtgcacgaa ccccccgttc agcccgaccg ctgcgcctta tccggtaact atcgtcttga    11640
gtccaacccg gtaagacacg acttatcgcc actggcagca gccactggta acaggattag    11700
cagagcgagg tatgtaggcg gtgctacaga gttcttgaag tggtggccta actacggcta    11760
cactagaagg acagtatttg gtatctgcgc tctgctgaag ccagttacct tcggaaaaag    11820
agttggtagc tcttgatccg gcaaacaaac caccgctggt agcggtggtt tttttgtttg    11880
caagcagcag attacgcgca gaaaaaaagg atctcaagaa gatcctttga tcttttctac    11940
ggggtctgac gctcagtgga acgaaaactc acgttaaggg attttggtca tgagattatc    12000
aaaaaggatc ttcacctaga tccttttaaa ttaaaaatga agttttaaat caatctaaag    12060
tatatatgag taaacttggt ctgacagtta ccaatgctta atcagtgagg cacctatctc    12120
agcgatctgt ctatttcgtt catccatagt tgcctgactc cccgtcgtgt agataactac    12180
gatacgggag ggcttaccat ctggccccag tgctgcaatg ataccgcgag acccacgctc    12240
accggctcca gatttatcag caataaacca gccagccgga agggccgagc gcagaagtgg    12300
tcctgcaact ttatccgcct ccatccagtc tattaattgt tgccgggaag ctagagtaag    12360
tagttcgcca gttaatagtt tgcgcaacgt tgttgccatt gctgcagggg gggggggggg    12420 ggggggacttc cattgttcat tccacggaca aaaacagaga aggaaacga cagaggccaa    12480 aaagcctcgc tttcagcacc tgtcgtttcc tttcttttca gagggtattt taaataaaaa    12540
cattaagtta tgacgaagaa gaacggaaac gccttaaacc ggaaaatttt cataaatagc    12600
gaaaacccgc gaggtcgccg ccccgtaacc taacctgtcg gatcaccgga aaggacccgt    12660
aaagtgataa tgattatcat ctacatatca caacgtgcgt ggaggccatc aaaccacgtc    12720
aaataatcaa ttatgacgca ggtatcgtat taattgatct gcatcaactt aacgtaaaaa    12780
caacttcaga caatacaaat cagcgacact gaatacgggg caacctcatg tccccccccc    12840 cccccccct gcaggcatcg tggtgtcacg ctcgtcgttt ggtatggctt cattcagctc    12900
cggttcccaa cgatcaaggc gagttacatg atccccatg ttgtgcaaaa aagcggttag    12960
ctccttcggt cctccgatcg ttgtcagaag taagttggcc gcagtgttat cactcatggt    13020
tatggcagca ctgcataatt ctcttactgt catgccatcc gtaagatgct tttctgtgac    13080
tggtgagtac tcaaccaagt cattctgaga atagtgtatg cggcgaccga gttgctcttg    13140
cccggcgtca cacgggata taccgcgcc acatagcaga actttaaaag tgctcatcat    13200
tggaaaacgt tcttcggggc gaaaactctc aaggatctta ccgctgttga gatccagttc    13260
gatgtaaccc actcgtgcac ccaactgatc ttcagcatct tttactttca ccagcgtttc    13320
tgggtgagca aaaacaggaa ggcaaaatgc cgcaaaaaag gaataagggc gacacggaa    13380 atgttgaata ctcatactct tcctttttca atattattga agcatttatc agggttattg    13440
tctcatgagc ggatacatat ttgaatgtat ttagaaaaat aaacaaatag gggttccgcg    13500
cacatttccc cgaaaagtgc cacctgacgt ctaagaaacc attattatca tgacattaac    13560
ctataaaaat aggcgtatca cgaggccctt tcgtcttcaa gaattcggag cttttgccat    13620
```

```
tctcaccgga ttcagtcgtc actcatggtg atttctcact tgataacctt attttttgacg   13680
agggggaaatt aataggttgt attgatgttg dacgagtcgg aatcgcagac cgataccagg    13740
atcttgccat cctatggaac tgcctcggtg agttttctcc ttcattacag aaacggcttt    13800
ttcaaaaata tggtattgat aatcctgata tgaataaatt gcagtttcat ttgatgctcg    13860
atgagttttt ctaatcagaa ttggttaatt ggttgtaaca ctggcagagc attacgctga    13920
cttgacggga cggcggcttt gttgaataaa tcgaactttt gctgagttga aggatcagat    13980
cacgcatctt cccgacaacg cagaccgttc cgtggcaaag caaaagttca aaatcaccaa    14040
ctggtccacc tacaacaaag ctctcatcaa ccgtggctcc ctcactttct ggctggatga    14100
tggggcgatt caggcctggt atgagtcagc aacaccttct tcacgaggca gacctcagcg    14160
ccagaaggcc gccagagagg ccgagcgcgg ccgtgaggct tggacgctag gcagggcat    14220
gaaaaagccc gtagcgggct gctacgggcg tctgacgcgg tggaagggg gaggggatgt    14280
tgtctacatg gctctgctgt agtgagtggg ttgcgctccg gcagcggtcc tgatcaatcg    14340
tcacccttc tcggtccttc aacgttcctg acaacgagcc tccttttcgc caatccatcg    14400
acaatcaccg cgagtccctg ctcgaacgct cgtccggac cggcttcgtc gaaggcgtct    14460
atcgcggccc gcaacagcgg cgagagcgga gcctgttcaa cggtgccgcc gcgctcgccg    14520
gcatcgctgt cgccggcctg ctcctcaagc acggcccaa cagtgaagta gctgattgtc    14580
atcagcgcat tgacggcgtc cccggccgaa aaacccgcct cgcagaggaa gcgaagctgc    14640
gcgtcggccg tttccatctg cggtgcgccc ggtcgcgtgc cggcatggat gcgcgcgcca    14700
tcgcggtagg cgagcagcgc ctgcctgaag ctgcgggcat tcccgatcag aaatgagcgc    14760
cagtcgtcgt cggctctcgg caccgaatgc gtatgattct ccgccagcat ggcttcggcc    14820
agtgcgtcga gcagcgcccg cttgttcctg aagtgccagt aaagcgccgg ctgctgaacc    14880
cccaaccgtt ccgccagttt gcgtgtcgtc agaccgtcta cgccgacctc gttcaacagg    14940
tccagggcgg cacggatcac tgtattcggc tgcaactttg tcatgcttga cactttatca    15000
ctgataaaca taatatgtcc accaacttat cagtgataaa gaatccgcgc gttcaatcgg    15060
accagcggag gctggtccgg aggccagacg tgaaacccaa cataccctg atcgtaattc    15120
tgagcactgt cgcgctcgac gctgtcggca tcggcctgat tatgccggtg ctgccgggcc    15180
tcctgcgcga tctggttcac tcgaacgacg tcaccgccca ctatggcatt ctgctggcgc    15240
tgtatgcgtt ggtgcaattt gcctgcgcac ctgtgctggg cgcgctgtcg gatcgtttcg    15300
ggcggcggcc aatcttgctc gtctcgctgg ccggcgccac tgtcgactac gccatcatgg    15360
cgacagcgcc tttcctttgg gttctctata tcgggcggat cgtggccggc atcaccgggg    15420
cgactggggc ggtagccggc gcttatattg ccgatatcac tgatggcgat gagcgcgcgc    15480
ggcacttcgg cttcatgagc gcctgtttcg ggttcgggat ggtcgcggga cctgtgctcg    15540
gtgggctgat gggcggtttc tcccccacg ctccgttctt cgccgcggca gccttgaacg    15600
gcctcaattt cctgacgggc tgtttccttt tgccggagtc gcacaaaggc gaacgccggc    15660
cgttacgccg ggaggctctc aacccgctcg cttcgttccg gtgggccgg gcatgaccg    15720
tcgtcgccgc cctgatggcg gtcttcttca tcatgcaact tgtcggacag gtgccggccg    15780
cgctttgggt cattttcggc gaggatcgct ttcactggga cgcgaccacg atcggcattt    15840
cgcttgccgc atttggcatt ctgcattcac tcgcccaggc aatgatcacc ggccctgtag    15900
ccgcccggct cggcgaaagg cgggcactca tgctcggaat gattgccgac ggcacaggct    15960
```

```
acatcctgct tgccttcgcg acacggggat ggatggcgtt cccgatcatg gtcctgcttg   16020
cttcgggtgg catcggaatg ccggcgctgc aagcaatgtt gtccaggcag gtggatgagg   16080
aacgtcaggg gcagctgcaa ggctcactgg cggcgctcac cagcctgacc tcgatcgtcg   16140 gaccctcct cttcacggcg atctatgcgg cttctataac aacgtggaac gggtgggcat    16200
ggattgcagg cgctgccctc tacttgctct gcctgccggc gctgcgtcgc gggctttgga   16260
gcggcgcagg gcaacgagcc gatcgctgat cgtggaaacg ataggcctat gccatgcggg   16320
tcaaggcgac ttccggcaag ctatacgcgc cctaggagtg cggttggaac gttggcccag   16380
ccagatactc ccgatcacga gcaggacgcc gatgatttga agcgcactca gcgtctgatc   16440
caagaacaac catcctagca acacggcggt ccccgggctg agaaagccca gtaaggaaac   16500
aactgtaggt tcgagtcgcg agatcccccg gaaccaaagg aagtaggtta aacccgctcc   16560
gatcaggccg agccacgcca ggccgagaac attggttcct gtaggcatcg ggattggcgg   16620
atcaaacact aaagctactg gaacgagcag aagtcctccg gccgccagtt gccaggcggt   16680
aaaggtgagc agaggcacgg gaggttgcca cttgcgggtc agcacggttc cgaacgccat   16740
ggaaaccgcc cccgccaggc ccgctgcgac gccgacagga tctagcgctg cgtttggtgt   16800
caacaccaac agcgccacgc ccgcagttcc gcaaatagcc cccaggaccg ccatcaatcg   16860
tatcgggcta cctagcagag cggcagagat gaacacgacc atcagcggct gcacagcgcc   16920
taccgtcgcc gcgaccccgc ccggcaggcg gtagaccgaa ataaacaaca agctccagaa   16980
tagcgaaata ttaagtgcgc cgaggatgaa gatgcgcatc caccagattc ccgttggaat   17040
ctgtcggacg atcatcacga gcaataaacc cgccggcaac gcccgcagca gcataccggc   17100
gacccctcgg cctcgctgtt cgggctccac gaaaacgccg gacagatgcg ccttgtgagc   17160
gtccttgggg ccgtcctcct gtttgaagac cgacagccca atgatctcgc cgtcgatgta   17220
ggcgccgaat gccacggcat ctcgcaaccg ttcagcgaac gcctccatgg gcttttctc    17280 ctcgtgctcg taaacggacc cgaacatctc tggagctttc ttcagggccg acaatcggat   17340
ctcgcggaaa tcctgcacgt cggccgctcc aagccgtcga atctgagcct taatcacaat   17400
tgtcaatttt aatcctctgt ttatcggcag ttcgtagagc gcgccgtgcg tcccgagcga   17460
tactgagcga agcaagtgcg tcgagcagtg cccgcttgtt cctgaaatgc cagtaaagcg   17520
ctggctgctg aacccccagc cggaactgac cccacaaggc cctagcgttt gcaatgcacc   17580
aggtcatcat tgacccaggc gtgttccacc aggccgctgc ctcgcaactc ttcgcaggct   17640
tcgccgacct gctcgcgcca cttcttcacg cgggtggaat ccgatccgca catgaggcgg   17700
aaggtttcca gcttgagcgg gtacggctcc cggtgcgagc tgaaatagtc gaacatccgt   17760
cgggccgtcg gcgacagctt gcggtacttc tcccatatga atttcgtgta gtggtcgcca   17820
gcaaacagca cgacgatttc ctcgtcgatc aggacctggc aacgggacgt tttcttgcca   17880
cggtccagga cgcggaagcg gtgcagcagc gacaccgatt ccaggtgccc aacgcggtcg   17940
gacgtgaagc ccatcgccgt cgcctgtagg cgcgacaggc attcctcggc cttcgtgtaa   18000
taccggccat tgatcgacca gcccaggtcc tggcaaagct cgtagaacgt gaaggtgatc   18060
ggctcgccga taggggtgcg cttcgcgtac tccaacacct gctgccacac cagttcgtca   18120
tcgtcggccc gcagctcgac gccggtgtag gtgatcttca cgtccttgtt gacgtggaaa   18180
atgaccttgt tttgcagcgc ctcgcgcggg attttcttgt tgcgcgtggt gaacagggca   18240
gagcgggccg tgtcgtttgg catcgctcgc atcgtgtccg gccacggcgc aatatcgaac   18300
aaggaaagct gcatttcctt gatctgctgc ttcgtgtgtt tcagcaacgc ggcctgcttg   18360
```

```
gcctcgctga cctgttttgc caggtcctcg ccggcggttt ttcgcttctt ggtcgtcata   18420
gttcctcgcg tgtcgatggt catcgacttc gccaaacctg ccgcctcctg ttcgagacga   18480
cgcgaacgct ccacggcggc cgatggcgcg ggcagggcag ggggagccag ttgcacgctg   18540
tcgcgctcga tcttggccgt agcttgctgg accatcgagc cgacggactg gaaggtttcg   18600
cggggcgcac gcatgacggt gcggcttgcg atggtttcgg catcctcggc ggaaaacccc   18660
gcgtcgatca gttcttgcct gtatgccttc cggtcaaacg tccgattcat tcaccctcct   18720
tgcgggattg ccccgactca cgccggggca atgtgccctt attcctgatt tgacccgcct   18780
ggtgccttgg tgtccagata atccacctta tcggcaatga agtcggtccc gtagaccgtc   18840
tggccgtcct tctcgtactt ggtattccga atcttgccct gcacgaatac cagcgacccc   18900
ttgcccaaat acttgccgtg ggcctcggcc tgagagccaa acacttgat gcggaagaag   18960 tcggtgcgct cctgcttgtc gccggcatcg ttgcgccact cttcattaac cgctatatcg   19020
aaaattgctt gcggcttgtt agaattgcca tgacgtacct cggtgtcacg ggtaagatta   19080
ccgataaact ggaactgatt atggctcata tcgaaagtct ccttgagaaa ggagactcta   19140
gtttagctaa acattggttc cgctgtcaag aactttagcg gctaaaattt tgcgggccgc   19200
gaccaaaggt gcgaggggcg gcttccgctg tgtacaacca gatattttc accaacatcc   19260 ttcgtctgct cgatgagcgg ggcatgacga aacatgagct gtcggagagg gcaggggttt   19320
caatttcgtt tttatcagac ttaaccaacg gtaaggccaa cccctcgttg aaggtgatgg   19380
aggccattgc cgacgccctg gaaactcccc tacctcttct cctggagtcc accgaccttg   19440
accgcgaggc actcgcggag attgcgggtc atcctttcaa gagcagcgtg ccgcccggat   19500
acgaacgcat cagtgtggtt ttgccgtcac ataaggcgtt tatcgtaaag aaatggggcg   19560
acgacacccg aaaaagctg cgtggaaggc tctgacgcca agggttaggg cttgcacttc    19620
cttctttagc cgctaaaacg gcccccttctc tgcgggccgt cggctcgcgc atcatatcga   19680
catcctcaac ggaagccgtg ccgcgaatgg catcgggcgg gtgcgctttg acagttgttt   19740
tctatcagaa ccccctacgtc gtgccggttcg attagctgtt tgtcttgcag gctaaacact   19800
ttcggtatat cgtttgcctg tgcgataatg ttgctaatga tttgttgcgt aggggttact   19860
gaaaagtgag cgggaaagaa gagtttcaga ccatcaagga gcgggccaag cgcaagctgg   19920
aacgcgacat gggtgcggac ctgttggccg cgctcaacga cccgaaaacc gttgaagtca   19980
tgctcaacgc ggacggcaag gtgtggcacg aacgccttgg cgagccgatg cggtacatct   20040
gcgacatgcg gcccagccag tcgcaggcga ttatagaaac ggtggccgga ttccacggca   20100
aagaggtcac gcggcattcg cccatcctgg aaggcgagtt ccccttggat ggcagccgct   20160
ttgccggcca attccgccg gtcgtggccg cgccaacctt tgcgatccgc aagcgcgcgg   20220
tcgccatctt cacgctggaa cagtacgtcg aggcgggcat catgacccgc gagcaatacg   20280
aggtcattaa aagcgccgtc gcggcgcatc gaaacatcct cgtcattggc ggtactggct   20340
cgggcaagac cacgctcgtc aacgcgatca tcaatgaaat ggtcgccttc aacccgtctg   20400
agcgcgtcgt catcatcgag gacaccggcg aaatccagtg cgccgcagag aacgccgtcc   20460
aataccacac cagcatcgac gtctcgatga cgctgctgct caagacaacg ctgccgtatgc   20520 gccccgaccg catcctggtc ggtgaggtac gtggccccga agcccttgat ctgttgatgg   20580
cctggaacac cggggcatgaa ggaggtgccg ccacccctgca cgcaaacaac cccaaagcgg   20640
gcctgagccg gctcgccatg cttatcagca tgcacccgga ttcaccgaaa cccattgagc   20700
```

```
cgctgattgg cgaggcggtt catgtggtcg tccatatcgc caggacccct agcggccgtc    20760
gagtgcaaga aattctcgaa gttcttggtt acgagaacgg ccagtacatc accaaaaccc    20820
tgtaaggagt atttccaatg acaacggctg ttccgttccg tctgaccatg aatcgcggca    20880
ttttgttcta ccttgccgtg ttcttcgttc tcgctctcgc gttatccgcg catccggcga    20940
tggcctcgga aggcaccggc ggcagcttgc catatgagag ctggctgacg aacctgcgca    21000
actccgtaac cggcccggtg gccttcgcgc tgtccatcat cggcatcgtc gtcgccggcg    21060
gcgtgctgat cttcggcggc gaactcaacg ccttcttccg aaccctgatc ttcctggttc    21120
tggtgatggc gctgctggtc ggcgcgcaga acgtgatgag caccttcttc ggtcgtggtg    21180
ccgaaatcgc ggccctcggc aacggggcgc tgcaccaggt gcaagtcgcg gcggcggatg    21240
ccgtgcgtgc ggtagcggct ggacggctcg cctaatcatg gctctgcgca cgatccccat    21300
ccgtcgcgca ggcaaccgag aaaacctgtt catgggtggt gatcgtgaac tggtgatgtt    21360
ctcgggcctg atggcgtttg cgctgatttt cagcgcccaa gagctgcggg ccaccgtggt    21420
cggtctgatc ctgtggttcg gggcgctcta tgcgttccga atcatggcga aggccgatcc    21480
gaagatgcgg ttcgtgtacc tgcgtcaccg ccggtacaag ccgtattacc ggcccgctc     21540 gaccccgttc cgcgagaaca ccaatagcca agggaagcaa taccgatgat ccaagcaatt    21600
gcgattgcaa tcgcgggcct cggcgcgctt ctgttgttca tcctctttgc ccgcatccgc    21660
gcggtcgatg ccgaactgaa actgaaaaag catcgttcca aggacgccgg cctggccgat    21720
ctgctcaact acgccgctgt cgtcgatgac ggcgtaatcg tgggcaagaa cggcagcttt    21780
atggctgcct ggctgtacaa gggcgatgac aacgcaagca gcaccgacca gcagcgcgaa    21840
gtagtgtccg cccgcatcaa ccaggccctc gcgggcctgg aagtgggtg gatgatccat    21900 gtggacgccg tgcggcgtcc tgctccgaac tacgcggagc ggggcctgtc ggcgttccct    21960
gaccgtctga cggcagcgat tgaagaagag cgctcggtct tgccttgctc gtcggtgatg    22020
tacttcacca gctccgcgaa gtcgctcttc ttgatggagc gcatggggac gtgcttggca    22080
atcacgcgca ccccccggcc gttttagcgg ctaaaaaagt catggctctg ccctcgggcg    22140
gaccacgccc atcatgacct tgccaagctc gtcctgcttc tcttcgatct tcgccagcag    22200
ggcgaggatc gtggcatcac cgaaccgcgc cgtgcgcggg tcgtcggtga ccagagtttt    22260
cagcaggccg cccaggcggc ccaggtcgcc attgatgcgg gccagctcgc ggacgtgctc    22320
atagtccacg acgcccgtga ttttgtagcc ctggccgacg gccagcaggt aggccgacag    22380
gctcatgccg gccgccgccg ccttttcctc aatcgctctt cgttcgtctg gaaggcagta    22440
caccttgata ggtgggctgc ccttcctggt tggcttggtt tcatcagcca tccgcttgcc    22500
ctcatctgtt acgccggcgg tagccggcca gcctcgcaga gcaggattcc cgttgagcac    22560
cgccaggtgc gaataaggga cagtgaagaa ggaacacccg ctcgcgggtg gcctacttc     22620 acctatcctg cccggctgac gccgttggat acaccaagga aagtctacac gaaccctttg    22680
gcaaaatcct gtatatcgtg cgaaaaagga tggatatacc gaaaaaatcg ctataatgac    22740
cccgaagcag ggttatgcag cggaaaagcg ctgcttccct gctgttttgt ggaatatcta    22800
ccgactggaa acaggcaaat gcaggaaatt actgaactga ggggacaggc gagagacgat    22860
gccaaagagc tacaccgacg agctggccga gtgggttgaa tcccgcgcgg ccaagaagcg    22920
ccggcgtgat gaggctgcgg ttgcgttcct ggcggtgagg gcggatgtcg aggcggcgtt    22980
agcgtccggc tatgcgctcg tcaccatttg ggagcacatg cggaaacgg  ggaaggtcaa     23040 gttctcctac gagacgttcc gctcgcacgc caggcggcac atcaaggcca agcccgccga    23100
```

```
tgtgcccgca ccgcaggcca aggctgcgga acccgcgccg gcacccaaga cgccggagcc   23160
acggcggccg aagcaggggg gcaaggctga aaagccggcc cccgctgcgg ccccgaccgg   23220
cttcaccttc aacccaacac cggacaaaaa ggatctactg taatggcgaa aattcacatg   23280
gttttgcagg gcaagggcgg ggtcggcaag tcggccatcg ccgcgatcat tgcgcagtac   23340
aagatggaca aggggcagac acccttgtgc atcgacaccg acccggtgaa cgcgacgttc   23400
gagggctaca aggccctgaa cgtccgccgg ctgaacatca tggccggcga cgaaattaac   23460
tcgcgcaact tcgacaccct ggtcgagctg attgcgccga ccaaggatga cgtggtgatc   23520
gacaacggtg ccagctcgtt cgtgcctctg tcgcattacc tcatcagcaa ccaggtgccg   23580
gctctgctgc aagaaatggg gcatgagctg gtcatccata ccgtcgtcac cggcggccag   23640
gctctcctgg acacggtgag cggcttcgcc cagctcgcca gccagttccc ggccgaagcg   23700
cttttcgtgg tctggctgaa cccgtattgg gggcctatcg agcatgaggg caagagcttt   23760
gagcagatga aggcgtacac ggccaacaag gcccgcgtgt cgtccatcat ccagattccg   23820
gccctcaagg aagaaaccta cggccgcgat ttcagcgaca tgctgcaaga gcggctgacg   23880
ttcgaccagg cgctggccga tgaatcgctc acgatcatga cgcggcaacg cctcaagatc   23940
gtgcggcgcg gcctgtttga acagctcgac gcggcggccg tgctatgagc gaccagattg   24000
aagagctgat ccgggagatt gcggccaagc acggcatcgc cgtcggccgc gacgacccgg   24060
tgctgatcct gcataccatc aacgcccggc tcatggccga cagtgcggcc aagcaagagg   24120
aaatccttgc cgcgttcaag gaagagctgg aagggatcgc ccatcgttgg ggcgaggacg   24180
ccaaggccaa agcggagcgg atgctgaacg cggccctggc ggccagcaag gacgcaatgg   24240
cgaaggtaat gaaggacagc gccgcgcagg cggccgaagc gatccgcagg gaaatcgacg   24300
acggccttgg ccgccagctc gcggccaagg tcgcggacgc cggcgcgtg gcgatgatga   24360 acatgatcgc cggcggcatg gtgttgttcg cggccgccct ggtggtgtgg gcctcgttat   24420
gaatcgcaga ggcgcagatg aaaaagcccg gcgttgccgg gctttgtttt tgcgttagct   24480
gggcttgttt gacaggccca agctctgact gcgcccgcgc tcgcgctcct gggcctgttt   24540
cttctcctgc tcctgcttgc gcatcagggc ctggtgccgt cgggctgctt cacgcatcga   24600
atcccagtcg ccggccagct cgggatgctc cgcgcgcatc ttgcgcgtcg ccagttcctc   24660
gatcttgggc gcgtgaatgc ccatgccttc cttgatttcg cgcaccatgt ccagccgcgt   24720
gtgcagggtc tgcaagcggg cttgctgttg ggcctgctgc tgctgccagg cggccttgt   24780 acgcggcagg acagcaagc cggggggcatt ggactgtagc tgctgcaaac gcgcctgctg   24840
acggtctacg agctgttcta ggcggtcctc gatgcgctcc acctggtcat gctttgcctg   24900
cacgtagagc gcaagggtct gctggtaggt ctgctcgatg ggcgcggatt ctaagagggc   24960
ctgctgttcc gtctcggcct cctgggccgc ctgtagcaaa tcctcgccgc tgttgccgct   25020 ggactgctt actgccgggg actgctgttg ccctgctcgc gccgtcgtcg cagttcggct   25080
tgcccccact cgattgactg cttcatttcg agccgcagcg atgcgatctc ggattgcgtc   25140
aacggacggg gcagcgcgga ggtgtccggc ttctccttgg gtgagtcggt cgatgccata   25200
gccaaaggtt tccttccaaa atgcgtccat tgctggaccg tgtttctcat tgatgcccgc   25260
aagcatcttc ggcttgaccg ccaggtcaag cgcgccttca tgggcggtca tgacggacgc   25320
cgccatgacc ttgccgccgt tgttctcgat gtagccgcgt aatgaggcaa tggtgccgcc   25380
catcgtcagc gtgtcatcga caacgatgta cttctggccg gggatcacct cccctcgaa   25440
```

```
agtcgggttg aacgccaggc gatgatctga accggctccg gttcgggcga ccttctcccg   25500
ctgcacaatg tccgtttcga cctcaaggcc aaggcggtcg ccagaacga ccgccatcat    25560
ggccggaatc ttgttgttcc ccgccgcctc gacggcgagg actgaacga tgcggggctt    25620
gtcgtcgccg atcagcgtct tgagctgggc aacagtgtcg tccgaaatca ggcgctcgac   25680
caaattaagc gccgcttccg cgtcgccctg cttcgcagcc tggtattcag gctcgttggt   25740
caaagaacca aggtcgccgt tgcgaaccac cttcgggaag tctccccacg gtgcgcgctc   25800
ggctctgctg tagctgctca agacgcctcc cttttagcc gctaaaactc taacgagtgc    25860
gcccgcgact caacttgacg cttcggcac ttacctgtgc cttgccactt gcgtcatagg    25920
tgatgctttt cgcactcccg atttcaggta ctttatcgaa atctgaccgg gcgtgcatta   25980
caaagttctt ccccacctgt tggtaaatgc tgccgctatc tgcgtggacg atgctgccgt   26040
cgtggcgctg cgacttatcg gccttttggg ccatatagat gttgtaaatg ccaggtttca   26100
gggccccggc tttatctacc ttctggttcg tccatgcgcc ttggttctcg gtctggacaa   26160
ttctttgccc attcatgacc aggaggcggt gtttcattgg gtgactcctg acggttgcct   26220
ctggtgttaa acgtgtcctg gtcgcttgcc ggctaaaaaa agccgacct cggcagttcg    26280
aggccggctt ccctagagc cgggcgcgtc aaggttgttc catctatttt agtgaactgc    26340
gttcgattta tcagttactt tcctcccgct ttgtgtttcc tcccactcgt ttccgcgtct   26400
agccgacccc tcaacatagc ggcctcttct tgggctgcct ttgcctcttg ccgcgcttcg   26460
tcacgctcgg cttgcaccgt cgtaaagcgc tcggcctgcc tggccgcctc ttgcgccgcc   26520
aacttcctt gctcctggtg ggcctcggcg tcggcctgcg ccttcgcttt caccgctgcc    26580
aactccgtgc gcaaactctc cgcttcgcgc ctggtggcgt cgcgctcgcc gcgaagcgcc   26640
tgcatttcct ggttggccgc gtccaggtc ttgcggctct cttctttgaa tgcgcgggcg    26700
tcctggtgag cgtagtccag ctcggcgcgc agctcctgcg ctcgacgctc cacctcgtcg   26760
gcccgctgcg tcgccagcgc ggcccgctgc tcggctcctg ccaggcggt gcgtgcttcg    26820
gccagggctt gccgctggcg tgcggccagc tcggccgcct cggcggcctg ctgctctagc   26880
aatgtaacgc gcgcctgggc ttcttccagc tcgcgggcct cgcctcgaa ggcgtcggcc    26940
agctccccgc gcacggcttc caactcgttg cgctcacgat cccagccggc ttgcgctgcc   27000
tgcaacgatt cattggcaag ggcctgggcg gcttgccaga gggcggccac ggcctggttg   27060
ccggcctgct gcaccgcgtc cggcacctgg actgccagcg gggcggcctg cgccgtgcgc   27120
tggcgtcgcc attcgcgcat gccggcgctg gcgtcgttca tgttgacgcg gcggccctta   27180
cgcactgcat ccacggtcgg gaagttctcc cggtcgcctt gctcgaacag ctcgtccgca   27240
gccgcaaaaa tgcggtcgcg cgtctctttg ttcagttcca tgttggctcc ggtaattggt   27300
aagaataata atactcttac ctaccttatc agcgcaagag tttagctgaa cagttctcga   27360
cttaacggca ggttttttag cggctgaagg gcaggcaaaa aaagcccgc acggtcggcg    27420
ggggcaaagg gtcagcggga agggattag cgggcgtcgg gcttcttcat gcgtcgggc    27480
cgcgcttctt gggatggagc acgacgaagc gcgcacgcgc atcgtcctcg gccctatcgg   27540
cccgcgtcgc ggtcaggaac ttgtcgcgcg ctaggtcctc cctggtgggc accaggggca   27600
tgaactcggc ctgctcgatg taggtccact ccatgaccgc atcgcagtcg aggccgcgtt   27660
ccttcaccgt ctcttgcagg tcgcggtacg cccgctcgtt gagcggctgg taacgggcca   27720
attggtcgta aatggctgtc ggccatgagc ggcctttcct gttgagccag cagccgacga   27780
cgaagccggc aatgcaggcc cctggcacaa ccaggccgac gccgggggca ggggatggca   27840
```

```
gcagctcgcc aaccaggaac cccgccgcga tgatgccgat gccggtcaac cagcccttga   27900
aactatccgg ccccgaaaca cccctgcgca ttgcctggat gctgcgccgg atagcttgca   27960
acatcaggag ccgtttcttt tgttcgtcag tcatggtccg ccctcaccag ttgttcgtat   28020
cggtgtcgga cgaactgaaa tcgcaagagc tgccggtatc ggtccagccg ctgtccgtgt   28080
cgctgctgcc gaagcacggc gaggggtccg cgaacgccgc agacggcgta tccggccgca   28140
gcgcatcgcc cagcatggcc ccggtcagcg agccgccggc caggtagccc agcatggtgc   28200
tgttggtcgc cccggccacc agggccgacg tgacgaaatc gccgtcattc cctctggatt   28260
gttcgctgct cggcggggca gtgcgccgcg ccggcggcgt cgtggatggc tcgggttggc   28320
tggcctgcga cggccggcga aaggtgcgca gcagctcgtt atcgaccggc tgcggcgtcg   28380
gggccgccgc cttgcgctgc ggtcggtgtt ccttcttcgg ctcgcgcagc ttgaacagca   28440
tgatcgcgga aaccagcagc aacgccgcgc ctacgcctcc cgcgatgtag aacagcatcg   28500
gattcattct tcggtcctcc ttgtagcgga accgttgtct gtgcgcgcg ggtggcccgc   28560 gccgctgtct ttggggatca gccctcgatg agcgcgacca gtttcacgtc ggcaaggttc   28620
gcctcgaact cctggccgtc gtcctcgtac ttcaaccagg catagccttc cgccggcggc   28680
cgacggttga ggataaggcg ggcagggcgc tcgtcgtgct cgacctggac gatggccttt   28740
ttcagcttgt ccgggtccgg ctccttcgcg ccctttcct tggcgtcctt accgtcctgg    28800
tcgccgtcct cgccgtcctg gccgtcgccg gcctccgcgt cacgctcggc atcagtctgg   28860
ccgttgaagg catcgacggt gttgggatcg cggcccttct cgtccaggaa ctcgcgcagc   28920
agcttgaccg tgccgcgcgt gatttcctgg gtgtcgtcgt caagccacgc ctcgacttcc   28980
tccgggcgct tcttgaaggc cgtcaccagc tcgttcacca cggtcacgtc gcgcacgcgg   29040
ccggtgttga acgcatcggc gatcttctcc ggcaggtcca gcagcgtgac gtgctgggtg   29100
atgaacgccg gcgacttgcc gatttccttg gcgatatcgc ctttcttctt gcccttcgcc   29160
agctcgcggc caatgaagtc ggcaatttcg cgcggggtca gctcgttgcg ttgcaggttc   29220
tcgataacct ggtcggcttc gttgtagtcg ttgtcgatga acgccgggat ggacttcttg   29280
ccggcccact tcgagccacg gtagcggcgg gcgccgtgat tgatgatata gcggcccggc   29340
tgctcctggt tctcgcgcac cgaaatgggt gacttcaccc cgcgctcttt gatcgtggca   29400
ccgatttccg cgatgctctc cggggaaaag ccggggttgt cggccgtccg cggctgatgc   29460
ggatcttcgt cgatcaggtc caggtccagc tcgatagggc cggaaccgcc ctgagacgcc   29520
gcaggagcgt ccaggaggct cgacaggtcg ccgatgctat ccaaccccag gccggacggc   29580
tgcgccgcgc ctgcggcttc ctgagcggcc gcagcggtgt ttttcttggt ggtcttggct   29640
tgagccgcag tcattgggaa atctccatct tcgtgaacac gtaatcagcc agggcgcgaa   29700 cctcttttcga tgccttgcgc gcggccgttt tcttgatctt ccagaccggc acaccggatg   29760
cgagggcatc ggcgatgctg ctgcgcaggc caacggtggc cggaatcatc atcttgggt    29820 acgcggccag cagctcggct tggtggcgcg cgtggcgcgg attccgcgca tcgaccttgc   29880
tgggcaccat gccaaggaat tgcagcttgg cgttcttctg gcgcacgttc gcaatggtcg   29940
tgaccatctt cttgatgccc tggatgctgt acgcctcaag ctcgatgggg acagcacat    30000 agtcggccgc gaagagggcg gccgccaggc cgacgccaag ggtcggggcc gtgtcgatca   30060
ggcacacgtc gaagccttgg ttcgccaggg ccttgatgtt cgccccgaac agctcgcggg   30120
cgtcgtccag cgacagccgt tcggcgttcg ccagtaccgg gttggactcg atgagggcga   30180
```

```
ggcgcgcggc ctggccgtcg ccggctgcgg gtgcggtttc ggtccagccg ccggcaggga    30240
cagcgccgaa cagcttgctt gcatgcaggc cggtagcaaa gtccttgagc gtgtaggacg    30300
cattgccctg ggggtccagg tcgatcacgg caacccgcaa gccgcgctcg aaaaagtcga    30360
aggcaagatg cacaagggtc gaagtcttgc cgacgccgcc tttctggttg gccgtgacca    30420
aagttttcat cgtttggttt cctgtttttt cttggcgtcc gcttcccact tccggacgat    30480
gtacgcctga tgttccggca gaaccgccgt tacccgcgcg tacccctcgg gcaagttctt    30540
gtcctcgaac gcggcccaca cgcgatgcac cgcttgcgac actgcgcccc tggtcagtcc    30600
cagcgacgtt gcgaacgtcg cctgtggctt cccatcgact aagacgcccc gcgctatctc    30660
gatggtctgc tgccccactt ccagccctg  atcgcctcc tggaactggc tttcggtaag    30720
ccgtttcttc atggataaca cccataattt gctccgcgcc ttggttgaac atagcggtga    30780
cagccgccag cacatgagag aagtttagct aaacatttct cgcacgtcaa cacctttagc    30840
cgctaaaact cgtccttggc gtaacaaaac aaaagcccgg aaaccgggct ttcgtctctt    30900
gccgcttatg gctctgcacc cggctccatc accaacaggt cgcgcacgcg cttcactcgg    30960
ttgcggatcg acactgccag cccaacaaag ccggttgccg ccgccgccag gatcgcgccg    31020
atgatgccgg ccacaccggc catcgcccac caggtcgccg ccttccggtt ccattcctgc    31080
tggtactgct tcgcaatgct ggacctcggc tcaccatagg ctgaccgctc gatggcgtat    31140
gccgcttctc cccttggcgt aaacccagc  gccgcaggcg gcattgccat gctgcccgcc    31200
gctttcccga ccacgacgcg cgcaccaggc ttgcggtcca gccttcggc  cacggcgagc    31260 tgcgcaagga cataatcagc cgccgacttg gctccacgcg cctcgatcag ctcttgcact    31320
cgcgcgaaat ccttggcctc cacggccgcc atgaatcgcg cacgcggcga aggctccgca    31380
gggccggcgt cgtgatcgcc gccgagaatg cccttcacca agttcgacga cacgaaaatc    31440
atgctgacgg ctatcaccat catgcagacg gatcgcacga acccgctgaa ttgaacacga    31500
gcacggcacc cgcgaccact atgccaagaa tgcccaaggt aaaaattgcc ggccccgcca    31560
tgaagtccgt gaatgccccg acggccgaag tgaagggcag gccgccaccc aggccgccgc    31620
cctcactgcc cggcacctgg tcgctgaatg tcgatgccag cacctgcggc acgtcaatgc    31680
ttccgggcgt cgcgctcggg ctgatcgccc atcccgttac tgccccgatc ccggcaatgg    31740
caaggactgc cagcgctgcc attttttggg tgaggccgtt cgcggccgag gggcgcagcc    31800
cctgggggga tgggaggccc gcgttagcgg gccgggaggg ttcgagaagg ggggcaccc    31860 cccttcggcg tgcgcggtca cgcgcacagg gcgcagccct ggttaaaaac aaggtttata    31920
aatattggtt taaaagcagg ttaaaagaca ggttagcggt ggccgaaaaa cgggcggaaa    31980
cccttgcaaa tgctggattt tctgcctgtg gacagcccct caaatgtcaa taggtgcgcc    32040
cctcatctgt cagcactctg cccctcaagt gtcaaggatc gcgcccctca tctgtcagta    32100
gtcgcgcccc tcaagtgtca ataccgcagg gcacttatcc ccaggcttgt ccacatcatc    32160
tgtgggaaac tcgcgtaaaa tcaggcgttt tcgccgattt gcgaggctgg ccagctccac    32220
gtcgccggcc gaaatcgagc ctgcccctca tctgtcaacg ccgcgccggg tgagtcggcc    32280
cctcaagtgt caacgtccgc ccctcatctg tcagtgaggg ccaagttttc cgcgaggtat    32340
ccacaacgcc ggcggccgcg gtgtctcgca cacggcttcg acggcgtttc tggcgcgttt    32400
gcagggccat agacgccgc  cagcccagcg gcgagggcaa ccagcccggt gagcgtcgga    32460
aaggcgctaa gcccgta    gcgacgcgga gaggggcgag acaagccaag ggcgcaggct    32520
cgatgcgcag cacgacatag ccggttctcg caaggacgag aatttccctg cggtgcccct    32580
```

```
caagtgtcaa tgaaagtttc aacgcgagc cattcgcgag agccttgagt ccacgctaga   32640
tgagagcttt gttgtaggtg gaccagttgg tgattttgaa cttttgcttt gccacggaac   32700
ggtctgcgtt gtcgggaaga tgcgtgatct gatccttcaa ctcagcaaaa gttcgattta   32760
ttcaacaaag ccacgttgtg tctcaaaatc tctgatgtta cattgcacaa gataaaaata   32820
tatcatcatg aacaataaaa ctgtctgctt acataaacag taatacaagg ggtgttatga   32880
gccatattca acgggaaacg tcttgctcga ctctagagct cgttcctcga ggaacggtac   32940
ctgcggggaa gcttacaata atgtgtgttg ttaagtcttg ttgcctgtca tcgtctgact   33000
gactttcgtc ataaatcccg gcctccgtaa cccagctttg ggcaagctca cggatttgat   33060
ccggcggaac gggaatatcg agatgccggg ctgaacgctg cagttccagc tttcccttc   33120 gggacaggta ctccagctga ttgattatct gctgaagggt cttggttcca cctcctggca   33180
caatgcgaat gattacttga gcgcgatcgg gcatccaatt ttctcccgtc aggtgcgtgg   33240
tcaagtgcta caaggcacct ttcagtaacg agcgaccgtc gatccgtcgc cgggatacgg   33300
acaaaatgga gcgcagtagt ccatcgaggg cggcgaaagc ctcgccaaaa gcaatacgtt   33360
catctcgcac agcctccaga tccgatcgag ggtcttcggc gtaggcagat agaagcatgg   33420
atacattgct tgagagtatt ccgatggact gaagtatggc ttccatcttt tctcgtgtgt   33480
ctgcatctat ttcgagaaag cccccgatgc ggcgcaccgc aacgcgaatt gccatactat   33540
ccgaaagtcc cagcaggcgc gcttgatagg aaaaggtttc atactcggcc gatcgcagac   33600
gggcactcac gaccttgaac ccttcaactt tcagggatcg atgctggttg atggtagtct   33660
cactcgacgt ggctctggtg tgttttgaca tagcttcctc caaagaaagc ggaaggtctg   33720
gatactccag cacgaaatgt gcccgggtag acggatggaa gtctagccct gctcaatatg   33780
aaatcaacag tacatttaca gtcaatactg aatatacttg ctacatttgc aattgtctta   33840
taacgaatgt gaaataaaaa tagtgtaaca acgcttttac tcatcgataa tcacaaaaac   33900
atttatacga acaaaaatac aaatgcactc cggtttcaca ggataggcgg gatcagaata   33960
tgcaactttt gacgttttgt tctttcaaag ggggtgctgg caaaaccacc gcactcatgg   34020
gcctttgcgc tgctttggca aatgacggta aacgagtggc cctctttgat gccgacgaaa   34080
accggcctct gacgcgatgg agagaaaacg ccttacaaag cagtactggg atcctcgctg   34140
tgaagtctat tccgccgacg aaatgcccct tcttgaagca gcctatgaaa atgccgagct   34200
cgaaggattt gattatgcgt tggccgatac gcgtggcggc tcgagcgagc tcaacaacac   34260
aatcatcgct agctcaaacc tgcttctgat ccccaccatg ctaacgccgc tcgacatcga   34320
tgaggcacta tctacctacc gctacgtcat cgagctgctg ttgagtgaaa atttggcaat   34380
tcctacagct gttttgcgcc aacgcgtccc ggtcggccga ttgacaacat cgcaacgcag   34440
gatgtcagag acgctagaga gccttccagt tgtaccgtct cccatgcatg aaagagatgc   34500
atttgccgcg atgaaagaac gcggcatgtt gcatcttaca ttactaaaca cgggaactga   34560
tccgacgatg cgcctcatag agaggaatct tcggattgcg atggaggaag tcgtggtcat   34620
ttcgaaactg atcagcaaaa tcttggaggc ttgaagatgg caattcgcaa gcccgcattg   34680
tcggtcggcg aagcacggcg gcttgctggt gctcgacccg agatccacca tcccaacccg   34740
acacttgttc cccagaagct ggacctccag cacttgcctg aaaaagccga cgagaaagac   34800
cagcaacgtg agcctctcgt cgccgatcac atttacagtc ccgatcgaca acttaagcta   34860
actgtggatg cccttagtcc acctccgtcc ccgaaaaagc tccaggtttt tctttcagcg   34920
```

```
cgaccgcccg cgcctcaagt gtcgaaaaca tatgacaacc tcgttcggca atacagtccc    34980
tcgaagtcgc tacaaatgat tttaaggcgc gcgttggacg atttcgaaag catgctggca    35040
gatggatcat ttcgcgtggc cccgaaaagt tatccgatcc cttcaactac agaaaaatcc    35100
gttctcgttc agacctcacg catgttcccg gttgcgttgc tcgaggtcgc tcgaagtcat    35160
tttgatccgt tggggttgga gaccgctcga gctttcggcc acaagctggc taccgccgcg    35220
ctcgcgtcat tctttgctgg agagaagcca tcgagcaatt ggtgaagagg gacctatcgg    35280 aaccctcac caaatattga gtgtaggttt gaggccgctg gccgcgtcct cagtcacctt    35340
ttgagccaga taattaagag ccaaatgcaa ttggctcagg ctgccatcgt cccccgtgc    35400 gaaacctgca cgtccgcgtc aaagaaataa ccggcacctc ttgctgtttt tatcagttga    35460
gggcttgacg gatccgcctc aagtttgcgg cgcagccgca aaatgagaac atctatactc    35520
ctgtcgtaaa cctcctcgtc gcgtactcga ctggcaatga aagttgctc gcgcgataga    35580 acgtcgcggg gtttctctaa aaacgcgagg agaagattga actcacctgc cgtaagtttc    35640
acctcaccgc cagcttcgga catcaagcga cgttgcctga gattaagtgt ccagtcagta    35700
aaacaaaaag accgtcggtc tttggagcgg acaacgttgg ggcgcacgcg caaggcaacc    35760
cgaatgcgtg caagaaactc tctcgtacta acggcttag cgataaaatc acttgctcct    35820
agctcgagtg caacaacttt atccgtctcc tcaaggcggt cgccactgat aattatgatt    35880
ggaatatcag actttgccgc cagatttcga acgatctcaa gcccatcttc acgacctaaa    35940
tttagatcaa caaccacgac atcgaccgtc gcggaagaga gtactctagt gaactgggtg    36000
ctgtcggcta ccgcggtcac tttgaaggcg tggatcgtaa ggtattcgat aataagatgc    36060
cgcatagcga catcgtcatc gataagaaga acgtgtttca acggctcacc tttcaatcta    36120
aaatctgaac cctgttcac agcgcttgag aaattttcac gtgaaggatg tacaatcatc    36180
tccagctaaa tgggcagttc gtcagaattg cggctgaccg cggatgacga aaatgcgaac    36240
caagtatttc aattttatga caaaagttct caatcgttgt tacaagtgaa acgcttcgag    36300
gttacagcta ctattgatta aggagatcgc ctatggtctc gccccggcgt cgtgcgtccg    36360
ccgcgagcca gatctcgcct acttcataaa cgtcctcata ggcacggaat ggaatgatga    36420
catcgatcgc cgtagagagc atgtcaatca gtgtgcgatc ttccaagcta gcaccttggg    36480
cgctactttt gacaagggaa aacagtttct tgaatccttg gattggattc gcgccgtgta    36540
ttgttgaaat cgatcccgga tgtcccgaga cgacttcact cagataagcc catgctgcat    36600
cgtcgcgcat ctcgccaagc aatatccggt ccggccgcat acgcagactt gcttggagca    36660
agtgctcggc gctcacagca cccagcccag caccgttctt ggagtagagt agtctaacat    36720
gattatcgtg tggaatgacg agttcgagcg tatcttctat ggtgattagc ctttcctggg    36780
gggggatggc gctgatcaag gtcttgctca ttgttgtctt gccgcttccg gtagggccac    36840
atagcaacat cgtcagtcgg ctgacgacgc atgcgtgcag aaacgcttcc aaatccccgt    36900
tgtcaaaatg ctgaaggata gcttcatcat cctgattttg gcgtttcctt cgtgtctgcc    36960
actggttcca cctcgaagca tcataacggg aggagacttc tttaagacca gaaacacgcg    37020
agcttggccg tcgaatggtc aagctgacgg tgcccgaggg aacggtcggc ggcagacaga    37080
tttgtagtcg ttcaccacca ggaagttcag tggcgcagag ggggttacgt ggtccgacat    37140
cctgctttct cagcgcgccc gctaaaatag cgatatcttc aagatcatca taagagacgg    37200
gcaaaggcat cttggtaaaa atgccggctt ggcgcacaaa tgcctctcca ggtcgattga    37260
tcgcaatttc ttcagtcttc gggtcatcga gccattccaa aatcggcttc agaagaaagc    37320
```

```
gtagttgcgg atccacttcc atttacaatg tatcctatct ctaagcggaa atttgaattc    37380
attaagagcg gcggttcctc ccccgcgtgg cgccgccagt caggcggagc tggtaaacac    37440
caaagaaatc gaggtcccgt gctacgaaaa tggaaacggt gtcaccctga ttcttcttca    37500
gggttggcgg tatgttgatg gttgccttaa gggctgtctc agttgtctgc tcaccgttat    37560
tttgaaagct gttgaagctc atcccgccac ccgagctgcc ggcgtaggtg ctagctgcct    37620
ggaaggcgcc ttgaacaaca ctcaagagca tagctccgct aaaacgctgc cagaagtggc    37680
tgtcgaccga gcccggcaat cctgagcgac cgagttcgtc cgcgcttggc gatgttaacg    37740
agatcatcgc atggtcaggt gtctcggcgc gatcccacaa cacaaaaacg cgcccatctc    37800
cctgttgcaa gccacgctgt atttcgccaa caacggtggt gccacgatca agaagcacga    37860
tattgttcgt tgttccacga atatcctgag gcaagacaca ctttacatag cctgccaaat    37920
ttgtgtcgat tgcggtttgc aagatgcacg gaattattgt cccttgcgtt accataaaat    37980
cggggtgcgg caagagcgtg gcgctgctgg gctgcagctc ggtgggtttc atacgtatcg    38040
acaaatcgtt ctcgccggac acttcgccat tcggcaagga gttgtcgtca cgcttgcctt    38100
cttgtcttcg gcccgtgtcg ccctgaatgg cgcgtttgct gacccettga tcgccgctgc    38160 tatatgcaaa aatcggtgtt tcttccggcc gtggctcatg ccgctccggt tcgcccctcg    38220
gcggtagagg agcagcaggc tgaacagcct cttgaaccgc tggaggatcc ggcggcacct    38280
caatcggagc tggatgaaat ggcttggtgt tgttgcgat caaagttgac ggcgatgcgt    38340
tctcattcac cttcttttgg cgcccaccta gccaaatgag gcttaatgat aacgcgagaa    38400
cgacacctcc gacgatcaat ttctgagacc ccgaaagacg ccggcgatgt tgtcggaga    38460 ccagggatcc agatgcatca acctcatgtg ccgcttgctg actatcgtta ttcatccctt    38520 cgccccttc aggacgcgtt tcacatcggg cctcaccgtg cccgtttgcg gcctttggcc    38580
aacgggatcg taagcggtgt tccagataca tagtactgtg tggccatccc tcagacgcca    38640
acctcgggaa accgaagaaa tctcgacatc gctcccttta actgaatagt tggcaacagc    38700
ttccttgcca tcaggattga tggtgtagat ggagggtatg cgtacattgc ccggaaagtg    38760
gaataccgtc gtaaatccat tgtcgaagac ttcgagtggc aacagcgaac gatcgccttg    38820
ggcgacgtag tgccaattac tgtccgccgc accaagggct gtgacaggct gatccaataa    38880
attctcagct ttccgttgat attgtgcttc cgcgtgtagt ctgtccacaa cagccttctg    38940
ttgtgcctcc cttcgccgag ccgccgcatc gtcggcgggg taggcgaatt ggacgctgta    39000
atagagatcg ggctgctctt tatcgaggtg ggacagagtc ttggaactta tactgaaaac    39060
ataacggcgc atcccggagt cgcttgcggt tagcacgatt actggctgag gcgtgaggac    39120
ctggcttgcc ttgaaaaata gataatttcc ccgcggtagg gctgctagat cttttgctatt    39180 tgaaacggca accgctgtca ccgtttcgtt cgtggcgaat gttacgacca aagtagctcc    39240
aaccgccgtc gagaggcgca ccacttgatc gggattgtaa gccaaataac gcatgcgcgg    39300
atctagcttg cccgccattg gagtgtcttc agcctccgca ccagtcgcag cggcaaataa    39360
acatgctaaa atgaaaagtg ctttttctgat catggttcgc tgtggcctac gtttgaaacg    39420
gtatcttccg atgtctgata ggaggtgaca accagacctg ccgggttggt tagtctcaat    39480
ctgccgggca agctggtcac cttttcgtag cgaactgtcg cggtccacgt actcaccaca    39540
ggcattttgc cgtcaacgac gagggtcctt ttatagcgaa tttgctgcgt gcttggagtt    39600
acatcatttg aagcgatgtg ctcgacctcc accctgccgc gtttgccaag aatgacttga    39660
```

-continued

```
ggcgaactgg gattgggata gttgaagaat tgctggtaat cctggcgcac tgttggggca    39720
ctgaagttcg ataccaggtc gtaggcgtac tgagcggtgt cggcatcata actctcgcgc    39780
aggcgaacgt actcccacaa tgaggcgtta acgacggcct cctcttgagt tgcaggcaat    39840
cgcgagacag acacctcgct gtcaacggtg ccgtccggcc gtatccatag atatacgggc    39900
acaagcctgc tcaacggcac cattgtggct atagcgaacg cttgagcaac atttcccaaa    39960
atcgcgatag ctgcgacagc tgcaatgagt ttggagagac gtcgcgccga tttcgctcgc    40020
gcggtttgaa aggcttctac ttccttatag tgctcggcaa ggctttcgcg cgccactagc    40080
atggcatatt caggccccgt catagcgtcc acccgaattg ccgagctgaa gatctgacgg    40140
agtaggctgc catcgcccca cattcagcgg gaagatcggg cctttgcagc tcgctaatgt    40200
gtcgtttgtc tggcagccgc tcaaagcgac aactaggcac agcaggcaat acttcataga    40260
attctccatt gaggcgaatt tttgcgcgac ctagcctcgc tcaacctgag cgaagcgacg    40320
gtacaagctg ctggcagatt gggttgcgcc gctccagtaa ctgcctccaa tgttgccggc    40380
gatcgccggc aaagcgacaa tgagcgcatc ccctgtcaga aaaacatat cgagttcgta     40440
aagaccaatg atcttggccg cggtcgtacc ggcgaaggtg attacaccaa gcataagggt    40500
gagcgcagtc gcttcggtta ggatgacgat cgttgccacg aggtttaaga ggagaagcaa    40560
gagaccgtag gtgataagtt gcccgatcca cttagctgcg atgtcccgcg tgcgatcaaa    40620
aatatatccg acgaggatca gaggcccgat cgcgagaagc actttcgtga gaattccaac    40680
ggcgtcgtaa actccgaagg cagaccagag cgtgccgtaa aggacccact gtgcccttg     40740
gaaagcaagg atgtcctggt cgttcatcgg accgatttcg gatgcgattt tctgaaaaac    40800
ggcctgggtc acggcgaaca ttgtatccaa ctgtgccgga acagtctgca gaggcaagcc    40860
ggttacacta aactgctgaa caaagtttgg gaccgtcttt tcgaagatgg aaaccacata    40920
gtcttggtag ttagcctgcc caacaattag agcaacaacg atggtgaccg tgatcacccg    40980
agtgataccg ctacgggtat cgacttcgcc gcgtatgact aaaataccct gaacaataat    41040
ccaaagagtg acacaggcga tcaatggcgc actcaccgcc tcctggatag tctcaagcat    41100
cgagtccaag cctgtcgtga aggctacatc gaagatcgta tgaatggccg taaacggcgc    41160
cggaatcgtg aaattcatcg attggacctg aacttgactg gtttgtcgca taatgttgga    41220
taaaatgagc tcgcattcgg cgaggatgcg ggcggatgaa caaatcgccc agccttaggg    41280
gagggcacca aagatgacag cggtcttttg atgctccttg cgttgagcgg ccgcctcttc    41340
cgcctcgtga aggccggcct gcgcggtagt catcgttaat aggcttgtcg cctgtacatt    41400
ttgaatcatt gcgtcatgga tctgcttgag aagcaaacca ttggtcacgg ttgcctgcat    41460
gatattgcga gatcgggaaa gctgagcaga cgtatcagca ttcgccgtca gcgtttgtc     41520
catcgtttcc agattgtcag ccgcaatgcc agcgctgttt gcggaaccgg tgatctgcga    41580
tcgcaacagg tccgcttcag catcactacc cacgactgca cgatctgtat cgctggtgat    41640
cgcacgtgcc gtggtcgaca ttggcattcg cggcgaaaac atttcattgt ctaggtcctt    41700
cgtcgaagga tactgatttt tctggttgag cgaagtcagt agtccagtaa cgccgtaggc    41760
cgacgtcaac atcgtaacca tcgctatagt ctgagtgaga ttctccgcag tcgcgagcgc    41820
agtcgcgagc gtctcagcct ccgttgccgg gtcgctaaca acaaactgcg cccgcgcggg    41880
ctgaatatat agaaagctgc aggtcaaaac tgttgcaata agttgcgtcg tcttcatcgt    41940
ttcctacctt atcaatcttc tgcctcgtgg tgacgggcca tgaattcgct gagccagcca    42000
gatgagttgc cttcttgtgc ctcgcgtagt cgagttgcaa agcgcaccgt gttggcacgc    42060
```

```
cccgaaagca cggcgacata ttcacgcata tcccgcagat caaattcgca gatgacgctt   42120
ccactttctc gtttaagaag aaacttacgg ctgccgaccg tcatgtcttc acggatcgcc   42180
tgaaattcct tttcggtaca tttcagtcca tcgacataag ccgatcgatc tgcggttggt   42240
gatggataga aaatcttcgt catacattgc gcaaccaagc tggctcctag cggcgattcc   42300
agaacatgct ctggttgctg cgttgccagt attagcatcc cgttgttttt tcgaacggtc   42360
aggaggaatt tgtcgacgac agtcgaaaat ttagggttta acaaataggc gcgaaactca   42420
tcgcagctca tcacaaaacg gcggccgtcg atcatggctc caatccgatg caggagatat   42480
gctgcagcgg gagcgcatac ttcctcgtat tcgagaagat gcgtcatgtc gaagccgta    42540 atcgacggat ctaactttac ttcgtcaact tcgccgtcaa atgcccagcc aagcgcatgg   42600
ccccggcacc agcgttggag ccgcgctcct gcgccttcgg cgggcccatg caacaaaaat   42660
tcacgtaacc ccgcgattga acgcatttgt ggatcaaacg agagctgacg atggatacca   42720
cggaccagac ggcggttctc ttccggagaa atcccacccc gaccatcact ctcgatgaga   42780
gccacgatcc attcgcgcag aaaatcgtgt gaggctgctg tgttttctag gccacgcaac   42840
ggcgccaacc cgctgggtgt gcctctgtga agtgccaaat atgttcctcc tgtggcgcga   42900
accagcaatt cgccaccccg gtccttgtca aagaacacga ccgtacctgc acggtcgacc   42960
atgctctgtt cgagcatggc tagaacaaac atcatgagcg tcgtcttacc cctcccgata   43020
ggcccgaata ttgccgtcat gccaacatcg tgctcatgcg ggatatagtc gaaaggcgtt   43080
ccgccattgg tacgaaatcg ggcaatcgcg ttgccccagt ggcctgagct ggcgccctct   43140
ggaaagtttt cgaaagagac aaaccctgcg aaattgcgtg aagtgattgc gccagggcgt   43200
gtgcgccact taaaattccc cggcaattgg gaccaatagg ccgcttccat accaatacct   43260
tcttggacaa ccacggcacc tgcatccgcc attcgtgtcc gagcccgcgc gccctgtcc    43320 ccaagactat tgagatcgtc tgcatagacg caaaggctca aatgatgtga gcccataacg   43380
aattcgttgc tcgcaagtgc gtcctcagcc tcggataatt tgccgatttg agtcacggct   43440
ttatcgccgg aactcagcat ctggctcgat ttgaggctaa gtttcgcgtg cgcttgcggg   43500
cgagtcagga acgaaaaact ctgcgtgaga acaagtggaa aatcgaggga tagcagcgcg   43560
ttgagcatgc ccggccgtgt ttttgcaggg tattcgcgaa acgaatagat ggatccaacg   43620
taactgtctt ttggcgttct gatctcgagt cctcgcttgc cgcaaatgac tctgtcggta   43680
taaatcgaag cgccgagtga gccgctgacg accggaaccg gtgtgaaccg accagtcatg   43740
atcaaccgta gcgcttcgcc aatttcggtg aagagcacac cctgcttctc gcggatgcca   43800
agacgatgca ggccatacgc tttaagagag ccagcgacaa catgccaaag atcttccatg   43860
ttcctgatct ggcccgtgag atcgtttttcc cttttccgc ttagcttggt gaacctcctc   43920
tttaccttcc ctaaagccgc ctgtgggtag acaatcaacg taaggaagtg ttcattgcgg   43980
aggagttggc cggagagcac gcgctgttca aaagcttcgt tcaggctagc ggcgaaaaca   44040
ctacggaagt gtcgcggcgc cgatgatggc acgtcggcat gacgtacgag gtgagcatat   44100
attgacacat gatcatcagc gatattgcgc aacagcgtgt tgaacgcacg acaacgcgca   44160
ttgcgcattt cagtttcctc aagctcgaat gcaacgccat caattctcgc aatggtcatg   44220
atcgatccgt cttcaagaag gacgatatgg tcgctgaggt ggccaatata agggagatag   44280
atctcaccgg atctttcggt cgttccactc gcgccgagca tcacaccatt cctctcccc    44340 gtggggaac cctaattgga tttgggctaa cagtagcgcc cccccaaact gcactatcaa    44400
```

```
tgcttcttcc cgcggtccgc aaaaatagca ggacgacgct cgccgcattg tagtctcgct    44460
ccacgatgag ccgggctgca aaccataacg gcacgagaac gacttcgtag agcgggttct    44520
gaacgataac gatgacaaag ccggcgaaca tcatgaataa ccctgccaat gtcagtggca    44580
ccccaagaaa caatgcgggc cgtgtggctg cgaggtaaag ggtcgattct tccaaacgat    44640
cagccatcaa ctaccgccag tgagcgtttg gccgaggaag ctcgcccaa acatgataac    44700 aatgccgccg acgacgccgg caaccagccc aagcgaagcc cgcccgaaca tccaggagat    44760
cccgatagcg acaatgccga gaacagcgag tgactggccg aacggaccaa ggataaacgt    44820
gcatatattg ttaaccattg tggcggggtc agtgccgcca cccgcagatt gcgctgcggc    44880
gggtccggat gaggaaatgc tccatgcaat tgcaccgcac aagcttgggg cgcagctcga    44940
tatcacgcgc atcatcgcat tcgagagcga gaggcgattt agatgtaaac ggtatctctc    45000
aaagcatcgc atcaatgcgc acctccttag tataagtcga ataagacttg attgtcgtct    45060
gcggatttgc cgttgtcctg gtgtggcggt ggcggagcga ttaaaccgcc agcgccatcc    45120
tcctgcgagc ggcgctgata tgaccccaa acatcccacg tctcttcgga ttttagcgcc    45180
tcgtgatcgt cttttggagg ctcgattaac gcgggcacca gcgattgagc agctgtttca    45240
acttttcgca cgtagccgtt tgcaaaaccg ccgatgaaat taccggtgtt gtaagcggag    45300
atcgcccgac gaagcgcaaa ttgcttctcg tcaatcgttt cgccgcctgc ataacgactt    45360
ttcagcatgt ttgcagcggc agataatgat gtgcacgcct ggagcgcacc gtcaggtgtc    45420
agaccgagca tagaaaaatt tcgagagttt atttgcatga ggccaacatc cagcgaatgc    45480
cgtgcatcga gacggtgcct gacgacttgg gttgcttggc tgtgatcttg ccagtgaagc    45540
gtttcgccgg tcgtgttgtc atgaatcgct aaaggatcaa agcgactctc cacccttagct    45600 atcgccgcaa gcgtagatgt cgcaactgat ggggcacact tgcgagcaac atggtcaaac    45660
tcagcagatg agagtggcgt ggcaaggctc gacgaacaga aggagaccat caaggcaaga    45720
gaaagcgacc ccgatctctt aagcatacct tatctcctta gctcgcaact aacaccgcct    45780
ctcccgttgg aagaagtgcg ttgttttatg ttgaagatta tcgggagggt cggttactcg    45840
aaaattttca attgcttctt tatgatttca attgaagcga gaaacctcgc ccggcgtctt    45900
ggaacgcaac atggaccgag aaccgcgcat ccatgactaa gcaaccggat cgacctattc    45960
aggccgcagt tggtcaggtc aggctcagaa cgaaaatgct cggcgaggtt acgctgtctg    46020
taaacccatt cgatgaacgg gaagcttcct tccgattgct cttggcagga atattggccc    46080
atgcctgctt gcgctttgca aatgctctta tcgcgttggt atcatatgcc ttgtccgcca    46140
gcagaaacgc actctaagcg attatttgta aaaatgtttc ggtcatgcgg cggtcatggg    46200
cttgacccgc tgtcagcgca agacggatcg gtcaaccgtc ggcatcgaca acagcgtgaa    46260
tcttggtggt caaaccgcca cgggaacgtc ccatacagcc atcgtcttga tcccgctgtt    46320
tcccgtcgcc gcatgttggt ggacgcggac acaggaactg tcaatcatga cgacattcta    46380
tcgaaagcct tggaaatcac actcagaata tgatcccaga cgtctgcctc acgccatcgt    46440
acaaagcgat tgtagcaggt tgtacaggaa ccgtatcgat caggaacgtc tgcccagggc    46500
gggcccgtcc ggaagcgcca caagatgaca ttgatcaccc cgtcaacgc gcggcacgcg    46560 acgcggctta tttgggaaca aaggactgaa caacagtcca ttcgaaatcg gtgacatcaa    46620
agcggggacg ggttatcagt ggcctccaag tcaagcctca atgaatcaaa atcagaccga    46680
tttgcaaacc tgatttatga gtgtgcggcc taaatgatga aatcgtcctt ctagatcgcc    46740
tccgtggtgt agcaacacct cgcagtatcg ccgtgctgac cttggccagg gaattgactg    46800
```

```
gcaagggtgc tttcacatga ccgctctttt ggccgcgata gatgatttcg ttgctgcttt   46860
gggcacgtag aaggagagaa gtcatatcgg agaaattcct cctggcgcga gagcctgctc   46920
tatcgcgacg gcatcccact gtcgggaaca gaccggatca ttcacgaggc gaaagtcgtc   46980
aacacatgcg ttataggcat cttcccttga aggatgatct tgttgctgcc aatctggagg   47040
tgcggcagcc gcaggcagat gcgatctcag cgcaacttgc ggcaaaacat ctcactcacc   47100
tgaaaaccac tagcgagtct cgcgatcaga cgaaggcctt ttacttaacg acacaatatc   47160
cgatgtctgc atcacaggcg tcgctatccc agtcaatact aaagcggtgc aggaactaaa   47220
gattactgat gacttaggcg tgccacgagg cctgagacga cgcgcgtaga cagttttttg   47280
aaatcattat caaagtgatg gcctccgctg aagcctatca cctctgcgcc ggtctgtcgg   47340
agagatgggc aagcattatt acggtcttcg cgcccgtaca tgcattggac gattgcaggg   47400
tcaatggatc tgagatcatc cagaggattg ccgcccttac cttccgtttc gagttggagc   47460
cagcccctaa atgagacgac atagtcgact tgatgtgaca atgccaagag agagatttgc   47520
ttaacccgat ttttttgctc aagcgtaagc ctattgaagc ttgccggcat gacgtccgcg   47580
ccgaaagaat atcctacaag taaaacattc tgcacaccga aatgcttggt gtagacatcg   47640
attatgtgac caagatcctt agcagtttcg cttggggacc gctccgacca gaaataccga   47700
agtgaactga cgccaatgac aggaatccct tccgtctgca gataggtacc atcgatagat   47760
ctgctgcctc gcgcgtttcg gtgatgacgg tgaaaacctc tgacacatgc agctcccgga   47820
gacggtcaca gcttgtctgt aagcggatgc cgggagcaga caagcccgtc agggcgcgtc   47880
agcgggtgtt ggcgggtgtc ggggcgcagc catgacccag tcacgtagcg atagcggagt   47940
gtatactggc ttaactatgc ggcatcagag cagattgtac tgagagtgca ccatatgcgg   48000
tgtgaaatac cgcacagatg cgtaaggaga aaataccgca tcaggcgctc ttccgcttcc   48060
tcgctcactg actcgctgcg ctcggtcgtt cggctgcggc gagcggtatc agctcactca   48120
aaggcggtaa tacggttatc cacagaatca ggggataacg caggaaagaa catgtgagca   48180
aaaggccagc aaaaggccag gaaccgtaaa aaggccgcgt tgctggcgtt tttccatagg   48240
ctccgccccc ctgacgagca tcacaaaaat cgacgctcaa gtcagaggtg gcgaaacccg   48300
acaggactat aaagatacca ggcgtttccc cctggaagct ccctcgtgcg ctctcctgtt   48360
ccgaccctgc cgcttaccgg atacctgtcc gcctttctcc cttcgggaag cgtggcgctt   48420
tctcatagct cacgctgtag gtatctcagt tcggtgtagg tcgttcgctc caagctgggc   48480
tgtgtgcacg aaccccccgt tcagcccgac cgctgcgcct tatccggtaa ctatcgtctt   48540
gagtccaacc cggtaagaca cgacttatcg ccactggcag cagccactgg taacaggatt   48600
agcagagcga ggtatgtagg cggtgctaca gagttcttga agtggtggcc taactacggc   48660
tacactagaa ggacagtatt tggtatctgc gctctgctga gccagttacc ttcggaaaa   48720 agagttggta gctcttgatc cggcaaacaa accaccgctg gtagcggtgg tttttttgtt   48780
tgcaagcagc agattacgcg cagaaaaaaa ggatctcaag aagatccttt gatcttttct   48840
acggggtctg acgctcagtg gaacgaaaac tcacgttaag ggattttggt catgagatta   48900
tcaaaaagga tcttcaccta gatccttta aattaaaaat gaagttttaa atcaatctaa   48960
agtatatatg agtaaacttg gtctgacagt taccaatgct taatcagtga ggcacctatc   49020
tcagcgatct gtctatttcg ttcatccata gttgcctgac tccccgtcgt gtagataact   49080
acgatacggg agggcttacc atctggcccc agtgctgcaa tgataccgcg agacccacgc   49140
```
tcaccggctc cagatttatc agcaataaac cagccagccg aagggccga gcgcagaagt 49200 ggtcctgcaa ctttatccgc ctccatccag tctattaatt gttgccggga agctagagta 49260
agtagttcgc cagttaatag tttgcgcaac gttgttgcca ttgctgcagg gggggggggg 49320
gggggggact tccattgttc attccacgga caaaaacaga gaaggaaac gacagaggcc 49380 aaaaagcctc gctttcagca cctgtcgttt cctttctttt cagagggtat tttaaataaa 49440
aacattaagt tatgacgaag aagaacggaa acgccttaaa ccggaaaatt ttcataaata 49500
gcgaaaaccc gcgaggtcgc cgccccggtc ggatcaccgg aaaggacccg taaagtgata 49560
atgattatca tctacatatc acaacgtgcg tggaggccat caaaccacgt caaataatca 49620
attatgacgc aggtatcgta ttaattgatc tgcatcaact taacgtaaaa acaacttcag 49680
acaatacaaa tcagcgacac tgaatacggg gcaacctcat gtcccccccc ccccccccc 49740 tgcaggcatc gtggtgtcac gctcgtcgtt tggtatggct tcattcagct ccggttccca 49800
acgatcaagg cgagttacat gatcccccat gttgtgcaaa aaagcggtta gctccttcgg 49860
tcctccgatc gttgtcagaa gtaagttggc cgcagtgtta tcactcatgg ttatggcagc 49920
actgcataat tctcttactg tcatgccatc cgtaagatgc ttttctgtga ctggtgagta 49980
ctcaaccaag tcattctgag aatagtgtat gcggcgaccg agttgctctt gcccggcgtc 50040
aacacgggat aataccgcgc cacatagcag aactttaaaa gtgctcatca ttggaaaacg 50100
ttcttcgggg cgaaaactct caaggatctt accgctgttg agatccagtt cgatgtaacc 50160
cactcgtgca cccaactgat cttcagcatc ttttactttc accagcgttt ctgggtgagc 50220
aaaaacagga aggcaaaatg ccgcaaaaaa gggaataagg gcgacacgga aatgttgaat 50280
actcatactc ttccttttc aatattattg aagcatttat cagggttatt gtctcatgag 50340
cggatacata tttgaatgta tttagaaaaa taaacaaata ggggttccgc gcacatttcc 50400
ccgaaaagtg ccacctgacg tctaagaaac cattattatc atgacattaa cctataaaaa 50460
taggcgtatc acgaggccct ttcgtcttca agaattggtc gacgatcttg ctgcgttcgg 50520
atattttcgt ggagttcccg ccacagaccc ggattgaagg cgagatccag caactcgcgc 50580
cagatcatcc tgtgacggaa cttttggcgcg tgatgactgg ccaggacgtc ggccgaaaga 50640
gcgacaagca gatcacgctt ttcgacagcg tcggatttgc gatcgaggat ttttcggcgc 50700
tgcgctacgt ccgcgaccgc gttgagggat caagccacag cagcccactc gaccttctag 50760
ccgacccaga cgagccaagg gatcttttg gaatgctgct ccgtcgtcag gctttccgac 50820
gtttgggtgg ttgaacagaa gtcattatcg tacggaatgc caagcactcc cgaggggaac 50880
cctgtggttg gcatgcacat acaaatggac gaacggataa accttttcac gccctttaa 50940 atatccgtta ttctaataaa cgctcttttc tcttag 50976

<210> SEQ ID NO 136
<211> LENGTH: 1000
<212> TYPE: DNA
<213> ORGANISM: Zea mays

<400> SEQUENCE: 136
tgccacgcaa actaaaaggc aaattctaca ggacagcaat ccggccggct atgttgtatg 60
gagcagaatg ttggcccact aaaagacgac atgtccaaca actaagtgtg gcagagatgc 120
gtatgttgcg ctggatatgt ggccacacaa ggagagatcg agtccggaat gatgatatac 180
gagagagagt aggagtggcg ccaattgagg agaagcttat gcaacatcgc ttgagatggt 240
ttggacatat ccaacgaaga cctgaagagg caccagtgca tatcggaata attaggcgtc 300

```
ccgaaaatgt gaagagaggt agaggtcgac caactttgac gtggacagag gctgtgaaga      360
gagacctgaa ggagtggaat aatgacaaag agctcgccgc agataggaag gggtggaagt      420
gtgcaattca cgtgccagaa ccctgattga tagtttcgct tttcctcctt aatcgtttga      480
ccttttcttg tgtccatttt agatcttgct ggtccttgtg ggttttatct cttttatgtg      540
tttccccgtt tcgttgtttt cggttctcct ttgcctttgt ttcccttttc tgttctttgg      600
gggttgagct ctgaggtttt catacggggt ttcatctcta gcctacccca acgtgcttgg      660
gacaaaaagg ctttgttgtt gttgttgttg ttgtatctgt atcctaaaag gtgagagaga      720
agggttatta agaaaaaccc tcgtcgctgg ccactgaagg ccgggcccaa tttagaacct      780
agacctgctg ccaccgcact acaagaccga ggcctaaaag gcccatcagg aggcgcatcg      840
gcgaatgccc caaactaaaa ccctaccccg gcaagtatat atatcctccc aacctcagtt      900
cttgttccca ttatcacggc ggcggtggcg gagcgtaagg cgaaggagta gcagcagcag      960
gcggcgccga gtagcggctc cccatctcga gcttgccacc                           1000

<210> SEQ ID NO 137
<211> LENGTH: 855
<212> TYPE: DNA
<213> ORGANISM: Zea mays

<400> SEQUENCE: 137
gtaaggttcc cttccctcct ccctcacac ccctgttcgt gttccttcgg atcggatctc       60
agtggtgatg ttagacgtcc gcggctgcct acgtagtggc attgccgccc gaaaggtttg      120
tttaggtggg gtagatccga aacaggccgg atctggacca tgtccgcggc ggggcggcgg      180
gacttgatcg cgtagctgtc gtgtgcattt ctccctacca gtggcggaat cggcgatgtg      240
gacctaaggg ctaaggctta tctgctgcct tgaccatttc gtcgctgaca aaaacaaagt      300
gacaatcatg ccgttctctg tttgtttatc tggatcgtta ttacgctgtg aatcctgcga      360
tatgtggcta agtgattttt cttcttttc tgggggcagt ttagcctttg acccagtcct      420
aggtgtggtc actaggactg tgtagcatga tgagtgaggt tgcagcaggc tgattgctag      480
tggacgtttt ttccccaatt tgttaggttt tcacgctcca ggttgtgcaa gtaattttgc      540
tagtgattgt gtgatccatc ttcaacgttg aaccttgttt ttccccctaa aaccccccaac     600 aggaaatctt gccccgactt ctattgcaaa aattgtaacg cttagcaccc tgattgactc      660
aattcctgtc actaggcatg ctcggtcaaa agcagatgat ttaccactta gaaactgccc      720
tgcccctgct ttccacatag catttcgaac tttttgacta ctattgacac cccccctaact    780 tgccgaacta tttctctctt cagctactat ttacctagtt ataattacat aaatgtttgt      840
gtgtatcttg tgcag                                                      855

<210> SEQ ID NO 138
<211> LENGTH: 884
<212> TYPE: DNA
<213> ORGANISM: Zea mays

<400> SEQUENCE: 138
gtgaggcatc cgatcgattt ttctttcttt ctttactaca ctccttcgcg atatggggac       60
ggcactcggt agtggcgtga ggtgcggtaa atcgcgttag tttagttgta gggtttgatc      120
gcttcggggg ggaccggggg ttgggcttcc cgtgttgaac cgtcaatcgg acgtagtagt      180
agtgcggatt cggggtttga tcgacggaaa gaggggttgt ccgcactctt ggtgtggtta      240
```

```
tagggttttg cgatttgttt gtctgtgtag gcccgtttcg tctcggggag tagattttca      300
ttgctactac caatccctat gtgctttggt gaacacgtat tttggtctgt atatggttta      360
aacgtgaaga ctatggtagt gtgagaccat gatttggatc ctttctgtg  gcattatagt     420 taaaatcgtg aggatctatc ttttagcgct tagggtattg ttatagacga gatcccctct      480
ttgggctcta aaaatagcaa gaaaaggaca tcttttgggc aagttaacgt cctgtattat      540
tctgaacgag atctgtttac tttcttataa gtttgatgtt ttggtctgga atatggttgc      600
gttcatcgtc caattagtgt gtttgcagta tgtgttggtg tagttcctct gtgggcattt      660
tgtggcccca gaaatgatag attttaagaa aggtttaggc agaaggggat cttaagtgtt      720
gtccagtaca aagtaacaat ttgtagcact tgtttctttt cttttgtttg actatatgaa      780
atttcggcca tgtaattgtt tcaaaataat aagatcgaat agtgttgcac actacttccc      840
agtcctatgt atacttatca gattttcct  ctttgatatt tcag                      884

<210> SEQ ID NO 139
<211> LENGTH: 1487
<212> TYPE: DNA
<213> ORGANISM: zea mays

<400> SEQUENCE: 139
ccggctatac cgctcccgcc ctcgtttttc agtaaaaaaa atatggtaat ggaagtggga       60
gagagttttt ccaactgttt ccgatcgttt tcatccctat ctataaacat ccacatgagt      120
aggggaggcg gggtggcgag tggacgacac tgtagccaac ctaaggacca aagctttagc      180
cttaaccatt gcaccatgtg tcgcttattg ttatatagag tatataaatg tatatagtaa      240
caatttgaaa attaaaatta aaatcatgat tgaataaaaa tctcatttaa ataaaaaatt      300
acatatatga tatatagaat tcataacaat gtacgagtaa ctaactagtt ctatacttaa      360
gcataaatag aaagcgtagc aatgtatgca cactttgcta gtcggatatt tagatactag      420
ttagaagtat taaatatagt ctaagtataa aactaattat atagatgagg actaaacagc      480
aagacgaacc tattaagttt aagtagtcca tggttcgtcc atgtaaaata aatatttgct      540
aataatagat taattagact taatagatcc atctcgtcgt ttagtcttta tctatataat      600
tacttttgta gttagactat attaattttt agtaattgac atttaaacat ccgatatgat      660
ccagacttga tgttagtcag gaaaaccaaa catcccctta accatattgg tcccaatttt      720
tggtgccttt acccatcaaa tgatattcac acaatcacac atctgggcct aactttcatc      780
gttgctgtcc acgacggcga cctggaggcg aggtcaattc cttggcccaa gcatagcttg      840
gagcttgcac gctaagaaga ggctctcgta ctctacaaac agtacagcac atacaggtga      900
caaaacgaca cacatcaacc agccaaataa taaatgagct tcttcatggg cacggcaagc      960
cgacaactac caacaagata caggtgacaa aaagaaaaca agaggccccc actcaccagt     1020
gggtcgtagg caacgcacgc ggacgcggtc cagcgggcga aagatcccc  gacttgcgcc     1080 caaagaagat acaggatcaa ggatttttaa ccgcagtttt ctattccacg accttatcca     1140
caccagcaga ttcgaaattc acggacaggc ccatggaccc ggcgaaagcc agcggtggtt     1200
cagcccctga cgtgcgggtc ccactctcca gccgcaccgc ctagagaggc agaggcatcc     1260
cttcgcgtgg aagcaaacga ggcgtgataa agtgggggctc ctcggtcccg gcgttggccg    1320
catcgacact cgccgcgcac caccaccacc gctgcggctc acggctacgc agcccgctct     1380
cccgaccccc ccgtgccctc ctcttttgc  tactagcaca tagagtttcg cccgaatcga    1440
tcgccgactg actccgctag ggttcggccc gatcgccgct tcgtcct                  1487
```

<210> SEQ ID NO 140
<211> LENGTH: 629
<212> TYPE: DNA
<213> ORGANISM: zea mays

<400> SEQUENCE: 140

```
atcctctgaa tgtgctgtgt tgagagtttt ttctagttgc tctgcaagga tatagaacaa      60
tgttctaaga ctaccatgtt tttaagtctg cctgatgctt ataattcatg aacgattttt     120
gcagctagct gtaatgtgac tatttatctt atctgcttgt tcaaccctgt tgtcgtgtgt     180
tgattctctg tttcatggtc ttttcactcg acagaaacag ttatttctta agaacttcac     240
cattatattc acagctgtga actatgatat tggaagtctt tggtcatttt tcgttgaact     300
attttgctga aagtttttc cgagaaagat gccagaccgg tctccgatct aagaatggcc      360
ataactgatg agcatcacaa ggtatatatt agttgatcaa atgtctttga gtacatctgt     420
ttgacacagc ttatttttag cttcttcaca tatttaagca tagcttattt ttagcttctt     480
ttaatattta agcagaagtt ttactaaact ggtagcatct ccagcagctt attagttcag     540
ctgactctta aatgaactaaaagcagcca acaagtataa gctattttt accagtttct       600
tagataactt gtttttctaa caaatagtg                                      629
```

<210> SEQ ID NO 141
<211> LENGTH: 607
<212> TYPE: DNA
<213> ORGANISM: zea mays

<400> SEQUENCE: 141

```
gccatcagtc gttgaagctg ctgctgtatc tgggttatct agtgtctctg ccattgccca      60
tggatggtgc tgtcttcaa agtatttgta tggtttgtgt cgtgagtcgt gactgagctg     120
gtttcatgga ccagttgtgt tctcgttacc caaaactatc gtgcgaccgc atatggctta     180
atcatgaata aatgttgttt gaatttaaac tattcgctga atattgttgt ttttttgtcat   240
gtcagttaat gttactaaat tggttgcctt ctaattttg tttactggtg tttgtcgcac     300
cttatctttt tactgtatgt ttacttcagg ttctggcagt ctcatttttt gtgactagtt    360
aaaacttaca gctaaaaaaa tgcagttttt cattttcatt tgaagtttga ttagagctat   420
tgataccgga ccatcaggtt aggttagttg tgcatagaat cataaatatt aatcatgttt   480
tctatgaatt aagtcaaact tgaaagtctg gctgaatata gtttctatga atcatattga   540
tatacatgtt tgattatttg ttttgctatt agctatttac tttggtgaat ctatataggc   600
ttatgca                                                              607
```

<210> SEQ ID NO 142
<211> LENGTH: 646
<212> TYPE: DNA
<213> ORGANISM: zea mays

<400> SEQUENCE: 142

```
cgcttttagt atggcctcgg aaacatggcc tgcctgttgc tagtagaaag ctagcactgc      60
ccttttggta agggcgtttc aggagcactg tgctggacta tatagagaga tgctcctctg     120
tgactgtgac cacctcacgt tctgcgtact ctgtaatctg gtaggatgcc tgtctctatc     180
atgattcatg aaggacgatt ggtctgtctt ttttttatcg tgctatttat taatcgtgta    240
aatgtactag cgaagggaag gcactggtag ctaggttagc tcgagtccgg atggaatgat    300
```

```
aatgctacta atacaaacaa tgccgtagtg tgtgtgtgta tttatcaact cgcgtgtcat    360
cacgtccgtt aagttgccgc tggtatctcc ctccctgtcg gtggcgcgta ttctcggcgc    420
actcctctga accagcatga attcagagca aggtagaggg gcctgtaaac cgtccaccat    480
ctgtctagct gttcttggta gaacacttgc agagattctc agctctctct ctctctctct    540
ctctctctct ctctctctcg tcccgtccta gcggacaagc ggagtggggc tccctcgctc    600
tgtgtcactg cttgctgcat cgctgaaagc ggtagatgcg gcggta                  646

<210> SEQ ID NO 143
<211> LENGTH: 936
<212> TYPE: DNA
<213> ORGANISM: zea mays

<400> SEQUENCE: 143
agatcgtgtg ctatctaagt atatattcgt aaataatgag acggctgtgc cactgcggtg     60
cagccctggt gcgtctcaga gcttgcttat ggtgaactct tcgtgttagg tttcttcctt    120
atatctgtcg tgtctgcggt gtcgatgaac tatctagtat gtggagcgtg tgcgtctcag    180
cagttaccct gccatgccac gtggactggc tgtcgtgcct actgtctgtt accatgtata    240
tatataaaaa atgatgcgtg gaccaatgtt tgatgctggc gctcttgccc tcgtgataat    300
gtattagcgg ttggcttgtt gcttgcttgt cagccccagg taaatcttgc tgcttgcttt    360
gcttgcagaa gcgagcgtct gcacgtacgt aatcaggata actgtatgca gcgatttggt    420
gatatgcact gccagtggag tttgcttcac aaagaatgga atggaacctg gcgaccctac    480
gtggagtttg cgcaccgatg taaggagctg gaggccggct ccgaggacta ttgcttccac    540
ttcctatatg tggcacgctg aagggcaatg ccgtgtttta gttgaaattt tggccagtcc    600
acgagcaatg tggtgtttct actctctgta tctctactaa tattaccaaa atcaaatcct    660
ctgattatct ctacctgtct ttatcagcca ttggtatttt gggtgtgtgt gtgtttcatc    720
tttatctacg tgcttctgta gaaagatggc aggcaaaatc gttgggttg tagttgtagg    780 tagtagctac aaagagacga gacttgggag gtgattatct tttgtagagt gaatagcttg    840
aatgaataac cgtttgtgtc tatgtaggac ccactgaata ttcaggagaa aaactgttgt    900
catatattgc gtgctattca agctcgcttc tgcctt                              936

<210> SEQ ID NO 144
<211> LENGTH: 16437
<212> TYPE: DNA
<213> ORGANISM: Artificial sequence
<220> FEATURE:
<223> OTHER INFORMATION: Vector sequence

<400> SEQUENCE: 144
gtttacccgc caatatatcc tgtcaaacac tgatagttta aactgaaggc gggaaacgac     60
aatctgatca tgagcggaga attaagggag tcacgttatg accccgccg atgacgcggg    120 acaagccgtt ttacgtttgg aactgacaga accgcaacgt tgaaggagcc actcagcaag    180
ctggtacgat tgtaatacga ctcactatag gcgaattga gcgctgttta acgctcttc    240 aactggaaga gcggttacca gagctggtca cctttgtcca ccaagatgga actgcggcct    300
cgaagctggc gcgccgtgca gcgtgacccg gtcgtgcccc tctctagaga taatgagcat    360
tgcatgtcta agttataaaa aattaccaca tatttttttt gtcacacttg tttgaagtgc    420
agtttatcta tctttataca tatatttaaa ctttactcta cgaataatat aatctatagt    480
actacaataa tatcagtgtt ttagagaatc atataaatga acagttagac atggtctaaa    540
```

```
ggacaattga gtattttgac aacaggactc tacagtttta tcttttagt gtgcatgtgt      600 tctccttttt ttttgcaaat agcttcacct atataatact tcatccattt tattagtaca      660
tccatttagg gtttagggtt aatggttttt atagactaat ttttttagta catctatttt      720
attctatttt agcctctaaa ttaagaaaac taaaactcta ttttagtttt tttatttaat      780
aatttagata taaaatagaa taaaataaag tgactaaaaa ttaaacaaat accctttaag      840
aaattaaaaa aactaaggaa acattttct tgtttcgagt agataatgcc agcctgttaa       900
acgccgtcga cgagtctaac ggacaccaac cagcgaacca gcagcgtcgc gtcgggccaa      960
gcgaagcaga cggcacggca tctctgtcgc tgcctctgga cccctctcga gagttccgct     1020
ccaccgttgg acttgctccg ctgtcggcat ccagaaattg cgtggcggag cggcagacgt     1080
gagccggcac ggcaggcggc ctcctcctcc tctcacggca ccggcagcta cggggggattc    1140 cttcccacc gctccttcgc tttccttcc tcgcccgccg taataaatag acacccctc       1200 cacccctct ttccccaacc tcgtgttgtt cggagcgcac acacacacaa ccagatctcc     1260
cccaaatcca cccgtcggca cctccgcttc aaggtacgcc gctcgtcctc cccccccccc     1320
ctctctacct tctctagatc ggcgttccgg tccatgcatg gttagggccc ggtagttcta    1380
cttctgttca tgtttgtgtt agatccgtgt ttgtgttaga tccgtgctgc tagcgttcgt     1440
acacggatgc gacctgtacg tcagacacgt tctgattgct aacttgccag tgtttctctt    1500
tggggaatcc tgggatggct ctagccgttc cgcagacggg atcgatttca tgatttttt      1560 tgtttcgttg catagggttt ggtttgccct tttccttat ttcaatatat gccgtgcact      1620
tgtttgtcgg gtcatctttt catgcttttt tttgtcttgg ttgtgatgat gtggtctggt    1680
tgggcggtcg ttctagatcg gagtagaatt ctgtttcaaa ctacctggtg gatttattaa    1740
ttttggatct gtatgtgtgt gccatacata ttcatagtta cgaattgaag atgatggatg    1800
gaaatatcga tctaggatag gtatacatgt tgatgcgggt tttactgatg catatacaga    1860 gatgctttt gttcgcttgg ttgtgatgat gtggtgtggt tgggcggtcg ttcattcgtt     1920
ctagatcgga gtagaatact gtttcaaact acctggtgta tttattaatt ttggaactgt    1980
atgtgtgtgt catacatctt catagttacg agtttaagat ggatggaaat atcgatctag    2040
gataggtata catgttgatg tgggttttac tgatgcatat acatgatggc atatgcagca    2100
tctattcata tgctctaacc ttgagtacct atctattata taaacaagt atgttttata     2160 attattttga tcttgatata cttggatgat ggcatatgca gcagctatat gtggattttt    2220
ttagccctgc cttcatacgc tatttatttg cttggtactg tttcttttgt cgatgctcac    2280
cctgttgttt ggtgttactt ctgcaggtcg actttaactt agcctaggat ccacacgaca    2340
ccatggtccg tcctgtagaa accccaaccc gtgaaatcaa aaaactcgac ggcctgtggg    2400
cattcagtct ggatcgcgaa aactgtggaa ttgatcagcg ttggtgggaa agcgcgttac    2460
aagaaagccg ggcaattgct gtgccaggca gttttaacga tcagttcgcc gatgcagata    2520
ttcgtaatta tgcgggcaac gtctggtatc agcgcgaagt ctttataccg aaaggttggg    2580
caggccagcg tatcgtgctg cgtttcgatg cggtcactca ttacggcaaa gtgtgggtca    2640
ataatcagga agtgatggag catcagggcg gctatacgcc atttgaagcc gatgtcacgc    2700
cgtatgttat tgccgggaaa agtgtacgta agtttctgct tctaccttg atatatat       2760 aataattatc attaattagt agtaaatata tattcaaat atttttttca aaataaaaga      2820
atgtagtata tagcaattgc ttttctgtag tttataagtg tgtatatttt aatttataac    2880
```

```
ttttctaata tatgaccaaa atttgttgat gtgcaggtat caccgtttgt gtgaacaacg    2940
aactgaactg gcagactatc ccgccgggaa tggtgattac cgacgaaaac ggcaagaaaa    3000
agcagtctta cttccatgat ttctttaact atgccggaat ccatcgcagc gtaatgctct    3060
acaccacgcc gaacacctgg gtggacgata tcaccgtggt gacgcatgtc gcgcaagact    3120
gtaaccacgc gtctgttgac tggcaggtgg tggccaatgg tgatgtcagc gttgaactgc    3180
gtgatgcgga tcaacaggtg gttgcaactg gacaaggcac tagcgggact ttgcaagtgg    3240
tgaatccgca cctctggcaa ccgggtgaag gttatctcta tgaactgtgc gtcacagcca    3300
aaagccagac agagtgtgat atctacccgc ttcgcgtcgg catccggtca gtggcagtga    3360
agggcgaaca gttcctgatt aaccacaaac cgttctactt tactggcttt ggtcgtcatg    3420
aagatgcgga cttgcgtggc aaaggattcg ataacgtgct gatggtgcac gaccacgcat    3480
taatggactg gattggggcc aactcctacc gtacctcgca ttacccttac gctgaagaga    3540
tgctcgactg ggcagatgaa catggcatcg tggtgattga tgaaactgct gctgtcggct    3600
ttaacctctc tttaggcatt ggtttcgaag cgggcaacaa gccgaaagaa ctgtacagcg    3660
aagaggcagt caacggggaa actcagcaag cgcacttaca ggcgattaaa gagctgatag    3720
cgcgtgacaa aaaccaccca agcgtggtga tgtggagtat tgccaacgaa ccggatacccc    3780 gtccgcaagg tgcacgggaa tatttcgcgc cactggcgga agcaacgcgt aaactcgacc    3840
cgacgcgtcc gatcacctgc gtcaatgtaa tgttctgcga cgtcacacc gataccatca    3900 gcgatctctt tgatgtgctg tgcctgaacc gttattacgg atggtatgtc caaagcggcg    3960
atttggaaac ggcagagaag gtactggaaa agaacttct ggcctggcag gagaaactgc    4020
atcagccgat tatcatcacc gaatacggcg tggatacgtt agccgggctg cactcaatgt    4080
acaccgacat gtggagtgaa gagtatcagt gtgcatggct ggatatgtat caccgcgtct    4140
ttgatcgcgt cagcgccgtc gtcggtgaac aggtatggaa tttcgccgat tttgcgacct    4200
cgcaaggcat attgcgcgtt ggcggtaaca agaaagggat cttcactcgc gaccgcaaac    4260
cgaagtcggc ggcttttctg ctgcaaaaac gctggactgg catgaacttc ggtgaaaaac    4320
cgcagcaggg aggcaaacaa ggtaccgatc catggcctcc tccgaggacg tcatcaagga    4380
gttcatgcgc ttcaaggtgc gcatggaggg ctccgtgaac ggccacgagt cgagatcga    4440 gggcgagggc gagggccgcc cctacgaggg cacccagacc gccaagctga aggtgaccaa    4500
gggcggcccc ctgcccttcg cctgggacat cctgtccccc cagttccagt acggctccaa    4560
ggtgtacgtg aagcacccg ccgacatccc cgactacaag aagctgtcct tccccgaggg    4620
cttcaagtgg gagcgcgtga tgaacttcga ggacggcggc gtggtgaccg tgacccagga    4680
ctcctccctg caggacggct ccttcatcta caaggtgaag ttcatcggcg tgaacttccc    4740
ctccgacggc cccgtaatgc agaagaagac tatgggctgg gaggcctcca ccgagcgcct    4800 gtaccccgc gacggcgtgc tgaagggcga gatccacaag gccctgaagc tgaaggacgg    4860
cggccactac ctggtggagt tcaagtccat ctacatggcc aagaagcccg tgcagctgcc    4920
cggctactac tacgtggact ccaagctgga catcacctcc cacaacgagg actacaccat    4980
cgtggagcag tacgagcgcg ccgagggccg ccaccacctg ttcctgtagg ccggccatc    5040 aacaactctc ctggcgcacc atcgtcggct acagcctcgg tgacgtgggg caacctagac    5100
ttgtccatct tctggattgg ccaacttaat taatgtatga aataaaagga tgcacacata    5160
gtgacatgct aatcactata atgtgggcat caaagttgtg tgttatgtgt aattactagt    5220
tatctgaata aaagagaaag agatcatcca tatttcttat cctaaatgaa tgtcacgtgt    5280
```

```
ctttataatt ctttgatgaa ccagatgcat ttcattaacc aaatccatat acatataaat    5340
attaatcata tataattaat atcaattggg ttagcaaaac aaatctagtc taggtgtgtt    5400
ttgcgaattg cggccgcgat ctgagcttct agaggatccc catcgatggg ccccggccga    5460
agcttgcatg cctgcagtgc agcgtgaccc ggtcgtgccc ctctctagag ataatgagca    5520
ttgcatgtct aagttataaa aaattaccac atattttttt tgtcacactt gtttgaagtg    5580
cagtttatct atctttatac atatatttaa actttactct acgaataata taatctatag    5640
tactacaata atatcagtgt tttagagaat catataaatg aacagttaga catggtctaa    5700
aggacaattg agtattttga caacaggact ctacagtttt atcttttttag tgtgcatgtg   5760
ttctcctttt tttttgcaaa tagcttcacc tatataatac ttcatccatt ttattagtac    5820
atccatttag ggtttagggt taatggtttt tatagactaa tttttttagt acatctattt    5880
tattctattt tagcctctaa attaagaaaa ctaaaactct attttagttt ttttatttaa    5940
taatttagat ataaaataga ataaaataaa gtgactaaaa attaaacaaa taccctttaa    6000
gaaattaaaa aaactaagga aacattttc ttgtttcgag tagataatgc cagcctgtta     6060
aacgccgtcg acgagtctaa cggacaccaa ccagcgaacc agcagcgtcg cgtcgggcca    6120
agcgaagcag acggcacggc atctctgtcg ctgcctctgg accctctcg agagttccgc     6180
tccaccgttg gacttgctcc gctgtcggca tccagaaatt gcgtggcgga gcggcagacg    6240
tgagccggca cggcaggcgg cctcctcctc ctctcacggc accggcagct acggggatt     6300
cctttcccac cgctccttcg ctttcccttc ctcgcccgcc gtaataaata gacacccct     6360
ccacaccctc ttccccaac ctcgtgttgt tcggagcgca cacacacaca accagatctc     6420
ccccaaatcc acccgtcggc acctccgctt caaggtacgc cgctcgtcct ccccccccc    6480
cctctctacc ttctctagat cggcgttccg gtccatgcat ggttagggcc cggtagttct    6540
acttctgttc atgtttgtgt tagatccgtg tttgtgttag atccgtgctg ctagcgttcg    6600
tacacggatg cgacctgtac gtcagacacg ttctgattgc taacttgcca gtgtttctct    6660
ttggggaatc ctgggatggc tctagccgtt ccgcagacgg gatcgatttc atgatttttt    6720
ttgtttcgtt gcatagggtt tggtttgccc ttttcctta tttcaatata tgccgtgcac     6780
ttgtttgtcg ggtcatcttt tcatgctttt tttttgtcttg gttgtgatga tgtggtctgg   6840
ttgggcggtc gttctagatc ggagtagaat tctgtttcaa actacctggt ggatttatta   6900
attttggatc tgtatgtgtg tgccatacat attcatagtt acgaattgaa gatgatggat    6960
ggaaatatcg atctaggata ggtatacatg ttgatgcggg ttttactgat gcatatacag    7020
agatgctttt tgttcgcttg gttgtgatga tgtggtgtgg ttgggcggtc gttcattcgt    7080
tctagatcgg agtagaatac tgtttcaaac tacctggtgt atttattaat tttgaactg      7140
tatgtgtgtg tcatacatct tcatagttac gagtttaaga tggatggaaa tatcgatcta   7200
ggataggtat acatgttgat gtgggtttta ctgatgcata tacatgatgg catatgcagc    7260
atctattcat atgctctaac cttgagtacc tatctattat aataaacaag tatgttttat    7320
aattattttg atcttgatat acttggatga tggcatatgc agcagctata tgtggatttt    7380
tttagccctg ccttcatacg ctattttatt gcttggtact gtttcttttg tcgatgctca    7440
ccctgttgtt tggtgttact tctgcaggtc gactttaact tagcctagga tccacacgac    7500
accatgtccc ccgagcgccg ccccgtcgag atccgcccgg ccaccgccgc cgacatggcc    7560
gccgtgtgcg acatcgtgaa ccactacatc gagacctcca ccgtgaactt ccgcaccgag    7620
```

```
ccgcagaccc cgcaggagtg gatcgacgac ctggagcgcc tccaggaccg ctaccgtgg      7680
ctcgtggccg aggtggaggg cgtggtggcc ggcatcgcct acgccggccc gtggaaggcc      7740
cgcaacgcct acgactggac cgtggagtcc accgtgtacg tgtcccaccg ccaccagcgc      7800
ctcggcctcg gctccaccct ctacacccac ctcctcaaga gcatggaggc ccagggcttc      7860
aagtccgtgg tggccgtgat cggcctcccg aacgaccgt ccgtgcgcct ccacgaggcc      7920
ctcggctaca ccgcccgcgg caccctccgc gccgccggct acaagcacgg cggctggcac      7980
gacgtcggct tctggcagcg cgacttcgag ctgccggccc cgccgcgccc ggtgcgcccg      8040
gtgacgcaga tctgagtcga aacctagact tgtccatctt ctggattggc caacttaatt      8100
aatgtatgaa ataaaaggat gcacacatag tgacatgcta atcactataa tgtgggcatc      8160
aaagttgtgt gttatgtgta attactagtt atctgaataa aagagaaaga gatcatccat      8220
atttcttatc ctaaatgaat gtcacgtgtc tttataattc tttgatgaac cagatgcatt      8280
tcattaacca aatccatata catataaata ttaatcatat ataattaata tcaattgggt      8340
tagcaaaaca aatctagtct aggtgtgttt tgcgaatgcg gccgccaccg cggtggagct      8400
cgaattcatt ccgattaatc gtggcctctt gctcttcagg atgaagagct atgtttaaac      8460
gtgcaagcgc tactagacaa ttcagtacat taaaaacgtc cgcaatgtgt tattaagttg      8520
tctaagcgtc aatttgttta caccacaata tatcctgcca ccagccagcc aacagctccc      8580
cgaccggcag ctcggcacaa aatcaccact cgatacaggc agcccatcag tccgggacgg      8640
cgtcagcggg agagccgttg taaggcggca gactttgctc atgttaccga tgctattcgg      8700
aagaacggca actaagctgc cgggtttgaa acacggatga tctcgcggag ggtagcatgt      8760
tgattgtaac gatgacagag cgttgctgcc tgtgatcaaa tatcatctcc ctcgcagaga      8820
tccgaattat cagccttctt attcatttct cgcttaaccg tgacaggctg tcgatcttga      8880
gaactatgcc gacataatag gaaatcgctg gataaagccg ctgaggaagc tgagtggcgc      8940
tatttcttta gaagtgaacg ttgacgatcg tcgggcccag gtagaatccg cctgagtcgc      9000
aagggtgact tcgcctatat tggacgacgg cgcgcagagg gcgacctctt tttgggttac      9060
gattgtagga ttatcactaa aacaatacat gaacatattc aaatggcaat ctctctaagg      9120
cattggaaat aaatacaaat aacagttggg tggagttttt cgacctgagg gcgttaacct      9180
tctgttaacc taaaagctct tgcccaaaca gcagaatcgg cgctaattgc cagcggcgga      9240
acttttccag tttcgcgaaa aatatcgcca ctggcaagga atgggtttga gatggcgaag      9300
tctgtcctaa aagcagcgcc tgtagttgta gggttgacgg ccttgatgga gcgtcatgcc      9360
gatgccctct cgagccaact tcaagcacat catcttaagg ttttcccgcc gcattccgag      9420
aagggcattc gaacattcgg gccatcggag gcgtccaagc tgctcggcgt tggcgagtca      9480
tatttacggc agaccgcgtc tgagatgcca gagttgaatg ttagcatgag cccgggtggc      9540
aggcgaatgt tctcaattga agatatccat gtgattcgga agtatatgga tcaggtcggc      9600
cgcgggaacc ggcgctacct gccacatcgt cgaggcggcg agcagcttca ggttatctct      9660
gtgatgaatt tcaaaggtgg gtcgggtaag accaccaccg ccgcgcatct ggcgcagtac      9720
ctcgctatgc gcggatatcg agtcttggcc attgatctcg atcctcaagc gagccttcct      9780
gcactctttg ggagccaacc ggagacggac gttgcccga acgaaacgct ctacggcgct      9840
ataaggtatg atgatgagca ggtggcaatc gaacgagtcg tccgagggac ttacattccc      9900
gacctccacc tgattcctgg taaccttgag ctgatggagt ttgaacacga tacgccacgc      9960
gcgctgatga accgcaaaga gggcgacacg ctcttttatg gtcgcatcag ccaagtaatt     10020
```

```
gaagatatcg cggataacta tgacgtcgtg gtcatcgact gccctcccca gcttgggtat   10080
ctcacgctat ccgcattgac tgcggcgacg tccattcttg tcacggtcca tccgcagatg   10140
ctggatgtga tgtcgatgaa ccagtttctg gcaatgacat cgaacctttt gcgtgaaatc   10200
gagaatgctg cgccaagtt caagtttaat tggatgcgct atctgataac ccgtttcgaa   10260
ccgagcgacg gaccacagaa ccaaatggta ggttatctgc ggtcgatttt tggcgaaaat   10320
gtcctcaatt ttccgatgct taaaaccacc gcggtttcgg acgctggcct gacaaaccag   10380
actctattcg aagtggagcg tggcctgttc acgcgctcga cctatgatcg agccttggag   10440
gcgatgaacg ccgtcaacga cgagatcgaa acactgatca aaaaagcatg gggtaggccc   10500
acatgagccg gaagcacatc cttggcgtct caactgacgc ccctgagacg tcgcccgccg   10560
acaataggac ggcaaagaac cgctccatgc cgctcctcgg cgtaacaagg aaggagcgcg   10620
atccggcaac gaagctcaca gcgaacattg gtaacgcact gcgagagcaa aacgatcgtc   10680
ttagccgtgc cgaagagatc gagcggcgtc tcgctgaagg tcaggcagtg atagagttgg   10740
atgcctcgtc aatagaaccg tctttcgtgc aggatcgtat gcgagggac attgacgggc   10800 tccttacttc gatccgggaa caaggacagc aagtcccaat ccttgtgcga ccgcatccga   10860
gccagccggg ccgatatcag gttgccttcg gccaccgccg gctacgcgcc gtttcagaac   10920
tcggacttcc ggtcagagcg gtcgttcgcg aactgacgga cgagcaagtg gtcgtagcac   10980
agggtcagga aaacaatgag cgcgaagatc ttaccttcat cgaaaaggcg cgcttcgcac   11040
atcgcctgaa caggcagttt tctcgagaga ttgtcatcgc cgcgatgtcg atcgacaaga   11100
gcaatttgtc caagatgctt ctgctcgttg acgccctccc ctctgaactg accgatgcta   11160
ttggtgccgc tcctggtgtt ggacggccga gttggcaaca acttgccgag ctgattgaga   11220
aagtttcttc accggccgac gtggctaaat atgctatgtc ggaggaagtt caagcgctgc   11280
catcggcaga acgattcaag gcggtgatcg ctagtctgaa gcccagtcgg gttgcgcgtg   11340
gacttcccga ggtcatggcc accccagacg gcaccagaat tgcacaggtg acgcagagca   11400
aggccaaact ggaaatcacg attgacagga aggcgacgcc cgattttgcg accttcgtgc   11460
tcgatcatgt gccagcgctg tatcaagcgt accacgctga gaaccaacgg aaacggggag   11520
agtaaaccgc aaaagaaaag agcccctca acgtcgccgt cgcggaagcc cttctgtctc   11580
tctagcgcga acagaatcgc atttcctcga atcctcgtca agagttttta gcgccgtttt   11640
ggtgagctga tttcctttgc ctgctgaaag gtgaaagatg atgcagacag gaagtgtaac   11700
gacgccattc gggcggcggc caatgacgct tgcgcttgtg cggcgccaga cggcgctggc   11760
cgatatcaaa caaggcaaga cagcggacaa gtggaaggtc tttagagacg cgtccgcggc   11820
tatgaaacta cttggaatcc agtccaacag tcttgccgtc cttgatgcgc tattgagctt   11880
tcacccggaa acggagttgc gtcaggaggc acagctgatc gtcttcccgt cgaatgctca   11940
gcttgccctt cgggcgcatg ggatggctgg cgcgactttg cgtaggcaca tcgccatgct   12000
cgtggagtca ggcttgatcg tccggaagga tagcgccaac ggaaagcgtt acgctcgtaa   12060
ggatggcgct ggtcagatcg agcgcgcgtt tggcttcgat ttgtctccgc ttctcgcgcg   12120
gtccgaagag ctagcgatga tggcacagca ggtgatggcc gatcgagcag cattcaggat   12180
ggccaaagaa agtctgacga tttgccgacg ggacgttcgg aagctaatta cggcagctat   12240
ggaagaggga gcgagggcg actggcaagc tgtcgaggaa gtctatgtgg aacttgtggg   12300
tagaattcca cgcgccccga cgcttgctga tgtagagtca attctcgaag agatgtggat   12360
```

```
gctccaggaa gagataatca accggttgga aattagagac aattcagaaa ataatagcac    12420
caatgctgcc cagagcgagc agcacataca gaattcaaaa cccgaatccg ttaatgaact    12480
tgaacctcgc tctgaaaagg agcagggcgc taagccgagt gaaatagacc gggcaaggag    12540
cgagccgata aaagcgttcc ccctcgggat gatcctgaaa gcatgcccga ccattggcaa    12600
ttatgggccg agcggtgcgg ttgctagctg gcgtgacctc atgtcggctg cggtggtggt    12660
tcggtctatg ctgggggtca gcccgtcggc ttaccaagac gcgtgtgagg caatgggacc    12720
ggagaatgcg gcagcagcga tggcgtgcat tttggagcga gcgaacttca tcaattcgcc    12780
cgggggctat ctccgagatc tgacacggcg gagcgagctt gggaagtttt cacttggccc    12840
gatgataatg gcgctcttga aggctagcgg gcaggggacg ttgcggtttg gctagaatta    12900
gcgagtatgg agcaggatgg tctgtggtca gctgaccaca gacctaatag gttgaaaaca    12960
tgagcgtttt ttggatgatc gacagaccat ccgattcccg gagtaccaag cgtgctctga    13020
tgggagcgat aacattactc aacaagcacg aaggccccat gccgatcgtt gatcgtgaag    13080
gagagcctgc tctacatgcg gcggtatttt gccggccgag gcatgtagtc gcggagcact    13140
gcctatttac tgccctaggc acaaacgttg actcttggat cgagctggca gacaaagcaa    13200
taacccacac agaggacgat taatggctga cgaagagatc cagaatccgc cggacggtac    13260
tgctgctgcc gaagttgagc cggctgctcc tagaggtaga agagcaaaga aagcaccagc    13320
cgaaacagcc cgcacgggat cgttcaaatc cgtgaagccg aaaacccgcg gcctcagcaa    13380
ccgagaaaaa ctggagaaga tcggtcaaat cgaagctcag gtcgctggcg gcgcaacctt    13440
gaaggacgcc gttaagatcg tgggtatttc cgttcagacc tattatcaat ggaagagagc    13500
tgcggttcaa cctgtctcac agaatccggc cgtgtctgtt tcagttgacg atgaactcgg    13560
cgagttcatc caactcgagg aggaaaatat gcatggcatg cccgttccat acagaagctg    13620
ggcgaacaaa cgatgctcgc cttccagaaa accgaggatg cgaaccactt catccggggt    13680
cagcaccacc ggcaagcgcc gcgacggccg aggtcttccg atctcctgaa gccagggcag    13740
atccgtgcac agcaccttgc cgtagaagaa cagcaaggcc gccaatgcct gacgatgcgt    13800
ggagaccgaa accttgcgct cgttcgccag ccaggacaga aatgcctcga cttcgctgct    13860
gcccaaggtt gccgggtgac gcacaccgtg gaaacggatg aaggcacgaa cccagtggac    13920
ataagcctgt tcggttcgta agctgtaatg caagtagcgt atgcgctcac gcaactggtc    13980
cagaaccttg accgaacgca gcggtggtaa cggcgcagtg gcggttttca tggcttgtta    14040
tgactgtttt tttgggggtac agtctatgcc tcgggcatcc aagcagcaag cgcgttacgc    14100
cgtgggtcga tgtttgatgt tatggagcag caacgatgtt acgcagcagg gcagtcgccc    14160
taaaacaaag ttaaacatca tgagggaagc ggtgatcgcc gaagtatcga ctcaactatc    14220
agaggtagtt ggcgtcatcg agcgccatct cgaaccgacg ttgctggccg tacatttgta    14280
cggctccgca gtggatggcg gcctgaagcc acacagtgat attgatttgc tggttacggt    14340
gaccgtaagg cttgatgaaa caacgcggcg agctttgatc aacgaccttt tggaaacttc    14400
ggcttcccct ggagagagcg agattctccg cgctgtagaa gtcaccattg ttgtgcacga    14460
cgacatcatt ccgtggcgtt atccagctaa gcgcgaactg caatttggag aatggcagcg    14520
caatgacatt cttgcaggta tcttcgagcc agccacgatc gacattgatc tggctatctt    14580
gctgacaaaa gcaagagaac atagcgttgc cttggtaggt ccagcggcgg aggaactctt    14640
tgatccggtt cctgaacagg atctatttga ggcgctaaat gaaaccttaa cgctatggaa    14700
ctcgccgccc gactgggctg gcgatgagcg aaatgtagtg cttacgttgt cccgcatttg    14760
```

```
gtacagcgca gtaaccggca aaatcgcgcc gaaggatgtc gctgccgact gggcaatgga    14820
gcgcctgccg gcccagtatc agcccgtcat acttgaagct agacaggctt atcttggaca    14880
agaagaagat cgcttggcct cgcgcgcaga tcagttggaa gaatttgtcc actacgtgaa    14940
aggcgagatc accaaggtag tcggcaaata atgtctaaca attcgttcaa gccgacgccg    15000
cttcgcggcg cggcttaact caagcgttag atgcactata cgtaaccaac tagtgcgctc    15060
ttccgcttcc tcgctcactg actcgctgcg ctcggtcgtt cggctgcggc gagcggtatc    15120
agctcactca aaggcggtaa tacggttatc cacagaatca ggggataacg caggaaagaa    15180
catgtgagca aaaggccagc aaaaggccag gaaccgtaaa aaggccgcgt tgctggcgtt    15240
tttccatagg ctccgccccc ctgacgagca tcacaaaaat cgacgctcaa gtcagaggtg    15300
gcgaaacccg acaggactat aaagatacca ggcgtttccc cctggaagct ccctcgtgcg    15360
ctctcctgtt ccgaccctgc cgcttaccgg atacctgtcc gcctttctcc cttcgggaag    15420
cgtggcgctt tctcatagct cacgctgtag gtatctcagt tcggtgtagg tcgttcgctc    15480
caagctgggc tgtgtgcacg aacccccgt tcagcccgac cgctgcgcct tatccggtaa    15540
ctatcgtctt gagtccaacc cggtaagaca cgacttatcg ccactggcag cagccactgg    15600
taacaggatt agcagagcga ggtatgtagg cggtgctaca gagttcttga agtggtggcc    15660
taactacggc tacactagaa ggacagtatt tggtatctgc gctctgctga gccagttac    15720 cttcggaaaa agagttggta gctcttgatc cggcaaacaa accaccgctg gtagcggtgg    15780
tttttttgtt tgcaagcagc agattacgcg cagaaaaaaa ggatctcaag aagatccttt    15840
gatcttttct acggggtctg acgctcagtg gaacgaaaac tcacgttaag ggattttggt    15900
catgagatta tcaaaaagga tcttcaccta gatccttta aattaaaaat gaagcgtacc    15960
gacgatcttg ctgcgttcgg atattttcgt ggagttcccg ccacagaccc ggattgaagg    16020
cgagatccag caactcgcgc cagatcatcc tgtgacggaa ctttggcgcg tgatgactgg    16080
ccaggacgtc ggccgaaaga gcgacaagca gatcacgctt ttcgacagcg tcggatttgc    16140
gatcgaggat ttttcggcgc tgcgctacgt ccgcgaccgc gttgagggat caagccacag    16200
cagcccactc gaccttctag ccgacccaga cgagccaagg gatcttttg gaatgctgct    16260 ccgtcgtcag gctttccgac gtttgggtgg ttgaacagaa gtcattatcg cacggaatgc    16320
caagcactcc cgaggggaac cctgtggttg gcatgcacat acaaatggac gaacggataa    16380 acctttttcac gcccttttaa atatccgatt attctaataa acgctctttt ctcttag     16437
```

<210> SEQ ID NO 145
<211> LENGTH: 17
<212> TYPE: DNA
<213> ORGANISM: Artificial Sequence
<220> FEATURE:
<223> OTHER INFORMATION: MPSS promiscuous tag

<400> SEQUENCE: 145

```
gatcaaaaaa aaaaaaa                                                        17
```

```
<210> SEQ ID NO 146
<211> LENGTH: 8
<212> TYPE: DNA
<213> ORGANISM: Artificial Sequence
<220> FEATURE:
<223> OTHER INFORMATION: Motif consensus sequence

<400> SEQUENCE: 146 ydratcyg                                                                8
```

REGULATORY SEQUENCES FOR MODULATING TRANSGENE EXPRESSION IN PLANTS

CROSS REFERENCE TO RELATED APPLICATIONS

This application is a Continuation of U.S. application Ser. No. 16/429,846, filed Jun. 3, 2019, now U.S. Pat. No. 11,242,535, which is a Continuation of U.S. application Ser. No. 15/660,390, filed Jul. 26, 2017, now patented as U.S. Pat. No. 10,344,290, which is a Continuation of U.S. application Ser. No. 14/660,076, filed Mar. 17, 2015, now abandoned, which is a Continuation of U.S. application Ser. No. 13/701,848, filed Dec. 4, 2012, now abandoned, which is a 371 of International Application No. PCT/US11/39691, filed Jun. 9, 2011, now expired, which claims the benefit of U.S. Provisional Application No. 61/372,515, filed Aug. 11, 2010, now expired, and Indian Provisional Application No. 1340/DEL/2010, filed Jun. 9, 2010, now expired, the entire contents of each is herein incorporated by reference.

REFERENCE TO SEQUENCE LISTING SUBMITTED ELECTRONICALLY

The official copy of the sequence listing is submitted electronically via EFSWeb as an ASCII formatted sequence listing with a file named BB1787USCNT4 ST25.txt created on Dec. 13, 2021 and having a size of 276 kilobytes and is filed concurrently with the specification. The sequence listing contained in this ASCII formatted document is part of the specification and is herein incorporated by reference in its entirety.

FIELD OF INVENTION

The present invention relates to the generation of transgenic plants, particularly to the use of promoter and intron sequences to regulate gene expression in plants.

BACKGROUND

Recent advances in plant genetic engineering have opened new doors to engineer plants to have improved characteristics or traits. These transgenic plants characteristically have recombinant DNA constructs in their genome that have a protein-coding region operably linked to at least one regulatory region that is the promoter. The promoter can be a strong or weak promoter, or a constitutive or tissue-specific promoter. Besides the promoter, the expression level of the gene product can be modulated by other regulatory elements such as introns. Introns are intervening, non-coding sequences that are present in most eukaryotic genes. Introns have been reported to affect the levels of gene expression. This effect is known as Intron Mediated Enhancement (IME) of gene expression (Lu et al., *Mol Genet Genomics* (2008) 279:563-572). Callis et al. (*Genes Dev.* 1987 1:1183-1200) showed that the presence of the first intron from maize alcohol dehydrogenase-1 (Adh1) gene increased the expression levels of transgenes in cultured maize cells up to 100-fold when compared to intronless constructs. Mascarenkas et al. (*Plant Mol. Biol.,* 1990, 15: 913-920) showed that other introns from the maize Adh1 gene could also increase heterologous gene expression in maize protoplasts. Vasil et al. (*Plant Physiol.,* 1989, 91:1575-15790) reported that the constructs containing Shrunken-1 (Sh-1) first intron had much higher expression levels of the reporter gene in plant protoplasts, when compared to the constructs with promoter alone, or to constructs with promoter and Adh-1 first intron. Identifying novel regulatory sequences can lead to finer modulation of gene expression in transgenic plants.

Plant genetic engineering has advanced to introducing multiple traits into commercially important plants, also known as gene stacking. This is accomplished by multigene transformation, where multiple genes are transferred to create a transgenic plant that might express a complex phenotype, or multiple phenotypes. But it is important to modulate or control the expression of each transgene optimally. The regulatory elements such as the promoter and the terminator sequences need to be diverse, to avoid introducing into the same transgenic plant repetitive sequences, which has been correlated with undesirable negative effects on transgene expression and stability (Peremarti et al (2010) *Plant Mol Biol* 73:363-378; Mette et al (1999) *EMBO J* 18:241-248; Mette et al (2000) *EMBO J* 19:5194-5201; Mourrain et al (2007) *Planta* 225:365-379, U.S. Pat. Nos. 7,632,982, 7,491,813, 7,674,950, PCT Application No. PCT/US2009/046968). Therefore it is important to discover and characterize novel regulatory elements that can be used to express heterologous nucleic acids in important crop species. Diverse regulatory regions can be used to control the expression of each transgene optimally.

SUMMARY

The present invention relates to regulatory sequences for modulating gene expression in plants. Recombinant DNA constructs comprising regulatory sequences are provided. Recombinant DNA constructs comprising intron sequences acting as enhancers of gene expression and endogenous promoter and terminator sequences corresponding to these intron sequences are provided.

Another embodiment of the invention is a recombinant DNA construct comprising an intron operably linked to a promoter and a terminator wherein the intron comprises a nucleotide sequence that has at least 95% sequence identity to SEQ ID NO: 4, 8, 13, 19, 52, 53, 56, 57, 58, 101, 102, 103, 104, 118, 137 or 138. In another embodiment, the intron comprises the nucleotide sequence of SEQ ID NO: 4, 8, 13, 19, 52, 53, 56, 57, 58, 101, 102, 103, 104, 118, 137 or 138.

One embodiment of the invention is a recombinant DNA construct comprising an intron operably linked to a promoter and a terminator wherein the promoter comprises a nucleotide sequence that has at least 95% sequence identity to SEQ ID NO: 105-117, 119, 136 or 139. In another embodiment, the promoter comprises the nucleotide sequence of SEQ ID NO: 105-117, 119, 136 or 139.

One embodiment of the invention is a recombinant DNA construct comprising an intron operably linked to a promoter and a terminator wherein the terminator comprises a nucleotide sequence that has at least 95% sequence identity to SEQ ID NOS: 140, 141, 142 or 143. In another embodiment, the terminator comprises the nucleotide sequence of SEQ ID NO: 140, 141, 142 or 143.

One embodiment of the invention is a recombinant DNA construct comprising an intron operably linked to a promoter and a terminator wherein the intron comprises a nucleotide sequence that has at least 95% identity to SEQ ID NOS: 4, 8, 13, 19, 52, 53, 56, 57, 58, 101, 102, 103, 104, 118, 137 or 138; and the promoter comprises a nucleotide sequence that has at least 95% identity to SEQ ID NOS: 105, 106, 107, 108, 109, 110, 111, 112, 113, 114, 115, 116, 117, 119, 136 or 139.

One embodiment of the invention is a recombinant DNA construct comprising an intron operably linked to a promoter and a terminator wherein the intron comprises a nucleotide sequence that has at least 95% identity to SEQ ID NO: 4, 8, 13, 19, 52, 53, 56, 57, 58, 101, 102, 103, 104, 118, 137 or 138; the promoter sequence has at least 95% identity to SEQ ID NO: 105, 106, 107, 108, 109, 110, 111, 112, 113, 114, 115, 116, 117, 119, 136 or 139; and the terminator has at least 95% sequence identity to SEQ ID NO: 140, 141, 142 or 143.

In one embodiment of the current invention, the intron is operably linked to the promoter, and is present downstream of the promoter, in the recombinant DNA constructs described herein. One embodiment of the present invention includes a recombinant DNA construct comprising an intron described in the present invention, operably linked to a promoter and a heterologous polynucleotide, wherein the intron can act as enhancer of expression of the heterologous polynucleotide.

Another embodiment of the invention encompasses a recombinant DNA construct comprising an intron wherein the intron sequence comprises at least one copy of the 8-bp sequence motif of SEQ ID NO: 99; or contains at least one copy of the 8-bp sequence motif of SEQ ID NO: 99 and at least one copy of the 5-bp sequence motif of SEQ ID NO: 100, wherein the intron is capable of enhancing expression of a heterologous polynucleotide in a transgenic plant. The intron sequence can also comprise more than one copy of SEQ ID NO: 99, or can comprise one or more than one copy of SEQ ID NO: 99 and more than one copy of SEQ ID NO: 100.

Another embodiment of this invention is a method to identify novel introns that are useful for enhancing expression of a heterologous polynucleotide in a plant cell, the method comprising the steps of scanning a plurality of introns from plants for presence of SEQ ID NO: 99, selecting a sequence that contains at least one copy of SEQ ID NO: 99, measuring the efficacy of the identified intron to enhance expression of a heterologous polynucleotide in a plant.

Another embodiment of the invention is a method for identifying novel intronic sequences for enhancing transgene expression in monocotyledonous plants by identifying sequences orthologous to SEQ ID NO: 4, 8, 13, 19, 52, 53, 56, 57, 58, 101, 102, 103, 104, 118, 137 or 138; and measuring the enhancing effect of the identified intron on the expression of an operably linked heterologous polynucleotide.

Another embodiment of the current invention includes the promoter and the terminator sequences that are endogenously linked to the introns identified using the methods described in the current invention.

Another embodiment of the current invention is a method for modulating expression of a heterologous polynucleotide in a monocotyledonous plant comprising the steps of: (a) introducing into a regenerable plant cell a recombinant DNA construct comprising a promoter and a heterologous polynucleotide wherein each is operably linked to an intron, wherein the intron comprises either (i) a nucleotide sequence that is orthologous to SEQ ID NO: 4, 8, 13, 19, 52, 53, 56, 57, 58, 101, 102, 103, 104, 118, 137 or 138; or (ii) a nucleotide sequence that contains least one copy of a sequence motif identical to SEQ ID NO: 99; and (b) regenerating a transgenic plant from a regenerable monocotyledonous plant cell after step (a) wherein the transgenic plant comprises the recombinant DNA construct; and (c) obtaining a progeny plant derived from the transgenic plant of step (b), wherein said progeny plant comprises the recombinant DNA construct and exhibits enhanced expression of the heterologous polynucleotide when compared to a plant comprising a corresponding recombinant DNA construct without the intron sequence.

In another embodiment, this invention concerns a vector, cell, plant, or seed comprising a recombinant DNA construct comprising the regulatory sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the regulatory sequences described in the present invention is a monocotyledonous plant. In another embodiment, the plant comprising the regulatory sequences described in the present invention is a maize plant.

BRIEF DESCRIPTION OF DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. § 1.822.

Figure 1:
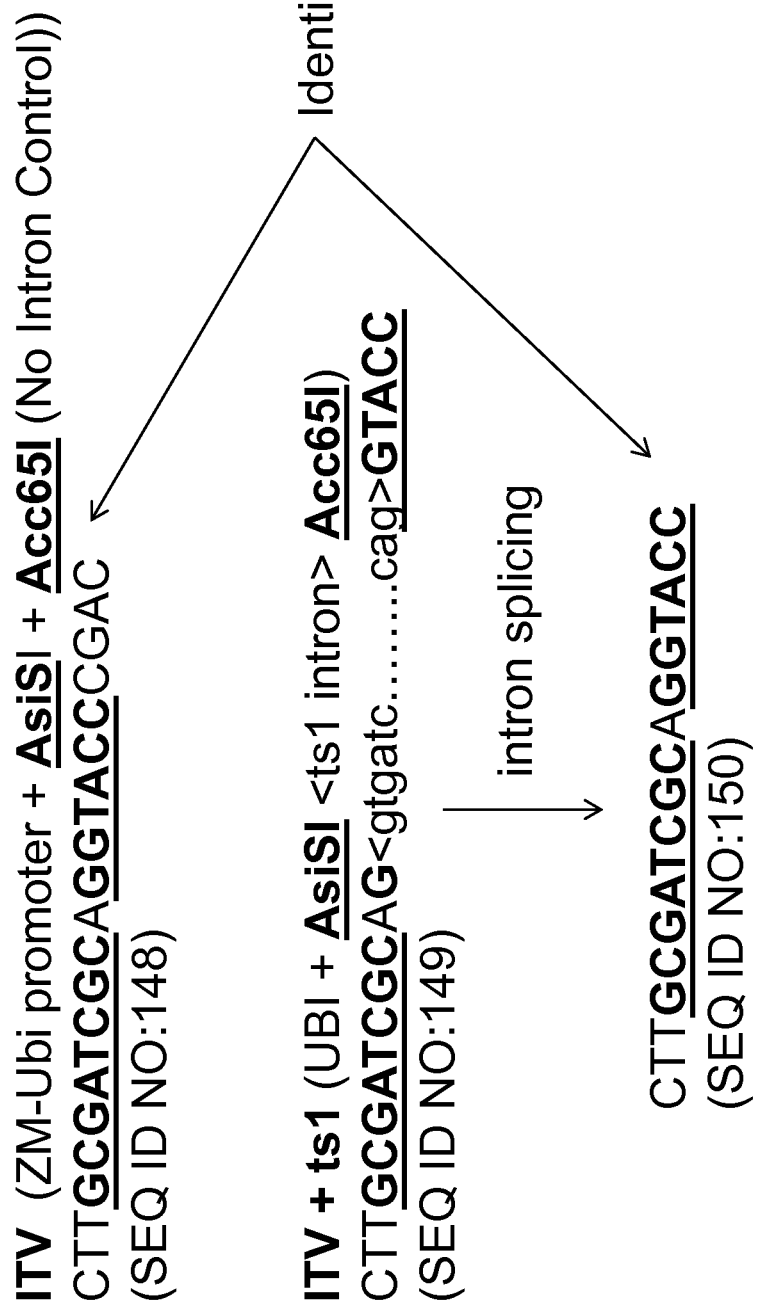
FIG. 1 is a schematic representation of the vector used for testing introns showing the location of restriction sites used to clone introns relative to the maize ubiquitin promoter, as described in Example 2.
Figure 2:
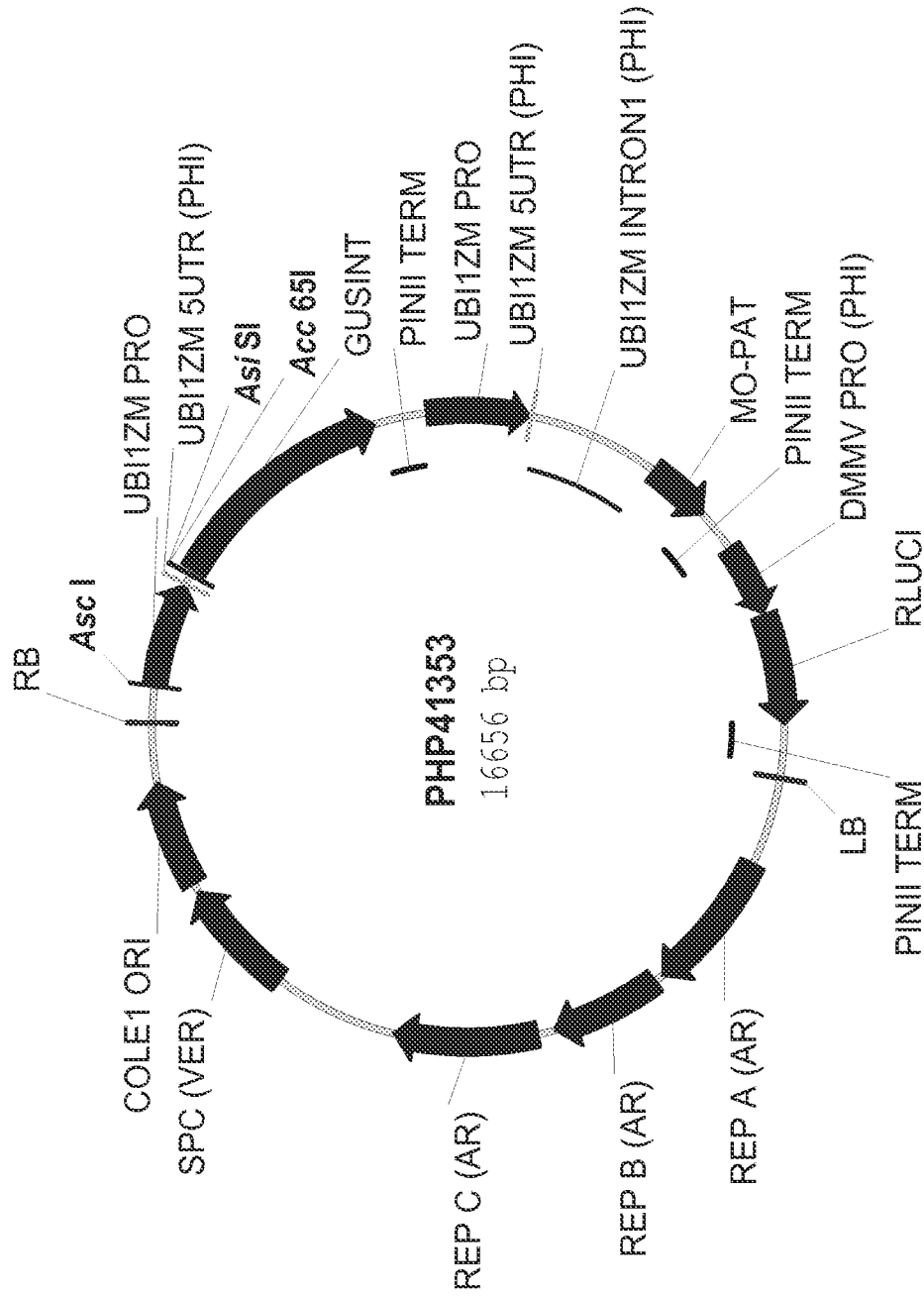
FIG. 2 shows the map of PHP 41353, the ITVUR-2 vector used for testing intron-mediated enhancement of gene expression.

SEQ ID NO: 1 is the sequence of the maize ubiquitin promoter.

SEQ ID NO: 2 is the sequence of the first intron from maize ubiquitin gene.

SEQ ID NO: 3 is the nucleotide sequence of PHP41353, ITVUR-2 vector.

SEQ ID NOS: 4-19 and SEQ ID NOS: 52-58, SEQ ID NO: 118, SEQ ID NOS: 137 and 138 are sequences of introns that were tested to identify expression-enhancing introns, and are described in Table 1 below.

SEQ ID NOS: 105-113, SEQ ID NO: 119 and SEQ ID NOS: 136 and 139 are the sequences of promoters identified for the enhancing introns as described in Example 10 and Example 11, and are described in Table 1 below.

SEQ ID NOS: 140-143 given in Table 1 are the sequences of the endogenous terminators for the introns TS1, TS2, TS13 and TS27, identified as explained in Example 13.

TABLE 1

| SEQ ID NO | Name | Intron/ Promoter | Enhancing/Non-Enhancing Intron |
|---|---|---|---|
| 4 | TS1 | Intron | Enhancing |
| 5 | TS4 | Intron | Non-Enhancing |
| 6 | TS5 | Intron | Non-Enhancing |
| 7 | TS6 | Intron | Non-Enhancing |
| 8 | TS7 | Intron | Enhancing* |
| 9 | TS8 | Intron | Non-Enhancing |
| 10 | TS10 | Intron | Non-Enhancing |
| 11 | TS11 | Intron | Non-Enhancing |
| 12 | TS12 | Intron | Non-Enhancing |
| 13 | TS13 | Intron | Enhancing |
| 14 | TS14 | Intron | Non-Enhancing |
| 15 | TS15 | Intron | Non-Enhancing |
| 16 | TS16 | Intron | Non-Enhancing |
| 17 | TS17 | Intron | Non-Enhancing |
| 18 | TS24 | Intron | Non-Enhancing |
| 19 | TS27 | Intron | Enhancing* |
| 52 | i1 | Intron | Enhancing |
| 53 | i2 | Intron | Enhancing |
| 54 | i3 | Intron | Non-Enhancing |
| 55 | i4 | Intron | Non-Enhancing |
| 56 | i5 | Intron | Enhancing |
| 57 | i6 | Intron | Enhancing |
| 58 | i7 | Intron | Enhancing |
| 105 | pTS1 | Promoter | Promoter identified for SEQ ID NO: 4 |
| 106 | pTS7 | Promoter | Promoter identified for SEQ ID NO: 8 |
| 107 | pTS13 | Promoter | Promoter identified for SEQ ID NO: 13 |
| 108 | pTS27 | Promoter | Promoter identified for SEQ ID NO: 19 |
| 109 | pi1 | Promoter | Promoter identified for SEQ ID NO: 52 |
| 110 | pi2 | Promoter | Promoter identified for SEQ ID NO: 53 |
| 111 | pi5 | Promoter | Promoter identified for SEQ ID NO: 56 |
| 112 | pi6 | Promoter | Promoter identified for SEQ ID NO: 57 |
| 113 | pi7 | Promoter | Promoter identified for SEQ ID NO: 58 |
| 118 | TS2 | Intron | Enhancing |
| 119 | pTS2 | Promoter | Promoter identified for SEQ ID NO: 118 |
| 136 | pTS1v | Promoter | Promoter sequence cloned for SEQ ID NO: 4 |
| 137 | TS7v | Intron | Enhancing |
| 138 | TS27v | Intron | Enhancing |
| 139 | pTS27v | Promoter | Promoter sequence cloned for SEQ ID NO: 19 |
| 140 | tTS1 | Terminator | Terminator identified for SEQ ID NO: 4 |
| 141 | tTS2 | Terminator | Terminator identified for SEQ ID NO: 118 |
| 142 | tTS13 | Terminator | Terminator identified for SEQ ID NO: 13 |
| 143 | tTS27 | Terminator | Terminator identified for SEQ ID NO: 19 |

*based on results from variants

SEQ ID NOS: 20-51 are the primers used for cloning introns as described in Table 2 in Example 3.

SEQ ID NO: 59 is the sequence of the vector PHP38808, used for testing intron-mediated enhancement of gene expression as described in Example 7. SEQ ID NO: 60 is the sequence of PHP34651, the vector containing GATEWAY® attR recombination sites and a PAT expression cassette used for LR reactions to generate the final expression vectors for introns, as described in Example 7.

SEQ ID NOS: 61-94 are the oligonucleotides used for generating introns by oligonucleotide stacking as described in Table 4 in Example 7.

SEQ ID NO: 95 is the sequence for first intron of adh1 gene.

SEQ ID NO: 96 is the sequence for intron 6 for adh1 gene.

SEQ ID NO: 97 is the sequence for intron 1 for shrunken1 (Sh-1) gene

SEQ ID NO: 98 is the sequence for ubi intron 1 used for computational analyses as described in Example 8.

SEQ ID NO: 99 is the sequence of the 8-bp motif identified as described in Example 8.

SEQ ID NO: 100 is the sequence of the 5-bp motif identified as described in Example 8.

SEQ ID NOS: 101-104 are the intron sequences containing the 8-bp motif (SEQ ID NO: 99), as described in Example 9.

SEQ ID NOS: 114-117 are the promoter sequences identified from the introns of SEQ ID NOS: 101-104 respectively, as described in Examples 9 and 10.

SEQ ID NOS: 120-128 are the sequences of the primers used for cloning the promoters and introns, as described in Table 7.

SEQ ID NOS: 129-134 are the primer and probe sequences for qPCR, as described in Table 9 and Table 10.

SEQ ID NO: 135 is the sequence of the PHP42365 vector that contains ZmUbi promoter and ZmUbi intron.

SEQ ID NO: 144 is the sequence of the PHP49597 vector (terminator test vector or TTV).

SEQ ID NO: 145 corresponds to the nucleotide sequence GATCAAAAAAAAAAAAA of a 'promiscuous' MPSS tags.

SEQ ID NO: 146 corresponds to the nucleotide sequence of a consensus motif sequence, which encompasses variations of the motif sequence given in SEQ ID NO: 99.

The sequence descriptions and Sequence Listing attached hereto comply with the rules governing nucleotide and/or amino acid sequence disclosures in patent applications as set forth in 37 C.F.R. § 1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. § 1.822.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth. As Used Herein:

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably to refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from an mRNA template using the enzyme reverse transcriptase. The cDNA can be single-stranded or converted into the double-stranded form using the Klenow fragment of DNA polymerase I.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Mature" protein refers to a post-translationally processed polypeptide; i.e., one from which any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

The term "insecticidal gene" and "insect resistance gene" are used interchangeably herein.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A "favorable allele" is the allele at a particular locus that confers, or contributes to, a desirable phenotype, e.g., increased cell wall digestibility, or alternatively, is an allele that allows the identification of plants with decreased cell wall digestibility that can be removed from a breeding program or planting ("counterselection"). A favorable allele of a marker is a marker allele that segregates with the favorable phenotype, or alternatively, segregates with the unfavorable plant phenotype, therefore providing the benefit of identifying plants.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, WI). Unless stated otherwise, multiple alignment of the sequences provided herein were performed using the Clustal V method of alignment (Higgins and Sharp, *CABIOS*. 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

The present invention includes a polynucleotide comprising: (i) a nucleic acid sequence of at least 90%, 91%, 92%, 93%, 94%, 95%, 96%, 97%, 98%, 99%, or 100% sequence identity, based on the Clustal V method of alignment, when compared to SEQ ID NOS: 4, 8, 13, 19, 52, 53, 56, 57, 58, 101-119, 136-143; or (ii) a full complement of the nucleic acid sequence of (i), wherein the polynucleotide acts as a regulator of gene expression in a plant cell.

Standard recombinant DNA and molecular cloning techniques used herein are well known in the art and are described more fully in Sambrook, J., Fritsch, E. F. and Maniatis, T. *Molecular Cloning: A Laboratory Manual*;

Cold Spring Harbor Laboratory Press: Cold Spring Harbor, 1989 (hereinafter "Sambrook").

Regulatory Sequences:

A recombinant DNA construct (including a suppression DNA construct) of the present invention may comprise at least one regulatory sequence.

"Regulatory sequences" or "regulatory elements" are used interchangeably and refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, but are not limited to, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, but are not limited to, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter.

A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present invention which causes the desired temporal and spatial expression.

Promoters which are seed or embryo-specific and may be useful in the invention include, but are not limited to, soybean Kunitz trypsin inhibitor (Kti3, Jofuku and Goldberg, *Plant Cell* 1:1079-1093 (1989)), patatin (potato tubers) (Rocha-Sosa, M., et al. (1989) *EMBO J.* 8:23-29), convicilin, vicilin, and legumain (pea cotyledons) (Rerie, W. G., et al. (1991) *Mol. Gen. Genet.* 259:149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci. U.S.A.* 82:3320-3324), phytohaemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564), and sporamin (sweet potato tuberous root) (Hattori, T., et al. (1990) *Plant Mol. Biol.* 14:595-604). Promoters of seed-specific genes operably linked to heterologous coding regions in chimeric gene constructions maintain their temporal and spatial expression pattern in transgenic plants. Such examples include, but are not limited to, *Arabidopsis thaliana* 2S seed storage protein gene promoter to express enkephalin peptides in *Arabidopsis* and *Brassica napus* seeds (Vanderkerckhove et al., *Bio/Technology* 7:L929-932 (1989)), bean lectin and bean beta-phaseolin promoters to express luciferase (Riggs et al., *Plant Sci.* 63:47-57 (1989)), and wheat glutenin promoters to express chloramphenicol acetyl transferase (Colot et al., *EMBO J* 6:3559-3564 (1987)).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, but are not limited to, for example, promoters regulated by light, heat, stress, flooding or drought, phytohormones, wounding, or chemicals such as ethanol, jasmonate, salicylic acid, or safeners.

For instance, introns of the present invention can be combined with inducible promoters to enhance their activity without affecting their inducibility characteristics.

A minimal or basal promoter is a polynucleotide molecule that is capable of recruiting and binding the basal transcription machinery. One example of basal transcription machinery in eukaryotic cells is the RNA polymerase II complex and its accessory proteins.

Plant RNA polymerase II promoters, like those of other higher eukaryotes, are comprised of several distinct "cis-acting transcriptional regulatory elements," or simply "cis-elements," each of which appears to confer a different aspect of the overall control of gene expression. Examples of such cis-acting elements include, but are not limited to, such as TATA box and CCAAT or AGGA box. The promoter can roughly be divided in two parts: a proximal part, referred to as the core, and a distal part. The proximal part is believed to be responsible for correctly assembling the RNA polymerase II complex at the right position and for directing a basal level of transcription, and is also referred to as "minimal promoter" or "basal promoter". The distal part of the promoter is believed to contain those elements that regulate the spatio-temporal expression. In addition to the proximal and distal parts, other regulatory regions have also been described, that contain enhancer and/or repressors elements The latter elements can be found from a few kilobase pairs upstream from the transcription start site, in the introns, or even at the 3' side of the genes they regulate (Rombauts, S. et al. (2003) *Plant Physiology* 132:1162-1176, Nikolov and Burley, (1997) *Proc Natl Acad Sci USA* 94: 15-22), Tjian and Maniatis (1994) *Cell* 77: 5-8; Fessele et al., 2002 *Trends Genet* 18: 60-63, Messing et al., (1983) *Genetic Engineering of Plants: an Agricultural Perspective*, Plenum Press, NY, pp 211-227).

When operably linked to a heterologous polynucleotide sequence, a promoter controls the transcription of the linked polynucleotide sequence.

In an embodiment of the present invention, the "cis-acting transcriptional regulatory elements" from the promoter sequence disclosed herein can be operably linked to "cis-acting transcriptional regulatory elements" from any heterologous promoter. Such a chimeric promoter molecule can be engineered to have desired regulatory properties. In an embodiment of this invention a fragment of the disclosed promoter sequence that can act either as a cis-regulatory sequence or a distal-regulatory sequence or as an enhancer sequence or a repressor sequence, may be combined with either a cis-regulatory or a distal regulatory or an enhancer sequence or a repressor sequence or any combination of any of these from a heterologous promoter sequence.

In a related embodiment, a cis-element of the disclosed promoter may confer a particular specificity such as conferring enhanced expression of operably linked polynucleotide molecules in certain tissues and therefore is also capable of regulating transcription of operably linked polynucleotide molecules. Consequently, any fragment, portion, or region of the promoter comprising the polynucleotide sequence shown in SEQ ID NO: 105, 106, 107, 108, 109, 110, 111, 112, 113, 114, 115, 116, 117, 119, 136 or 139 can be used as a regulatory polynucleotide molecule.

Promoter fragments that comprise regulatory elements can be added, for example, fused to the 5' end of, or inserted within, another promoter having its own partial or complete regulatory sequences (Fluhr et al., *Science* 232:1106-1112, 1986; Ellis et al., *EMBO J.* 6:11-16, 1987; Strittmatter and Chua, Proc. Nat. Acad. Sci. USA 84:8986-8990, 1987; Poulsen and Chua, *Mol. Gen. Genet.* 214:16-23, 1988; Comai et al., *Plant Mol. Biol.* 15:373-381, 1991; 1987; Aryan et al., *Mol. Gen. Genet.* 225:65-71, 1991).

Cis elements can be identified by a number of techniques, including deletion analysis, i.e., deleting one or more nucleotides from the 5' end or internal to a promoter; DNA binding protein analysis using DNase I footprinting; methylation interference; electrophoresis mobility-shift assays, in vivo genomic footprinting by ligation-mediated PCR; and other conventional assays; or by sequence similarity with known cis element motifs by conventional sequence comparison methods. The fine structure of a cis element can be further studied by mutagenesis (or substitution) of one or more nucleotides or by other conventional methods (see for example, *Methods in Plant Biochemistry and Molecular Biology*, Dashek, ed., CRC Press, 1997, pp. 397-422; and *Methods in Plant Molecular Biology*, Maliga et al., eds., Cold Spring Harbor Press, 1995, pp. 233-300).

Cis elements can be obtained by chemical synthesis or by cloning from promoters that include such elements, and they can be synthesized with additional flanking sequences that contain useful restriction enzyme sites to facilitate subsequent manipulation. Promoter fragments may also comprise other regulatory elements such as enhancer domains, which may further be useful for constructing chimeric molecules.

Methods for construction of chimeric and variant promoters of the present invention include, but are not limited to, combining control elements of different promoters or duplicating portions or regions of a promoter (see for example, U.S. Pat. Nos. 4,990,607; 5,110,732; and 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In an embodiment of the present invention, the promoters disclosed herein can be modified. Those skilled in the art can create promoters that have variations in the polynucleotide sequence. The polynucleotide sequence of the promoters of the present invention as shown in SEQ ID NOS: 105-113, 119, 136 or 139, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

The present invention encompasses functional fragments and variants of the promoter sequences disclosed herein.

A "functional fragment" of a regulatory sequence herein is defined as any subset of contiguous nucleotides of any of the regulatory sequences disclosed herein, that can perform the same, or substantially similar function as the full length promoter sequences disclosed herein.

A "functional fragment of a promoter" with substantially similar function to a full length promoter disclosed herein refers to a functional fragment that retains largely the same level of activity as the full length promoter sequence and exhibits the same pattern of expression as the full length promoter sequence.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Enhancer sequences refer to the sequences that can increase gene expression. These sequences can be located upstream, within introns or downstream of the transcribed region. The transcribed region is comprised of the exons and the intervening introns, from the promoter to the transcription termination region. The enhancement of gene expression can be through various mechanisms which include, but are not limited to, increasing transcriptional efficiency, stabilization of mature mRNA and translational enhancement.

Recombinant DNA constructs of the present invention may also include other regulatory sequences, including but not limited to, translation leader sequences, introns, and polyadenylation recognition sequences. In another embodiment of the present invention, a recombinant DNA construct of the present invention further comprises an enhancer or silencer.

An "intron" is an intervening sequence in a gene that is transcribed into RNA and then excised in the process of generating the mature mRNA. The term is also used for the excised RNA sequences. An "exon" is a portion of the sequence of a gene that is transcribed and is found in the mature messenger RNA derived from the gene, and is not necessarily a part of the sequence that encodes the final gene product.

Many genes exhibit enhanced expression on inclusion of an intron in the transcribed region, especially when the intron is present within the first 1 kb of the transcription start site. The increase in gene expression by presence of an intron can be at both the mRNA (transcript abundance) and protein levels. The mechanism of this Intron Mediated Enhancement (IME) in plants is not very well known (Rose et al., *Plant Cell*, 20: 543-551(2008) Le-Hir et al, *Trends Biochem Sci.* 28: 215-220 (2003), Buchman and Berg, *Mol. Cell Biol.* (1988) 8:4395-4405; Callis et al., *Genes Dev.* 1(1987):1183-1200).

An "enhancing intron" is an intronic sequence present within the transcribed region of a gene which is capable of enhancing expression of the gene when compared to an intronless version of an otherwise identical gene. An enhancing intronic sequence might also be able to act as an enhancer when located outside the transcribed region of a gene, and can act as a regulator of gene expression independent of position or orientation (Chan et. al. (1999) *Proc. Natl. Acad. Sci.* 96: 4627-4632; Flodby et al. (2007) *Biochem. Biophys. Res. Commun.* 356: 26-31).

Short consensus sequences or motifs can be identified from the intron sequences experimentally identified to be enhancing introns. These motifs can be used to scan and help identify more gene-expression enhancing introns. A motif capable of conferring transgene expression in male reproductive tissue in dicot plants has been described in US application No. US2007/020436.

An 8-bp sequence (SEQ ID NO: 99) and a 5-bp sequence (SEQ ID NO: 100) that can be used for identifying novel enhancing introns have been described in this application. Some variations of the 8-bp sequence can also be useful for identifying enhancing introns. The useful variations from the 8-bp motif (SEQ ID NO: 99) described herein can occur mainly at the first three positions. The last 5 bp of the sequence are highly conserved. Also, the variations from the 8-bp consensus (SEQ ID NO: 99) occur at maximum two out of 8 positions at any one time. In the event of more than 2 bp being different than the consensus, the enhancing intron might have additional copies of either the 5-bp (SEQ ID NO: 100) or the 8-bp motif (SEQ ID NO: 99).

The motif variations can be represented as a consensus motif sequence, Y[R/T]RATCYG (SEQ ID NO: 146). The first position can be any of the two pyrimidine bases, C or T. The second position can be substituted by an A, G or T. The third position can be a purine. The ATC core is the most highly conserved region, and does not exhibit any variability.

An intron sequence can be added to the 5' untranslated region, the protein-coding region or the 3' untranslated region to increase the amount of the mature message that accumulates in the cytosol.

The intron sequences can be operably linked to a promoter. Promoters may be derived in their entirety from a native gene, or be composed of different elements derived from different promoters found in nature, or even comprise synthetic DNA segments.

Sequences orthologous to an intron are sequences that are present in orthologous genes at the same position as the intron in the original gene sequence.

The tissue expression patterns of the genes can be determined using the RNA profile database of the Massively Parallel Signature Sequencing (MPSS™). This proprietary database contains deep RNA profiles of more than 250 libraries and from a broad set of tissue types. The MPSS™ transcript profiling technology is a quantitative expression analysis that typically involves 1-2 million transcripts per cDNA library (Brenner S. et al., (2000). *Nat Biotechnol* 18: 630-634, Brenner S. et al. (2000) *Proc Natl Acad Sci USA* 97: 1665-1670). It produces a 17-base high quality usually gene-specific sequence tag usually captured from the 3'-most DpnII restriction site in the transcript for each expressed gene. The use of this MPSS data including statistical analyses, replications, etc, has been described previously (Guo M et al. (2008) *Plant Mol Biol* 66: 551-563).

IMEter is a word-based discriminator that can do a computational analysis as to whether an intron can act as an enhancer of gene expression or not. The IMeter scoring system is described in Rose, A. B. (2004). Plant J. 40_744-751, and Rose et al (2008) *Plant Cell* 20: 543-551.

"Transcription terminator", "termination sequences", or "terminator" as described herein refer to DNA sequences located downstream of a coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" refers to a polynucleotide sequence that, when operably linked to the 3' end of a second polynucleotide sequence that is to be expressed, is capable of terminating transcription from the second polynucleotide sequence and facilitating efficient 3' end processing of the messenger RNA resulting in addition of poly A tail. Transcription termination is the process by which RNA synthesis by RNA polymerase is stopped and both the processed messenger RNA and the enzyme are released from the DNA template.

Improper termination of an RNA transcript can affect the stability of the RNA, and hence can affect protein expression. Variability of transgene expression is sometimes attributed to variability of termination efficiency (Bieri et al (2002) *Molecular Breeding* 10: 107-117). As used herein, the terms "bidirectional transcriptional terminator" and "bidirectional terminator" refer to a transcription terminator sequence that has the capability of terminating transcription in both 5' to 3', and 3' to 5' orientations. A single sequence element that acts as a bidirectional transcriptional terminator can terminate transcription from two convergent genes.

The present invention encompasses functional fragments and variants of the terminator sequences disclosed herein.

A "functional fragment of a terminator" with substantially similar function to the full length terminator disclosed herein refers to a functional fragment that retains the ability to terminate transcription largely to the same level as the full length terminator sequence. A recombinant construct comprising a heterologous polynucleotide operably linked to a "functional fragment" of the terminator sequence disclosed herein exhibits levels of heterologous polynucleotide expression substantially similar to a recombinant construct comprising a heterologous polynucleotide operably linked to the full length terminator sequence.

A "variant terminator", as used herein, is the sequence of the terminator or the sequence of a functional fragment of a terminator containing changes in which one or more nucleotides of the original sequence is deleted, added, and/or substituted, while substantially maintaining terminator function. One or more base pairs can be inserted, deleted, or substituted internally to a terminator, without affecting its activity. Fragments and variants can be obtained via methods such as site-directed mutagenesis and synthetic construction.

These terminator functional fragments will comprise at least about 20 contiguous nucleotides, preferably at least about 50 contiguous nucleotides, more preferably at least about 75 contiguous nucleotides, even more preferably at least about 100 contiguous nucleotides of the particular terminator nucleotide sequence disclosed herein. Such fragments may be obtained by use of restriction enzymes to cleave the naturally occurring terminator nucleotide sequences disclosed herein; by synthesizing a nucleotide sequence from the naturally occurring terminator DNA sequence; or may be obtained through the use of PCR technology. See particularly, Mullis et al., *Methods Enzymol.* 155:335-350 (1987), and Higuchi, R. In PCR Technology: Principles and Applications for DNA Amplifications; Erlich, H. A., Ed.; Stockton Press Inc.: New York, 1989. Again, variants of these terminator fragments, such as those resulting from site-directed mutagenesis, are encompassed by the compositions of the present invention.

The terms "substantially similar" and "corresponding substantially" as used herein refer to nucleic acid fragments, particularly regulatory sequences, wherein changes in one or more nucleotide bases do not substantially alter the ability of the regulatory sequence to perform the same function as the corresponding full length sequence disclosed herein. These terms also refer to modifications, including deletions and variants, of the nucleic acid sequences of the instant invention by way of deletion or insertion of one or more nucleotides that do not substantially alter the functional properties of the resulting sequence relative to the initial, unmodified sequence. It is therefore understood, as those skilled in the art will appreciate, that the invention encompasses more than the specific exemplary sequences.

As will be evident to one of skill in the art, any heterologous polynucleotide of interest can be operably linked to the regulatory sequences described in the current invention. Examples of polynucleotides of interest that can be operably linked to the regulatory sequences described in this invention include, but are not limited to, polynucleotides comprising other regulatory elements such as introns, enhancers, promoters, translation leader sequences, protein coding regions such as disease and insect resistance genes, genes conferring nutritional value, genes conferring yield and heterosis increase, genes that confer male and/or female sterility, antifungal, antibacterial or antiviral genes, and the like. Likewise, the regulatory sequences described in the current invention can be used to regulate transcription of any nucleic acid that controls gene expression. Examples of nucleic acids that could be used to control gene expression include, but are not limited to, antisense oligonucleotides, suppression DNA constructs, or nucleic acids encoding transcription factors.

Embodiments of the Invention are:

The present invention relates to regulatory sequences for modulating gene expression in plants. Recombinant DNA constructs comprising regulatory sequences are provided. Recombinant DNA constructs comprising intron sequences acting as enhancers of gene expression and endogenous promoter and terminator sequences corresponding to these intron sequences are provided.

Another embodiment of the invention is a recombinant DNA construct comprising an intron operably linked to a promoter and a terminator wherein the intron comprises a nucleotide sequence that has at least 95% sequence identity to SEQ ID NO: 4, 8, 13, 19, 52, 53, 56, 57, 58, 101, 102, 103, 104, 118, 137 or 138. In another embodiment, the intron comprises the nucleotide sequence of SEQ ID NO: 4, 8, 13, 19, 52, 53, 56, 57, 58, 101, 102, 103, 104, 118, 137 or 138.

One embodiment of the invention is a recombinant DNA construct comprising an intron operably linked to a promoter and a terminator wherein the promoter comprises a nucleotide sequence that has at least 95% sequence identity to SEQ ID NO: 105-117, 119, 136 or 139. In another embodiment, the promoter comprises the nucleotide sequence of SEQ ID NO: 105-117, 119, 136 or 139.

One embodiment of the invention is a recombinant DNA construct comprising an intron operably linked to a promoter and a terminator wherein the terminator comprises a nucleotide sequence that has at least 95% sequence identity to SEQ ID NOS: 140, 141, 142 or 143. In another embodiment, the terminator comprises the nucleotide sequence of SEQ ID NO: 140, 141, 142 or 143.

One embodiment of the invention is a recombinant DNA construct comprising an intron operably linked to a promoter and a terminator wherein the intron comprises a nucleotide sequence that has at least 95% identity to SEQ ID NOS: 4, 8, 13, 19, 52, 53, 56, 57, 58, 101, 102, 103, 104, 118, 137 or 138; and the promoter comprises a nucleotide sequence that has at least 95% identity to SEQ ID NOS: 105, 106, 107, 108, 109, 110, 111, 112, 113, 114, 115, 116, 117, 119, 136 or 139.

One embodiment of the invention is a recombinant DNA construct comprising an intron operably linked to a promoter and a terminator wherein the intron comprises a nucleotide sequence that has at least 95% identity to SEQ ID NO: 4, 8, 13, 19, 52, 53, 56, 57, 58, 101, 102, 103, 104, 118, 137 or 138; the promoter sequence has at least 95% identity to SEQ ID NO: 105, 106, 107, 108, 109, 110, 111, 112, 113, 114, 115, 116, 117, 119, 136 or 139; and the terminator has at least 95% sequence identity to SEQ ID NO: 140, 141, 142 or 143.

In one embodiment of the current invention, the intron is operably linked to the promoter, and is present downstream of the promoter, in the recombinant DNA constructs described herein. One embodiment of the present invention includes a recombinant DNA construct comprising an intron described in the present invention, operably linked to a promoter and a heterologous polynucleotide, wherein the intron can act as enhancer of expression of the heterologous polynucleotide.

Another embodiment of the invention encompasses a recombinant DNA construct comprising an intron wherein the intron sequence comprises at least one copy of the 8-bp sequence motif of SEQ ID NO. 99; or contains at least one copy of the 8-bp sequence motif of SEQ ID NO: 99 and at least one copy of the 5-bp sequence motif of SEQ ID NO: 100, wherein the intron is capable of enhancing expression of a heterologous polynucleotide in a transgenic plant. The intron sequence can also comprise more than one copy of SEQ ID NO: 99, or can comprise one or more than one copy of SEQ ID NO: 99 and more than one copy of SEQ ID NO: 100.

Another embodiment of this invention is a method to identify novel introns that are useful for enhancing expression of a heterologous polynucleotide in a plant cell, the method comprising the steps of scanning a plurality of introns from plants for presence of SEQ ID NO: 99, selecting a sequence that contains at least one copy of SEQ ID NO: 99, measuring the efficacy of the identified intron to enhance expression of a heterologous polynucleotide in a plant.

Another embodiment of the invention is a method for identifying novel intronic sequences for enhancing transgene expression in monocotyledonous plants by identifying sequences orthologous to SEQ ID NO: 4, 8, 13, 19, 52, 53, 56, 57, 58, 101, 102, 103, 104, 118, 137 or 138; and measuring the enhancing effect of the identified intron on the expression of an operably linked heterologous polynucleotide.

Another embodiment of the current invention includes the promoter and the terminator sequences that are endogenously linked to the introns identified using the methods described in the current invention.

Another embodiment of the current invention is a method for modulating expression of a heterologous polynucleotide in a monocotyledonous plant comprising the steps of: (a) introducing into a regenerable plant cell a recombinant DNA construct comprising a promoter and a heterologous polynucleotide wherein each is operably linked to an intron, wherein the intron comprises either (i) a nucleotide sequence that is orthologous to SEQ ID NO: 4, 8, 13, 19, 52, 53, 56, 57, 58, 101, 102, 103, 104, 118, 137 or 138; or (ii) a nucleotide sequence that contains least one copy of a sequence motif identical to SEQ ID NO: 99; and; (b) regenerating a transgenic plant from a regenerable monocotyledonous plant cell after step (a) wherein the transgenic plant comprises the recombinant DNA construct; and (c) obtaining a progeny plant derived from the transgenic plant of step (b), wherein said progeny plant comprises the recombinant DNA construct and exhibits enhanced expression of the heterologous polynucleotide when compared to a plant comprising a corresponding recombinant DNA construct without the intron sequence.

In another embodiment, this invention concerns a vector, cell, plant, or seed comprising a recombinant DNA construct comprising the regulatory sequences described in the present invention.

The invention encompasses regenerated, mature and fertile transgenic plants comprising the recombinant DNA constructs described above, transgenic seeds produced therefrom, T1 and subsequent generations. The transgenic plant cells, tissues, plants, and seeds may comprise at least one recombinant DNA construct of interest.

In one embodiment, the plant comprising the regulatory sequences described in the present invention is a monocotyledonous plant. In another embodiment, the plant comprising the regulatory sequences described in the present invention is a maize plant.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Identification of Candidate Gene Expression/Transcript-Enhancing First Introns Introns that may enhance transcript abundance were sought from among a set of maize genes which (a) had first introns near the N-terminus of the transcript, and (b) had high level transcript abundance. A subset of maize genes were identified whose models were deemed to be complete. This assessment was done using a combination of maize public B73 BAC sequences plus a proprietary EST transcript assembly in an analysis comparing the predicted gene structures and the predicted transcript open reading frames (ORFs) in relation to public reference proteins plus some manual curations. Only full-length transcripts were considered; that is, those with complete protein coding regions. This set did not represent all maize genes, and there was some redundancy in the list.

This set of gene models was then analyzed versus a body of over 250 MPSS mRNA transcript profiling samples produced from a variety of maize tissues and treatments. The MPSS profiling technology produces a 17-bp tag sequence beginning with GATC. These tags were matched to the gene set via the full-length transcript, and those genes which (a) had an MPSS tag matching the plus strand of the transcript, and (b) had a measured expression level of at least 1000 ppm (parts per million) in at least one of the MPSS samples, were retained. In this way a working set of 3131 genes was produced. Using the maize BAC genomic sequence to analyze these 3131 genes, a subset of genes was produced that (a) contained an intron, and (b) contained an intron which was located within the 5'UTR or within the first 300 nucleotides of the ORF. This resulted in a subset of 1185 genes for further consideration.

This set of 1185 candidate genes was then filtered down by a number of criteria. Duplicates were removed. Introns without canonical GT-AG rules were excluded. Genes whose expression was defined by 'promiscuous' MPSS tags, such as GATCAAAAAAAAAAAAAA (SEQ ID NO: 145), and also MPSS tags matching repetitive elements, were removed. Genes whose first introns were greater than 2 kb were dropped. In addition, genes whose first introns' GC content were higher than 50% GC and/or the intron T (=U) content was below 25% were removed. In addition, the IMeter score for the first intron had to be positive. The (Meter scoring system is described in Rose, A. B. (2004) *Plant J.* 40:744-751. This resulted in an interim set of remaining 331 candidates. This set was then further manually winnowed down to 86 by positively considering a combinations of factors but chiefly: (a) the breadth of diverse tissue expression and (b) the ratio of the (Meter score to intron length.

This set of 86 introns was one prioritized pool from which introns were drawn for functional testing of whether they enhance transcript abundance. Seventeen of these 86 were tested.

Example 2

Creation of an Intron Testing Vector with Maize Ubiquitin Promoter

Figure 3:
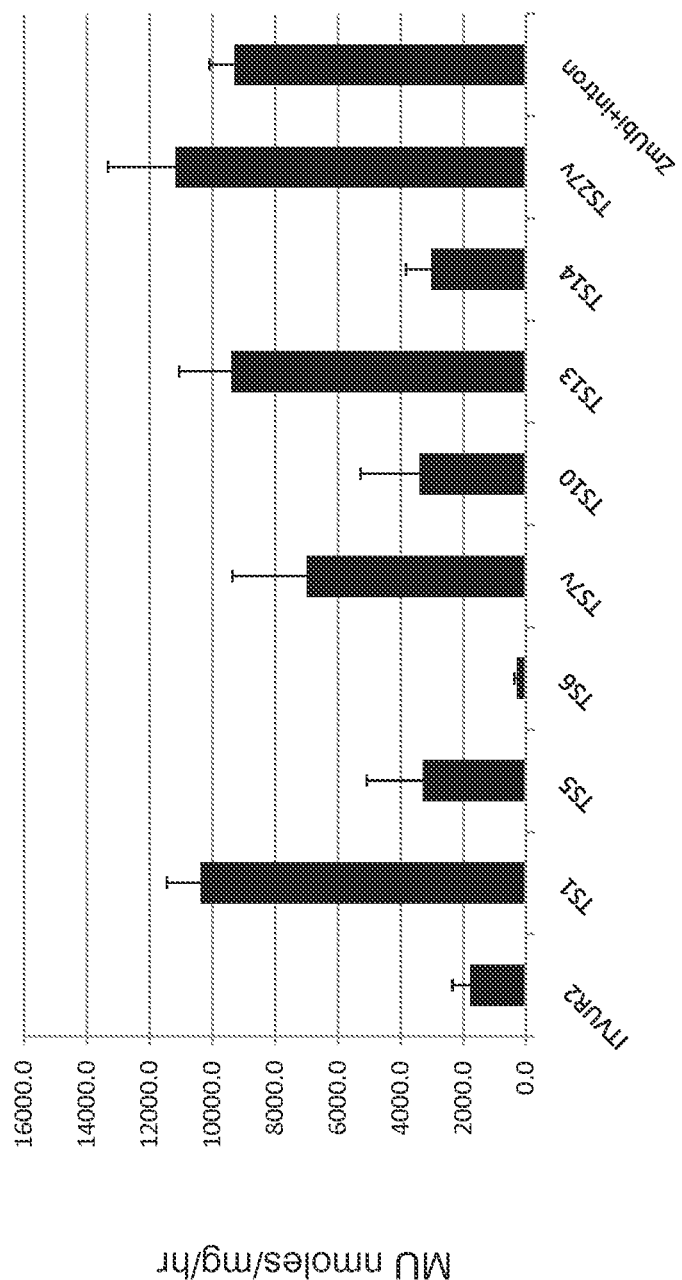
FIG. 3 shows quantitative analysis of GUS reporter gene expression in Maize Embryos infected with the respective constructs.

Maize ubi promoter (SEQ ID NO: 1) along with its intron (SEQ ID NO: 2) in the 5' UTR confers high level constitutive expression in monocot plants (Christensen, A. H., Sharrock, R. A. and Quail, P. H., *Plant Mol. Biol.* 18,675-89, 1992). This high-level expression is dependent on the first intron in the 5' UTR. Removal of this intron results in a >4-fold reduction in expression measured by transient assays (FIG. 3). We created a plant transformation vector where the maize ubiquitin promoter together with its endogenous intron drives *E. coli* β-glucuronidase (GUS) reporter gene expression. We then replaced the maize ubiquitin intron with two restriction sites, AsiS1 and Acc65I to allow the insertion of novel introns and test their ability to enhance reporter gene expression driven by the ubiquitin promoter (SEQ ID NO: 1) (FIG. 1).

Example 3

Intron Amplification and Cloning

*Zea mays* B73 seeds were germinated in Petri plates and genomic DNA was made from seedling leaf tissue using the QIAGEN® DNEASY® Plant Maxi Kit (QIAGEN® Inc.) according to the manufacturer's instructions. DNA products were amplified with primers shown in Table 2 using genomic DNA as template with PHUSION™ DNA polymerase (New England Biolabs Inc.). The resulting DNA fragments were cloned into the intron testing vector ITVUR-2 (SEQ ID NO: 3), using standard molecular biology techniques (Sambrook et al.) or using INFUSION™ from (Clontech Inc.), and sequenced completely.

TABLE 2

| | Intron | | Forward Primer | Reverse Primer |
|---|---|---|---|---|
| Name | SEQ ID NO | Length (nt) | (SEQ ID NO) | (SEQ ID NO) |
| TS1 | 4 | 814 | 20 | 21 |
| TS4 | 5 | 727 | 22 | 23 |
| TS5 | 6 | 834 | 24 | 25 |
| TS6 | 7 | 982 | 26 | 27 |
| TS7v | 137 | 856 | 28 | 29 |
| TS8 | 9 | 1020 | 30 | 31 |
| TS10 | 10 | 841 | 32 | 33 |
| TS11 | 11 | 1044 | 34 | 35 |
| TS12 | 12 | 648 | 36 | 37 |
| TS13 | 13 | 632 | 38 | 39 |
| TS14 | 14 | 1405 | 40 | 41 |
| TS15 | 15 | 1361 | 42 | 43 |
| TS16 | 16 | 703 | 44 | 45 |
| TS17 | 17 | 1341 | 46 | 47 |
| TS24 | 18 | 1125 | 48 | 49 |
| TS27v | 138 | 884 | 50 | 51 |

All the constructs were mobilized into the *Agrobacterium* strain LBA4404/pSB1 and selected on Spectinomycin and tetracycline. *Agrobacterium* transformants were isolated and the integrity of the plasmid was confirmed by retransforming to *E. coli* or PCR analysis.

Example 4

Transient Transformation and Expression of Intron Constructs in Maize Embryos Infected with *Agrobacterium*

Preparation of *Agrobacterium* Suspension:

*Agrobacterium* was streaked out from −80° C. frozen aliquot onto a plate containing PHI-L medium and was cultured at 28° C. in the dark for 2 days. The PHI-L medium comprises 50 ml Stock Solution A, 50 ml/L stock Solution B, 900 ml Stock Solution C and spectinomycin (Sigma chemicals) was added to a concentration of 50 mg/L in sterile ddH2O (Stock Solution A: K2HPO4 60 g/l, NaH2PO4 20 g/l, pH adjusted to 7.0 w/KOH and autoclaved; stock solution B: NH4Cl 20 g/l, MgSO4.7H2O 6 g/l, KCl 3 g/l, CaCl2 0.2 g/l, FeSO4.7H2O 50 mg/l; stock solution C: glucose 5 g/l, agar 15 g/l (#A-7049, Sigma Chemicals, St. Louis, Mo.) and was autoclaved.

The plate can be stored at 4° C. and used usually for about 1 month. A single colony was picked from the master plate and was streaked onto a plate containing PHI-M medium [Yeast Extract 5 g/l (Difco); Peptone 10 g/l (Difco); NaCl 5 g/l (Hi-Media); agar (Sigma Chemicals) 15 g/l; pH 6.8, containing 50 mg/l spectinomycin] and incubated at 28° C. in the dark for overnight.

Five ml of PHI-A, [CHU (N6) Basal salts (Sigma C-1416) 4 g/l; Erikson's vitamin solution (1000×, Sigma-1511) 1 ml/l; Thiamine.HCl (Sigma) 0.5 mg/l; 2,4-Dichloro phenoxyacetic acid (2,4-D, Sigma) 1.5 mg/l; L-Proline (Sigma) 0.69 g/l; Sucrose (Sigma) 68.5 g/l; Glucose (Sigma) 36 g/l; pH adjusted to 5.2 with KOH] was added to a 14 ml FALCON™ tube in a hood. About 3 full loops (5 mm loop size) *Agrobacterium* was collected from the plate and suspended in the tube, then the tube vortexed to make an even suspension. One ml of the suspension was transferred to a spectrophotometer tube and the OD of the suspension was adjusted to 0.72 at 550 nm by adding either more *Agrobacterium* or more of the same suspension medium, for an *Agrobacterium* concentration of approximately $0.5 \times 10^9$ cfu/ml. The final *Agrobacterium* suspension was aliquoted into 2 ml microcentrifuge tubes, each containing 1 ml of the suspension. The suspension was then used as soon as possible.

Embryo Isolation, Infection and Co-Cultivation:

About 2 ml of the same medium (PHI-A) which is used for the *Agrobacterium* suspension was added into a 2 ml microcentrifuge tube. Immature embryos were isolated from a sterilized ear with a sterile spatula and dropped directly into the medium in the tube. A total of 25 embryos are placed in the tube. The optimal size of the embryos was about 1.7-2.0 mm. The entire medium was drawn off and 1 ml of *Agrobacterium* suspension was added to the embryos and the tube was vortexed for 30 sec. The tube was allowed to stand for 5 min in the hood. The suspension of *Agrobacterium* and embryos was poured into a Petri plate containing co-cultivation medium PHI-B [CHU(N6) Basal salts (Sigma C-1416) 4 g/l; Eriksson's vitamin solution (1000×, Sigma-1511) 1 ml/l; Thiamine.HCl 0.5 mg/l; 2,4-D 1.5 mg/l; L-Proline 0.69 g/l; GELRITE® (Sigma) 3 g/l; Sucrose 30 g/l; pH adjusted to 5.8 with KOH; Post sterilization, Silver nitrate (0.85 mg/l) and acetosyringone (100 mM) were added after cooling the medium to 45° C.]. Any embryos left in the tube were transferred to the plate using a sterile spatula. The *Agrobacterium* suspension was drawn off and the embryos placed axis side down on the media. The plate was sealed with PARAFILM® and was incubated in the dark at 23-25° C. for about 3 days of co-cultivation.

Resting of Co-Cultivated Embryos:

For the resting step, all the embryos were transferred to a new plate containing PHI-C medium [CHU(N6) Basal salts (Sigma C-1416) 4 g/l; Eriksson's vitamin solution (1000×, Sigma-1511) 1 ml/l; Thiamine.HCl 0.5 mg/l; 2,4-D 1.5 mg/l; L-Proline 0.69 g/l; Sucrose 30 g/l; MES buffer (Sigma) 0.5 g/l; agar (Sigma 1-7049) 8 g/l; pH adjusted to 5.8 with KOH; Post sterilization, Silver nitrate (0.85 mg/l) and carbenicillin (100 mg/l) were added after cooling the medium to 45° C.]. The plates were sealed with PARAFILM® and incubated in the dark at 28° C. for 3-5 days.

Histochemical and Fluorometric GUS Analysis:

Transformed embryos were taken for expression analysis after 3 days of resting. Ten embryos for each construct were used for histochemical GUS staining using standard protocols (Janssen and Gardner, *Plant Mol. Biol.* (1989) 14:61-72) and two pools of 5 each were used to do quantitative assays using MUG substrate using standard protocols [Jefferson, R. A., Nature. 342:837-838 (1989); Jefferson, R. A., Kavanagh, T. A. & Bevan, M. W. *EMBO J.* 6:3901-3907 (1987)] (FIG. 3). Introns TS1 (SEQ ID NO: 4), TS7v (SEQ ID NO: 137), TS13 (SEQ ID NO: 13) and TS27v (SEQ ID NO: 138) all enhanced the GUS reporter gene expression between 3 to 5 fold when compared to the ubiquitin promoter alone without any intron. The level of enhancement is comparable to that of the maize ubiquitin first intron. Introns TS4, TS5, TS6, TSB, TS10, TS11, TS12, TS14, TS15, TS16, TS17 and TS24 did not enhance expression (Data shown for TS5, TS6, TS10 and TS14 in FIG. 3).

Example 5

Transient Transformation and Expression of Intron Constructs in Rice Calli Via *Agrobacterium*

Preparation of *Agrobacterium* Suspension:

*Agrobacterium* was streaked out from −80° C. frozen aliquot onto a plate containing YEB medium and was cultured at 28° C. in the dark for 2 days. The YEB medium comprises (MgSO4 (Hi-Media) 0.2 g/l; K2HPO4 (Fisher Scientific) 0.5 g/l; Mannitol 10 g/l; NaCl 0.1 g/l; Yeast Extract 0.4 g/l; Agar 15 g/l). *Agrobacterium* cultures harboring the intron constructs were cultured one day prior to rice calli infection in YEB broth. A large swipe of *Agrobacterium* growth was inoculated into 7.5 ml of YEB broth in FALCON™ tubes. Then in the next morning OD of each culture was measured at 550 nm. Cultures were centrifuged at 4000 rpm for 10 minutes. Supernatant was discarded and the pellet was resuspended in PHI-L supplemented with Acetosyringone at 100 μM. Another spin was given to *Agrobacterium* cultures at 4000 rpm for 10 min and the pellets were resuspended in PHI-L supplemented with Acetosyringone at 100 μM and the OD was adjusted to 1.0 by adding either more *Agrobacterium* or more of the same suspension medium, for an *Agrobacterium* concentration of approximately $0.5 \times 10^9$ cfu/ml.

Rice Callus Induction, Infection and Co-Cultivation:

15 to 21 days old Rice calli which were grown on callus induction medium, PHI-R [CHU(N6) Basal salts (Sigma C-1416) 4 g/l; Eriksson's vitamin solution (1000×, Sigma-1511) 1 ml/l; Thiamine.HCl 0.5 mg/l; 2,4-D 2.0 mg/l; L-Proline 0.69 g/l; Casein hydrolysate (Sigma) 300 mg/l; Sucrose (Sigma) 30 g/l; GELRITE® (Sigma) 4 g/l; pH adjusted to 5.8 with KOH]. Coleoptile of the rice calli was removed and calli were spliced to the size of approximately 2 to 3 mm. Spliced calli were transferred to the FALCON™ tubes containing *Agrobacterium* cultures and infected for 15 minutes with gentle intermittent shaking. The liquid *Agrobacterium* culture was decanted and the wet calli were taken out and blotted on sterile WHATMAN® filter paper No 4. Subsequently, the calli were transferred onto co-cultivation medium, PHI-R supplemented with Acetosyringone (Sigma) at 100 μM. The infected calli were co-cultivated in dark at 21° C. for 72 hours.

Resting of Co-Cultivated Rice Calli:

The co-cultivation was terminated by washing in sterile water containing carbenicillin (Sigma, 400 mg/l). Calli were washed with gentle intermittent shaking in the antibiotic solution for 15 minutes. The wet calli were blotted on WHATMAN® filter paper No 4. The dried calli were transferred to resting/callusing medium, PHI-R in which carbenicillin (400 mg/l) was added after cooling the medium to 45° C. after sterilization. The plates were sealed with PARAFILM® and incubated in the dark at 28° C. for 3-5 days.

Figure 4:
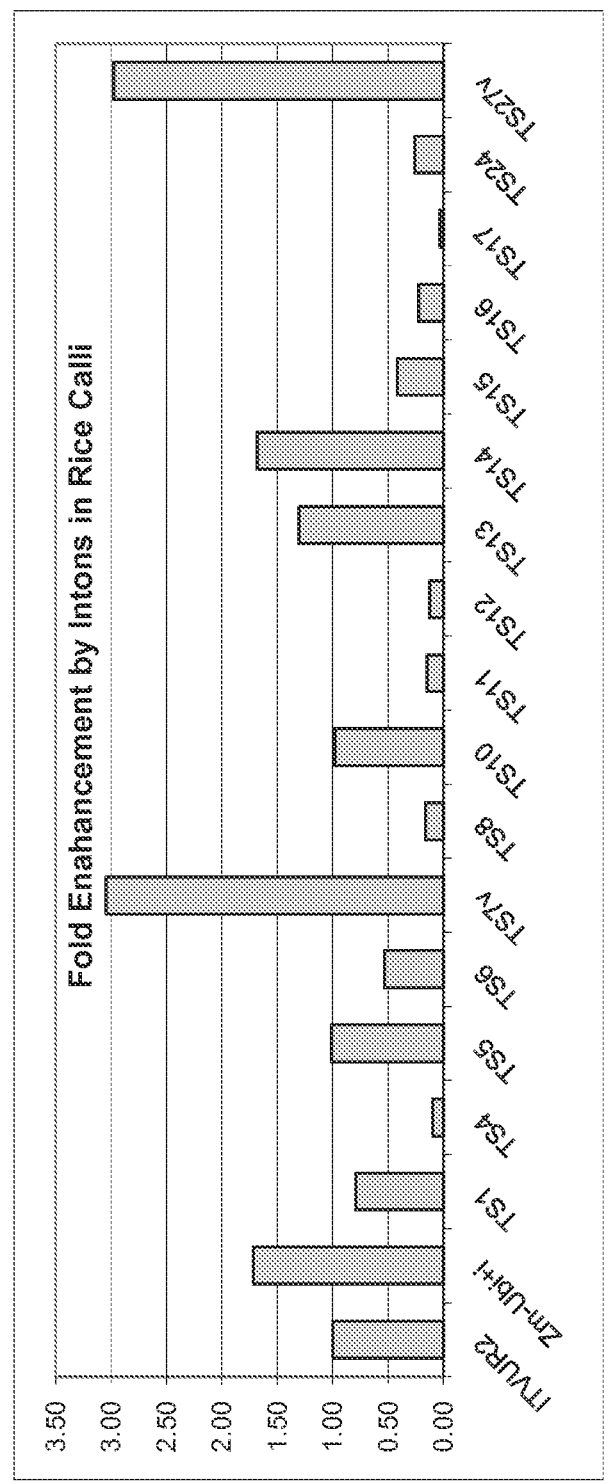
FIG. 4 shows the fold enhancement of GUS reporter gene expression in rice calli infected with intron constructs when compared with the control vector ITVUR-2.

Histochemical and Fluorometric GUS Analysis:

After 3 days, calli were taken for expression analysis. For each construct 20 calli were infected and 8 calli were used for histochemical GUS staining using X-Gluc solution and another eight calli were taken for GUS quantitation using standard protocol (Jefferson et al., EMBO J. 6:3901-3907, 1987). TS7v (SEQ ID NO: 137) and TS27v (SEQ ID NO: 138) were able to enhance GUS reporter expression from the maize ubiquitin promoter (SEQ ID NO: 1) (FIG. 4).

Example 6

Description of Constitutive Promoter Selection Via MPSS Samples

Promoter candidates were identified using a set of 241 proprietary expression profiling experiments run on the MPSS (Massively Parallel Signature Sequencing) technology platform provided by Lynx Therapeutics. The 241 samples from corn consisted of various tissue samples spanning most of the range of corn tissues and developmental stages. Each experiment resulted in approximately 20,000 unique sequence tags of 17 bp length from a single tissue sample. Typically these tags could be matched to one or a few transcript sequences from the proprietary "Unicorn" EST assembly set. A query of the MPSS database was performed looking for tags that were observed in 240 or more of the 241 samples. We identified 111 tags that met the criteria and chose 22 that were observed at an expression level of 1 or greater PPM (Parts Per Million tags) in all 241 experiments for further development. 21 of these 22 tags mapped to a single gene based on the transcript set. We took the top 6 candidates from this list and identified the 1500 bp of promoter regions and the first intron, defined as the first intron in the transcript from the 5' end, (i1(SEQ ID NO: 52), i2(SEQ ID NO: 53), i3(SEQ ID NO: 54), i5(SEQ ID NO: 56), i6(SEQ ID NO: 57) and i7(SEQ ID NO: 58). In addition we also included one second intron (i4; SEQ ID NO: 55) to the list. All introns were evaluated for intron-mediated enhancement of expression from CYMV promoter.

Example 7

Enhancement Activity of Introns in Transient Expression System

To determine whether the experimental introns function to enhance promoter activity in plant tissue, transient infiltration assays using the maize suspension cell line, BMS (Black Mexican Sweet), were performed. These *Agrobacterium*-mediated assays, known in the art, provide a rapid screening method to evaluate the enhancement capability of the introns.

The introns were cloned into an expression vector downstream of the Citrus Yellow Mosaic virus promoter and upstream of the coding region of an insecticidal gene described in US2007/0202089 A1. The insecticidal gene acted as a reporter for expression. A vector with no intron between the promoter and coding region was included to provide a baseline control for expression. A vector (SEQ ID NO: 59; PHP38808) with the Adh1 intron1 was also included to provide a comparison for the level of increased expression by each experimental intron. The Adh1 intron has been shown to enhance the expression of foreign genes in plant tissue (Callis et al. (1987) *Genes and Development*: 1183-1200; Kyozuka et al. (1990) *Maydica* 35: 353-357). Each expression vector also contained an expression cassette for phosphinothricin acetyl transferase (PAT).

Transiently transformed BMS cells were evaluated for expression by both northern blot analysis for RNA accumulation and ELISA analysis for protein accumulation. If the experimental introns, particularly introns i1 (SEQ ID NO: 52), i2 (SEQ ID NO: 53), i5 (SEQ ID NO: 56), i6 (SEQ ID NO: 57), and i7 (SEQ ID NO: 58), exhibited intron mediated enhancement of expression, the increased expression would be reflected at both the RNA and protein levels.

Figure 5:
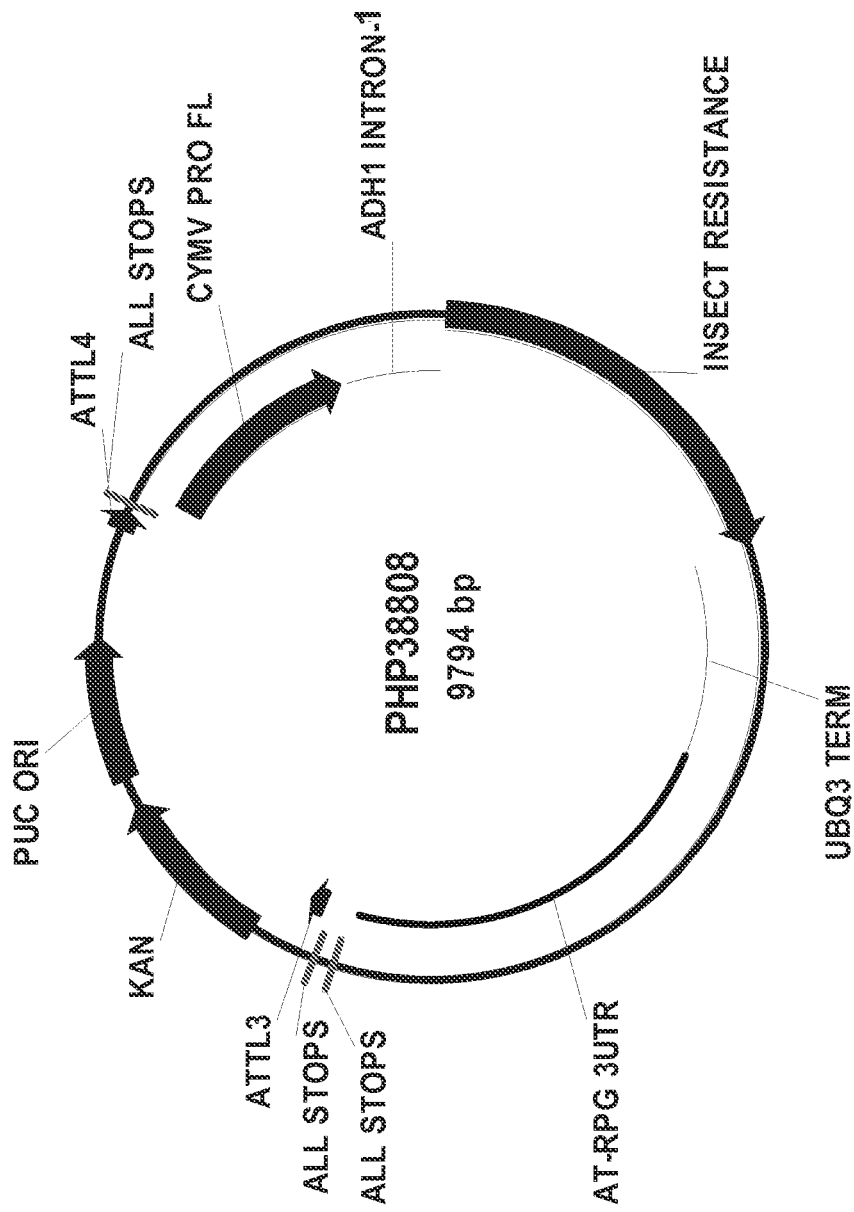
FIG. 5 shows the map of PHP38808, the vector with CYMV promoter and ADH1 intron, used for testing intron-mediated enhancement of gene expression, as described in Example 7.

The ratio of expression for each intron cassette showed that introns i1, i2, i5, i6, and i7 had expression levels that were between 2.3 and 4.8 fold higher than the intronless control (Table 3). These increased expression levels were comparable to the control cassette (SEQ ID NO: 59, PHP38808; FIG. 5) containing the Adh1 intron. The ELISA values were standardized for differences in transformation efficiency between vectors by normalizing against PAT gene expression.

TABLE 3

ELISA Results Indicating Expression Levels of Insecticidal Gene (IG) and PAT in Constructs Containing Experimental Introns

| Intron | IG (ppm) | PAT (ppm) | IG/ PAT | Fold difference from no intron |
|---|---|---|---|---|
| none | 38.8 | 179.0 | 0.22 | N/A |
| ADH1 | 104.3 | 117.4 | 0.89 | 4.05 |
| i1 | 98.3 | 136.5 | 0.72 | 3.27 |
| i2 | 118.7 | 154.0 | 0.77 | 3.50 |
| i5 | 115.5 | 108.5 | 1.06 | 4.82 |
| i6 | 107.6 | 209.0 | 0.51 | 2.32 |
| i7 | 104.3 | 117.4 | 0.89 | 4.05 |

Figure 6:
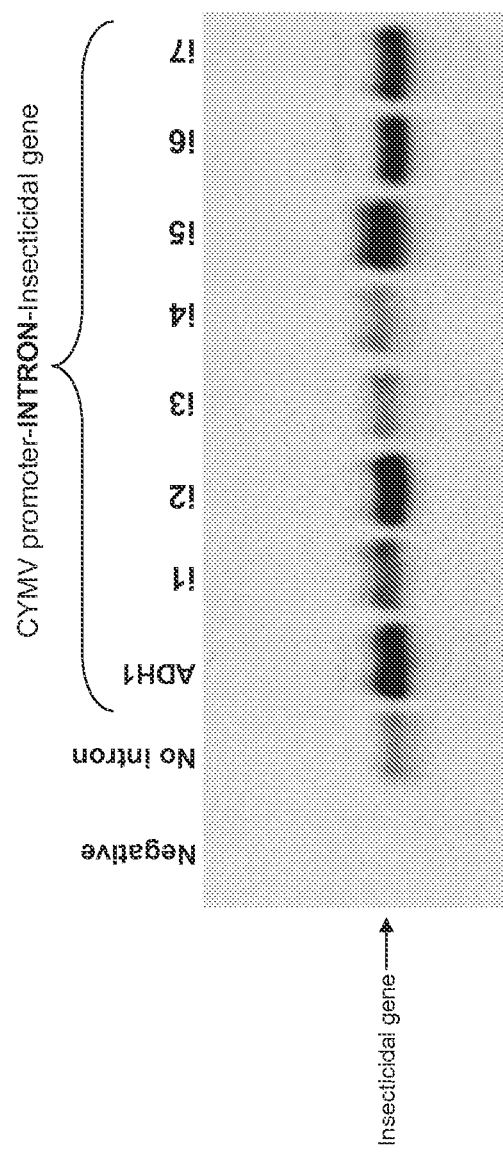
FIG. 6 shows the results of Northern blot of RNA extracted from infiltrated maize tissue culture material and probed with a digoxigenin-labeled DNA probe for the insecticidal gene used. Samples were loaded based on ELISA data to contain equal amounts of PAT.

To determine whether introns i1 (SEQ ID NO: 52), i2 (SEQ ID NO: 53), i5 (SEQ ID NO: 56), i6 (SEQ ID NO: 57), and i7 (SEQ ID NO: 58) resulted in increased mRNA levels, northern blot analysis was performed. RNA amounts for each vector were normalized against PAT expression prior to electrophoresis. The results of the analysis mirrored the ELISA results. Introns i1, i2, i5, i6, and i7 facilitated levels of reporter mRNA accumulation that were above that of the intronless cassette and comparable to the ADH1 cassette (see FIG. 6). These results show that i1, i2, i5, i6, and i7 (SEQ ID NOS: 52-53, 56-58 respectively) display intron-mediated enhancement of expression in this system.

Figure 7:
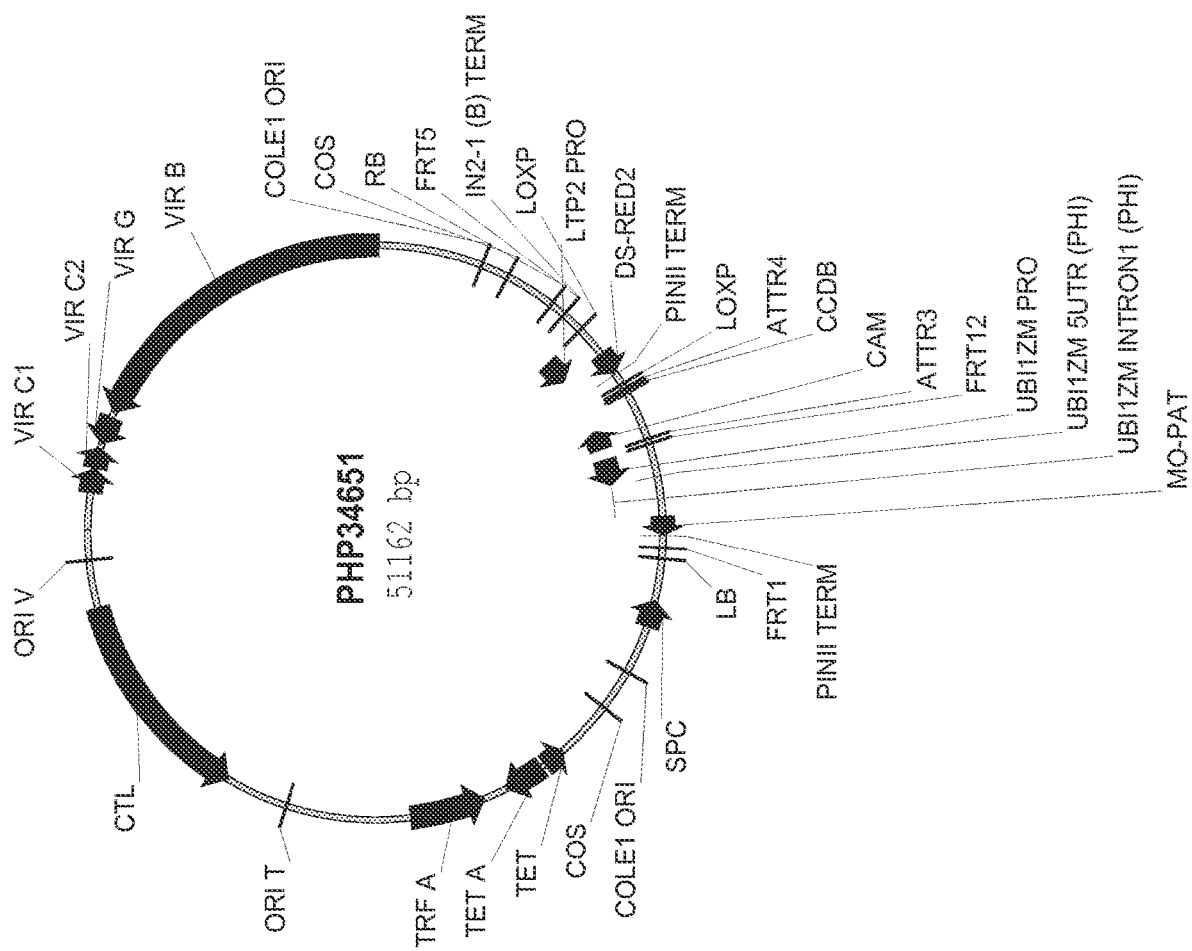
FIG. 7 shows the map of PHP34651, vector containing GATEWAY® attR recombination sites and a PAT expression cassette used for LR reactions to generate the final expression vectors for introns, as described in Example 7.
Figure 8:
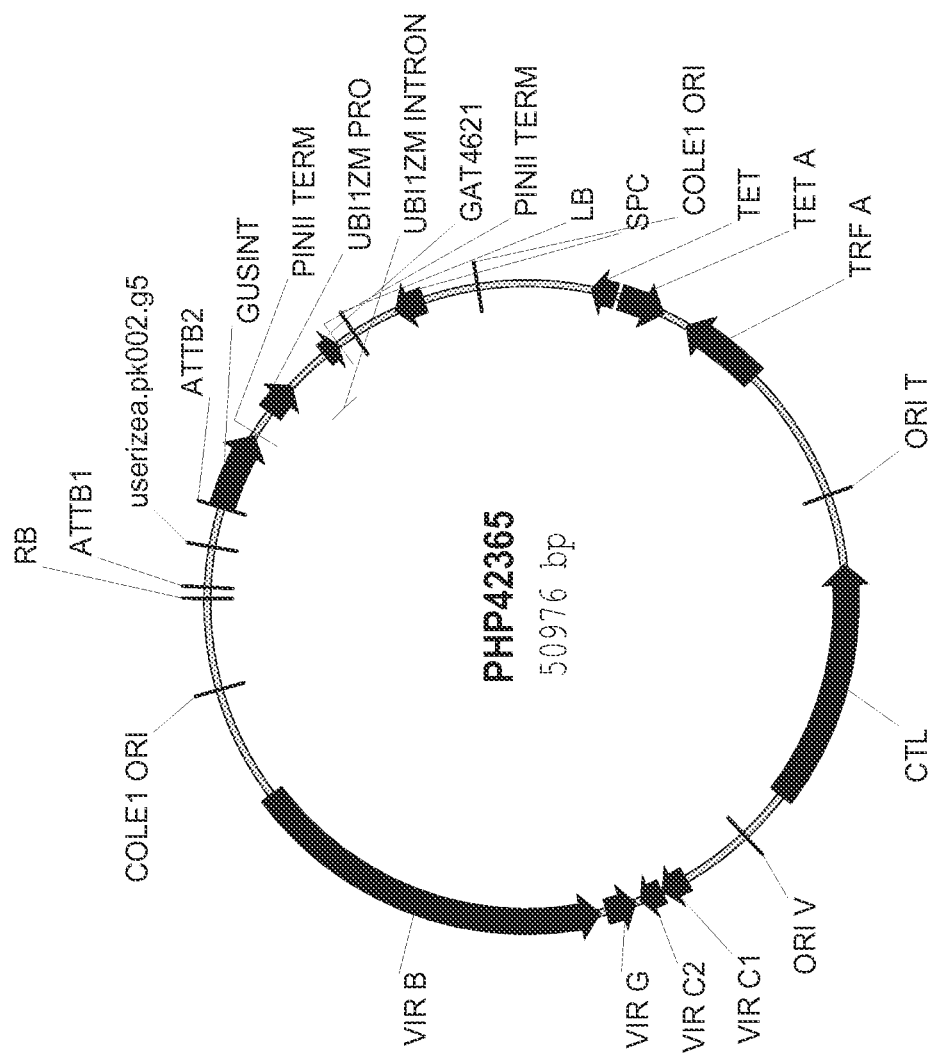
FIG. 8 shows the map of PHP42365, vector containing ZmUbi promoter and ZmUbi intron, for testing in stable transgenic rice plants, as described in Example 11.

Materials and Methods:

Introns i1 (SEQ ID NO: 52), i2 (SEQ ID NO: 53), i3 (SEQ ID NO: 54), i4 (SEQ ID NO: 55) and i5 (SEQ ID NO: 56) were generated using a method known in the art as oligonucleotide stacking. Oligos and primers (Table 4) synthesized by IDT (Integrated DNA Technologies, Inc. Coralville, IA) were resuspended in distilled water to a concentration of 100 µM. Equal amounts of each oligonucleotide were mixed to create a total volume of 10 µl. The flanking primers for PCR amplification were also mixed equally to a volume of 10 µl. Two microliters of the oligonucleotide mix and 10 µl of the primer mix were combined for PCR using the HotStart Herculase system from Stratagene. PCR was performed using 10 µl Herculase buffer, 2 µl of 25 nM dNTPs, 1.2 µl of the oligo and primer mixture, 1 µl 100 mM MgSO4, 2 µl DMSO, 1 µl HotStart Herculase enzyme, and 82.8 µl of distilled water. PCR conditions were 96° C. for 3 minutes, then 35 cycles at 94° C. for 30 s, 60° C. for 30 s, and 72° C. for 1 min., followed by 72° C. for 10 min. Reactions were stored at 4° C. Introns i6 and i7 were synthesized by GENEART, Inc., Burlingame, CA To clone introns i1 (SEQ ID NO: 52), i2 (SEQ ID NO: 53), i6 (SEQ ID NO: 57), and i7 (SEQ ID NO: 58), the starting product was cut with the restriction enzymes ECoRV (5' end) and BamHI (3' end). Intron i5 (SEQ ID NO: 56), was cut with EcoRV (5' end) and BglII (3' end). A plasmid containing a cassette (SEQ ID NO: 59, PHP38808; FIG. 5) with the CYMV promoter the ADH1 intron and an insecticidal gene flanked by GATEWAY® (INVITROGEN™) attL recombination sites was cut with EcoRV and BamHI to remove the ADH1 intron and allow the experimental introns to be ligated into the cut plasmid. The resulting vectors (entry vectors, PHP38811, PHP38813, PHP38815, PHP38817, PHP38819, PHP38821, PHP38823 for i1, i2, i3, i4, i5, i6, i7 respectively) were used in LR reactions with a larger plasmid (PHP34651, FIG. 7, SEQ ID NO: 60) containing GATEWAY® attR recombination sites and a PAT expression cassette to generate the final expression vectors (destination vectors PHP38812, PHP38814, PHP38816, PHP38818, PHP38820, PHP38822 and PHP38824 respectively for introns i1, i2, i3, i4, i5, i6, i7, i8 and i9). These vectors were used to transform competent *Agrobacterium tumefaciens* cells, which were then used to transiently transform BMS cells.

TABLE 4

Primers and Oligonucleotides Used for Oligonucleotide Stacking

| Oligo/Primer SEQ ID NO: | (Used for) Intron | Sense/ Antisense | Flanking Primer/Oligonucleotide |
|---|---|---|---|
| 61 | i1 | Sense | Flanking Primer |
| 62 | i1 | Sense | Oligonucleotide |
| 63 | i1 | Sense | Oligonucleotide |
| 64 | i1 | Sense | Oligonucleotide |
| 65 | i1 | Antisense | Oligonucleotide |
| 66 | i1 | Antisense | Oligonucleotide |
| 67 | i1 | Antisense | Oligonucleotide |
| 68 | i1 | Antisense | Flanking Primer |
| 69 | i2 | Sense | Flanking Primer |
| 70 | i2 | Sense | Oligonucleotide |
| 71 | i2 | Sense | Oligonucleotide |
| 72 | i2 | Sense | Oligonucleotide |
| 73 | i2 | Antisense | Oligonucleotide |
| 74 | i2 | Antisense | Oligonucleotide |
| 75 | i2 | Antisense | Oligonucleotide |
| 76 | i2 | Antisense | Flanking Primer |
| 77 | i3 | Sense | Flanking Primer |
| 78 | i3 | Sense | Oligonucleotide |
| 79 | i3 | Sense | Oligonucleotide |
| 80 | i3 | Antisense | Oligonucleotide |
| 81 | i3 | Antisense | Oligonucleotide |
| 82 | i3 | Antisense | Flanking Primer |
| 83 | i4 | Sense | Flanking Primer |
| 84 | i4 | Sense | Oligonucleotide |

TABLE 4-continued

Primers and Oligonucleotides Used for Oligonucleotide Stacking

| Oligo/Primer SEQ ID NO: | (Used for) Intron | Sense/ Antisense | Flanking Primer/Oligonucleotide |
|---|---|---|---|
| 85 | i4 | Sense | Oligonucleotide |
| 86 | i4 | Antisense | Oligonucleotide |
| 87 | i4 | Antisense | Oligonucleotide |
| 88 | i4 | Antisense | Flanking Primer |
| 89 | i5 | Sense | Flanking Primer |
| 90 | i5 | Sense | Oligonucleotide |
| 91 | i5 | Sense | Oligonucleotide |
| 92 | i5 | Antisense | Oligonucleotide |
| 93 | i5 | Antisense | Oligonucleotide |
| 94 | i5 | Antisense | Flanking Primer |

RNA was extracted from infiltrated tissue culture material using the QIAGEN® RNA Maxiprep kit. Based on ELISA data for PAT, RNA samples were loaded on an agarose gel (1% Lonza SeaKem LE agarose) to contain equal parts per million of PAT to normalize for variations in transformation efficiency. After electrophoresis, samples on the gel were transferred to a nylon membrane via capillary transfer overnight using the WHATMAN® TurboBlotter system standard protocol. RNA was crosslinked to the membrane by UV light. Prehybridization and hybridization steps were performed following the manufacturer's protocol for Roche DIG Easy Hyb solution (catalog #11603558001). The blot was prehybridized at 50° C. in Roche DIG Easy Hyb solution, then was probed overnight at 50° C. with a mixture of digoxigenin-labeled DNA probes for the insecticidal and PAT gene in Roche DIG Easy Hyb solution. Probes were generated using Roche PCR DIG Probe Synthesis Kit (Roche catalog #11636090910). The blot was washed twice for five minutes each at room temperature in low stringency buffer (2×SSC+0.1% SDS), then washed twice for 15 minutes each at 50° C. in high stringency buffer (0.1×SSC+0.1% SDS).

For detection, the Roche DIG Wash and Block Buffer Set (catalog #11585762001) was used. The membrane was washed for 2 minutes at room temperature in wash buffer, and then blocked in block solution for 30 minutes at room temperature. A 1:10,000 dilution of anti-digoxigenin-AP antibody (Roche catalog #11093274910, 0.75 U/µl) in 50 ml block solution was added to the blot for 30 minutes. The blot was washed twice for 15 minutes each at room temperature in wash buffer, and then equilibrated in 50 ml of detection buffer for 3 minutes. Blot was incubated at room temperature for 5 minutes with 3 ml of CSPD (Roche catalog #1755633001), and then incubated at 37° C. for 10 minutes. Detection was done with film at 37° C.

Example 8

Identification of Unique Motif from Maize First Introns Using the Experimental Dataset of Tested Enhancing Introns Computational analysis was performed to identify unique motifs that were present in the 9 enhancing introns identified as explained in Examples 4 and 7 and Table 1 (TS1, TS7, TS13, TS27, i1, i2, i5, i6, i7(SEQ ID NOS: 4, 8, 13, 19, 52, 53, 56, 57, and 58 respectively)). The proprietary promoter REAPer tool was adapted to look for possibly conserved motifs. The promoter REAPer tool is a regulatory element identification tool that relies on the conserved word approach. It is described in the U.S. patent application Ser. No. 12/534,471. The introns were searched in both directions using sets of 3-6 introns at a time. When candidates were found, they were used to search all the introns.

The introns were divided into the following categories. "All Enhancing Introns" are the 9 introns (new enhancing introns) described in Table 1 and experimentally shown to be enhancing gene expression (TS1, TS7, TS13, TS27, i1, i2, i5, i6, and i7 (SEQ ID NOS: 4, 8, 13, 19, 52, 53, 56, 57, and 58 respectively), plus four known enhancing introns (Adh1_intron1(SEQ ID NO: 95), Adh1_intron 6 (SEQ ID NO: 96), Sh-1_intron 1 (SEQ ID NO: 97) and Ubi1ZM_intron (SEQ ID NO: 98) Callis, J. et al (1987) Genes Dev. 1: 1183-1200, Vasil, V. et al (1989) Plant Physiol. 91; 1575-1579, Christensen, A. H. et al (1992) Plant Mol. Biol. 18: 675-689, Jeong, Y. M. et al (2009) Plant Sci. 176:58-65). The 10 "non-enhancing introns" are 10 introns found not to enhance gene expression in transient maize assays as explained in Examples 4 and 7 and Table 1 (SEQ ID NOS: 5-7, 9, 11, 12, 17, 18, 54, and 55).

The 8-bp sequence CAGATCTG (SEQ ID NO: 99) or its variations were found in all the enhancing introns except TS27. The exact 8-bp sequence CAGATCTG was found in 2 out of the 9 enhancing introns identified (SEQ ID NOS: 52 and 53), but was not found in any of the 10 non-enhancing introns (SEQ ID NOS: 5-79, 11, 12, 17, 18, 54, and 55). A subset of this sequence ATCTG (SEQ ID NO: 100) was also present in 8 out of 9 enhancing introns (SEQ ID NOS: 4, 8, 13, 52, 53, 56, 57 and 58), and was also found to be present in the four known enhancing introns (SEQ ID NOS: 95-98). The frequency of occurrence of these motifs was normalized to the intron length (Table 6).

The variations of the 8-bp sequence CAGATCTG are mainly in the first 3 base pairs. The motif variations can be represented as the consensus sequence, Y[R/T]RATCYG (SEQ ID NO: 146). The first position can be any of the two pyrimidine bases, C or T. The second position can be substituted by an A, G or T and the third position can any purine. The last 5 base pairs of the sequence, that is the sequence ATCTG is highly conserved.

Statistical Analyses of Motif Frequencies:

A number of simple frequency statistics were determined for the introns. The statistics are shown in Tables 5 and 6.

TABLE 5

| Intron Classification | Intron Count | Aggregate Nts | Average Intron Length |
|---|---|---|---|
| All Enhancing Introns | 13 | 7716 | 594 |
| New Enhancing Introns | 9 | 4813 | 535 |
| Other Enhancing Introns | 4 | 2903 | 726 |
| Non-Enhancing Introns | 10 | 7888 | 789 |
| Non-Tested Introns | 1066 | 933097 | 875 |

TABLE 6

| Intron Classification | Total Introns Containing CAGATCTG | Total Introns Containing ATCTG | Frequency Intron Contains CAGATCTG | Frequency Intron Contains ATCTG |
| --- | --- | --- | --- | --- |
| All Enhancing Introns | 2 | 12 | 0.15 | 0.92 |
| New Enhancing Introns | 2 | 8 | 0.22 | 0.89 |
| Other Enhancing Introns | 0 | 4 | 0.00 | 1.00 |
| Non-Enhancing Introns | 0 | 7 | 0.00 | 0.70 |
| Non-Tested Introns | 15 | 502 | 0.01 | 0.47 |
| Ratio All Enhancing/Non-Enhancing | | 1.71 | | 1.32 |
| Ratio New Enhancing/Non-Enhancing | | 1.14 | | 1.27 |

| Intron Classification | Total Occurrences CAGATCTG Either Strand | Total Occurrences ATCTG Either Strand | Gross Frequency CAGATCTG | Gross Frequency ATCTG |
| --- | --- | --- | --- | --- |
| All Enhancing Introns | 6 | 29 | 0.0008 | 0.0038 |
| New Enhancing Introns | 6 | 23 | 0.0012 | 0.0048 |
| Other Enhancing Introns | 0 | 6 | 0 | 0.00207 |
| Non-Enhancing Introns | 0 | 18 | 0 | 0.00228 |
| Non-Tested Introns | 15 | 1391 | 1.6075E-05 | 0.00149 |
| Ratio All Enhancing/Non-Enhancing | | 1.61 | | 1.647 |
| Ratio New Enhancing/Non-Enhancing | | 1.28 | | 2.094 |

| Intron Classification | Average Individual Frequency of CAGATCTG/kb | Average of Individual Intron Frequency of ATCTG/kb | SE Frequency CAGATCTG/kb | SE Frequency ATCTG/kb |
| --- | --- | --- | --- | --- |
| All Enhancing Introns | 0.0036 | 0.0094 | 0.0025 | 0.0004 |
| New Enhancing Introns | 0.0052 | 0.0124 | 0.0035 | 0.0050 |
| Other Enhancing Introns | 0.00000 | 0.00266 | 0.00000 | 0.00107 |
| Non-Enhancing Introns | 0.00000 | 0.00203 | 0.00000 | 0.00057 |
| Non-Tested Introns | 0.00013 | 0.00271 | 0.00005 | 0.00013 |
| Ratio All Enhancing/Non-Enhancing | | 4.62 | | |
| Ratio New Enhancing/Non-Enhancing | | 6.10 | | |

SE frequency is standard error of frequency. Gross frequency is simply the total occurrences divided by the aggregate nucleotides of all the introns in the set.

The 'all' 13 enhancing introns have 4.6-fold higher, and the 9 'new' enhancing introns have 6.1-fold higher frequencies of ATCTG relative to the non-enhancing introns on a mean frequency per kb of intron basis (See Tables 5 and 6 above).

Example 9

Identification of Novel Maize Introns with 8-bp Motif

From the initial set of 1085 introns explained in Example 1, 1066 introns that were still not tested experimentally were scanned computationally to identify the ones with the 8-bp motif. Four introns (SEQ ID NOS: 101-104) were found to contain the exact 8-bp motif and these are good candidates for being enhancing introns.

Example 10

Identifying Promoters of Expression-Enhancing Introns

It is likely that the expression enhancing introns from Examples 4, 7 and 9 perform optimally along with their endogenous promoters. To test this 1000 bp-2000 bp of promoter regions upstream of the start codon from the respective genes (SEQ ID NOS: 105-117, SEQ ID NOS: 136 and 139) were identified and these can be tested with the respective introns.

Cloning Endogenous Promoters of Expression Enhancing Introns

We amplified 1000 base pairs region of endogenous promoter, (using the primers given in Table 7) upstream of the start codon of the gene that carries TS1 intron as its first intron and cloned the pTS1v sequence (SEQ ID NO: 136) in ITVUR-2 vector (SEQ ID NO: 3, PHP41353) between AscI-AsiS1 restriction sites, followed by the TS1 intron (SEQ ID NO: 4) at AsiSI-Acc65I sites to create an endogenous promoter and intron combination (PHP50061). Similarly, we amplified a 1487 base pair region of endogenous promoter (pTS27v; SEQ ID NO: 139) upstream of the TS27 intron and cloned it in ITVUR-2 vector (SEQ ID NO: 3, PHP41353) at AscI-AsiS1 restriction sites, followed by the TS27v intron (SEQ ID NO: 138) at AsiSI-Acc65I sites to give us an endogenous promoter and intron combination (PHP52322).

Example 11

Cloning and Testing of TS2 Enhancing Intron and Corresponding Endogenous Promoter We tested another intron with potential gene expression enhancing properties. TS2 intron (SEQ ID NO: 118) was cloned into ITVUR-2 vector (SEQ ID NO: 3, PHP41353) using the same procedure as explained in Example 3 to create PHP50062. We created 2 more constructs to test the ability of the endogenous promoter upstream of the start codon of the gene that carries TS2 as its first intron to drive gene expression and ability of TS2 intron to enhance gene expression. We amplified 1077-bp of endogenous TS2 promoter (pTS2; SEQ ID NO: 119), as defined by the sequence upstream of the TS2 intron at the genomic location, and cloned that in ITVUR-2 vector (SEQ ID NO: 3) between AscI and NcoI sites (PHP500063). We also amplified the pTS2 promoter and TS2 intron sequence from the endogenous locus (1077 bp promoter (SEQ ID NO: 118)+1329 bp intron (SEQ ID NO: 119)) and cloned that between AscI and NcoI sites (PHP50111). The primers for these amplifying promoter and intron sequences to make these constructs are given in Table 2 and Table 7.

TABLE 7

| Cloned sequence | | Forward Primer | Reverse Primer |
|---|---|---|---|
| Promoter | Intron | (SEQ ID NO) | (SEQ ID NO) |
| — | TS2 (SEQ ID NO: 118) | 120 | 121 |
| pTS2 (SEQ ID NO: 119) | TS2 (SEQ ID NO: 118) | 122 | 123 |
| pTS2 (SEQ ID NO: 119) | — | 122 | 124 |
| pTS1v (SEQ ID NO: 136) | — | 125 | 126 |
| pTS27v (SEQ ID NO: 139) | — | 127 | 128 |

All the constructs were mobilized into the *Agrobacterium* strain LBA4404/pSB1 and selected on spectinomycin and tetracycline. *Agrobacterium* transformants were isolated and the integrity of the plasmid was confirmed by retransforming to *E. coli* or PCR analysis.

Example 12

Stable Transfection of Rice with Promoter and Intron Sequence Constructs

Transformation and Regeneration of Rice Callus via *Agrobacterium* Infection

*O. sativa* spp. *japonica* rice var. Nipponbare seeds are sterilized in absolute ethanol for 10 minutes then washed 3 times with water and incubated in 70% Sodium hypochlorite [Fisher Scientific-27908] for 30 minutes. The seeds are then washed 5 times with water and dried completely. The dried seeds are inoculated into NB-CL media [CHU(N6) basal salts (PhytoTechnology-C416) 4 g/l; Eriksson's vitamin solution (1000× PhytoTechnology-E330) 1 ml/l; Thiamine HCl (Sigma-T4625) 0.5 mg/l; 2,4-Dichloro phenoxyacetic acid (Sigma-D7299) 2.5 mg/l; BAP (Sigma-B3408) 0.1 mg/l; L-Proline (PhytoTechnology-P698) 2.5 g/l; Casein acid hydrolysate vitamin free (Sigma-C7970) 0.3 g/l; Myo-inositol (Sigma-I3011) 0.1 g/l; Sucrose (Sigma-S5390) 30 g/l; GELRITE® (Sigma-G1101.5000) 3 g/l; pH 5.8) and kept at 28° C. in dark for callus proliferation.

A single *Agrobacterium* colony containing a desired insert with the candidate sequences from a freshly streaked plate can be inoculated in YEB liquid media [Yeast extract (BD Difco-212750) 1 g/l; Peptone (BD Difco-211677) 5 g/l; Beef extract (Amresco-0114) 5 g/l; Sucrose (Sigma-S5390) 5 g/l; Magnesium Sulfate (Sigma-M8150) 0.3 g/l at pH-7.0] supplemented with Tetracycline (Sigma-T3383) 5 mg/l, Rifamysin 10 mg/l and Spectinomycin (Sigma-S650) 50 mg/l. The cultures are grown overnight at 28° C. in dark with continuous shaking at 220 rpm. The following day the cultures are adjusted to 0.5 Absorbance at 550 nm in PHI-A(CHU(N6) basal salts (PhytoTechnology-C416) 4 g/l; Eriksson's vitamin solution (1000× PhytoTechnology-E330) 1 ml/l; Thiamine HCl (Sigma-T4625) 0.5 mg/l; 2,4-Dichloro phenoxyacetic acid (Sigma-D7299) 2.5 mg/l, L-Proline (PhytoTechnology-P698) 0.69 mg/l; Sucrose (Sigma-S5390) 68.5 g/l; Glucose-36 g/l (Sigma-G8270); pH 5.8)) media supplemented with 200 µM Acetosyringone (Sigma-D134406) and incubated for 1 hour at 28° C. with continuous shaking at 220 rpm.

17-21 day old proliferating calli are transferred to a sterile culture flask and *Agrobacterium* solution prepared as described above was added to the flask. The suspension is incubated for 20 minutes with gentle shaking every 2 minutes. The *Agrobacterium* suspension is decanted carefully and the calli are placed on WHATMAN filter paper No—4. The calli are immediately transferred to NB-CC medium [NB-CL supplemented with 200 µM Acetosyringone (Sigma-D134406) and incubated at 21° C. for 72 hrs.

Culture Termination and Selection

The co-cultivated Calli are placed in a dry, sterile, culture flask and washed with 1 liter of sterile distilled water containing Cefotaxime (Duchefa-C0111.0025) 0.250 g/l and Carbenicillin (Sigma-C0109.0025) 0.4 g/l. The washes are repeated 4 times or until the solution appeared clear. The water is decanted carefully and the calli are placed on WHATMAN filter paper No—4 and dried for 30 minutes at room temperature. The dried calli are transferred to NB-RS medium [NB-CL supplemented with Cefotaxime (Duchefa-C0111.0025) 0.25 g/l; and Carbenicillin (Sigma-C0109.0025) 0.4 g/l and incubated at 28° C. for 4 days.

The calli are then transferred to NB-SB media [NB-RS supplemented with Bialaphos (Meiji Seika K. K., Tokyo, Japan) 5 mg/l and incubated at 28° C. and subcultured into fresh medium every 14 days. After 40-45 days on selection, proliferating, Bialaphos resistant, callus events are easily observable.

Regeneration of Stably transformed Rice Plants from Transformed Rice Calli

Transformed callus events are transferred to NB-RG media [CHU(N6) basal salts (PhytoTechnology-C416) 4 g/l; N6 vitamins 1000×1 ml {Glycine (Sigma-47126) 2 g/l; Thiamine HCl (Sigma-T4625) 1 g/l; acid; Kinetin (Sigma-K0753) 0.5 mg/l; Casein acid hydrolysate vitamin free (Sigma-C7970) 0.5 g/l; Sucrose (Sigma-S5390) 20 g/l; Sorbitol (Sigma-S1876) 30 g/l, pH was adjusted to 5.8 and 4 g/l GELRITE® (Sigma-G1101.5000) was added. Post-sterilization 0.1 ml/l of CuSo4 (100 mM concentration, Sigma-C8027) and 100 ml/l 10×AA Amino acids pH free {Glycine (Sigma-G7126) 75 mg/l; L-Aspartic acid (Sigma-A9256) 2.66 g/l; L-Arginine (Sigma-A5006) 1.74 g/l; L-Glutamine (Sigma-G3126) 8.76 g/l} and incubated at 32° C. in light. After 15-20 days, regenerating plantlets can be transferred to magenta boxes or tubes containing NB-RT media [MS basal salts (PhytoTechnology-M524) 4.33 g/L; B5 vitamins 1 ml/l from 1000× stock {Nicotinic acid (Sigma-G7126) 1 g/l, Thiamine HCl (Sigma-T4625) 10 g/l)}; Myo-inositol (Sigma-I3011) 0.1 g/l; Sucrose (Sigma-S5390) 30 g/l; and IBA (Sigma-I5386) 0.2 mg/l; pH adjusted to 5.8]. Rooted plants obtained after 10-15 days can be hardened in liquid Y media [1.25 ml each of stocks A-F and water sufficient to make 1000 ml. Composition of individual stock solutions: Stock (A) Ammonium Nitrate (HIMEDIA-RM5657) 9.14 g/l, (B) Sodium hydrogen Phosphate (HIMEDIA-58282) 4.03 g, (C) Potassium Sulphate (HIMEDIA-29658-4B) 7.14 g, (D) Calcium Chloride (HIMEDIA-05080) 8.86 g, (E) Magnesium Sulphate (HIMEDIA-RM683) 3.24 g, (F) (Trace elements) Magnesium chloride tetra hydrate (HIMEDIA-10149) 15 mg, Ammonium Molybdate (HIMEDIA-271974B) 6.74 mg/l, Boric acid (Sigma-136768) 9.34 g/l, Zinc sulphate heptahydrate (Hi-Media-RM695) 0.35 mg/l, Copper Sulphate heptahydrate (HIMEDIA-C8027) 0.31 mg/l, Ferric chloride hexahydrate (Sigma-236489) 0.77 mg/l, Citric acid monohydrate (HIMEDIA-C4540) 0.119 g/l] at 28° C. for 10-15 days before transferring to greenhouse. Leaf samples are collected for histochemical GUS staining with 5-bromo-4-chloro-3-indolyl-β-D-glucuronide (X-Gluc), using standard protocols (Janssen and Gardner, *Plant Mol. Biol.* (1989) 14:61-72).

Transgenic plants are analyzed for copy number by southern blotting using standard procedure. All single copy events are transferred to individual pots and further analysis is performed only on these. For all the analysis leaf material from three independent one month old single copy $T_0$ events were taken.

Transgene Copy Number Determination by Quantitative PCR

Transgenic rice plants generated using different constructs were analyzed to determine the transgene copy number using TaqMan-based quantitative real-time PCR (qPCR) analysis. Genomic DNA was isolated from the leaf tissues collected from 10-day old T0 rice plants using the QIAGEN® DNEASY® Plant Maxi Kit (QIAGEN® Inc.) according to the manufacturer's instructions. DNA concentration was adjusted to 100 ng/µl and was used as a template for the qPCR reaction to determine the copy number. The copy number analysis was carried out by designing PCR primers and TaqMan probes for the target gene and for the endogenous glutathione reductase 5 (GR5) gene. The endogenous GR5 gene serves as an internal control to normalize the Ct values obtained for the target gene across different samples. In order to determine the relative quantification (RQ) values for the target gene, genomic DNA from known single and two copy calibrators for a given gene were also included in the experiment. Test samples and calibrators were replicated twice for accuracy. Non-transgenic control and no template control were also included in the reaction. The reaction mixture (for a 20 µl reaction volume) comprises 10 µl of 2×TaqMan universal PCR master mix (Applied Biosystems), 0.5 µl of 10 µM PCR primers and 0.5 µl of 10 µM TaqMan probe for both target gene and endogenous gene. Volume was adjusted to 19 µl using sterile Milli Q water and the reaction components were mixed properly and spun down quickly to bring the liquid to bottom of the tube. 19 µl of the reaction mix was added into each well of reaction plate containing 1 µl of genomic DNA to achieve a final volume of 20 µl. The plate was sealed properly using MicroAmp optical adhesive tape (Applied Biosystems) and centrifuged briefly before loading onto the Real time PCR system (7500 Real PCR system, Applied Biosystems). The amplification program used was: 1 cycle each of 50° C. for 2:00 min and 95° C. for 10:00 min followed by 40 repetitions of 95° C. for 15 sec and 58° C. for 1:00 min. After completion of the PCR reaction, the SDS v2.1 software (Applied Biosystems) was used to calculate the RQ values in the test samples with reference to single copy calibrator.

Stable transgenic rice events were generated with the constructs, PHP50063, PHP50111 PHP50062, PHP50061, PHP52322, and PHP42365 as given in Table 8. The primers used for amplifying the cloned promoter and intron sequences for these constructs are given in Table 2 and Table 7.

TABLE 8

Description of Promoter and Intron Elements in Constructs

| Construct | Intron | Promoter |
|---|---|---|
| PHP50063 | — | pTS2 (SEQ ID NO: 119) |

TABLE 8-continued

Description of Promoter and Intron Elements in Constructs

| Construct | Intron | Promoter |
|---|---|---|
| PHP50111 | TS2 (SEQ ID NO: 118) | pTS2 (SEQ ID NO: 119) |
| PHP50062 | TS2 (SEQ ID NO: 118) | Zm Ubi promoter |
| PHP50061 | TS1 (SEQ ID NO: 4) | pTS1v (SEQ ID NO: 136) |
| PHP52322 | TS27v (SEQ ID NO: 138) | pTS27v (SEQ ID NO: 139) |
| PHP42365 | Zm Ubi intron | Zm Ubi promoter |

The stable transgenic rice events generated with these constructs were subjected to TaqMan-based qPCR (quantitative PCR) analysis to determine the transgene copy number as described above. PCR primers and TaqMan probes designed for the GUS reporter gene and for the endogenous GR5 gene are listed in Table 9.

TABLE 9

Primer Sequences for qPCR

| Primer ID | SEQ ID NO: |
|---|---|
| GUS F primer | 129 |
| GUS R primer | 130 |
| GR5, F primer | 131 |
| GR5, R primer | 132 |

TABLE 10

Probe Sequences for qPCR

| | SEQ ID NO | Probe | Quencher |
|---|---|---|---|
| GUS | 133 | Fam | Tamra |
| GR5 | 134 | Vic | MGB |

All single copy events were transferred to individual pots and further analysis was performed on leaf material and panicle collected one month after transplanting in the greenhouse.

Qualitative and Quantitative Analysis of GUS Reporter Gene Expression in Stable Rice Events Both qualitative and quantitative GUS reporter gene expression analyses were carried out in triplicates on at least 5 independent single copy events for each construct. Leaf and panicle samples were collected for histochemical GUS staining with 5-bromo-4-chloro-3-indolyl-β-D-glucuronide (X-Gluc), using standard protocols (Janssen and Gardner, *Plant Mol. Biol.* (1989) 14:61-72) and for quantitative MUG assay using standard protocols (Jefferson, R. A., Nature. 342, 837-8 (1989); Jefferson, R. A., Kavanagh, T. A. & Bevan, M. W., *EMBO J.* 6, 3901-3907 (1987).

Figure 9:
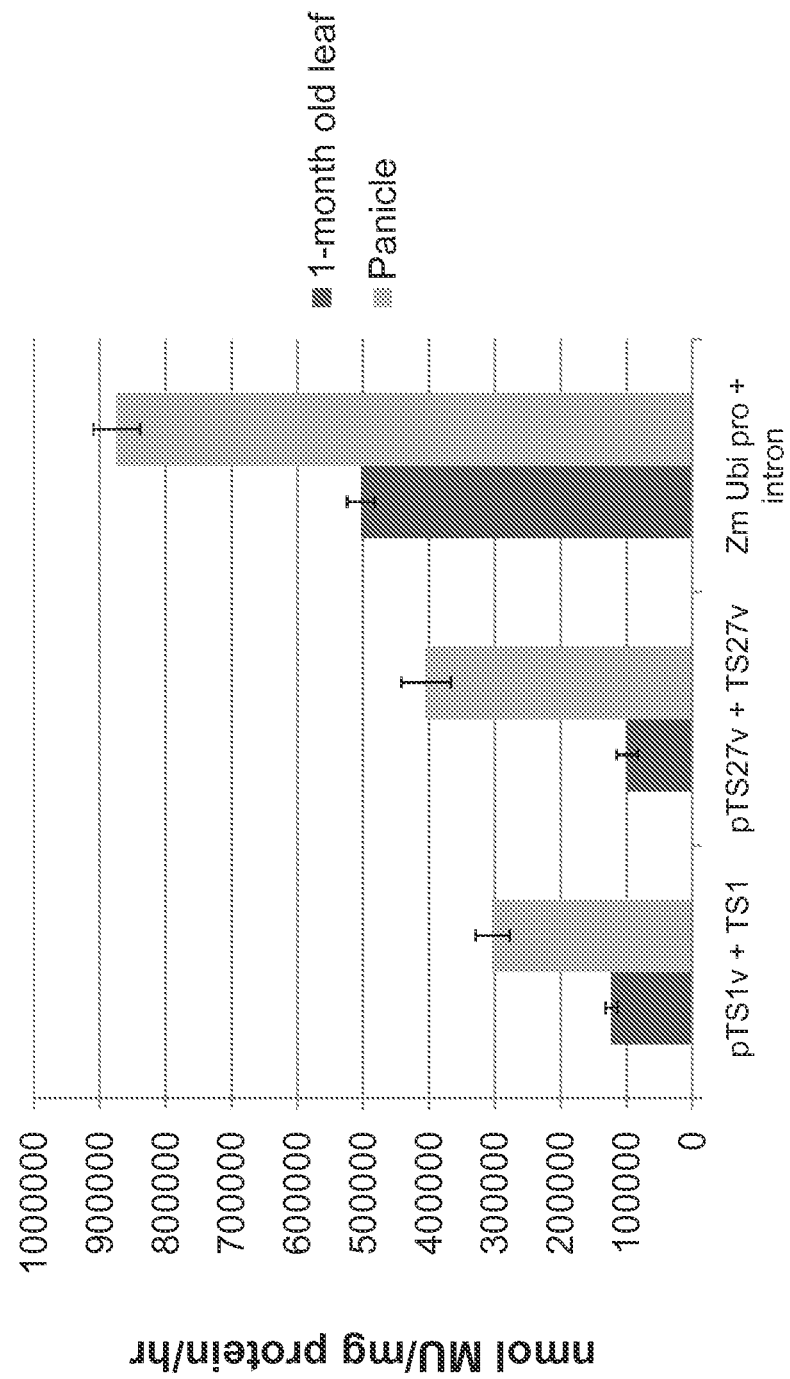
FIG. 9 shows MUG data from stable transgenic lines transformed with different constructs. Data represents the average of 5-8 independent single copy events±SE.

TS1 and TS27v when combined with their respective endogenous promoters (pTS1v+TS1 (PHP50061) and pTS27v+TS27v (PHP52322) were able to drive GUS expression in stable rice transgenic events (FIG. 9).

Figure 10:
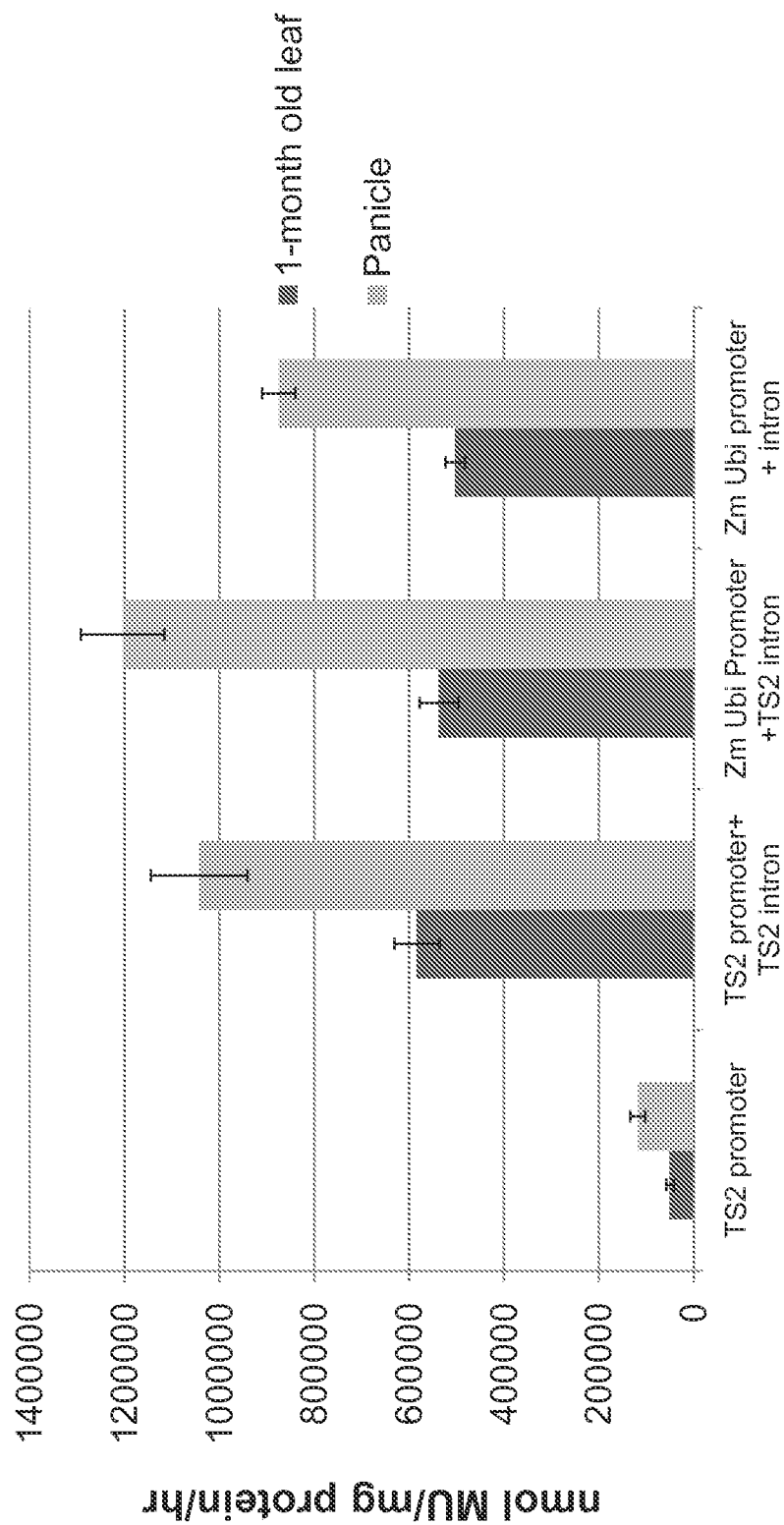
FIG. 10 shows MUG data from stable transgenic lines transformed with different constructs. Data represents the average of 5-8 independent single copy events±SE.

TS2 intron with its endogenous promoter (PHP50111) enhanced the GUS reporter gene expression by 11.6 fold in leaves and 8.9 fold in panicles compared to the TS2 promoter alone (PHP50063) driving the GUS reporter gene expression (FIG. 10) and the values obtained were comparable to the levels observed with maize ubiquitin promoter and intron (PHP42365) driving GUS in transgenic rice plants. There is a slight increase in the GUS reporter gene expression levels when the TS2 intron is cloned with maize Ubiquitin promoter (PHP50062) compared to the data obtained with maize ubiquitin intron cloned with maize ubiquitin promoter (FIG. 10).

Figure 11:
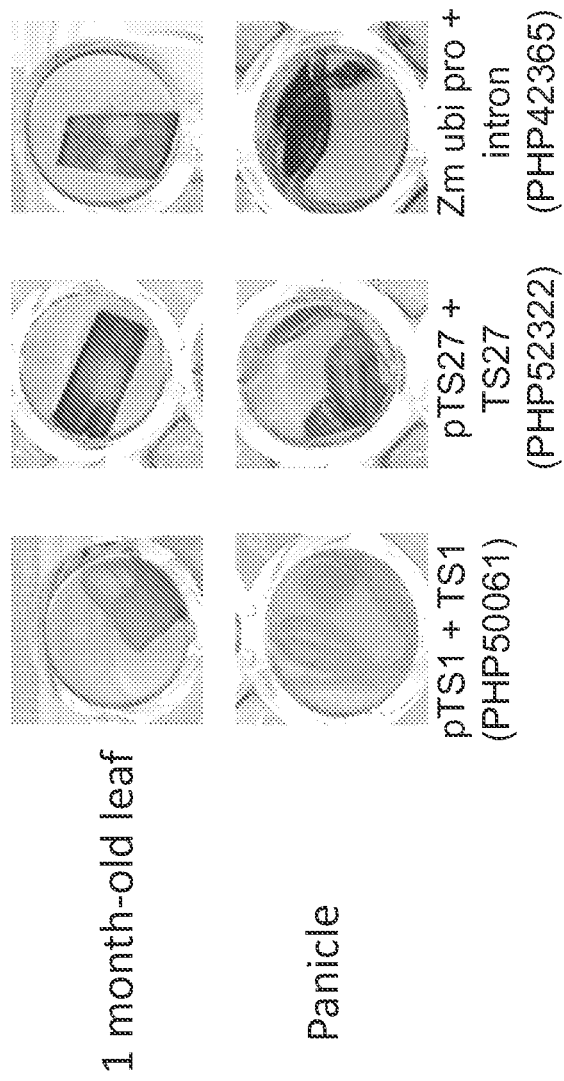
FIG. 11 shows histochemical data from leaves and panicles collected from stable transgenic lines transformed with different constructs. Representative images are shown for each construct analyzed.
Figure 12:
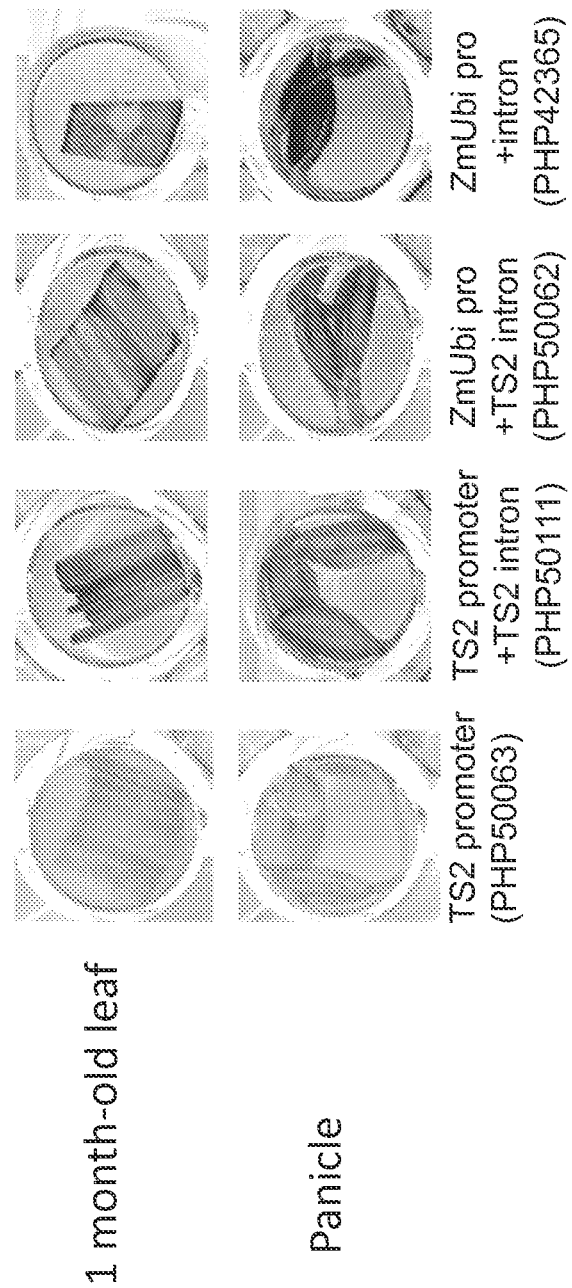
FIG. 12 shows histochemical data from leaves and panicles collected from stable transgenic lines transformed with different constructs. Representative images are shown for each construct analyzed.

GUS histochemical staining data were found to correlate very well with the quantitative GUS assay in all events. Representative images are shown in FIG. 10 and FIG. 11.

Example 13

Identification of Novel Terminator Sequences

Transcription terminators for the 4 genes comprising the expression enhancing introns TS1, TS2, TS13 and TS27v (SEQ ID NOS: 4, 118, 13 and 138 respectively) were identified, and were called tTS1 (SEQ ID NO: 140), tTS2 (SEQ ID NO: 141), tTS13 (SEQ ID NO: 142) and tTS27 (SEQ ID NO: 143). Terminator sequences were defined as 500-900 bp of sequence downstream of the translational stop codon of the respective genes.

Example 14

Amplification and Cloning of Terminator Sequences

Figure 13:
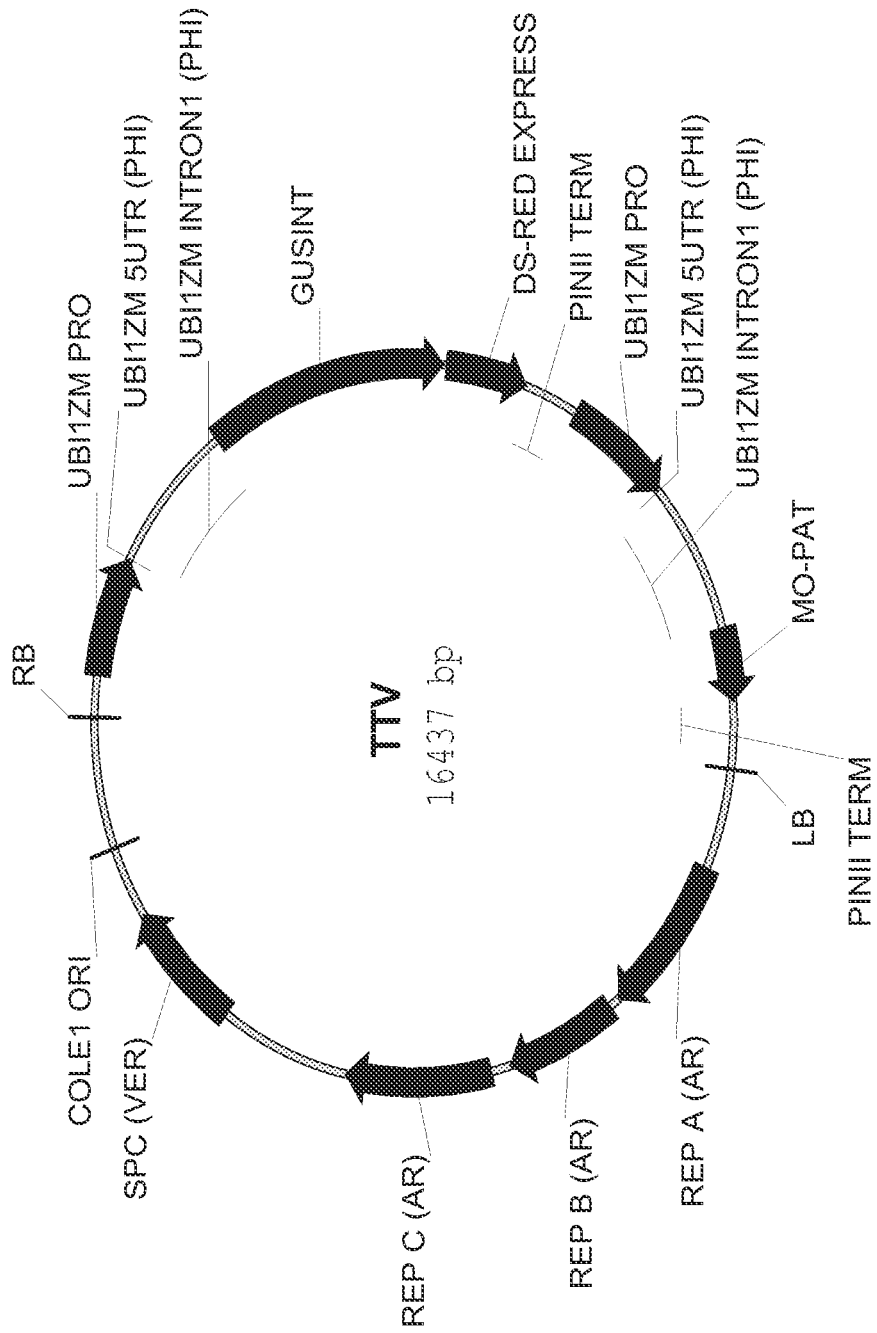
FIG. 13 is the schematic representation of the PHP49597 vector (terminator test vector).

We constructed a terminator test vector (TTV) (PHP49597-FIG. 13; SEQ ID NO: 144) carrying GUS (β-glucuronidase) reporter gene driven by the Maize Ubiquitin promoter using standard molecular biology techniques (Sambrook et al.). A promoterless Ds-RED coding sequence was included downstream of the GUS gene for measurement of transcription downstream of the cloned test terminator sequences (read-through transcripts). The Ds-Red sequence was followed by a Pin II terminator to enable termination and polyadenylation of all transcripts, so we could detect them by reverse-transcription-PCR (RT-PCR) using oligo dT primer. The Terminator test vector also carried a monocot-optimized Phosphinothricin acetyl transferase (MOPAT) gene as a plant selectable marker.

Candidate terminator sequences can be amplified from maize genomic DNA. The resulting DNA fragments can be cloned into the terminator test vector at Acc65I restriction site using IN-FUSION™ cloning (Clontech Inc.). All constructs will be transformed into *Agrobacterium* (LBA4404/pSB1)

Example 15

Rice Transformation with Candidate Terminator Sequences

The candidate maize terminator sequences tTS1, tTS2, tTS13 and tTS27 (SEQ ID NOS:140-143 respectively) will be tested for their ability to function as transcription terminators in stable rice transgenic plants generated by *Agrobacterium* mediated transformation as described in Example 12.

Example 16

Testing of Candidate Rice Terminator Sequences in Stably Transformed Rice Tissues ReverseTranscriptase-PCR (RT-PCR) and GUS assays can be done from stably transformed rice plant tissues, to test the ability of candidate maize terminator sequences tTS1, tTS2, tTS13 and tTS27 (SEQ ID NOS: 140-143 respectively) to prevent transcription read-through and to compare GUS expression Reverse Transcription PCR (RT-PCR) to Determine Transcription Read-Through RNA will be extracted from leaf tissue from multiple independent T0 events for each construct. cDNA can be synthesized using SuperScript® III First-Strand Synthesis System from Invitrogen. The level of GUS gene and read-through transcripts will be assayed using specific primers within GUS gene and DS-Red respectively. Transcript levels can also be measured by quantitative RT-PCR using primers and probes within GUS and DS-Red sequences.

Histochemical and Fluorometric GUS Analysis

Tissue samples from each independent stably transformed rice line can be stained for histochemical GUS analysis, with 5-bromo-4-chloro-3-indolyl-β-D-glucuronide (X-Gluc), using standard protocols (Janssen and Gardner, *Plant Mol. Biol.* (1989) 14:61-72). Tissue samples can also be used for quantitative MUG assay using standard protocols [Jefferson, R. A., *Nature.* 342:837-838 (1989); Jefferson, R. A., Kavanagh, T. A. & Bevan, M. W. *EMBO J.* 6:3901-3907 (1987)].

We claim:

1. A recombinant DNA construct comprising an intron operably linked to a promoter, a heterologous polynucleotide, and a terminator, wherein the intron comprises a nucleotide sequence that has at least 98% sequence identity to SEQ ID NO: 58.

2. The recombinant DNA construct of claim 1, wherein the promoter comprises a nucleotide sequence that has at least 98% identity to SEQ ID NO: 106.

3. The recombinant DNA construct of claim 2, wherein the terminator comprises a nucleotide sequence that has at least 98% identity to SEQ ID NO: 140.

4. The recombinant DNA construct of claim 1, wherein the intron comprises the nucleotide sequence of SEQ ID NO: 58.

5. The recombinant DNA construct of claim 2, wherein the promoter comprises the nucleotide sequence of SEQ ID NO: 106.

6. The recombinant DNA construct of claim 3, wherein the terminator comprises the nucleotide sequence of SEQ ID NO: 140.

7. The recombinant DNA construct of claim 1, wherein the intron enhances expression of the heterologous polynucleotide in a plant.

8. A recombinant DNA construct comprising an intron operably linked to a promoter and a heterologous polynucleotide, wherein the intron comprises a nucleotide sequence that comprises at least one copy of SEQ ID NO: 100, and wherein the intron is capable of enhancing expression of the heterologous polynucleotide in a monocotyledonous plant when compared to a corresponding recombinant DNA construct without the intron.

9. A plant comprising the recombinant DNA construct of claim 7.

10. A seed comprising the recombinant DNA construct of claim 7.

11. A plant comprising the recombinant DNA construct of claim 8.

12. A seed comprising the recombinant DNA construct of claim 8.

13. A method for modulating transgene expression in a plant comprising the steps of:
  (a) introducing into a regenerable plant cell the recombinant DNA construct of claim 1;
  (b) regenerating a transgenic plant from the regenerable plant cell after step (a), wherein the transgenic plant comprises the recombinant DNA construct; and
  (c) obtaining a progeny plant derived from the transgenic plant of step (b), wherein the progeny plant comprises the recombinant DNA construct and exhibits enhanced transgene expression when compared to a plant comprising in its genome the recombinant DNA construct without the corresponding intron sequence.

14. The method of claim 13 wherein said plant is a monocot.

* * * * *